(12) United States Patent
Studer et al.

(10) Patent No.: US 10,280,398 B2
(45) Date of Patent: May 7, 2019

(54) MIDBRAIN DOPAMINE (DA) NEURONS FOR ENGRAFTMENT

(71) Applicant: MEMORIAL SLOAN-KETTERING CANCER CENTER, New York, NY (US)

(72) Inventors: Lorenz Studer, New York, NY (US); Jae-Won Shim, New York, NY (US); Sonja Kriks, New York, NY (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 0 days.

(21) Appl. No.: 14/356,042

(22) PCT Filed: Nov. 2, 2012

(86) PCT No.: PCT/US2012/063339
§ 371 (c)(1),
(2) Date: May 2, 2014

(87) PCT Pub. No.: WO2013/067362
PCT Pub. Date: May 10, 2013

(65) Prior Publication Data
US 2015/0010514 A1 Jan. 8, 2015

Related U.S. Application Data

(60) Provisional application No. 61/555,828, filed on Nov. 4, 2011.

(51) Int. Cl.
| | |
|---|---|
| *C12N 5/02* | (2006.01) |
| *C12N 5/00* | (2006.01) |
| *C12N 5/0793* | (2010.01) |
| *A61K 35/30* | (2015.01) |
| *C12N 5/0797* | (2010.01) |

(52) U.S. Cl.
CPC ........... *C12N 5/0619* (2013.01); *A61K 35/30* (2013.01); *C12N 5/0623* (2013.01); *C12N 2501/01* (2013.01); *C12N 2501/119* (2013.01); *C12N 2501/13* (2013.01); *C12N 2501/15* (2013.01); *C12N 2501/16* (2013.01); *C12N 2501/41* (2013.01); *C12N 2501/415* (2013.01); *C12N 2501/999* (2013.01); *C12N 2506/02* (2013.01); *C12N 2506/45* (2013.01)

(58) Field of Classification Search
CPC .................................................... C12N 5/0619
See application file for complete search history.

(56) References Cited

U.S. PATENT DOCUMENTS

| | | | |
|---|---|---|---|
| 5,166,065 A | 11/1992 | Williams et al. | |
| 5,340,740 A | 8/1994 | Petitte et al. | |
| 5,453,357 A | 9/1995 | Hogan | |
| 5,523,226 A | 6/1996 | Wheeler | |
| 5,589,376 A | 12/1996 | Anderson et al. | |
| 6,610,540 B1 | 8/2003 | Csete et al. | |
| 6,787,356 B1 | 9/2004 | Studer et al. | |
| 6,833,269 B2 | 12/2004 | Carpenter | |
| 6,887,706 B2 | 5/2005 | Zhang et al. | |
| 7,005,252 B1 | 2/2006 | Thomson | |
| 7,011,828 B2 | 3/2006 | Reubinoff et al. | |
| 7,112,437 B2 | 9/2006 | Pera | |
| 7,211,434 B2 | 5/2007 | Van Der Kooy et al. | |
| 7,252,995 B2 | 8/2007 | Fu et al. | |
| 7,294,510 B2 | 11/2007 | Okano et al. | |
| 7,297,539 B2 | 11/2007 | Mandalam et al. | |

(Continued)

FOREIGN PATENT DOCUMENTS

| | | |
|---|---|---|
| CA | 2923592 A1 | 3/2015 |
| CN | 102191221 A | 9/2011 |
| EP | 1 645 286 A1 | 4/2006 |
| KR | 101331034 B1 | 11/2013 |

(Continued)

OTHER PUBLICATIONS

MacDonald (2009, Developmental Cell, 17:9-26).*
Katoh, Cancer Biology and Therapy, 2006, 5:1059-1064.*
Gordon, 2006, Journal of Biological Chemistry, 281:22429-22433.*
Willert, CSH Perspectives in Biology, 2012, 4:1-13.*
Wang, Stem Cells and Development, 2010, 19:1375-1383.*
Thomson et al. (PNAS, 92:7844-7848 (Aug. 1995)).*
NIH (Stem Cells: Scientific Progress and Future Research Directions, Department of Health and Human Services, Chapter 1, pp. 1-4, Jun. 2001).*

(Continued)

*Primary Examiner* — Valarie E Bertoglio
(74) *Attorney, Agent, or Firm* — Baker Botts L.L.P.

(57) ABSTRACT

The present invention relates to the field of stem cell biology, in particular the lineage specific differentiation of pluripotent or multipotent stem cells, which can include, but is not limited to, human embryonic stem cells (hESC) in addition to nonembryonic human induced pluripotent stem cells (hiPSC), somatic stem cells, stem cells from patients with a disease, or any other cell capable of lineage specific differentiation. Specifically described are methods to direct the lineage specific differentiation of hESC and/or hiPSC into floor plate midbrain progenitor cells and then further into large populations of midbrain fate FOXA2+LMX1A+TH+ dopamine (DA) neurons using novel culture conditions. The midbrain fate FOXA2+LMX1A+TH+ dopamine (DA) neurons made using the methods of the present invention are further contemplated for various uses including, but not limited to, use in in vitro drug discovery assays, neurology research, and as a therapeutic to reverse disease of, or damage to, a lack of dopamine neurons in a patient. Further, compositions and methods are provided for differentiating midbrain fate FOXA2+LMX1A+TH+ dopamine (DA) neurons from human pluripotent stem cells for use in disease modeling, in particular Parkinson's disease. Additionally, authentic DA neurons are enriched for markers, such as CD142, and A9 type neuronal cells.

14 Claims, 35 Drawing Sheets

(56) References Cited

U.S. PATENT DOCUMENTS

| | | |
|---|---|---|
| 7,332,336 B2 | 2/2008 | Ochiya et al. |
| 7,368,115 B2 | 5/2008 | Ohta et al. |
| 7,763,463 B2 | 7/2010 | Carpenter et al. |
| 7,892,830 B2 | 2/2011 | Bergendahl et al. |
| 8,153,422 B2 | 4/2012 | Isacson et al. |
| 8,153,428 B2 | 4/2012 | Carpenter et al. |
| 8,252,585 B2 | 8/2012 | Carpenter |
| 8,252,586 B2 | 8/2012 | Carpenter et al. |
| 8,323,971 B2 | 12/2012 | Pedersen et al. |
| 8,551,783 B2 | 10/2013 | Kim et al. |
| 8,642,334 B2 | 2/2014 | Chambers et al. |
| 8,883,502 B2 | 11/2014 | Zhang et al. |
| 8,932,857 B2 | 1/2015 | Yamanaka et al. |
| 9,249,389 B2 | 2/2016 | Isacson et al. |
| 9,453,198 B2 | 9/2016 | Studer et al. |
| 9,487,751 B2 | 11/2016 | Anderson et al. |
| 2003/0036195 A1 | 2/2003 | Studer et al. |
| 2003/0211605 A1 | 11/2003 | Lee et al. |
| 2004/0005704 A1 | 1/2004 | Csete et al. |
| 2004/0087478 A1 | 5/2004 | Gillen et al. |
| 2004/0214324 A1 | 10/2004 | Isacson et al. |
| 2005/0260747 A1 | 11/2005 | Reubinoff et al. |
| 2006/0078543 A1 | 4/2006 | Reubinoff et al. |
| 2007/0224650 A1 | 9/2007 | Jessell et al. |
| 2009/0035285 A1 | 2/2009 | Condie et al. |
| 2010/0009442 A1 | 1/2010 | Sasai et al. |
| 2010/0093090 A1 | 4/2010 | Deng et al. |
| 2010/0099772 A1 | 4/2010 | Bean et al. |
| 2011/0229441 A1 | 9/2011 | Benchoua et al. |
| 2012/0094381 A1 | 4/2012 | Chambers et al. |
| 2012/0142093 A1 | 6/2012 | Takahashi et al. |
| 2012/0148549 A1 | 6/2012 | Anderson et al. |
| 2012/0322146 A1 | 12/2012 | Carpenter et al. |
| 2013/0108669 A1 | 5/2013 | Cooper et al. |
| 2013/0183674 A1 | 7/2013 | Studer et al. |
| 2014/0199274 A1 | 7/2014 | Kim et al. |
| 2014/0248696 A1 | 9/2014 | Zhang et al. |
| 2014/0314721 A1 | 10/2014 | Semechkin et al. |
| 2015/0010514 A1 | 1/2015 | Studer et al. |
| 2015/0010515 A1 | 1/2015 | Schoeler et al. |
| 2015/0030570 A1 | 1/2015 | Pan et al. |
| 2015/0086481 A1 | 3/2015 | Ganat et al. |
| 2015/0087541 A1 | 3/2015 | Gonzalez et al. |
| 2015/0265652 A1 | 9/2015 | George et al. |
| 2015/0353888 A1 | 12/2015 | Inoue et al. |
| 2016/0108362 A1 | 4/2016 | Su et al. |
| 2016/0115444 A1 | 4/2016 | Studer et al. |
| 2016/0115448 A1 | 4/2016 | Studer et al. |
| 2016/0145582 A1 | 5/2016 | Yu |
| 2016/0201032 A1 | 7/2016 | Studer et al. |
| 2016/0326491 A1 | 11/2016 | Chambers et al. |

FOREIGN PATENT DOCUMENTS

| | | |
|---|---|---|
| WO | WO 2003/000868 A1 | 1/2003 |
| WO | WO 2007/113505 A2 | 10/2007 |
| WO | WO 2008/018190 A1 | 2/2008 |
| WO | WO 2009/099152 A1 | 8/2009 |
| WO | WO 2010/063848 A1 | 6/2010 |
| WO | WO 2010/096496 A2 | 8/2010 |
| WO | WO 2010/141622 A2 | 12/2010 |
| WO | WO 2011/019092 A1 | 2/2011 |
| WO | WO 2011/108766 A1 | 9/2011 |
| WO | WO 2011/159726 A2 | 12/2011 |
| WO | WO 2015/054526 A2 | 4/2015 |
| WO | WO 2015/143622 A1 | 10/2015 |
| WO | WO 2016/063985 A1 | 4/2016 |
| WO | WO 2016/162747 A2 | 10/2016 |

OTHER PUBLICATIONS

Eldar-Finkelman, 2011, Frontiers in molecular Neuroscience, 4:32:1-18. (Year: 2011).*

Wang (2010, PNAS, 107:9323-9328).*

Chambers, S. M. et al., "Highly efficient neural conversion of human ES and iPS cells by dual inhibition of SMAD signaling", Nature Biotechnology, vol. 27, No. 3, Mar. 1, 2009, pp. 275-280.

Cooper, O. et al., "Differentiation of human ES and Parkinson's disease iPS cells into ventral midbrain dopaminergic neurons requires a high activity form of SHH, FGF8a and specific regionalization by retinoic acid", Molecular and Cellular Neurosciences, vol. 45, No. 3, Nov. 1, 2010, pp. 258-266.

Fasano, C.A. et al., Efficient Derivation of Functional Floor Plate Tissue from Human Embryonic Stem Cells, Cell Stem Cell, Apr. 2, 2010, vol. 6, No. 4, pp. 336-347.

Joksimovic, M. et al., "Wnt antagonism of Shh facilitates midbrain floor plate neurogenesis", Developmental Biology, vol. 331, No. 2, Jul. 15, 2009, pp. 507-508.

Kriks, S. et al., Dopamine neurons derived from human ES cells efficiently engraft in animal models of Parkinson's disease, Nature, Nov. 6, 2011, vol. 480, No. 7378, pp. 547-551.

Extended European Search Report dated Mar. 10, 2015 issued in European Patent Application No. 12846715.6.

International Search Report dated Mar. 29, 2013 in International Patent Application No. PCT/US2012/063339.

Written Opinion of the International Searching Authority dated Mar. 29, 2013 in International Patent Application No. PCT/US2012/063339.

Chambers et al., "Combined small-molecule inhibition accelerates developmental timing and converts human pluripotent stem cells into nociceptors," 2012, Nature Biotechnology 30(7):715-720.

Crawford et al., "The Notch Response Inhibitor DAPT Enhances Neuronal Differentiation in Embryonic Stem Cell-Derived Embryoid Bodies Independently of Sonic Hedgehog Signaling," 2007, Developmental Dynamics 236:886-892.

Kirkeby et al., "Predictive Markers Guide Differentiation to Improve Graft Outcome in Clinical Translation of hESC Based Therapy for Parkinson's Disease," Cell Stem Cell, available online Oct. 27, 2016 (2016), downloaded Feb. 2, 2017 from <http://dx.doi.org/10.1016/j.stem/2016.09.004>.

Li et al., "Rapid induction and long-term self-renewal of primitive neural precursors from human embryonic stem cells by small molecule inhibitors," 2011, PNAS 108(20):8299-8304.

Placantonakis et al., "BAC Transgenesis in Human Embryonic Stem Cells as a Novel Tool to Define the Human Neural Lineage," 2009, Stem Cells 27:521-532.

Raymon et al., "Immortalized Human Dorsal Root Ganglion Cells Differentiate into Neurons with Nociceptive Properties," 1999, J. Neurosci. 19(13):5420-5428.

Steinbeck et al., "Optogenetics enables functional analysis of human embryonic stem cell-derived grafts in a Parkinson's disease model," 2015, Nature Biotechnology 33(2):204-209.

Tomishima et al., "Production of Green Fluorescent Protein Transgenic Embryonic Stem Cells Using the GENSAT Bacterial Artificial Chromosome," 2007, Stem Cells 25:39-45.

Woolf et al., "Nociceptors-Noxious Stimulus Detectors" 2007, Neuron 55:353-364.

Jin et al., "MAPK/ERK and Wnt/β-Catenin pathways are synergistically involved in proliferation of Sca-1 positive hepatic progenitor cells", Biochemical and Biophysical Research Communications 409:803-807 (2011).

Lin W. et al., "Foxa1 and Foxa2 function both upstream of and cooperatively with Lmx1a and Lmx1b in a feedforward loop promoting mesodiencephalic dopaminergic neuron development", Genome & Development Control, Developmental Biology 333:386-396 (2009).

Yu et al., "BMP type I receptor inhibition reduces heterotopic ossification", Nature Medicine 14(12):1363-1369 (2008).

U.S. Appl. No. 13/201,137 (U.S. Pat. No. 8,642,334), filed Nov. 10, 2011 (Feb. 4, 2014).

U.S. Appl. No. 13/697,274 (U.S. Pat. No. 9,453,198), filed Jan. 22, 2013 (Sep. 27, 2016).

U.S. Appl. No. 14/168,835 (US 2017/0130199), filed Jan. 30, 2014 (May 11, 2017).

U.S. Appl. No. 14/169,286 (US 2017/0159012), filed Jan. 31, 2014 (Jun. 8, 2017).

(56) References Cited

OTHER PUBLICATIONS

U.S. Appl. No. 14/922,110 (US 2016/0115448), filed Oct. 23, 2015 (Apr. 28, 2016).
U.S. Appl. No. 15/077,012 (US 2016/0201032), filed Mar. 22, 2016 (Jul. 14, 2016).
U.S. Appl. No. 13/201,137, Dec. 23, 2013 Issue Fee Payment.
U.S. Appl. No. 13/201,137, Sep. 24, 2013 Notice of Allowance.
U.S. Appl. No. 13/201,137, Sep. 17, 2013 Response after Final Action.
U.S. Appl. No. 13/201,137, Jul. 24, 2013 Final Office Action.
U.S. Appl. No. 13/201,137, Jun. 6, 2013 Response to Non-Final Office Action.
U.S. Appl. No. 13/201,137, Mar. 7, 2013 Non-Final Office Action.
U.S. Appl. No. 13/201,137, Jan. 24, 2013 Response to Restriction Requirement.
U.S. Appl. No. 13/201,137, Jan. 3, 2013 Restriction Requirement.
U.S. Appl. No. 13/697,274, Aug. 19, 2016 Issue Fee Payment.
U.S. Appl. No. 13/697,274, May 20, 2016 Notice of Allowance.
U.S. Appl. No. 13/697,274, Apr. 7, 2016 Request for Continued Examination (RCE).
U.S. Appl. No. 13/697,274, Mar. 24, 2016 Notice of Allowance.
U.S. Appl. No. 13/697,274, Mar. 24, 2016 Applicant Initiated Interview Summary.
U.S. Appl. No. 13/697,274, Mar. 22, 2016 Issue Fee Payment.
U.S. Appl. No. 13/697,274, Dec. 23, 2015 Notice of Allowance.
U.S. Appl. No. 13/697,274, Nov. 4, 2015 Response to Non-Final Office Action.
U.S. Appl. No. 13/697,274, May 5, 2015 Non-Final Office Action.
U.S. Appl. No. 13/697,274, Mar. 26, 2015 Response to Restriction Requirement.
U.S. Appl. No. 13/697,274, Dec. 26, 2014 Restriction Requirement.
U.S. Appl. No. 14/168,835, May 22, 2017 Non-Final Office Action.
U.S. Appl. No. 14/168,835, Jan. 27, 2017 Office of Petitions Decision.
U.S. Appl. No. 14/168,835, Sep. 15, 2016 Petition for review by the Office of Petitions.
U.S. Appl. No. 14/168,835, Mar. 15, 2016 Office of Petitions Decision.
U.S. Appl. No. 14/168,835, Nov. 26, 2014 Petition for review by the Office of Petitions.
U.S. Appl. No. 14/168,835, Sep. 30, 2014 Notice of Abandonment.
U.S. Appl. No. 14/169,286, Jun. 8, 2017 Restriction Requirement.
U.S. Appl. No. 14/169,286, Mar. 3, 2017 Office of Petitions Decision.
U.S. Appl. No. 14/169,286, Sep. 15, 2016 Petition for review by the Office of Petitions.
U.S. Appl. No. 14/169,286, Mar. 15, 2016 Office of Petitions Decision.
U.S. Appl. No. 14/169,286, Nov. 26, 2014 Petition for review by the Office of Petitions.
U.S. Appl. No. 14/169,286, Sep. 30, 2014 Notice of Abandonment.
U.S. Appl. No. 15/077,012, Jun. 12, 2017 Non-Final Office Action.
"DAPI Nucleic Acid Stain," Molecular Probes, Invitrogen, Ltd. pp. 1-5 (2006).
Agarwal et al., "Efficient Differentiation of Functional Hepatocytes from Human Embryonic Stem Cells," Stem Cells, 26:1117-1127 (2008).
Aoki, et al., "Sox10 Regulates the Development of Neural Crest-Derived Melanocytes in Xenopus," Developmental Biology, 259(1):19-33 (2003).
Bailey et al., "Sensory Organs: Making and Breaking the Pre-Placodal Region," Current Topics in Developmental Biology, 72:167-204 (2006).
Baker et al., "Establishing neuronal identity in vertebrate neurogenic placodes," Development, 127:3045-3056 (2000).
Baker et al., "Vertebrate cranial placodes I. Embryonic induction," Dev Biol., 232(1):1-61, pp. 1-30 (2001a).
Baker et al., "Vertebrate cranial placodes I. Embryonic induction," Dev Biol., 232(1):1-61, pp. 31-61(2001b).
Bansal et al., "Specific Inhibitor of FGF Receptor Signaling: FGF-2-Mediated Effects on Proliferation, Differentiation, and MAPK Activation Are Inhibited by PD 173074 in Oligodendrocyte-Lineage Cells," Journal of Neuroscience, Research, 74(4):486-493.
Barberi et al., "Derivation of engraftable skeletal myoblasts from human embryonic stem cells," Nat Med, 13(5):642-648 (2007).
Barberi et al., "Derivation of Multipotent Mesenchymal Precursors from Human Embryonic Stem Cells," PLoS Med, 2(6):e161 (2005).
Barberi et al., "Neural subtype specification of fertilization and nuclear transfer embryonic stem cells and application in parkinsonian mice," Nat Biotechnol. 10:1200-1207 (2003).
Bennett et al., "Regulation of Wnt Signaling During Adipogenesis," J Biol Chem., 277(34):30998-31004 (2002).
Bhattacharyya et al., "Hierarchy of regulatory events in sensory placode development," Curr Opin Genet Dev. 14(5):520-6 (2004).
Bouwmeester et al., "Cerberus is a head-inducing secreted factor expressed in the anterior endoderm of Spemann's organizer," Nature, 382:595-601 (1996).
Bradley et al., "Formation of germ-line chimaeras from embryo-derived teratocarcinoma cell lines," Nature 309:255-256 (1984).
Briscoe and Ericson, "The specification of neuronal identity by graded Sonic Hedgehog signalling," Semin Cell Dev Biol. 3:353-62 (1999).
Brivanlou and Darnell, "Signal Transduction and the Control of Gene Expression," Science, 295(5556):813-818 (2002).
Bystron et al., "The First Neurons of the Human Cerebral Cortex," Nat Neurosci., 9(7):880-886 (2006).
Cadigan and Liu, "Wnt Signaling: Complexity At the Surface," J Cell Sci., 119(Pt 3):395-402 (2006).
Callaerts et al., "*PAX-6* in Development and Evolution," Annu. Rev. Neurosci. 20:483-532 (1997).
Chambers et al., "Dual-SMAD Inhibition/WNT Activation-Based Methods to Induce Neural Crest and Derivatives from Human Pluripotent Stem Cells," Methods in Molecular Biology (2013) DOI 10.1007/7651_2013_59.
Charrier et al., "Dual origin of the floor plate in the avian embryo," Development 129:4785-4796 (2002).
Charron et al., "The Morphogen Sonic Hedgehog Is an Axonal Chemoattractant that Collaborates with Netrin-1 in Midline Axon Guidance," Cell 113:11-23 (2003).
Chen et al., "Immortalization and characterization of a nociceptive dorsal root ganglion sensory neuronal line," J Peripher Nerv Syst., 12(2):121-130 (2007).
Cuny et al., "Structure-Activity Relationship Study of Bone Morphogenetic Protein (BMP) Signaling Inhibitors," Bioorg Med Chem Lett., 18(15):4388-4392 (2008).
D'Amour et al., "Efficient differentiation of human embryonic stem cells to definitive endoderm," Nat Biotechnol, 23(12):1534-1541 (2005).
Dennis et al., "DAVID: Database for Annotation, Visualization, and Integrated Discovery," Genome Biology 4:R60 (2003).
Dezawa et al., "Potential of Bone Marrow Stromal Cells in Applications for Neuro-Degenerative, Neuro-Traumatic and Muscle Degenerative Diseases," Current Neuropharmacology, 3:257-266 (2005).
Doble and Woodgett, "GSK-3: Tricks of the Trade for a Multi-Tasking Kinase," Journal of Cell Science, 116(7):1175-1186 (2003).
Doetschman et al. "Establishment of Hamster Blastocyst-Derived Embryonic Stem (ES) Cells," Dev Biol., 127:224-227 (1988).
Dorsky et al., "Control of Neural Crest Cell Fate by the Wnt Signalling Pathway," Nature, 396(6709):370-373 (1998).
Dovey et al., "Functional Gamma-Secretase Inhibitors Reduce Beta-Amyloid Peptide Levels in Brain," J Neurochem., 76(1):173-181 (2001).
Ebendal et al., "Bone Morphogenetic Proteins and Their Receptors: Potential Functions in the Brain," Journal of Neuroscience, Research, 51(2):139-146 (1998).
Eiraku et al., "Self-organized formation of polarized cortical tissues from ESCs and its active manipulation by extrinsic signals," Cell Stem Cell, 3:519-53 (2008).
Elkabetz et al., "Human ES cell-derived neural rosettes reveal a functionally distinct early neural stem cell stage," Genes Dev., 22:152-165 Erratum (2008).

(56) References Cited

OTHER PUBLICATIONS

Elkabetz et al., "Human ES Cell-Derived Neural Rosettes Reveal a Functionally Distinct Early Neural Stem Cell Stage," Genes Dev., 22(2):152-165 (2008).
Erceg et al., "Human Embryonic Stem Cell Differentiation Toward Regional Specific Neural Precursors," Stem Cells, 27:78-87 (2009).
Ericson et al., "Two Critical Periods of Sonic Hedgehog Signaling Required for the Specification of Motor Neuron Identity," Cell, 87:661-673 (1996).
Evans et al., "Derivation and preliminary characterization of pluripotent cell lines from porcine and bovine blastocysts," Theriogenology, 33(1):125-128 (1990).
Evans et al., "Establishment in culture of pluripotential cells from mouse embryos," Nature, 292:154-156 (1981).
Fang et al., "Electrophysiological Differences Between Nociceptive and Non- Nociceptive Dorsal Root Ganglion Neurones in the Rat In Vivo," The Journal of Physiology, 565(3):927-943 (2005).
Fasano et al., "Bmi-1 cooperates with Foxg1 to maintain neural stem cell self-renewal in the fore brain," Genes Dev., 23:561-574 (2009).
Fasano et al., "Bmi-1 cooperates with Foxg1 to maintain neural stem cell self-renewal in the fore brain," Genes Dev., 23:561-574 Suppl. Fig. 1 (2009).
Fasano et al., "Bmi-1 cooperates with Foxg1 to maintain neural stem cell self-renewal in the fore brain," Genes Dev., 23:561-574 Suppl. Fig. 2 (2009).
Fasano et al., "Bmi-1 cooperates with Foxg1 to maintain neural stem cell self-renewal in the fore brain," Genes Dev., 23:561-574 Suppl. Fig. 3 (2009).
Fasano et al., "Bmi-1 cooperates with Foxg1 to maintain neural stem cell self-renewal in the fore brain," Genes Dev., 23:561-574 Suppl. Fig. 4 (2009).
Fasano et al., "Bmi-1 cooperates with Foxg1 to maintain neural stem cell self-renewal in the fore brain," Genes Dev., 23:561-574 Suppl. Fig. legends (2009).
Fasano et al., "Bmi-1 cooperates with Foxg1 to maintain neural stem cell self-renewal in the fore brain," Genes Dev., 23:561-574 Suppl. Materials (2009).
Fasano et al., "shRNA knockdown of Bmi-1 reveals a critical role for p21-Rb pathway in NSC self-renewal during development," Cell Stem Cell, 1:87-99 (2007).
George et al., "Nociceptive Sensory Neurons Derive From Contralaterally Migrating, Fate-Restricted Neural Crest Cells," Nat Neurosci., 10(10):1287-1293 (2007).
Gerdes et al., "Production of a Mouse Monoclonal Antibody Reactive With a Human Nuclear Antigen Associated With Cell Proliferation," Int J Cancer, 31(1):13-20 (1983).
Gerrero et al., "Bm-3.0: A POU-Domain Protein Expressed in the Sensory, Immune, and Endocrine Systems That Functions on Elements Distinct From Known Octamer Motifs," PNAS USA, 90(22):10841-10845 (1993).
Giles et al., "Pluripotency of Cultured Rabbit Inner Cell Mass Cells Detected by Isozyme Analysis and Eye Pigmentation of Fetuses Following Injection into Blastocysts or Morulae," Mol. Reprod and Dev., 36:130-138 (1993).
Glinka et al., "Dickkopf-1 is a member of a new family of secreted proteins and functions in head induction," Nature, 391:357-362 (1998).
Grappe et al., "Structural basis of BMP signalling inhibition by the cystine knot protein Noggin," Nature, 420:636-642 (2002).
Graves et al., "Derivation and Characterization of Putative Pluripotential Embryonic Stem Cells from Preimplantation Rabbit Embryos," Mol. Reprod and Dev., 36:424-433 (1993).
Hemmati-Brivanlou et al., "Follistatin, an Antagonist of Activin, is Expressed in the Spemann Organizer and Displays Direct Neuralizing Activity," Cell, 77:283-295 (1994).
Hendzel et al., "Mitosis-Specific Phosphorylation of Histone H3 Initiates Primarily Within Pericentromeric Heterochromatin During G2 and Spreads in an Ordered Fashion Coincident With Mitotic Chromosome Condensation," Chromosoma., 106(6):348-360 (1997).
Hogan, "Bone Morphogenetic Proteins: Multifunctional Regulators of Vertebrate Development," Genes Dev., 10(13):1580-1594 (1996).
Huang et al., "Bioinformatics enrichment tools: paths toward the comprehensive functional analysis of large gene lists," Nucleic Acids Res., 37(1):1-13 (2009).
Huang et al., "Systematic and integrative analysis of large gene lists using DAVID Bioinformatics Resources," Nat Protoc., 4(1):44-57 (2009).
Hunter et al., "Retinoic acid stimulates neurite outgrowth in the amphibian spinal cord," PNAS USA, 88:3666-3670 (1991).
Iannaccone et al., "Pluripotent Embryonic Stem Cells from the Rat Are Capable of Producing Chimeras," Dev. Biol. 163:288-292 (1994).
International search report dated Sep. 26, 2014 in International Application No. PCT/US2014/035760.
International Search Report dated Nov. 11, 2010 in International Patent Application No. PCT/US10/024487.
ISR PCT/US2011/037179 dated Feb. 24, 2012.
Ivanova et al., "Dissecting self-renewal in stem cells with RNA interference," Nature, 442:533-538 (2006).
Jeong et al., "A functional screen for sonic hedgehog regulatory elements across a 1 Mb interval identifies long-range ventral forebrain enhancers," Development, 133:7761-7772 (2005).
Jeong et al., "Distinct regulators of SHH transcription in the floor plate and notochord indicate separate origins for these tissues in the mouse node," Development, 130:3891-3902 (2003).
Jessell et al., "Polarity and patterning in the neural tube: the origin and function of the floor plate," Ciba Found Symp., 144:255-276, pp. 255-266 (1989a).
Jessell et al., "Polarity and patterning in the neural tube: the origin and function of the floor plate," CibaFound Symp., 144:255-276, pp. 267-276 (1989b).
Jessell et al., Polarity and patterning in the neural tube: the origin and function of the floor plate. Ciba Found Symp., (discussion) 144:276-280, 290-295 (1989).
Jessell, "Neuronal specification in the spinal cord: inductive signals and transcriptional codes," Nat Rev Genet., 1:20-29 (2000).
Joannides et al., "Automated Mechanical Passaging: A Novel and Efficient Method for Human Embryonic Stem Cell Expansion," Stem Cells, 24(2):230-235 (2006).
Joksimovic et al., "Wnt antagonism of SHH facilitates midbrain floor plate neurogenesis," Nat Neurosci., 12:125-131 (2009).
Kakegawa et al, International Association for Dental Research, General Session and Exhibition, Jun. 28-Jul. 1, Abstract #0267, Brisbane Australia.
Kawasaki et al., "Induction of Midbrain Dopaminergic Neurons from ES Cells by Stromal Cell-Derived Inducing Activity," Neuron, 28:31-40 (2000).
Kikuchi et al., "Multiplicity of the Interactions of Wnt Proteins and Their Receptors," Cell Signal, 19(4):659-671 (2007).
Kim et al., "Oct4-Induced Pluripotency in Adult Neural Stem Cells," Cell, 136:411-419 (2009).
Kim et al., "Robust Enhancement of Neural Differentiation From Human ES and iPS Cells Regardless of Their Innate Difference in Differentiation Propensity," Stem Cell Reviews and Reports, 6(2):270-281 (2010).
Kimura-Yoshida et al., "Crucial roles of Foxa2 in mouse anterior-posterior axis polarization via regulation of anterior visceral endoderm-specific genes," PNAS, 104:5919-59249 with Data Supplement Figs. Legends SFig. 5 and SFig. 6 (2006).
Kitao et al., "Neurogenesis of Subpopulations of Rat Lumbar Dorsal Root Ganglion Neurons Including Neurons Projecting to the Dorsal Column Nuclei," The Journal of Comparative Neurology, 371(2):249-257 (1996).
Kittappa et al, "The *foxa2* Gene Controls the Birth and Spontaneous Degeneration of Dopamine Neurons in Old Age," PLoS Biol., 5(12):e325 (2007).
Kodama et al., "Neurogenic Potential of Progenitors Derived from Human Circulating CD14+ Monocytes," Immunol. Cell Biol., 84(2):209-217 (2006).
Laflamme et al., "Cardiomyocytes derived from human embryonic stem cells in pro-survival factors enhance function of infarcted rat hearts," Nat Biotechnol., 25(9):1015-1024 (2007).

(56) References Cited

OTHER PUBLICATIONS

Lee et al., "Directed Differentiation and Transplantation of Human Embryonic Stem Cell-Derived Motoneurons," Stem Cells, 25:1931-1939 (2007).
Lee et al., "Instructive Role of Wnt/B-Catenin in Sensory Fate Specification in Neural Crest Stem Cells," Science, 303(5660):1020-1023 (2004).
Lee et al., "Isolation and Directed Differentiation of Neural Crest Stem Cells Derived From Human Embryonic Stem Cells," Nat Biotechnol., 25(12):1468-1475 (2007).
Lee et al., "Modeling Pathogenesis and Treatment of Familial Dysautonomia using Patient-Specific iPSCs," Nature, 461(7262):402-406 (2009).
Lee et al., "The Expression and Posttranslational Modification of a Neuron-Specific B-Tubulin Isotype During Chick Embryo genesis," Cell Motility and the Cytoskeleton, 17(2):118-132 (1990).
Letinic et al., "Origin of GABAergic neurons in the human neocortex," Nature, 2002, vol. 417, No. 6889, pp. 645-649.
Li et al., "Directed differentiation of ventral spinal progenitors and motor neurons from human embryonic stem cells by small molecules," Stem Cells, 4:886-893 (2008).
Li et al., "Specification of Motoneurons From Human Embryonic Stem Cells," Nat Biotechnol., 23(2):215-221 (2005).
Lois et al., "Germline Transmission and Tissue-Specific Expression of Transgenes Delivered by Lentiviral Vectors," Science, 295:868-872 (2002).
Lyuksyutova et al., "Anterior-Posterior Guidance of Commissural Axons by Wnt-Frizzled Signaling," Science, 302:1984-1988 (2003).
Ma et al., "Neurogenin1 and Neurogenin2 Control Two Distinct Waves of Neurogenesis in Developing Dorsal Root Ganglia," Genes Dev., 13(13):1717-1728 (1999).
Marmigere and Ernfors, "Specification and Connectivity of Neuronal Subtypes in the Sensory Lineage," Nat Rev Neurosci., 8(2):114-127 (2007).
Maroof et al., "Directed differentiation and functional maturation of cortical interneurons from human embryonic stem cells", Cell Stem Cell, Epub. May 2, 2013, vol. 12, No. 5, pp. 559-572.
Martin, "Isolation of a pluripotent cell line from early mouse embryos cultured in medium conditioned by teratocarcinoma stem cells," PNAS USA, 78(12):7634-7638 (1981).
Matise et al., "Gli2 is required for induction of floor plate and adjacent cells, but not most ventral neurons in the mouse central nervous system," Development, 125:2759-2770 (1998).
Mehler et al., "Bone Morphogenetic Proteins in the Nervous System," Trends Neurosci., 20(7):309-317 (1997).
Menendez et al., "Wnt signaling and a Smad pathway blockade direct the differentiation of human pluripotent stem cells to multi potent neural crest cells," PNAS, 2011, vol. 108, No. 48, pp. 19240-19245.
Mizuseki et al., "Generation of neural crest-derived peripheral neurons and floor plate cells from mouse and primate embryonic stem cells," PNAS USA, 100:5828-5833 (2003).
Mizuseki et al., "Generation of neural crest-derived peripheral neurons and floor plate cells from mouse and primate embryonic stem cells," PNAS USA, 100:5828-5833 Supporting Information List (2003).
Mizuseki et al., "Generation of neural crest-derived peripheral neurons and floor plate cells from mouse and primate embryonic stem cells," PNAS USA, 100:5828-5833 Supporting Materials and Methods (2003).
Mizuseki et al., "Generation of neural crest-derived peripheral neurons and floor plate cells from mouse and primate embryonic stem cells," PNAS USA, 100:5828-5833 Supporting Information Fig. 6 (2003).
Mizuseki et al., "Generation of neural crest-derived peripheral neurons and floor plate cells from mouse and primate embryonic stem cells," PNAS USA, 100:5828-5833 Supporting Fig. 6 (2003).
Mizuseki et al., "Generation of neural crest-derived peripheral neurons and floor plate cells from mouse and primate embryonic stem cells," PNAS USA, 100:5828-5833 Supporting Information Fig. 7 (2003).
Mizuseki et al., "Generation of neural crest-derived peripheral neurons and floor plate cells from mouse and primate embryonic stem cells," PNAS USA, 100:5828-5833 Supporting Fig. 7 (2003).
Mizuseki et al., "Generation of neural crest-derived peripheral neurons and floor plate cells from mouse and primate embryonic stem cells," PNAS USA, 100:5828-5833 Supporting Information Fig. 8 (2003).
Mizuseki et al., "Generation of neural crest-derived peripheral neurons and floor plate cells from mouse and primate embryonic stem cells," PNAS USA, 100:5828-5833 Supporting Fig. 8 (2003).
Mizuseki et al., "Generation of neural crest-derived peripheral neurons and floor plate cells from mouse and primate embryonic stem cells," PNAS USA, 100:5828-5833 Supporting Information Fig. 9 (2003).
Mizuseki et al., "Generation of neural crest-derived peripheral neurons and floor plate cells from mouse and primate embryonic stem cells," PNAS USA, 100:5828-5833 Supporting Fig. 9 (2003).
Mukhopadhyay et al., "Dickkopf1 is required for embryonic head induction and limb morphogenesis in the mouse," Dev Cell, 3:423-434 (2001).
Mullor et al., "Pathways and consequences: Hedgehog signaling in human disease," Trends Cell Biol 12:562-569 (2002).
Munoz-Sanjuan et al., "Neural Induction, The Default Model and Embryonic Stem Cells," Nat Rev Neurosci., 3:271-280 (2002).
Notarianni et al., "Maintenance and differentiation in culture of pluripotential embryonic cell lines from pig blastocysts," J. Reprod. Fert. Suppl., 41:51-56 (1990).
Ono et al., "Differences in neurogenic potential in floor plate cells along an anteroposterior location: midbrain dopaminergic neurons originate from mesencephalic floor plate cells," Development, 134:3213-3225 (2007).
Ono et al., "Differences in neurogenic potential in floor plate cells along an anteroposterior location: midbrain dopaminergic neurons originate from mesencephalic floor plate cells," Development, 134:3213-3225 Data Supplement (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 1 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 2 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 3 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 4 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 5 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 6 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 7 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 8 (2007).

(56) References Cited

OTHER PUBLICATIONS

Papapetrou et al., "Stoichiometric and Temporal Requirements of Oct4, Sox2, Klf4, and c-Myc Expression for Efficient Human Ipsc Induction and Differentiation," PNAS USA, 106(31):12759-12764 (2009).
Paterson et al., "Preclinical Studies of Fibroblast Growth Factor Receptor 3 As a Therapeutic Target in Multiple Myeloma," Br. J. Haematol., 124(5):595-603 (2004).
Patten et al., "Distinct modes of floor plate induction in the chick embryo," Development, 130:4809-4821 (2003).
Perrier et al., "Derivation of midbrain dopamine neurons from human embryonic stem cells," PNAS USA, 101:12543-12548 (2004).
Perrier et al., "Derivation of midbrain dopamine neurons from human embryonic stem cells," PNAS USA, 101:12543-12548 Supporting Materials, Methods, Supplemental Data, and Supporting Fig. 6 (2004).
Placzek and Briscoe, "The Floor Plate: Multiple Cells, Multiple Signals," Nat. Rev. Neurosci., 6:230-240 (2005).
Placzek et al., "Induction of floor plate differentiation by contact-dependent, homeogenetic signals," Development, 117:205-218 (1993).
Placzek, "The role of the notochord and floor plate in inductive interactions," Curr Opin Genet Dev., 5:499-506 (1995).
Reubinoff et al., "Neural progenitors from human embryonic stem cells," Nature Biotechnology, 19:1134-1140 (2001).
Roelink et al., "Floor plate and motor neuron induction by *vhh-1*, a vertebrate homolog of hedgehog expressed by the notochord," Cell, 76:761-775 (1994).
Saha et al., "Technical Challenges in Using Human Induced Pluripotent Stem Cells to Model Disease," Cell Stem Cell, 5(6):584-595 (2009).
Sasai et al., "Xenopus *chordin*: a Novel Dorsalizing Factor Activated by Organizer-Specific Homeobox Genes," Cell, 79(5):779-790 (1994).
Schlosser et al., "Development of Neurogenic Placodes in *Xenopus laevis*," The Journal of Comparative Neurology, 418:121-146 (2000).
Schlosser et al., "Induction and Specification of Cranial Placodes," Dev Biol., 294(2):303-351 (2006) A: pp. 303-327.
Schlosser et al., "Induction and Specification of Cranial Placodes," Dev Biol., 294(2):303-351 (2006) B: pp. 328-351.
Shen et al., "The timing of cortical neurogenesis is encoded within lineages of individual progenitor cells," Nat Neurosci., 9:743-751 (2006).
Shirasaki et al., "Guidance of cerebellofugal axons in the rat embryo: directed growth toward the floor plate and subsequent elongation along the longitudinal axis," Neuron, 14:961-972 (1995).
Smith et al., "Expression Cloning of noggin, a New Dorsalizing Factor Localized to the Spemann organizer in Xenopus Embryos," Cell, 70:829-840 (1992).
Smith et al., "Inhibition of Activin/Nodal signaling promotes specification of human embryonic stem cells into neuroectoderm," Dev Biol., 313:107-117 (2008).
Streit, "Early development of the cranial sensory nervous system: from a common field to individual placodes," Dev Biol., 276:1-15 (2004).
Sukoyan et al., "Embryonic Stem Cells Derived from Morulae, Inner Cell Mass, and Blastocysts of Mink: Comparisons of Their Pluripotencies," Mol. Reprod. Dev., 36:148-158 (1993).
Sukoyan et al., "Isolation and Cultivation of Blastocyst-Derived Stem Cell Lines from American Mink (*Mustela vison*)," Mol. Reprod. Dev., 33:418-431 (1992).
Sumi et al., "Defining early lineage specification of human embryonic stem cells by the orchestrated balance of canonical Wnt/β-catenin, Activin/Nodal and BMP signaling," Development, 135:2969-2979 (2008).
Sun et al., "A Central Role for Islet1 in Sensory Neuron Development Linking Sensory and Spinal Gene Regulatory Programs," Nat Neurosci., 11(11):1283-1293 (2008).
Sun et al., "Design, Synthesis, and Evaluations of Substituted 3-[(3- or 4-Carboxyethylpyrrol-2-yl)Methylidenyl]indolin-2-ones As Inhibitors of VEGF, FGF, and PDGF Receptor Tyrosine Kinases," J Med Chem., 42(25):5120-5130 (1999).
Suter et al., "A Sox1 to Pax6 switch drives neuroectoderm to radial glia progression during differentiation of mouse embryonic stem cells," Stem Cells, 27(1):49-58 (2009).
Takahashi et al., "Induction of Pluripotent Stem Cells from Adult Human Fibroblasts by Defined Factors," Cell, 131:861-872 (2007).
Takahashi et al., "Induction of Pluripotent Stem Cells From Mouse Embryonic and Adult Fibroblast Cultures by Defined Factors," Cell, 126(4):663-676 (2006).
Tanaka et al., "FGF-Induced Vesicular Release of Sonic Hedgehog and Retinoic Acid in Leftward Nodal Flow Is Critical for Left-Right Determination," Nature, 435(7039):172-177 (2005).
Tesar et al., "New cell lines from mouse epiblast share defining features with human embryonic stem cells," Nature, 448:196-199 (2007).
Theos et al., "The Silver Locus Product Pmell 7/Gp100/Silv/Me20: Controversial in Name and in Function," Pigment Cell Res., 18(5):322-336 (2005).
Valenzuela et al., "Identification of Mammalian Noggin and Its Expression in the Adult Nervous System," J. Neurosci., 15(9):6077-6084 (1995).
Vallier et al., "Nodal Inhibits Differentiation of Human Embryonic Stem Cells Along the Neuroectodermal Default Pathway," Dev Biol., 275(2):403-421 (2004).
Venezia et al., "Molecular Signatures of Proliferation and Quiescence in Hematopoietic Stem Cells," PLoS Biol., 2(10):e301 (2004).
Vierbuchen et al., "Direct Conversion of Fibroblasts to Functional Neurons by Defined Factors," Nature, 463(7284):1035-1041 (2010).
Wang et al., "Noggin and bFGF cooperate to maintain the pluripotency of human embryonic stem cells in the absence of feeder layers," Biochem Biophys Res Commun., 330:934-942 (2005).
Watanabe et al., "A ROCK inhibitor permits survival of dissociated human embryonic stem cells," Nat. Biotechnol., 25(6):681-686 (2007).
Watanabe et al., "Directed differentiation of telencephalic precursors from embryonic stem cells," Nat. Neuro., 3:288-296 (2005).
Weinstein et al., "Neural Induction," Annu Rev Cell Dev Biol., 15:411-433, pp. 411-424 (1999a).
Weinstein et al., "Neural Induction," Annu Rev Cell Dev Biol., 15:411-433, pp. 425-433 (1999b).
Wichterle et al., "Directed Differentiation of Embryonic Stem Cells into Motor Neurons," Cell, 110:385-397 (2002).
Xu et al., "Basic FGF and suppression of BMP signaling sustain undifferentiated proliferation of human ES cells," Nat Methods, 2:185-190 (2005).
Xu et al., "BMP4 initiates human embryonic stem cell differentiation to trophoblast," Nat Biotechnol., 20(12):1261 (2002).
Xu et al., "*NANOG* is a Direct Target of TGFβ/Activin-Mediated SMAD Signaling in Human ESCs," Cell Stem Cell, 3:196-206 (2008).
Yamashita et al., "Bone Morphogenetic Protein Receptors," Bone, 19(6):569-574 (1996).
Yan et al., "Directed Differentiation of Dopaminergic Neuronal Subtypes from Human Embryonic Stem Cells," Stem Cells, 23(6):781-790 (2005).
Zhang and Zhang, "Differentiation of Neural Precursors and Dopaminergic Neurons from Human Embryonic Stem Cells," Methods Mal Biol., 584:355-366 (2010).
Zhang et al., "In vitro differentiation of transplantable neural precursors from human embryonic stem cells," Nature Biotechnology, 19:1129-1133 (2001).
Zhou et al., "High-Efficiency Induction of Neural Conversion in Human ESCs and Human Induced Pluripotent Stem Cells With a Single Chemical Inhibitor of Transforming Growth Factor Beta Superfamily Receptors," Stem Cells, 28(10):1741-1750 (2010).
Zhu et al., "Functional Smoothened Is Required for Expression of Gli3 in Colorectal Carcinoma Cells," Cancer Letters, 207(2):205-214 (2004).
Zietlow et al., "The Survival of Neural Precursor Cell Grafts Is Influenced by In Vitro Expansion," Journal of Anatomy, 207(3):227-240 (2005).
Zoltewicz et al., "*oto* is a homeotic locus with a role in anteroposterior development that is partially redundant with Lim1," Development, 126:5085-5095 (1999).

(56) References Cited

OTHER PUBLICATIONS

U.S. Appl. No. 14/922,110, Jan. 3, 2018 Response to Restriction Requirement.
U.S. Appl. No. 14/922,110, Jul. 10, 2017 Restriction Requirement.
U.S. Appl. No. 15/077,012, Jan. 16, 2018 Response to Restriction Requirement.
U.S. Appl. No. 15/077,012, Nov. 3, 2017 Restriction Requirement.
U.S. Appl. No. 15/077,012, Sep. 12, 2017 Response to Non-Final Office Action.
El Maarouf et al., "Use of polysialic acid in repair of the central nervous system," PNAS 103(45):16989-16994 (2006).
U.S. Appl. No. 14/168,835, Apr. 25, 2018 Non-Final Office Action.
U.S. Appl. No. 14/168,835, Apr. 16, 2018 Applicant Initiated Interview Summary.
U.S. Appl. No. 14/168,835, Apr. 16, 2018 Request for Continued Examination (RCE).
U.S. Appl. No. 14/168,835, Apr. 10, 2018 Advisory Action.
U.S. Appl. No. 14/168,835, Mar. 16, 2018 Response after Final Action.
U.S. Appl. No. 14/168,835, Jan. 17, 2018 Final Office Action.
U.S. Appl. No. 14/168,835, Nov. 16, 2017 Response to Non-Final Office Action.
U.S. Appl. No. 14/169,286, May 11, 2018 Response to Non-Final Office Action.
U.S. Appl. No. 14/169,286, Feb. 12, 2018 Non-Final Office Action.
U.S. Appl. No. 14/169,286, Dec. 4, 2017 Response to Non-Final Office Action.
U.S. Appl. No. 14/169,286, Sep. 6, 2017 Non-Final Office Action.
U.S. Appl. No. 14/169,286, Aug. 8, 2017 Response to Restriction Requirement.
U.S. Appl. No. 14/922,110, May 17, 2018 Non-Final Office Action.
U.S. Appl. No. 15/077,012, Mar. 22, 2018 Notice of Allowance.
Brevini et al., "No shortcuts to pig embryonic stem cells," Theriogenology, 74:544-550 (2010).
Cai et al., "BMP and TGF-β pathway mediators are critical upstream regulators of Wnt signaling during midbrain dopamine differentiation in human pluripotent stem cells," Developmental Biology, 376:62-73 (2013).
Lupo et al., "Multiple roles of Activin/Nodal, bone morphogenetic protein, fibroblast growth factor and Wnt/β-catenin signaling in the anterior neural patterning of adherent human embryonic stem cell cultures," Open Biol., 3:120167 (2013) (13 pages).
Maroof et al., "Prospective Isolation of Cortical Interneuron Precursors from Mouse Embryonic Stem Cells," J. Neurosci, 30(13):4667-4675 (2010).
Munoz et al., "Constraints to Progress in Embryonic Stem Cells from Domestic Species," Stem Cell Rev. and Rep., 5:6-9 (2009).
Oliveri, "Epigenetic dedifferentiation of somatic cells into pluripotency: cellular alchemy in the age of regenerative medicine?" Regen. Med., 2(5):795-816 (2007).
Paris et al., "Equine embryos and embryonic stem cells: Defining reliable markers of pluripotency," Theriogenology, 74:516-524 (2010).
Patel et al., "Advances in Reprogramming Somatic Cells to Induced Pluripotent Stem Cells," Stem Cell Rev., 6(3):367-380 (2010).
Stem Cell: Scientific Progress and Future Research Directions, Department of Health and Human Services, Chapter 4, pp. 23-42, Jun. 2001.
Andersson et al., "Identification of Intrinsic Determinants of Midbrain Dopamine Neurons," Cell 124:393-405 (2006).
Deng et al., "Specific and integrated roles of Lmx1a, Lmx1b and Phox2a in ventral midbrain development," Development 138:3399-3408 (2011).

\* cited by examiner

Figure 8
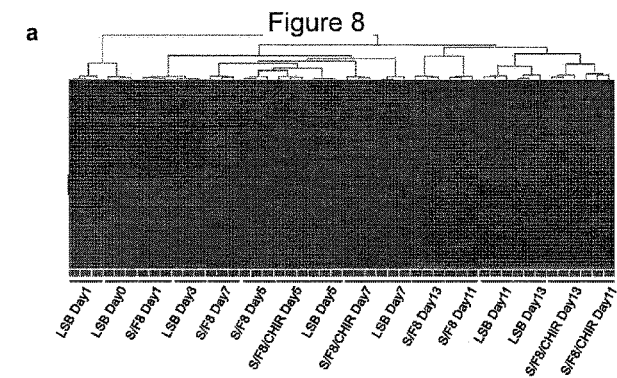
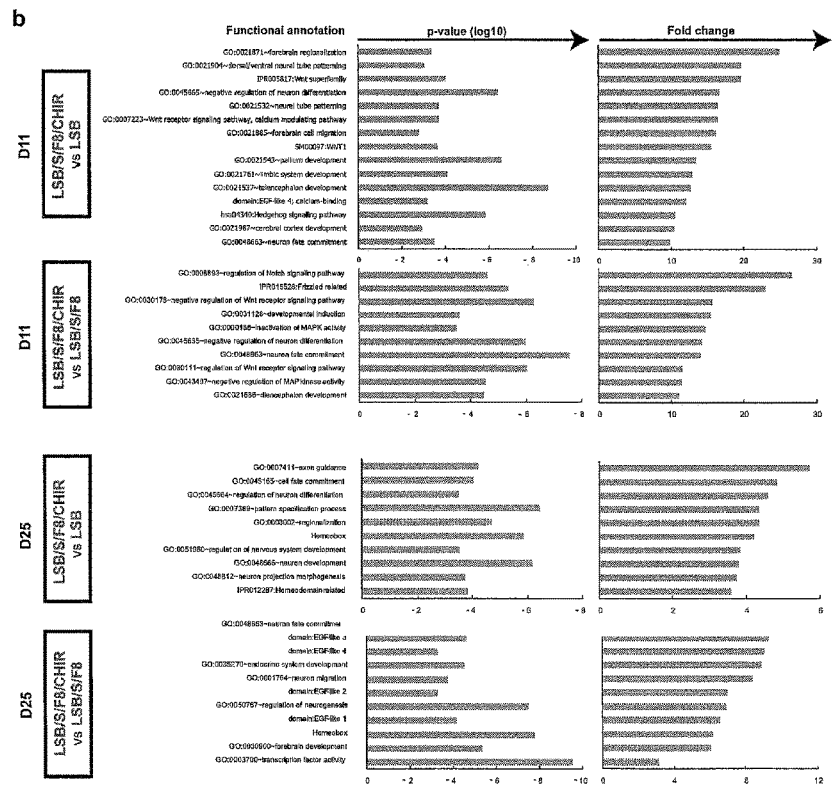
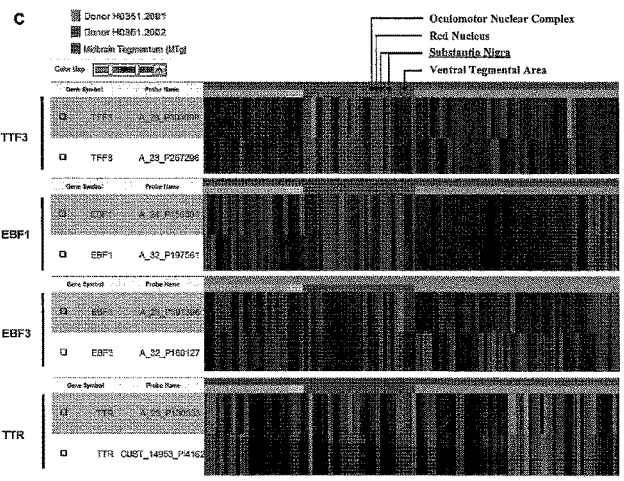

Figure 15
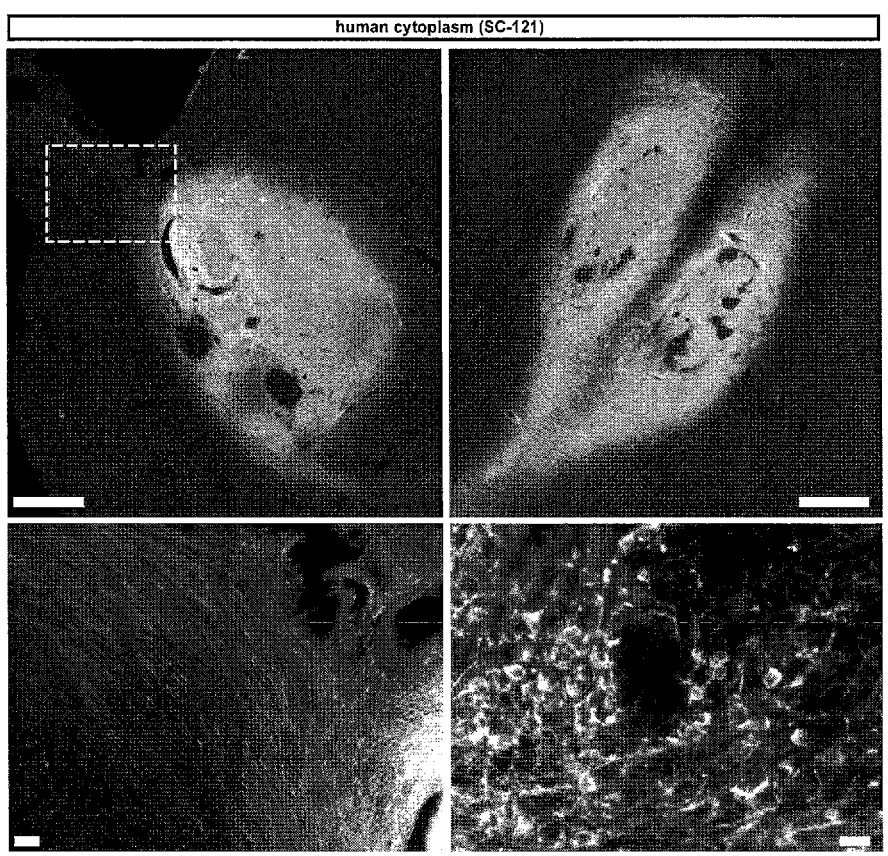
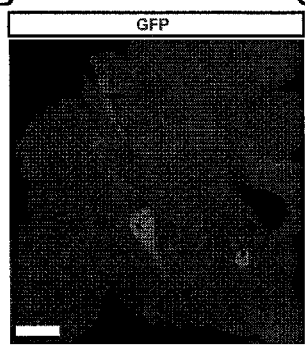
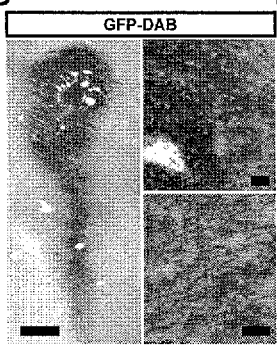
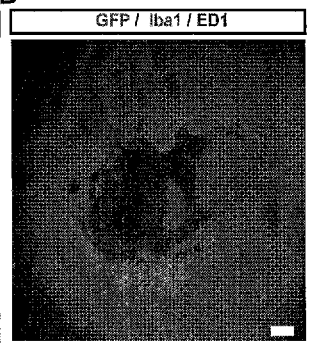

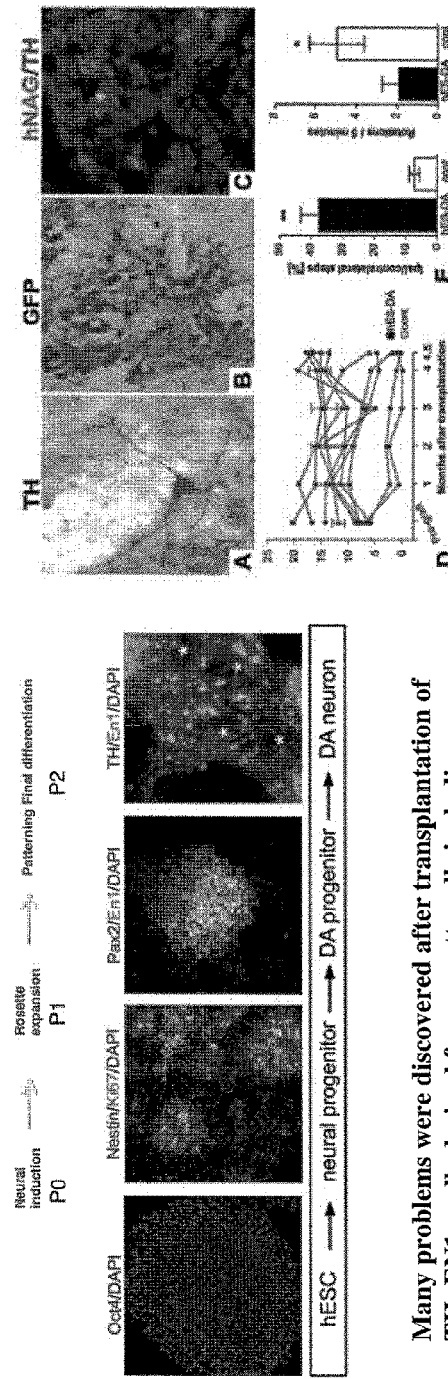

Fig. 16
Derivation of TH+En1+ cells from hESCs using MS5 feeder cells and rosette cell intermediates.

Many problems were discovered after transplantation of TH+EN1+ cells derived from rosette cells including poor viability of the cells in vivo, loss of the original transplanted phenotype, concerns about inappropriate cell growth, such as teratomas and growth of inappropriate neural types.

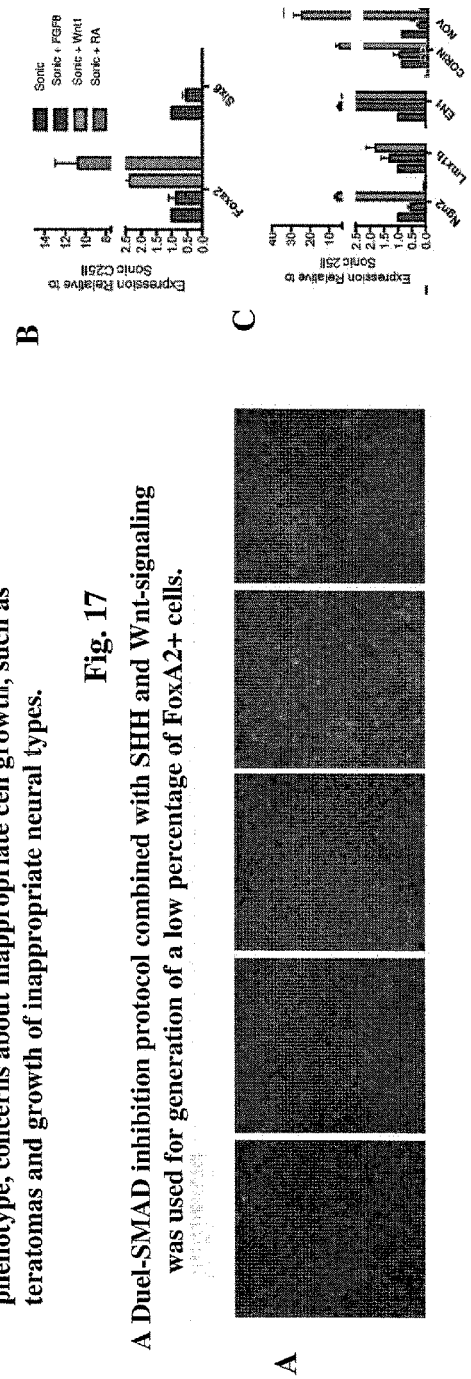

Fig. 17

A Duel-SMAD inhibition protocol combined with SHH and Wnt-signaling was used for generation of a low percentage of FoxA2+ cells.

Green color =    Red color =

MIDBRAIN DOPAMINE (DA) NEURONS FOR ENGRAFTMENT

This application is a U.S. National Stage Application under 35 U.S.C. § 371 of International Patent Application No. PCT/US2012/063339 filed 2 Nov. 2012, which claims the benefit of priority to U.S. Provisional Patent Application No. 61/555,828 filed 4 Nov. 2011, the disclosures of all of which are hereby incorporated by reference in their entireties. The International Application was published on 10 May 2013 as WO 2013/067362.

GOVERNMENT LICENSE RIGHTS

This invention was made with government support under grant numbers NS047085 and NS052671 awarded by the National Institutes of Health. The Government has certain rights in the invention.

FIELD OF THE INVENTION

The present invention relates to the field of stem cell biology, in particular the lineage specific differentiation of pluripotent or multipotent stem cells, which can include, but is not limited to, human embryonic stem cells (hESC) in addition to nonembryonic human induced pluripotent stem cells (hiPSC), somatic stem cells, stem cells from patients with a disease, or any other cell capable of lineage specific differentiation. Specifically described are methods to direct the lineage specific differentiation of hESC and/or hiPSC into floor plate midbrain progenitor cells and then further into large populations of midbrain fate FOXA2+LMX1A+TH+ dopamine (DA) neurons using novel culture conditions. The midbrain fate FOXA2+LMX1A+TH+ dopamine (DA) neurons made using the methods of the present invention are further contemplated for various uses including, but not limited to, use in in vitro drug discovery assays, neurology research, and as a therapeutic to reverse disease of, or damage to, a lack of dopamine neurons in a patient. Further, compositions and methods are provided for differentiating midbrain fate FOXA2+LMX1A+TH+ dopamine (DA) neurons from human pluripotent stem cells for use in disease modeling, in particular Parkinson's disease. Additionally, authentic DA neurons are enriched for markers, such as CD142, and A9 type neuronal cells.

BACKGROUND OF THE INVENTION

Cell populations that retain the ability to differentiate into numerous specialized cell types are useful for developing large numbers of lineage specific differentiated cell populations. These cell populations that retain a capability for further differentiation into specialized cells contain pluripotent cells. Pluripotent cells may be from embryonic and/or nonembryonic somatic stem cell origin.

These lineage specific differentiated cell populations are contemplated to find use in cell replacement therapies for patients with diseases resulting in a lose of function of a defined cell population. In addition to their direct therapeutic value, lineage specific differentiated cells are also valuable research tools for a variety of purposes including in vitro screening assays to identify, confirm, and test for specification of function or for testing delivery of therapeutic molecules to treat cell lineage specific disease.

Previously embryonic and somatic stem cells were used as therapeutics and model systems for neurodegenerative diseases. Research and technological developments relating to directed differentiation of embryonic and somatic stem cells has taken place in the field of diseases of the central nervous system (CNS), such as for Huntington's, Alzheimer's, Parkinson's, and multiple sclerosis. However the results of these studies showed little capability of these cells used in vivo to allow the patient to recover neuronal function and often resulted in the growth of unwanted tumors in the patients.

Therefore there is a need for compositions and methods to obtain cell populations capable of being used both in research and as a therapeutic for treating diseases resulting in a loss of cells having a particular function.

SUMMARY OF THE INVENTION

The present invention relates to the field of stem cell biology, in particular the lineage specific differentiation of pluripotent or multipotent stem cells, which can include, but is not limited to, human embryonic stem cells (hESC) in addition to nonembryonic human induced pluripotent stem cells (hiPSC), somatic stem cells, stem cells from patients with a disease, or any other cell capable of lineage specific differentiation. Specifically described are methods to direct the lineage specific differentiation of hESC and/or hiPSC into floor plate midbrain progenitor cells and then further into large populations of midbrain fate FOXA2+LMX1A+TH+ dopamine (DA) neurons using novel culture conditions. The midbrain fate FOXA2+LMX1A+TH+ dopamine (DA) neurons made using the methods of the present invention are further contemplated for various uses including, but not limited to, use in in vitro drug discovery assays, neurology research, and as a therapeutic to reverse disease of, or damage to, a lack of dopamine neurons in a patient. Further, compositions and methods are provided for differentiating midbrain fate FOXA2+LMX1A+TH+ dopamine (DA) neurons from human pluripotent stem cells for use in disease modeling, in particular Parkinson's disease. Additionally, authentic DA neurons are enriched for markers, such as CD142, and A9 type neuronal cells.

A kit comprising a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling. In one embodiment, said first inhibitor is LDN-193189. In other embodiments, said first inhibitor is selected from the group consisting of LDN-193189, derivatives thereof and mixtures thereof. In one embodiment, said second inhibitor is SB431542. In other embodiments, said second inhibitor is selected from the group consisting of SB431542, derivatives thereof and mixtures thereof. In one embodiment, said third inhibitor is CHIR99021. In other embodiments, said third inhibitor is selected from the group consisting of CHIR99021, derivatives thereof and mixtures thereof. In one embodiment, said the kit further comprises an activator of Sonic hedgehog (SHH) signaling and an activator of fibroblast growth factor (FGF) 8 receptor family signaling. In one embodiment, said the kit further comprises brain-derived neurotrophic factor (BDNF), ascorbic acid (AA), glial cell line-derived neurotrophic factor, dibutyryl cAMP and transforming growth factor type β3. In one embodiment, said the kit further comprise antibodies selected from the group consisting of anti-tyrosine hydroxylase (TH), anti-forkhead box protein A2 (FOXA2), and anti-LIM homeobox transcription factor 1, alpha (LMX1A). In one embodiment, said the kit further comprises a cell selected from the group consisting of a stem cell, embryonic stem cell, induced pluripotent stem cell, and an engineered cell. In one embodiment, said the kit further comprises instructions for differentiating progenitor cells and midbrain fate FOXA2/LMX1A+ dopamine (DA) neurons. In one embodiment, said the kit further comprises instructions for obtaining a cell from a patient with Parkinson's disease (PD).

A composition, comprising, a cell population in contact with a first signaling inhibitor and a second signaling inhibitor, wherein greater than 40% of said cell population is positive for forkhead box protein A2 (FOXA2), wherein said cell population was previously contacted by a first signaling inhibitor, a third signaling inhibitor, and an activator of Sonic hedgehog (SHH) signaling, wherein said first inhibitor is capable of lowering transforming growth factor beta (TGFβ)/Activin-Nodal signaling, said second inhibitor is capable of lowering glycogen synthase kinase 3β (GSK3β) signaling for activation of wingless (Wnt) signaling and said third inhibitor is capable of lowering Small Mothers Against Decapentaplegic (SMAD) signaling. In one embodiment, said first inhibitor is a small molecule selected from the group consisting of LDN-193189, derivatives thereof and mixtures thereof. In one embodiment, said second inhibitor is selected from the group consisting of CHIR99021 and derivatives thereof. In one embodiment, said third inhibitor is selected from the group consisting of SB431542, derivatives thereof and mixtures thereof. In one embodiment, said activator of Sonic hedgehog (SHH) signaling is selected from the group consisting of Sonic hedgehog (SHH) C25II and smoothened (SMO) receptor small molecule agonist, wherein said agonist is purmorphamine. In some embodiments, said cell population was further previously contacted with Fibroblast growth factor 8 (FGF8). In one embodiment, said majority of cells comprising said cell population are forkhead box protein A2 (FOXA2)$^+$LIM+ homeobox transcription factor 1+, alpha (LMX1A),$^+$ NGN2+ and DDC+ floor plate midbrain progenitor cells. In one embodiment, said cell population is selected from the group consisting of a rodent cells, primate cells and human cells. In one embodiment, said cells are derived from Parkinson's disease (PD) patient cells. In one embodiment, said cell population is at least 50% positive for forkhead box protein A2 (FOXA2). In one embodiment, said cell population is at least 60% positive for forkhead box protein A2. In one embodiment, said cell population is at least 70% positive for forkhead box protein A2. In one embodiment, said cell population is at least 80% positive for forkhead box protein A2. In one embodiment, said cell population is at least 90% positive for forkhead box protein A2. In one embodiment, said cell population is at least 95% up to 100% positive for forkhead box protein A2.

A composition, comprising, an in vitro cell population wherein the majority of cells comprising said cell population are tyrosine hydroxylase (TH)$^+$forkhead box protein A2 (FOXA2)$^+$LIM homeobox transcription factor 1+, alpha (LMX1A)$^+$ floor plate midbrain dopamine (DA) neurons. In one embodiment, said greater than 40% of said floor plate midbrain dopamine (DA) neurons are tyrosine hydroxylase positive (TH+). In one embodiment, said cell population is at least 50% tyrosine hydroxylase positive. In one embodiment, said cell population is at least 60% tyrosine hydroxylase positive. In one embodiment, said cell population is at least 70% tyrosine hydroxylase positive. In one embodiment, said cell population is at least 80% tyrosine hydroxylase positive. In one embodiment, said cell population is at least 90% tyrosine hydroxylase positive. In one embodiment, said cell population is at least 95% up to 100% tyrosine hydroxylase positive. In some embodiments, said cell population comprises a majority of midbrain fate FOXA2/LMX1A+ dopamine (DA) neurons. In one embodiment, said floor plate midbrain dopamine (DA) neurons are positive for markers selected from the group consisting of nuclear receptor NURR1 (NR4A2), Neuron-specific class III beta-tubulin (Tuj1), TTF3, paired-like homeodomain 3 (PITX3), achaete-scute complex (ASCL), early B-cell factor 1 (EBF-1), early B-cell factor 3 (EBF-3) and transthyretin (TTR). In one embodiment, said midbrain fate FOXA2/LMX1A+ dopamine (DA) neuron population is positive for a molecule selected from the group consisting of DA, 3,4-Dihydroxy-Phenylacetic Acid (DOPAC) and homovanillic acid (HVA). In one embodiment, said marker is selected from the group consisting of a protein and a nucleic acid. In some embodiments, said midbrain fate FOXA2/LMX1A+ dopamine (DA) neuron population is capable of engrafting in vivo in a patient selected from the group consisting of a Parkinson disease (PD) patient. In one embodiment, said midbrain fate FOXA2/LMX1A+ dopamine (DA) neurons are capable of engrafting in vivo and providing dopamine (DA) neuronal function.

In some embodiments, the inventions provide a composition, comprising, a cell population in contact with LDN-193189 and CHIR99021, wherein greater than 40% of said cell population is positive for forkhead box protein A2 (FOXA2), and wherein said cell population was previously contacted by LDN-193189, SB431542, an activator of Sonic hedgehog (SHH) signaling and CHIR99021. In one embodiment, said activator of SONIC hedgehog (SHH) signaling is selected from the group consisting of Sonic hedgehog (SHH) C25II and purmorphamine. In one embodiment, said greater than 10% of said cell population is double positive for forkhead box protein A2 (FOXA2) and LIM homeobox transcription factor 1, alpha (LMX1A). In one embodiment, said majority of said cell population is a population of floor plate midbrain progenitor cells. In one embodiment, said cell population was previously contacted with fibroblast growth factor 8 (FGF8). In one embodiment, said cell population is selected from the group consisting of rodent cells, primate cells and human cells. In one embodiment, said human cells are cells from a patient with a neurological symptom of Parkinson's disease (PD). In one embodiment, said cell population is derived from an induced pluripotent stem cell (iPSC). In one embodiment, greater than 10% of said cell population is selected from the group consisting of double positive for forkhead box protein A2 (FOXA2)/LIM homeobox transcription factor 1, alpha (LMX1A) and double positive for forkhead box protein A2 (FOXA2)/orthodenticle homeobox 2 (OTX2).

In one embodiment, the inventions provide a method for inducing directed differentiation of cells into a population of floor plate midbrain progenitor cells, comprising, a) providing: i) a cell population, wherein said cell population is selected from the group consisting of a nonembryonic stem cell, an embryonic stem cell, an induced nonembryonic pluripotent cell and an engineered pluripotent cell; and ii) a first signaling inhibitor, a second signaling inhibitor, an activator of Sonic hedgehog (SHH) signaling and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β(GSK3β) signaling for activation of wingless (Wnt) signaling; b) contacting said cell population with said first and said second inhibitor, c) after contacting said cell population with said first and said second inhibitor further contacting said cells with said activator of Sonic hedgehog (SHH) signaling under conditions for differentiating a population of floor plate midbrain progenitor cells; and) after contacting said cell population with said activator of Sonic hedgehog (SHH) signaling further contacting said cells with said third inhibitor for differentiating said cell population into a population of floor plate midbrain progenitor cells. In one embodiment, said contact with said first and said second inhibitor is under conditions capable of resulting in said differentiated population of floor plate midbrain progenitor cells. In one embodiment, said contact with said first and said second inhibitor is within 1 hour of plating cells in vitro. In one embodiment, said contact with said first and said second inhibitor is within 48 hours of plating cells in vitro. In one embodiment, said contact with said first and said second inhibitor is within 62 hours of plating cells in vitro. In one embodiment, said contact of said cells with said activator of Sonic hedgehog (SHH) signaling is under conditions capable of resulting in said differentiated population of floor plate midbrain progenitor cells. In one embodiment, said contact of said cells with said activator of Sonic hedgehog (SHH) signaling is at least 24 hours up to 36 hours after contacting said cell population with said first and said second inhibitor. In one embodiment, said contact of said cells with said activator of Sonic hedgehog (SHH) signaling is up to 144 hours. In one embodiment, said contact of said cells with said third inhibitor is under conditions capable of resulting in said differentiated population of floor plate midbrain progenitor cells. In one embodiment, said contact of said cells with said third inhibitor is at least 24 hours up to 36 hours after contacting said cell population with said activator of Sonic hedgehog (SHH) signaling. In one embodiment, said contact of said cells with said third inhibitor is up to 192 hours. In one embodiment, said cell population is differentiated into said floor plate midbrain progenitor cells by at least day 11 after contacting said cells with said first and said second inhibitor. In one embodiment, said first inhibitor is SB431542. In one embodiment, said second inhibitor is LDN-193189. In one embodiment, said third inhibitor is CHIR99021. In one embodiment, said activator of Sonic hedgehog (SHH) signaling is selected from the group consisting of Sonic hedgehog (SHH) C25II and purmorphamine. In one embodiment, said method further provides Fibroblast growth factor 8 (FGF8) and contacting said cell population with said FGF8 under conditions capable of resulting in said differentiated population of floor plate midbrain progenitor cells. In one embodiment, said contact of said cells with said FGF8 is at least 24 up to 36 hours after contacting said cell population with said first and said second inhibitor. In one embodiment, said contact of said cells with said FGF8 is up to 144 hours. In one embodiment, said floor plate midbrain progenitor cell population comprises greater than 40% forkhead box protein A2 (FOXA2)$^+$ cells. In one embodiment, said floor plate midbrain progenitor cell population comprises greater than 40% forkhead box protein A2 (FOXA2)$^+$LIM homeobox transcription factor 1, alpha (LMX1A)$^+$ cells. In one embodiment, said method further comprises step e) contacting said population of floor plate midbrain progenitor cells with neuronal maturation medium, said medium comprising N2 medium, brain-derived neurotrophic factor (BDNF), ascorbic acid (AA), glial cell line-derived neurotrophic factor, dibutyryl cAMP (dbcAMP) and transforming growth factor type β3 for differentiation of floor plate midbrain progenitor cells into floor plate midbrain dopamine (DA) neurons. In one embodiment, said method further comprises step e) contacting said population of floor plate midbrain progenitor cells with neuronal maturation medium with B27 supplement for differentiation of floor plate midbrain progenitor cells into floor plate midbrain dopamine (DA) neurons. In one embodiment, said cells contacted with neurobasal medium with B27 supplement are contacted with brain-derived neurotrophic factor (BDNF), ascorbic acid (AA), glial cell line-derived neurotrophic factor, dibutyryl cAMP (dbcAMP) and transforming growth factor type β3 for differentiation of floor plate midbrain progenitor cells into floor plate midbrain dopamine (DA) neurons. In one embodiment, said floor plate midbrain dopamine (DA) neurons are forkhead box protein A2 (FOXA2)$^+$LIM homeobox transcription factor 1, alpha (LMX1A)$^+$, Nuclear receptor related 1 protein (NURR1)$^+$ and tyrosine hydroxylase (TH)$^+$. In one embodiment, greater than 40% of said floor plate midbrain dopamine (DA) neurons are tyrosine hydroxylase (TH)$^+$. In one embodiment, said population of floor plate midbrain dopamine (DA) neurons are differentiated by at least day 25 after contacting said cell population with said first and said second inhibitor. In one embodiment, said floor plate midbrain dopamine (DA) neurons are positive for markers that identify molecules. In one embodiment, said markers are selected from the group consisting of tyrosine hydroxylase (TH), forkhead box protein A2 (FOXA2), LIM homeobox transcription factor 1, dompamine, 3,4-Dihydroxy-Phenylacetic Acid (DOPAC) and homovanillic acid (HVA), alpha, nuclear receptor NURR1 (NR4A2), Neuron-specific class III beta-tubulin (Tuj1), TTF3, paired-like homeodomain 3 (PITX3), achaete-scute complex (ASCL), early B-cell factor 1 (EBF-1), early B-cell factor 3 (EBF-3), transthyretin (TTR), synapsin, dopamine transporter (DAT), and G-protein coupled, and inwardly rectifying potassium channel (Kir3.2/GIRK2). In one embodiment, said molecule is selected from the group consisting of a protein and a nucleic acid. In one embodiment, said molecule is identified using a marker selected from the group consisting of an antibody, a PCR primer, a nucleic acid sequence and an enzyme assay. In one embodiment, said floor plate midbrain dopamine (DA) neurons are capable of engrafting in vivo in a patient with Parkinson disease (PD) for providing dopamine (DA) neuronal function. In one embodiment, said method further comprises, providing, a patient in need of dopamine producing neurons, wherein said patient shows at least one neurological symptom, and the step of transplanting floor plate midbrain dopamine (DA) neurons into said patient for providing dopamine (DA) neuronal function. In one embodiment, said neurological symptoms are selected from the group consisting of tremor, bradykinesia (extreme slowness of movement), flexed posture, postural instability, and rigidity. In one embodiment, said patient shows a reduction of said neurological symptom. In one embodiment, said cell is selected from a rodent cell, a primate cell and a human cell. In one embodiment, said human cells are cells from a patient with a neurological symptom of Parkinson's disease (PD).

In one embodiment, the inventions provide a method of engrafting in vivo for therapeutic treatment, comprising, a) providing: i) a population of floor plate midbrain dopamine (DA) neurons wherein greater than 40% of said population expresses tyrosine hydroxylase (TH); and ii) a subject, wherein said subject shows at least one neurological symptom; and b) transplanting said floor plate midbrain dopamine (DA) neurons into said subject under conditions for allowing in vivo engraftment for providing dopamine (DA) neuronal function. In one embodiment, said neurological symptoms are selected from the group consisting of tremor, bradykinesia (extreme slowness of movement), flexed posture, postural instability and rigidity. In one embodiment, said subject shows reduction of said neurological symptom. In one embodiment, said population of floor plate midbrain dopamine (DA) neurons are derived from a population of floor plate midbrain progenitor cells treated according to methods of the present inventions. In one embodiment, said population of floor plate midbrain dopamine (DA) neurons are derived from a population of floor plate midbrain progenitor cells treated according to a method further comprising a step of contacting said population of floor plate midbrain progenitor cells with neuronal maturation medium, said medium comprising N2 medium, brain-derived neurotrophic factor (BDNF), ascorbic acid (AA), glial cell line-derived neurotrophic factor, dibutyryl cAMP and transforming growth factor type β3 for differentiation of floor plate midbrain progenitor cells into floor plate midbrain dopamine (DA) neurons. In one embodiment, said population of floor plate midbrain progenitor cells are derived from a cell population treated according to a method of the present inventions. In one embodiment, said population of floor plate midbrain progenitor cells are derived from a cell population treated according to a method for inducing directed differentiation of cells into a population of floor plate midbrain progenitor cells, comprising, a) providing: i) a cell population, wherein said cell population is selected from the group consisting of a nonembryonic stem cell, an embryonic stem cell, an induced nonembryonic pluripotent cell and an engineered pluripotent cell; and ii) a first signaling inhibitor, a second signaling inhibitor, an activator of Sonic hedgehog (SHH) signaling and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) signaling for activation of wingless (Wnt) signaling; b) contacting said cell population with said first and said second inhibitor, c) after contacting said cell population with said first and said second inhibitor further contacting said cells with said activator of Sonic hedgehog (SHH) signaling under conditions for differentiating a population of floor plate midbrain progenitor cells; and d) after contacting said cell population with said activator of Sonic hedgehog (SHH) signaling further contacting said cells with said third inhibitor for differentiating said cell population into a population of floor plate midbrain progenitor cells. In one embodiment, said population of floor plate midbrain dopamine (DA) neurons are derived from a cell population selected from the group consisting of animals, primates and humans. In one embodiment, said human cells are cells from a patient with a symptom of Parkinson's disease (PD).

In one embodiment, the inventions provide a composition, comprising, a cell population in contact with LDN-193189 and CHIR99021, wherein greater than 40% of said cell population is positive for forkhead box protein A2 (FOXA2), and wherein said cell population was previously contacted by LDN-193189, SB431542, an activator of Sonic hedgehog (SHH) signaling and CHIR99021, wherein said activator of Sonic hedgehog (SHH) signaling is selected from the group consisting of Sonic hedgehog (SHH) C25II and purmorphamine. In one embodiment, said cell population is at least 50% positive for forkhead box protein A2 (FOXA2). In one embodiment, said cell population is at least 60% positive for forkhead box protein A2. In one embodiment, said cell population is at least 70% positive for forkhead box protein A2. In one embodiment, said cell population is at least 80% positive for forkhead box protein A2. In one embodiment, said cell population is at least 90% positive for forkhead box protein A2. In one embodiment, said cell population is at least 95% up to 100% positive for forkhead box protein A2. In one embodiment, greater than 10% of said cell population is selected from the group consisting of double positive for forkhead box protein A2 (FOXA2)/LIM homeobox transcription factor 1, alpha (LMX1A) and double positive for forkhead box protein A2 (FOXA2)/orthodenticle homeobox 2 (OTX2). In one embodiment, said cell population is at least 20%, 30%, 40%, 50%, 60%, 70%, 80%, 90%, at least 95% up to 100% positive. In one embodiment, at least 20% of said cell population is positive for a marker selected from the group consisting of Nurr1+, CD142, DCSM1, CD63 and CD99. In some embodiments, said cell population is at least 30%, 40%, 50%, 60%, 70%, 80%, 90%, at least 95% up to 100% positive. In some embodiments, said cell population is at least 50%, 60%, 70%, 80%, 90%, at least 95% up to 100% positive. In one embodiment, said cell population is selected from the group consisting of rodent cells, primate cells, human cells and human cells from a patient with a neurological symptom of Parkinson's disease (PD).

In one embodiment, the inventions provide a method for inducing directed differentiation of cells into a population of floor plate midbrain progenitor cells, comprising, a) providing: i) a cell population, wherein said cell population is selected from the group consisting of a nonembryonic stem cell, an embryonic stem cell, an induced nonembryonic pluripotent cell and an engineered pluripotent cell; and ii) a first signaling inhibitor, a second signaling inhibitor, an activator of Sonic hedgehog (SHH) signaling and a third signaling inhibitor, wherein said first inhibitor is SB431542, said second inhibitor is LDN-193189, said activator of Sonic hedgehog (SHH) signaling is selected from the group consisting of Sonic hedgehog (SHH) C25II and a purmorphamine, and said third inhibitor is CHIR99021; b) contacting said cell population with said first and said second inhibitor, wherein said contact with said first and said second inhibitor is under conditions capable of resulting in said differentiated population of floor plate midbrain progenitor cells such that said contact with said first and said second inhibitor is within 48 hours of plating cells in vitro, c) after contacting said cell population with said first and said second inhibitor further contacting said cells with said activator of Sonic hedgehog (SHH) signaling under conditions for differentiating a population of floor plate midbrain progenitor cells; and d) after contacting said cell population with said activator of Sonic hedgehog (SHH) signaling further contacting said cells with said third inhibitor for differentiating said cell population into a population of floor plate midbrain progenitor cells. In one embodiment, contact of said cells with said activator of Sonic hedgehog (SHH) signaling is under conditions capable of resulting in said differentiated population of floor plate midbrain progenitor cells such that said contact of said cells with said activator of Sonic hedgehog (SHH) signaling is at least 24 hours and up to 36 hours after contacting said cell population with said first and said second inhibitor. In one embodiment, contact of said cells with said third inhibitor is under conditions capable of resulting in said differentiated population of floor plate midbrain progenitor cells such that said contact of said cells with said third inhibitor is at least 24 hours and up to 36 hours after contacting said cell population with said activator of Sonic hedgehog (SHH) signaling. In one embodiment, floor plate midbrain progenitor cell population comprises greater than 40% forkhead box protein A2 (FOXA2)+LIM homeobox transcription factor 1+, alpha (LMX1A)+ cells. In one embodiment, the method further comprises step e) contacting said population of floor plate midbrain progenitor cells with neuronal maturation medium, said medium comprising N2 medium, brain-derived neurotrophic factor (BDNF), ascorbic acid (AA), glial cell line-derived neurotrophic factor, dibutyryl cAMP and transforming growth factor type β3 for differentiation of floor plate midbrain progenitor cells into floor plate midbrain dopamine (DA) neurons. In one embodiment, said floor plate midbrain dopamine (DA) neurons are positive for sets of markers selected from the group consisting of forkhead box protein A2 (FOXA2)/LIM homeobox transcription factor 1 alpha (LMX1A)/tyrosine hydroxylase (TH); forkhead box protein A2/LIM homeobox transcription factor 1 alpha/tyrosine hydroxylase/CD142; forkhead box protein A2/LIM homeobox transcription factor 1 alpha/tyrosine hydroxylase/ Nuclear receptor related 1 protein (NURR1); forkhead box protein A2/LIM homeobox transcription factor 1 alpha/ tyrosine hydroxylase/CD142/Nuclear receptor related 1 protein and tyrosine hydroxylase/α-synuclein. In one embodiment, said method further comprises step f) sorting said floor plate midbrain dopamine (DA) neurons for CD142 expression into a population of cells at least 80% positive for CD142. In one embodiment, said floor plate midbrain dopamine (DA) neurons are positive for a marker that identifies a molecule selected from the group consisting of tyrosine hydroxylase (TH), forkhead box protein A2 (FOXA2), LIM homeobox transcription factor 1, dompamine, 3,4-Dihydroxy-Phenylacetic Acid (DOPAC) and homovanillic acid (HVA), alpha, nuclear receptor NURR1 (NR4A2), Neuron-specific class III beta-tubulin (Tuj1), TTF3, paired-like homeodomain 3 (PITX3), achaete-scute complex (ASCL), early B-cell factor 1 (EBF-1), early B-cell factor 3 (EBF-3), transthyretin (TTR), synapsin, dopamine transporter (DAT), and G-protein coupled, inwardly rectifying potassium channel (Kir3.2/GIRK2), CD142, DCSM1, CD63 and CD99. In one embodiment, the method further comprises, provides, a patient in need of dopamine producing neurons, and a step after e) treating said patient by transplanting said floor plate midbrain dopamine (DA) neurons for providing dopamine (DA) neuronal function. In one embodiment, said patient comprises at least one neurological symptom selected from the group consisting of tremor, bradykinesia (extreme slowness of movement), flexed posture, postural instability, and rigidity. In one embodiment, said patient is observed to have at least one neurological symptom selected from the group consisting of tremor, bradykinesia (extreme slowness of movement), flexed posture, postural instability, and rigidity. In one embodiment, said patient shows a reduction of at least one of said neurological symptom.

In one embodiment, the inventions provide a method of engrafting in vivo for therapeutic treatment, comprising, a) providing: i) a population of floor plate midbrain dopamine (DA) neurons wherein greater than 40% of said population expresses tyrosine hydroxylase (TH); and ii) a subject, wherein said subject shows at least one neurological symptom, wherein said neurological symptoms are selected from the group consisting of tremor, bradykinesia (extreme slowness of movement), flexed posture, postural instability and rigidity; and b) transplanting said floor plate midbrain dopamine (DA) neurons into said subject under conditions for allowing in vivo engraftment for providing dopamine (DA) neuronal function. In one embodiment, said subject shows reduction of at least one of said neurological symptom. In one embodiment, said population of floor plate midbrain dopamine (DA) neurons are derived from a population of cells further comprising a step of sorting said floor plate midbrain dopamine (DA) neurons for CD142 expression into a population of cells at least 80% positive for CD142. In one embodiment, said population of floor plate midbrain dopamine (DA) neurons are derived from a population of floor plate midbrain progenitor cells after a step of sorting said floor plate midbrain dopamine (DA) neurons for CD142 expression into a population of cells at least 80% positive for CD142. In one embodiment, said population of floor plate midbrain dopamine (DA) neurons are derived from a cell population selected from the group consisting of animals, primates, humans and a patient with a symptom of Parkinson's disease (PD). In one embodiment, said population of floor plate midbrain dopamine (DA) neurons are derived from a cell population isolated from the group consisting of animals, primates, humans and a patient with a symptom of Parkinson's disease (PD).

DEFINITIONS

As used herein, the term "disease modeling" refers to the process of using an experimental organism or in vitro cell cultures to mimic specific signs or symptoms observed in humans as a result of a disorder. In one embodiment, pluripotent stem cells derived from an animal model with a genetic mutation resulting in a neurological disorder, such as Parkinson's disease (PD), can be grown and differentiated into neural cells for identifying new characteristics of neurons related to PD. In one embodiment, human pluripotent stem cells derived from a person with a genetic mutation resulting in a neurological disorder, such as Parkinson's disease (PD) can be grown and differentiated into neural cells harboring a similar defect observed within the person.

As used herein, term "parkinsonism" refers to a group of diseases that are all linked to an insufficiency of dopamine in the basal ganglia which is a part of the brain that controls movement. Symptoms include tremor, bradykinesia (extreme slowness of movement), flexed posture, postural instability, and rigidity. A diagnosis of parkinsonism requires the presence of at least two of these symptoms, one of which must be tremor or bradykinesia. The most common form of parkinsonism is idiopathic, or classic, Parkinson's disease (PD), but for a significant minority of diagnoses, about 15 percent of the total, one of the Parkinson's plus syndromes (PPS) may be present. These syndromes also known as atypical parkinsonism, include corticobasal degeneration, Lewy body dementia, multiple systematrophy, and progressive supranuclear palsy. In general, Parkinson's disease involves the malfunction and death of vital nerve cells in the brain primarily in an area of the brain called the substantia nigra. Many of these vital nerve cells make dopamine, that as these neurons die off, the amount of dopamine resulting from differentiation in the brain decreases, leaving a person unable to control movement normally. The intestines also have dopamine cells that degenerate in Parkinson's disease patients, and this may be an important causative factor in the gastrointestinal symptoms that are part of the disease. A group of symptoms that an individual experiences varies from person to person. Primary motor signs of Parkinson's disease include the following: tremor of the hands, arms, legs, jaw and face, bradykinesia or slowness of movement, rigidity or stiffness of the limbs and trunk and postural instability or impaired balance and coordination.

As used herein, the term "subject" refers to a mammal (human and animal, i.e. non-human animals) that is to be the recipient of a particular treatment including any type of control. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, term "dopamine" refers to a chemical made by dopamine neurons that sends messages to the part of the brain containing neurons that control movement and coordination.

As used herein, the term "LSB" refers to a combination of two compounds LDN-193189 and SB431542 capable of lowering or blocking signaling consisting of transforming growth factor beta (TGFβ)/Activin-Nodal signaling and Small Mothers Against Decapentaplegic (SMAD) signaling in a cell.

As used herein, the term "SB431542" refers to a molecule capable of lowering or blocking transforming growth factor beta (TGFβ)/Activin-Nodal signaling with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

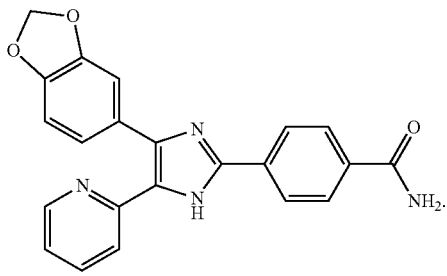 [SMILES: NC(=O)c1ccc(-c2nc(-c3ccc4c(c3)OCO4)c(-c3ccccn3)[nH]2)cc1]

In one exemplary, SB431542 is Stemolecule™ SB431542, Stemgent, Inc. Cambridge, Mass., United States.

As used herein, the term "LDN-193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$. LDN-193189 is capable of functioning as a SMAD signaling inhibitor. LDN-193189 is also a highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al. (2008) Nat Med 14:1363-1369; Cuny et al. (2008) Bioorg. Med. Chem. Lett. 18: 4388-4392, herein incorporated by reference).

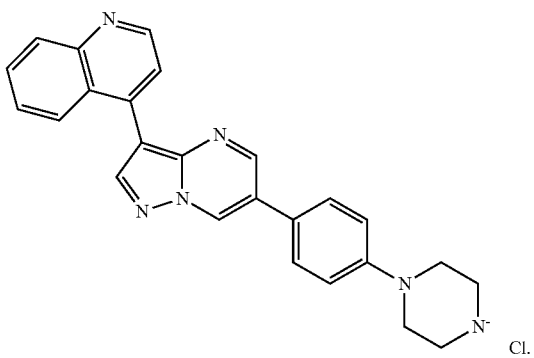

In one exemplary embodiment, LDN-193189 is Stemolecule™ LDN-193189, Stemgent, Inc. Cambridge, Mass., United States.

As used herein, the term "glycogen synthase kinase 3β inhibitor" or "GSK3β inhibitor" refers to a compound that inhibits a glycogen synthase kinase 3β enzyme, for example, see, Doble, et al., J Cell Sci. 2003; 116:1175-1186, herein incorporated by reference. For the purposes of the present inventions, a GSK3β inhibitor is capable of activating a WNT signaling pathway, see, for example, Cadigan, et al., J Cell Sci. 2006; 119:395-402; Kikuchi, et al., Cell Signaling. 2007; 19:659-671, herein incorporated by reference.

As used herein, the term "CHIR99021" or "CHIR" or "aminopyrimidine" or "3-[3-(2-Carboxyethyl)-4-methylpyrrol-2-methylidenyl]-2-indolinone" refers to IUPAC name 6-(2-(4-(2,4-dichlorophenyl)-5-(4-methyl-1H-imidazol-2-yl)pyrimidin-2-ylamino)ethylamino)nicotinonitrile.

CHIR99021 is one example of a small-molecule chemical inhibitor of glycogen synthase kinase 3β (GSK3β) that activates a WNT signaling pathway, and is highly selective, showing nearly thousand fold selectivity against a panel of related and unrelated kinases, with an $IC_{50}$=6.7 nM against human GSK3β and nanomolar $IC_{50}$ values against rodent GSK3β homologs.

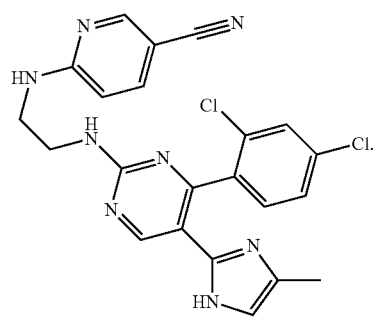 [SMILES: Cc1c[nH]c(-c2cnc(NCCNc3ccc(C#N)cn3)nc2-c2ccc(Cl)cc2Cl)n1]

In one exemplary embodiment, CHIR99021 is Stemolecule™ CHIR99021, Stemgent, Inc. Cambridge, Mass., United States.

As used herein, the term "purmorphamine" refers to a purine derivative, such as CAS Number: 483367-10-8, for one example see structure below, that activates the Hedgehog pathway including by targeting Smoothened.

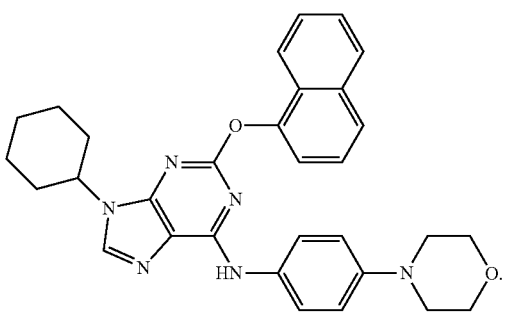 [SMILES: c1ccc2c(Oc3nc(Nc4ccc(N5CCOCC5)cc4)c4ncn(C5CCCCC5)c4n3)cccc2c1]

In one exemplary embodiment, purmorphamine is Stemolecule™ Purmorphamine, Stemgent, Inc. Cambridge, Mass., United States.

As used herein, the term "signaling" in reference to a "signal transduction protein" refers to proteins that are activated or otherwise affected by ligand binding to a membrane receptor protein or some other stimulus. Examples of signal transduction protein include a SMAD, a WNT complex protein, in another embodiment a WNT complex protein including beta-catenin, Sonic hedgehog (SHH), NOTCH, transforming growth factor beta (TGFβ), Activin, Nodal, glycogen synthase kinase 3β (GSK3β) proteins and the like. For many cell surface receptors or internal receptor proteins, ligand-receptor interactions are not directly linked to the cell's response. The ligand activated receptor must first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "LSB/S/F8/CHIR" or "LSB/SHH/FGF8/CHIR" refers to contacting cells with LDN-193189 and SB431542 (i.e. LSB) in addition to S, Sonic Hedgehog activator, F8, FGF8, and CHIR of the present inventions. In contrast to "LSB/S/F8" or "SHH/FGF8" or "SHH/FGF" which refers to contacting cells with LDN-193189 and SB431542 (i.e. LSB) in addition to S, Sonic Hedgehog activator, F8, FGF8 but without CHIR as in previously published methods. In similar abbreviations, LDN/SB" refers to contacting cells with LDN, LDN-193189 and SB, SB431542.

As used herein, the term "inhibit" or "block" means a reduction in the level of activity of a particular signaling pathway of a cell upon treatment with a compound (i.e. an inhibitor) compared to the activity of said signaling pathway of a cell that is left untreated with such compound or treated with a control.

As used herein, the term ""activate" means an increase in the level of activity of a particular signaling pathway of a cell upon treatment with a compound (i.e. an activator) compared to the activity of said signaling pathway of a cell that is left untreated with such compound or treated with a control. Any level of inhibition or activation of a particular signaling pathway is considered an embodiment of the invention if such inhibition or activation results in the directed differentiation of a stem cell.

As used herein, the term "Sma Mothers Against Decapentaplegic" or "Small Mothers Against Decapentaplegic" or "SMAD" refers to a signaling molecule.

As used herein, the term "WNT" or "wingless" in reference to a ligand refers to a group of secreted proteins (i.e. Int1 (integration 1) in humans) capable of interacting with a WNT receptor, such as a receptor in the Frizzled and LRPDerailed/RYK receptor family.

As used herein, the term "WNT" or "wingless" in reference to a signaling pathway refers to a signal pathway composed of Wnt family ligands and Wnt family receptors, such as Frizzled and LRPDerailed/RYK receptors, mediated with or without β-catenin. For the purposes described herein, a preferred WNT signaling pathway includes mediation by β-catenin, i.e. WNT/β-catenin.

As used herein, "canonical pathway" or "classical activation" in reference to WNT refers to one of the multiple Wnt downstream signal pathways, for example, in the canonical pathway a major effect of Wnt ligand binding to its receptor is the stabilization of cytoplasmic beta-catenin through inhibition of the beta-catenin degradation complex. Others Wnt pathways are non-canonical.

As one example, the small molecule CHIR affects a canonical Wnt signaling downstream pathway.

As used herein, the teen "Sonic hedgehog (SHH or Shh)" refers to a protein that is one of at least three proteins in the mammalian signaling pathway family called hedgehog, another is desert hedgehog (DHH) while a third is Indian hedgehog (IHH). Shh interacts with at least two transmembrane proteins by interacting with transmembrane molecules Patched (PTC) and Smoothened (SMO). Shh typically binds to PCT which then allows the activation of SMO as a signal transducer. In the absence of SHH, PTC typically inhibits SMO, which in turn activates a transcriptional repressor so transcription of certain genes does not occur. When Shh is present and binds to PTC, PTC cannot interfere with the functioning of SMO. With SMO uninhibited, certain proteins are able to enter the nucleus and act as transcription factors allowing certain genes to be activated (see, Gilbert, 2000 Developmental Biology (Sunderland, Mass.: Sinauer Associates, Inc., Publishers).

As used herein, the term "activator" or "activating" refers to small molecules, peptides, proteins and compounds for activating molecules resulting in directed differentiation of cells of the present inventions. Exemplary activators include but are not limited to: CHIR, Sonic hedgehog (SHH) C25II, a small molecule Smoothened agonist purmorphamine, fibroblast growth factor (FGF), etc.

As used herein, the term "activator of Sonic hedgehog (SHH) signaling" refers to any molecule or compound that activates a SHH signaling pathway including a molecule or compound that binds to PCT or a Smoothened agonist and the like. Examples of such compounds are a protein Sonic hedgehog (SHH) C25II and a small molecule Smoothened agonist purmorphamine.

As used herein, the term "Sonic hedgehog (SHH) C25II" refers to a recombinant N-Terminal fragment of a full-length murine sonic hedgehog protein capable of binding to the SHH receptor for activating SHH, one example is R and D Systems catalog number: 464-5H-025/CF.

As used herein, the term "signals" refer to internal and external factors that control changes in cell structure and function. They are chemical or physical in nature.

As used herein, the term "ligand" refers to molecules and proteins that bind to receptors (R), examples include but are not limited to transforming growth factor-beta, activins, nodal, bone morphogenic proteins (BMPs), etc.

As used herein, the term "inhibitor" or "signaling inhibitor" is in reference to inhibiting a signaling molecule or a signaling molecule's pathway, such as an inhibitor of SMAD signaling, inhibitor of glycogen synthase kinase 3β (GSK3β), refers to a compound or molecule (e.g., small molecule, peptide, peptidomimetic, natural compound, protein, siRNA, anti sense nucleic acid, aptamer, or antibody) that interferes with (i.e. reduces or suppresses or eliminates or blocks) the signaling function of the molecule or pathway. In other words, an inhibitor is any compound or molecule that changes any activity of a named protein (signaling molecule, any molecule involved with the named signaling molecule, a named associated molecule, such as a glycogen synthase kinase 3β (GSK3β)) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules. Thus in one embodiment, an inhibitor of the present inventions induces (changes) or alters differentiation from a default to a non-default cell type, for example, one of the methods of the present inventions comprising LDN/SB, CHIR and a SHH activator (which may inhibit glycogen synthase kinase 3β) differentiated progenitor cells into non-default neural progenitor cells. In a preferred embodiment, an inhibitor of the present inventions "alters" or "lowers" or "blocks" default signaling in order to direct cellular differentiation towards a nondefault cell type, such as described herein for differentiating floor plate midbrain progenitor cells and midbrain fate FOXA2/LMX1A+ dopamine (DA) neurons of the present inventions. Thus, an inhibitor of the present inventions is a natural compound or small molecule which changes signal molecule activity in a manner that contributes to differentiation of a starting cell population (day 0) into floor plate midbrain progenitor cells. When progenitor cells are contacted with inhibitors these small molecules may contribute to further differentiation into midbrain fate FOXA2/LMX1A+dopamine (DA) neurons of the present inventions Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. In some cases, an inhibitor is referred to as a "direct inhibitor" which refers to inhibiting a signaling target or a signaling target pathway by actually contacting the signaling target; for example, a direct inhibitor of a gamma secretase is a DAPT molecule that binds to the gamma secretase protein.

As used herein, the term "derivative" refers to a chemical compound with a similar core structure.

As used herein, the term "floor plate midbrain progenitor cell" in reference to an in vivo cell located in a midbrain, including during embryonic development of midbrain neurons, refers to a cell that may differentiate into a dopamine producing cell. In some embodiments, a "floor plate midbrain progenitor cell" refers to a cell in culture that is used to artificially produce a cultured cell in vitro that expresses overlapping or identical sets of markers when compared to markers expressed by in vivo cells, i.e. co-expression of the floor plate marker FOXA2 and the roof plate marker LMX1A, OTX2, NGN2, and DDC, such as in cultured cells of the present inventions around day 11 after initiation of directed differentiation as described herein. Preferably, a floor plate midbrain progenitor cell is "FOXA2+LMX1A+" or "FOXA2/LMX1A+". In some embodiments, low numbers of cells in a differentiated progenitor population are FOXA2/LMX1A/TH+.

As used herein, the term "floor-plate derived DA neurons" or "authentic midbrain DA neurons" or "midbrain fate FOXA2+LMX1A+ dopamine (DA) neurons" or "floor plate midbrain dopamine (DA) neuron" or "engraftable midbrain DA neuron" or "mDA neuron" or "FOXA2+LMX1A+TH+" or "FOXA2/LMX1A/TH" or "FOXA2+LMX1A+NURR1+TH+" or "FOXA2/LMX1A/NURR1/TH" refers to an engraftable midbrain DA neuron population obtained by methods described herein, typically around or by day 25 after initiating directed differentiation. In a preferred embodiment, "authentic midbrain DA neurons" are FOXA2+/LMX1A+/NURR1+/TH+. These neurons were labeled "engraftable" after transplantation experiments in mice and primates showing the capability of these neurons to reverse Parkinson-like neurological conditions with less interference from neural overgrowth and teratoma formation. The midbrain fate FOXA2/LMX1A+ dopamine (DA) neurons of the present inventions were maintained in vitro for several months while retaining engrafting capability.

As used herein, cells used for obtaining floor plate midbrain progenitor cells and midbrain fate FOXA2/LMX1A+ dopamine (DA) neurons are obtained from a variety of sources including embryonic and nonembryonic sources, for example, hESCs and nonembryonic hiPSCs, somatic stem cells, disease stem cells, i.e. isolated pluripotent cells and engineered derived stem cells isolated from Parkinson disease patients, cancer stem cells, human or mammalian pluripotent cells, etc.

As used herein, the term "stem cell" refers to a cell with the ability to divide for indefinite periods in culture and to give rise to specialized cells. A stem cell may be obtained from animals and patients, including humans; for example, a human stem cell refers to a stem cell that is human. A stem cell may be obtained from a variety of sources including embryonic and nonembryonic, such as umbilical cord cells, cells from children and cells from adults. For the purposes of the present inventions, adult stem cells in general refer to cells that were not originally obtained from a fetus, in other words, cells from babies, cast off umbilical cords, cast off placental cells, cells from children, cells from adults, etc.

As used herein, the term "umbilical cord blood stem cells" refer to stem cells collected from an umbilical cord at birth that have the capability to at least produce all of the blood cells in the body (hematopoietic).

As used herein, the term "somatic (adult) stem cell" refers to a relatively rare undifferentiated cell found in many organs and differentiated tissues with a limited capacity for both self renewal (in the laboratory) and differentiation. Such cells vary in their differentiation capacity, but it is usually limited to cell types in the organ of origin.

As used herein, the term "somatic cell" refers to any cell in the body other than gametes (egg or sperm); sometimes referred to as "adult" cells.

As used herein, the term "neural lineage cell" refers to a cell that contributes to the nervous system (both central and peripheral) or neural crest cell fates during development or in the adult. The nervous system includes the brain, spinal cord, and peripheral nervous system. Neural crest cell fates include cranial, trunk, vagal, sacral, and cardiac, giving rise to mesectoderm, cranial cartilage, cranial bone, thymus, teeth, melanocytes, iris pigment cells, cranial ganglia, dorsal root ganglia, sympathetic/parasympathetic ganglia, endocrine cells, enteric nervous system, and portions of the heart.

As used herein, the term "adult stem cell" refers to a somatic stem cell, for one example, a "hematopoietic stem cell" which refers to a stem cell in babies, children and adults, that gives rise to all red and white blood cells and platelets.

As used herein, the term "embryonic stem cell" refers to a primitive (undifferentiated) cell that is derived from one of several sources, including but not limited to a preimplantation-stage embryo, an artificially created embryo, i.e. by in vitro fertilization, etc., capable of dividing without differentiating for a prolonged period in culture, and are known to have the capability to develop into cells and or tissues of the three primary germ layers, the ectoderm, the mesoderm, and the endoderm.

As used herein, the term "endoderm" refers to a layer of the cells derived from the inner cell mass of the blastocyst; it has the capability to give rise to lungs, other respiratory structures, and digestive organs, or generally "the gut" "in vivo" and a variety of cell types in vitro.

As used herein, the term "embryonic stem cell line" refers to a population of embryonic stem cells that have been cultured under in vitro conditions that allow proliferation without differentiation for up to days, months to years, for example, cells in a human WA-09 cell line.

As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers, the ectoderm, the mesoderm, and the endoderm.

As used herein, the term "induced pluripotent stem cell" or "iPSC" refers to a type of pluripotent stem cell, similar to an embryonic stem cell, whereby somatic (adult) cells are reprogrammed to enter an embryonic stem cell-like state by being forced to express factors important for maintaining the "stemness" of embryonic stem cells (ESCs). Mouse iPSCs were reported in 2006 (Takahashi and Yamanaka), and human iPSCs were reported in late 2007 (Takahashi et al. and Yu et al.). Mouse iPSCs demonstrate important characteristics of pluripotent stem cells, including the expression of stem cell markers, the formation of tumors containing cells from all three germ layers, and the ability to contribute to many different tissues when injected into mouse embryos at a very early stage in development. Human iPSCs also express stem cell markers and are capable of generating cells characteristic of all three germ layers. Unlike an embryonic stem cell an iPSC is formed artificially by the introduction of certain embryonic genes (such as a OCT4, SOX2, and KLF4 transgenes) (see, for example, Takahashi and Yamanaka Cell 126, 663-676 (2006), herein incorporated by reference) into a somatic cell, for examples of cell lines from induced cells, C14, C72, and the like. Another example of an iPSC is an adult human skin cell, or fibroblast cell, transformed with using genes (OCT4, SOX2, NANOG, LIN28, and KLF4) cloned into a plasmid for example, see, Yu, et al., Science DOI: 10.1126/science.1172482, herein incorporated by reference.

As used herein, the term "totipotent" refers to an ability to give rise to all cell types of the body plus all of the cell types that make up the extraembryonic tissues such as the placenta.

As used herein, the term "multipotent" refers to an ability to develop into more than one cell type of the body.

As used herein, the term "pluripotent" refers to a cell having the ability to give rise to at least two but often numerous different cell types of the body. Pluripotent cells often generate a teratoma after injection into an immunosuppressed mouse.

As used herein, the term "pluripotent stem cell" refers to an ability of this cell to develop into at least two different cells types depending upon environmental factors, i.e. morphogens, growth factors, signaling molecules, either activators or inhibitors, etc. In some embodiments, a pluripotent stem cell refers to an ability of a cell to develop into any one of the three developmental germ layers of the organism including endoderm, mesoderm, and ectoderm.

As used herein, the term "specialized cell" refers to a type of cell that performs a specific function in multicellular organisms. For example, groups of specialized cells, such as neurons, work together to form a system, such as a nervous system.

As used herein, the term "neuroectoderm" refers to a cell or cell fate found early in development or during pluripotent stem cell differentiation that can give rise to cells of the neural lineage.

As used herein, the term "markers of cell proliferation" refers to the expression of molecules associated with rapidly cycling cells which are typically not present in mature slowly cycling or noncycling cells, i.e. actively dividing vs. cells with extended cycling times or noncycling cells. Examples of such markers include a Ki67 marker of cell proliferation (Gerdes, et al., *Int J Cancer* 31:13-20 (1983), herein incorporated by reference) and phospho-histone H3 markers of G2/M-phases of mitosis (Hendzel, et al., *Chromosoma* 106:348-360 (1997), herein incorporated by reference).

As used herein, the term "proliferation" refers to an increase in cell number.

As used herein, the term "differentiation" refers to a process whereby an unspecialized embryonic cell acquires the features of a specialized cell such as a specific type of neuron, brain cell, heart, liver, or muscle cell. Differentiation is controlled by the interaction of a cell's genes with the physical and chemical conditions outside the cell, usually through signaling pathways involving proteins embedded in the cell surface.

As used herein, the term "differentiation" as used with respect to cells in a differentiating cell system refers to the process by which cells differentiate from one cell type (e.g., a multipotent, totipotent or pluripotent differentiable cell) to another cell type such as a target-differentiated cell.

As used herein, the term "cell differentiation" refers to a pathway by which a less specialized cell (i.e. stem cell) develops or matures to possess a more distinct form and function (for example, an iPSC progressing into a neural crest progenitor to a cell of neuronal lineage to a floor plate midbrain progenitor cells to a midbrain fate FOXA2/LMX1A+ dopamine (DA) neurons of the present inventions).

As used herein, the term "undifferentiated" refers to a cell that has not yet developed into a specialized cell type.

As used herein, the term "default" or "passive" in reference to a cell differentiation pathway refers to a pathway where a less specialized cell becomes a certain differentiated cell type in culture, when not treated with certain compounds i.e. normal cell cultures conditions without contact with at least one morphogen. In other words, a default cell results when a cell is not contacted by a molecule capable of changing the differentiated cell type (i.e. a morphogen), for example cultures treated with LSB alone, but not an activator of SHH or an activator of Wnt for making a forkhead box protein A2 (FOXA2)+ cell of the present inventions, instead results in the expression of markers HES5, PAX6, LHX2, and EMX2. In contrast, "non-default" in reference to a cell refers to a differentiated cell type that results in a cell type that is different from a default cell, i.e. a non-default cell is a differentiated cell type resulting from a non-default conditions, such as cell of the present inventions, including a forkhead box protein A2 (FOXA2)+ neuronal cell, a floor plate midbrain progenitor cell and midbrain fate FOXA2/LMX1A+ dopamine (DA) neuron of the present inventions, etc. A default cell may also be a default cell after a cell has contact with a morphogen to become a non-default cell without a subsequent morphogenic compound, such as a non-default floor plate midbrain progenitor cell that subsequently becomes a default cell that is not a midbrain fate FOXA2/LMX1A+ dopamine (DA) neurons because of a lack of contact with a morphogen such as CHIR.

As used herein, the term "morphogen" refers to a compound that influences differentiation of a cell, i.e. determines, at least in part, cell fate. A morphogen also can influence a cell to differentiate into a non-default cell type.

As used herein, the term "directed differentiation" refers to a manipulation of stem cell culture conditions to induce differentiation into a particular (for example, desired) cell type, such as floor plate midbrain progenitor cells and midbrain fate FOXA2/LMX1A+ dopamine (DA) neurons of the present inventions. In one embodiment, the tam "directed differentiation" in reference to a cell refers to the use of small molecules, growth factor proteins, and other growth conditions to promote the transition of a cell from a pluripotent state into a more mature or specialized cell fate (e.g. central nervous system cell, neural cell, floor plate midbrain progenitor cell and midbrain fate FOXA2/LMX1A+ dopamine (DA) neuron of the present inventions, etc.). In one preferred embodiment, the beginning of directed differentiation is the contacting of a cell at day 0 with LDN/SB. A cell undergoing directed differentiation as described herein results in the formation of a non-default cell type of floor plate midbrain progenitor cells and midbrain fate FOXA2/LMX1A+ dopamine (DA) neurons of the present inventions.

As used herein, the term "inducing differentiation" in reference to a cell refers to changing the default cell type (genotype and/or phenotype) to a non-default cell type (genotype and/or phenotype). Thus "inducing differentiation in a stem cell" refers to inducing the cell to divide into progeny cells with characteristics that are different from the stem cell, such as genotype (i.e. change in gene expression as determined by genetic analysis such as a microarray) and/or phenotype (i.e. change in expression of a protein, such as forkhead box protein A2 (FOXA2) or a set of proteins, such as forkhead box protein A2 (FOXA2) and LIM homeobox transcription factor 1, alpha (LMX1A) positive (+) while negative (−) for PAX6).

As used herein, the term "fate" in reference to a cell, such as "cell fate determination" in general refers to a cell with a genetically determined lineage whose progeny cells are capable of becoming a variety of cell types or a few specific cell types depending upon in vivo or in vitro culture conditions. In other words, a cell's predetermined fate is determined by its environment to be destined for a particular differentiation pathway such that a cell becomes one cell type instead of another cell type, for example, a stem cell's progeny cells whose "neural fate" is to become a nerve cell instead of a muscle cell or a skin cell.

As used herein, the term "neurite outgrowth" or "neural outgrowth" refers to observation of elongated, membrane-enclosed protrusions of cytoplasm from cells.

As opposed to "neural overgrowth" which refers to unwanted unconstrained neural growth, i.e. uncontrolled growth of neurons, of transplanted cells at the site of engraftment. As used herein, the term "teratoma" refers to a noncancerous tumour from any tissue type growing from transplanted cells.

As used herein, the term "teratoma formation" refers to the unwanted growth of a variety of tissue types into noncancerous tumours from growth of transplanted cells.

As used herein, the term "dopamine neuron" or "dopaminergic neuron" in general refers to a cell capable of expressing dopamine. "Midbrain dopamine neurons" or "mDA" refer to presumptive dopamine expressing cells in forebrain structures and dopamine expressing cells in forebrain structures.

As used herein, the term "neural stem cell" refers to a stem cell found in adult neural tissue that can give rise to neurons and glial (supporting) cells. Examples of glial cells include astrocytes and oligodendrocytes.

As used herein, the term "floor plate" or "FP" or "fp" refers to a region of the neural tube in vivo that extends along the entire ventral midline also described as the unpaired ventral longitudinal zone of the neural tube or referred to as a signaling center of the neural tube. In other words, the neural tube was divided in different regions where the ventral cells closest to the midline constituted the floor plate. For one example of further cellular identification, chick midbrain FP can be divided into medial (MFP) and lateral (LFP) regions on the basis of gene expression, mode of induction and function. Floor plate cells are found in vivo in several areas of the developing embryo, for example floor plate cells in the midbrain, in the hindbrain, etc. In vivo, floor plate cells in the midbrain region are contemplated to give rise to cells that are different than cells differentiated from floor plate cells in other regions. One primary floor plate marker in the midbrain region is FOXA2.

As used herein, the term "roof plate" refers to the dorsal cells closest to the midline. One roof plate marker is LMX1A. During embryonic development, floor plate and roof plate cells are located at distinct positions in the CNS (ventral versus dorsal) with diametrically opposed patterning requirements for their induction.

As used herein, the term "midbrain" refers to a region of the developing vertebrate brain between the forebrain (anterior) and the hindbrain (posterior). The midbrain regions gives rise to many areas of the brain, including but not limited to reticular formation, which is part of the tegmentum, a region of the brainstem that influences motor functions, the crus cerebri, which is made up of nerve fibers connecting the cerebral hemispheres to the cerebellum, and a large pigmented nucleus called the substantia nigra. A unique feature of the developing midbrain is the co-expression of the floor plate marker FOXA2 and the roof plate marker LMX1A.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "cell culture" refers to a growth of cells in vitro in an artificial medium for research or medical treatment.

As used herein, the term "culture medium" refers to a liquid that covers cells in a culture vessel, such as a Petri plate, a multiwell plate, and the like, and contains nutrients to nourish and support the cells. Culture medium may also include growth factors added to induce desired changes in the cells.

As used herein, the term "neuronal maturation medium" or "BAGCT" medium refers to a culture medium comprising N2 medium, further comprising brain-derived neurotrophic factor (BDNF), ascorbic acid (AA), glial cell line-derived neurotrophic factor, dibutyryl cAMP and transforming growth factor type β3 for differentiating midbrain fate FOXA2/LMX1A+ dopamine (DA) neurons.

As used herein, the term "feeder layer" refers to a cell used in co-culture to maintain pluripotent stem cells. For human embryonic stem cell culture, typical feeder layers include mouse embryonic fibroblasts (MEFs) or human embryonic fibroblasts that have been treated to prevent them from dividing in culture.

As used herein, the term "passage" in reference to a cell culture, refers to the process in which cells are disassociated, washed, and seeded into new culture vessels after a round of cell growth and proliferation. The number of passages a line of cultured cells has gone through is an indication of its age and expected stability.

As used herein, the term "expressing" in relation to a gene or protein refers to making an mRNA or protein which can be observed using assays such as microarray assays, antibody staining assays, and the like.

As used herein, the term "paired box gene 6" or "PAX6" refers to a marker of a non-default neuroprogenitor cell.

As used herein, the term "TUJ1" or "neuron-specific class III beta-tubulin" in reference to a differentiating cell of the present inventions refers to a marker of early neural human cell differentiation, such as neural progenitor cells, and is found expressed in neurons of the PNS and CNS.

As used herein, the term "homodimer" in reference to a SMAD molecule refers to at least two molecules of SMAD linked together, such as by disulfide linkages.

As used herein, the term "contacting" cells with a compound of the present inventions refers to placing the compound in a location that will allow it to touch the cell in order to produce (obtain) "contacted" cells. The contacting may be accomplished using any suitable method. For example, in one embodiment, contacting is by adding the compound to a tube of cells. Contacting may also be accomplished by adding the compound to a culture of the cells.

As used herein, the term "attached cell" refers to a cell growing in vitro wherein the cell adheres to the bottom or side of the culture vessel, an attached cell may contact the vessel via extracellular matrix molecules and the like and requires the use of an enzyme for detaching this cell from the culture dish/container, i.e. trypsin, dispase, etc. An "attached cell" is opposed to a cell in a suspension culture that is not attached and does not require the use of an enzyme for removing cells from the culture vessel.

As used herein, the term "marker" or "cell marker" refers to a gene or protein that identifies a particular cell or cell type. A marker for a cell may not be limited to one marker, markers may refer to a "pattern" of markers such that a designated group of markers may identity a cell or cell type from another cell or cell type. For example, midbrain fate FOXA2/LMX1A+ dopamine (DA) neurons of the present inventions express one or more markers that distinguish a floor plate midbrain progenitor cell from a precursor less differentiated cell, i.e. forkhead box protein A2 (FOXA2) positive and LIM homeobox transcription factor 1, alpha (LMX1A) positive vs. HES5+ and PAX6+ cells, for example, as shown by exemplary gene expression patterns in FIGS. 1e and 1f.

As used herein, the term "positive" in relation to a cell, including a "positive cell" refers to a cell that expresses a marker, for one example, an antibody "stains" for that marker when using an antibody staining (detection) system or a nucleic acid sequence that hybridizes to the marker nucleic acid sequence as measured by a reporter molecule, i.e. a fluorescent molecule that attaches to double stranded nucleic acid sequences, in a detectable quantitative and/or qualitative amount above a control or comparative cell. For example, a cell positive for a marker such as forkhead box protein A2 (FOXA2), etc., refers to a cell that expresses FOXA2 mRNA and/or protein when detected in an assay, such as a gene array or antibody, respectively. Such as positive cell may be referred to as FOXA2+. When a cell is positive for more than one marker, such as when using the notation FOXA2/LMX1A+, the cell or the majority of the cell population is positive for both FOXA2 and LMX1A.

As used herein, the term "negative" in relation to a cell or cell population, including a "negative cell" refers to a cell or population absent detectable signal for a marker or signal at levels of control populations. For example, a cell failing to stain following contacting with a forkhead box protein A2 (FOXA2) antibody detection method or gene array that includes detection of a FOXA2 mRNA, etc., is FOXA2- or negative for FOXA2.

As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as β-galactosidase (lacZ gene).

As used herein, the term "GFP" refers to any green fluorescent protein DNA sequence capable of producing a fluorescent protein upon expression in a cell typically used as an indication marker for expression of a target gene. Examples of GFP include GFP sequences isolated from coelenterates, such as the Pacific jellyfish, *Aequoria Victoria*, and synthetic sequence derivatives thereof, such as "eGFP".

The term "sample" is used in its broadest sense. In one sense it can refer to a cell or tissue. In another sense, it is meant to include a specimen or culture obtained from any source and encompasses fluids, solids and tissues. Environmental samples include environmental material such as surface matter, soil, water, and industrial samples. These examples are not to be construed as limiting the sample types applicable to the present invention.

The terms "purified," "to purify," "purification," "isolated," "to isolate," "isolation," and grammatical equivalents thereof as used herein, refer to the reduction in the amount of at least one contaminant from a sample. For example, a desired cell type is purified by at least a 10%, preferably by at least 30%, more preferably by at least 50%, yet more preferably by at least 75%, and most preferably by at least 90%, with a corresponding reduction in the amount of undesirable cell types, for example, directed differentiation of the present inventions resulted in the desired increase in purity of differentiated floor plate midbrain progenitor cells or midbrain fate FOXA2/LMX1A+ dopamine (DA) neurons of the present inventions. In other words "purify" and its equivalents, refers to the removal of certain cells (e.g., undesirable cells) from a sample either mechanically, such as by flow cytometer cell sorting or through directed differentiation. For example, for differentiating a purified population of forkhead box protein A2 (FOXA2)+ LIM homeobox transcription factor 1, alpha (LMX1A)+ progenitor cells of the present inventions, progenitor cells are purified by removal of contaminating PAX6 neuronal cells by sorting a mixed cell population into double positive forkhead box protein A2 (FOXA2)+ LIM homeobox transcription factor 1, alpha (LMX1A)+ cells by flow cytometry; midbrain fate FOXA2/LMX1A+ dopamine (DA) neurons are also purified or "selected" from non-dopamine (DA) (default cells) by using a specified method of cell culture comprising compositions and methods of the present inventions. The removal or selection of non-midbrain fate FOXA2/LMX1A+ dopamine (DA) neuronal cells results in an increase in the percent of desired midbrain fate FOXA2/LMX1A+ dopamine (DA) neurons in the sample. Thus, purification of a cell type results in an "enrichment," i.e., an increase in the amount, of the desired cell, i.e. midbrain fate FOXA2/LMX1A+ dopamine (DA) neurons in the sample.

The term "naturally occurring" as used herein when applied to an object (such as cell, tissue, etc.) and/or chemical (such as a protein, amino acid sequence, nucleic acid sequence, codon, etc.) means that the object and/or compound are/were found in nature. For example, a naturally occurring cell refers to a cell that is present in an organism that can be isolated from a source in nature, such as an embryonic cell, wherein the cell has not been intentionally modified by man in the laboratory.

As used herein the term, "in vitro" refers to an artificial environment and to processes or reactions that occur within an artificial environment. In vitro environments exemplified, but are not limited to, test tubes and cell cultures.

As used herein the term, "in vivo" refers to the natural environment (e.g., an animal or a cell) and to processes or reactions that occur within a natural environment, such as embryonic development, cell differentiation, neural tube formation, etc.

The term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vivo, treatment and/or mutagenesis. A cell may derived from another cell, using for example chemical treatment, radiation, inducing new protein expression, for example, by infection with virus, transfection with DNA sequences, contacting (treating) with a morphogen, etc., and selection (such as by serial culture) of any cell type that is contained in cultured parent cells). A derived cell can be selected from a mixed population by virtue of response to a growth factor, cytokine, selected progression of cytokine treatments, adhesiveness, lack of adhesiveness, sorting procedure, and the like.

As used herein, the term "cell" refers to a single cell as well as to a population of (i.e., more than one) cells. The population may be a pure population comprising one cell type, such as a population of neuronal cells or a population of undifferentiated embryonic cells. Alternatively, the population may comprise more than one cell type, for example a mixed cell population. It is not meant to limit the number of cells in a population; for example, in one embodiment, a mixed population of cells may comprise at least one differentiated cell. In the present inventions, there is no limit on the number of cell types that a cell population may comprise.

As used herein, the term "highly enriched population" refers to a population of cells, such as a population of cells in a culture dish, expressing a marker at a higher percentage or amount than a comparison population, for example, treating a LSB contacted cell culture on day 1 with purmorphamine and on day 3 with CHIR results in a highly enriched population of floor plate midbrain progenitor cells compare to treatment with LSB alone. In other examples, an enriched population is a population resulting from sorting or separating cells expressing one or more markers from cells not expressing the desired marker, such as a CD142 enriched population, an A9 enriched population, and the like.

The term, "cell biology" or "cellular biology" refers to the study of a live cell, such as anatomy and function of a cell, for example, a cell's physiological properties, structure, organelles, and interactions with their environment, their life cycle, division and death.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "kit" refers to any delivery system for delivering materials. In the context of cell differentiation, a kit may refer to a combination of materials for contacting stem cells, such delivery systems include systems that allow for the storage, transport, or delivery of reaction reagents from one location to another in the appropriate containers (such as tubes, etc.) and/or supporting materials (e.g., buffers, written instructions for performing cell differentiation, etc.) (e.g., compounds, proteins, detection agents (such as antibodies that bind to tyrosine hydroxylase (TH), forkhead box protein A2 (FOXA2), LIM homeobox transcription factor 1, alpha (LMX1A), etc.), etc. For example, kits include one or more enclosures (e.g., boxes, or bags, test tubes, Eppendorf tubes, capillary tubes, multiwell plates, and the like) containing relevant reaction reagents for inhibiting signaling pathways, for example, an inhibitor for lowering transforming growth factor beta (TGFβ)/Activin-Nodal signaling, such as SB431542 (or SB431542 replacement), and the like, an inhibitor for lowering SMAD signaling, LDN-193189 (or LDN-193189 replacement), and the like, an inhibitor for lowering glycogen synthase kinase 3β (GSK3β), for one example, for activation of wingless (Wnt or Wnts) signaling otherwise known as a WNT signaling activator (WNT agonist), such as CHIR99021 (or CHIR99021 replacement), etc.), and the like, an activator of Sonic hedgehog (SHH) signaling (such as a smoothened (SMO) receptor small molecule agonist), for example, a Sonic hedgehog (SHH) C25II molecule, purmorphamine, and the like, a molecule with Fibroblast growth factor 8 (FGF8) activity, such as Fibroblast growth factor 8 (FGF8), etc., and neuronal maturation molecules, for example, brain-derived neurotrophic factor (BDNF), ascorbic acid (AA), glial cell line-derived neurotrophic factor, dibutyryl cAMP and transforming growth factor type β3, including molecules capable of replacing these components, and/or supporting materials. The reagents in the kit in one embodiment may be in solution, may be frozen, or may be lyophilized. The reagents in the kit in one embodiment may be in individual containers or provided as specific combinations, such as a combination of LSB (LDN-193189 with SB431542), Sonic hedgehog (SHH) C25II molecule with purmorphamine, Sonic hedgehog (SHH) C25II molecule with purmorphamine with CHIR99021 or purmorphamine with CHIR99021, neuronal maturation molecules and the like.

BRIEF DESCRIPTION OF THE DRAWINGS

FIGS. 3-1 and 3-2 shows an exemplary in vitro maturation, characterization and functional assessment of floor plate derived- versus rosette-derived midbrain DA neurons. FIG. 3-1: shows exemplary: a) Immunocytochemical analysis at day 50 of differentiation for TH (red), in combination with LMX1A (green, left panels), FOXA2 (blue, left panels) and NURR1 (green, right panels). b) Quantification of TH+, FOXA2+, LMX1+ and NURR1+ cells out of total cells in rosette-derived versus floor plate-derived (LSB/S/F8/CHIR) cultures. c) Quantification of serotonin+ (5-HT), and GABA+ neuronal subtypes at day 50 in floor plate- and rosette-derived DA neuron cultures. d,e) HPLC analysis for measuring DA and metabolites d) Representative chromatogram for the electrochemical detection of DA in a sample of floor plate-derived cultures. e) Comparison of DA, DOPAC and HVA levels between floor plate- versus rosette-derived cultures. f) Immunocytochemical analysis of floor plate-derived cultures (day 80) for TH (red) and synapsin (green). g-i) Electrophysiological analyses of floor plate cultures at day 80 of DA neuron differentiation. Phase contrast image of a patched neuron (g) and corresponding recordings (h). i) Power analysis showing membrane potential oscillations characteristic of DA neuron identity (2 to approximately 5 Hz). Significance levels for individual markers (panels b, c, e) are presented as a comparison of FP− versus rosette-derived cultures: Student's T-test: * $p<0.001$;  $p<0.01$; $p<0.05$). Scale bars correspond to 50 μm in (a), 20 μm in (f, upper panel), 5 μm in (f, lower panel) and 20 μm in (g) j: Maturation of mDA neurons in vitro (d65). TH positive neurons are still expressing FoxA2 and extend long fibers typical for mDA neurons, and k: DA release measurement by HPLC: d65 old TH+ neurons are functional in vitro. FIG. 3-2: shows an exemplary summary of cells produced by a floor plate based midbrain DA neuron protocol as described herein. a) In contrast to past strategies (for example, Perrier, A. L. et al. Derivation of midbrain dopamine neurons from human embryonic stem cells. Proc Natl Acad Sci USA 101, 12543-8 (2004)), the novel protocol described herein is based on generating LMX1A/FOXA2 positive midbrain floor plate (left panel) followed by neuronal conversion (middle panel) and DA neuron maturation (right panel). Mature floor plate generated DA neuron cells retain FOXA2/LMX1A expression.

FIG. 8 shows an exemplary analysis of genes differentially expressed in LSB/S/F8/CHIR treated versus LSB and LSB/S/F8 treated cultures at days 11 and 25 of differentiation. a) Hierarchical clustering of global gene expression data obtained from three conditions at days 0, 1, 3, 5, 7, 11 and 13 (samples were assessed in triplicates for each condition and each day). b) Gene enrichment analysis according to GO classes using DAVID; http://david.abcc.ncifcrf.gov. Comparisons at day 11 reveal enrichment for both SHH and WNT signaling in LSB/S/F8/CHIR condition in agreement with CHIR99021 mediated activation of canonical WNT signaling. Alternative cell fates such as "forebrain development" and "diencephalon" as well as "homeobox" are other GO terms highly enriched at days 11 and 25. c) Online validation using the Allen gene human expression data base (http://human.brain-map.org) for candidate markers enriched in midbrain DA neuron condition (LSB/S/F8/CHIR). TTF3, EBF1, EBF3 and TTR were expressed based on available human brain region specific microarray data. TTR, a classic transcriptional target of FOXA2 is only weakly expressed in adult substantia nigra, suggesting that its main role may be during development or that SHH treatment may cause artificially high TTR expression levels during in vitro differentiation.

FIG. 15 shows an exemplary histological analysis of floor plate-derived grafts in primate brain. Floor plate-derived DA neurons derived from H9 hESCs and from H9-GFP hESCs (day 25 cultures; 1.25×10$^6$ cells/tract, 3 tracts/per hemisphere, 6 tracts in total) were grafted into the striatum of adult MPTP lesioned rhesus monkeys (=2). a) Upper left and right panels: High-resolution image reconstructions of representative graft sites (1 month after transplantation). Graft cytoarchitecture is illustrated by immunohistochemistry for the human specific marker SC-121 (no cross-reactivity with non-human primate tissues). Lower left panel: SC-121+ fibers extending from graft core. Lower right panel: Higher resolution image of SC-121+ cells showing neuronal precursor morphologies. b) Analysis of GFP expression in graft cores further confirmed human identity of the cells complementing the SC-121 data. Note: For both animals, one hemisphere each was grafted with unmarked H9 derived cells while the other hemisphere received cells derived from H9-GFP cells (expression of GFP under control of EF1a promoter). c) Higher resolution image of the GFP+ graft using DAB detection showing numerous GFP+ cells at graft periphery exhibiting neuroblast morphology. d) Immunohistochemical analyses of areas in the graft core negative for GFP and SC-121. These areas contained large numbers of host microglia based on Iba1 expression (red) as well as few ED1+ macrophages (blue), suggesting persistent inflammation despite cyclosporine immunosuppression. Scale bars correspond to 500 µm in (a, top panel), 50 µm in (a, lower left panel), 20 µm in (a, lower right panel), 2 mm in (b), 500 µm in (c, left panel), 50 µm (c, upper right panel), 100 µm (c, lower right panel), 100 µm (d).

FIG. 16 shows an exemplary derivation of TH+ cells from hESCs using a previous MS5 feeder cell based method that differentiated cells into DA neuron-like cells via (through) rosette cell intermediates. Top) at P0 hESCs were contacted with molecules for beginning neural induction of Oct4+ cells into rosette cells using MS5 feeder cells (Perrier et al., 2004). At the P1 stage rosette cells were expanded by contacting cells with additional molecules for differentiating cells into cells at stage P2 with specific expression patterns including Pax2+/En1+ DA progenitor cells further differentiated into TH+/En1+ DA neurons. These cells were used for engraftment in 6OHDA lesion rats, immunosuppressed via cyclosporin A treatment. These transplantation studies showed very poor in vivo viability of DA-like neurons, including loss of the TH+ phenotype, and revealed concerns about further growth of unwanted, possibly lethal, cells for the grafted animals, i.e. teratomas, and growth of cells into inappropriate neural types that would cause additional medical problems for the patient. A: There were very small numbers of surviving TH+ neuron at 4.5 months after transplantation (<50 TH+ cells/animal) in grafts from rosette derived DA neuron precursors. However, in contrast to TH+ cells, GFP marked cells (GFP was driven by a ubiquitous promoter) did survive quite well after transplantation. This suggests that most surviving cells following transplantation were neural cells of non-DA neuron identity (16B). FIG. 16C: few graft-derived cells (hNA+ (green) co-express TH (red) suggesting that most grafted human cells adopt a non-DA neuron phenotype. Panels 16 D-E show that D-E, despite the very poor in vivo survival there was some (albeit very modest and highly variable) improvement in a few behavioral assays such as amphetamine induced rotations (D), cylinder test and spontaneous rotations (E).

FIG. 17 shows an exemplary protocol for derivation of low numbers of floor plate cells. A modified Dual-SMAD inhibition protocol generated floor plate (fp) cells. High concentrations of SHH were necessary for the induction of FoxA2+ fp cells and that addition of caudalizing patterning cues such as FGF8, Wnt1 or RA did not lead to decrease in FOXA2 expression but change in regional identity A) Left panel: Cells at day 11 of differentiation following treatment with NSB (Noggin/SB431542); left center panel: NSB+SHH (Sonic C25II) treatment; Center panel: NSB+SHH+RA; Center right pane: NSB+SHH+Wnt1; NSB+SHH+FGF8; Note: NSB only treatment does not induce FoxA2 expression. FoxA2+ floor plate cells are only induced in the presence of high dose SHH. Addition of RA. Wnt1 and FGF8 does not inhibit FoxA2 induction. B) qRT-PCR analysis for gene expression of FOXA2 and SIX6 showing maintenance (or even increase) of expression for FOXA2 following treatment with RA or FGF with a concomitant downregulation of SIX6 expression marking the most anterior floor plate like cells. C) Induction of gene expression for midbrain precursors and midbrain floor plate markers in the presence of FGF8 and Wnt1.

Figures 1, 24:
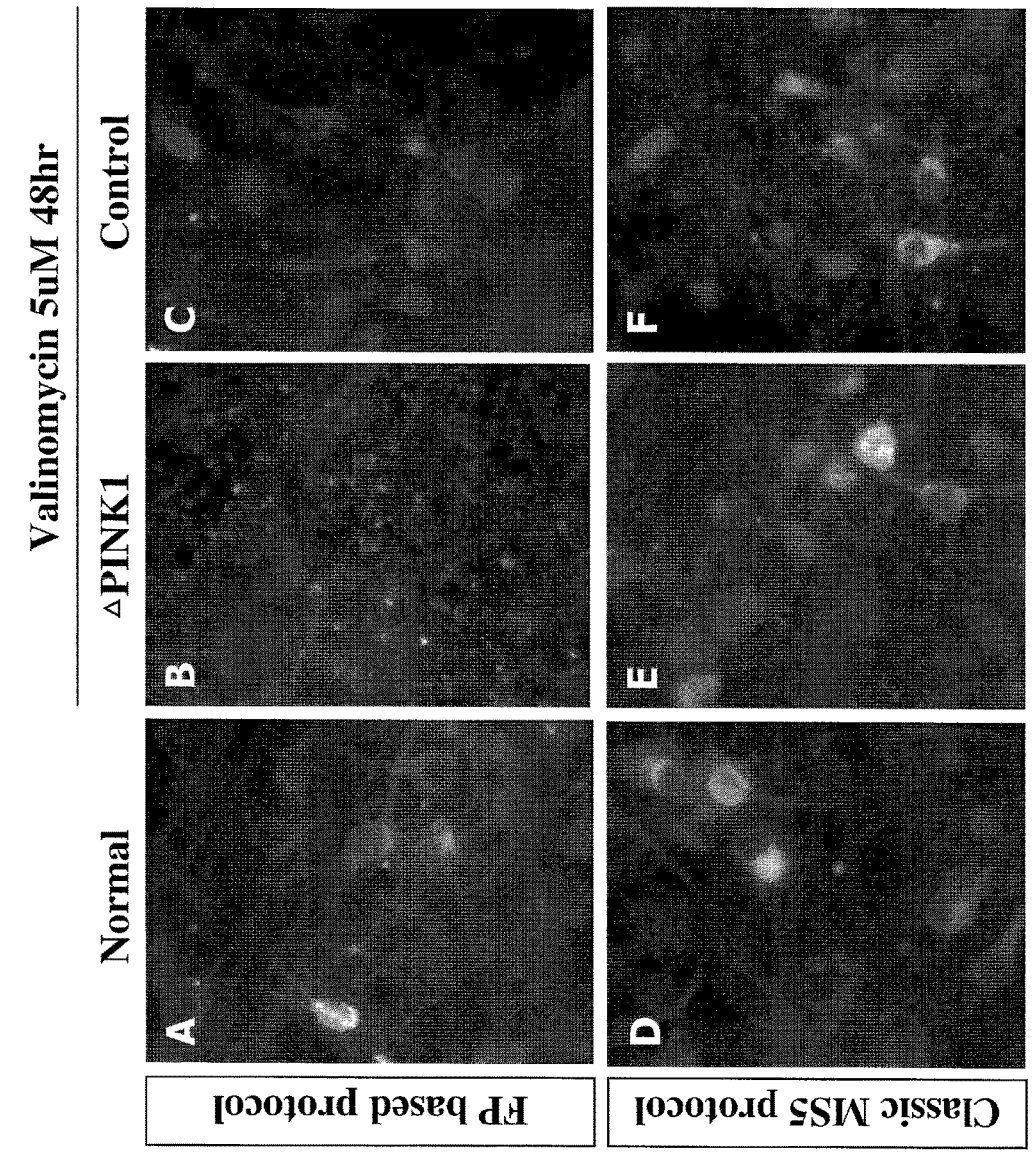
Figures 2, 24:
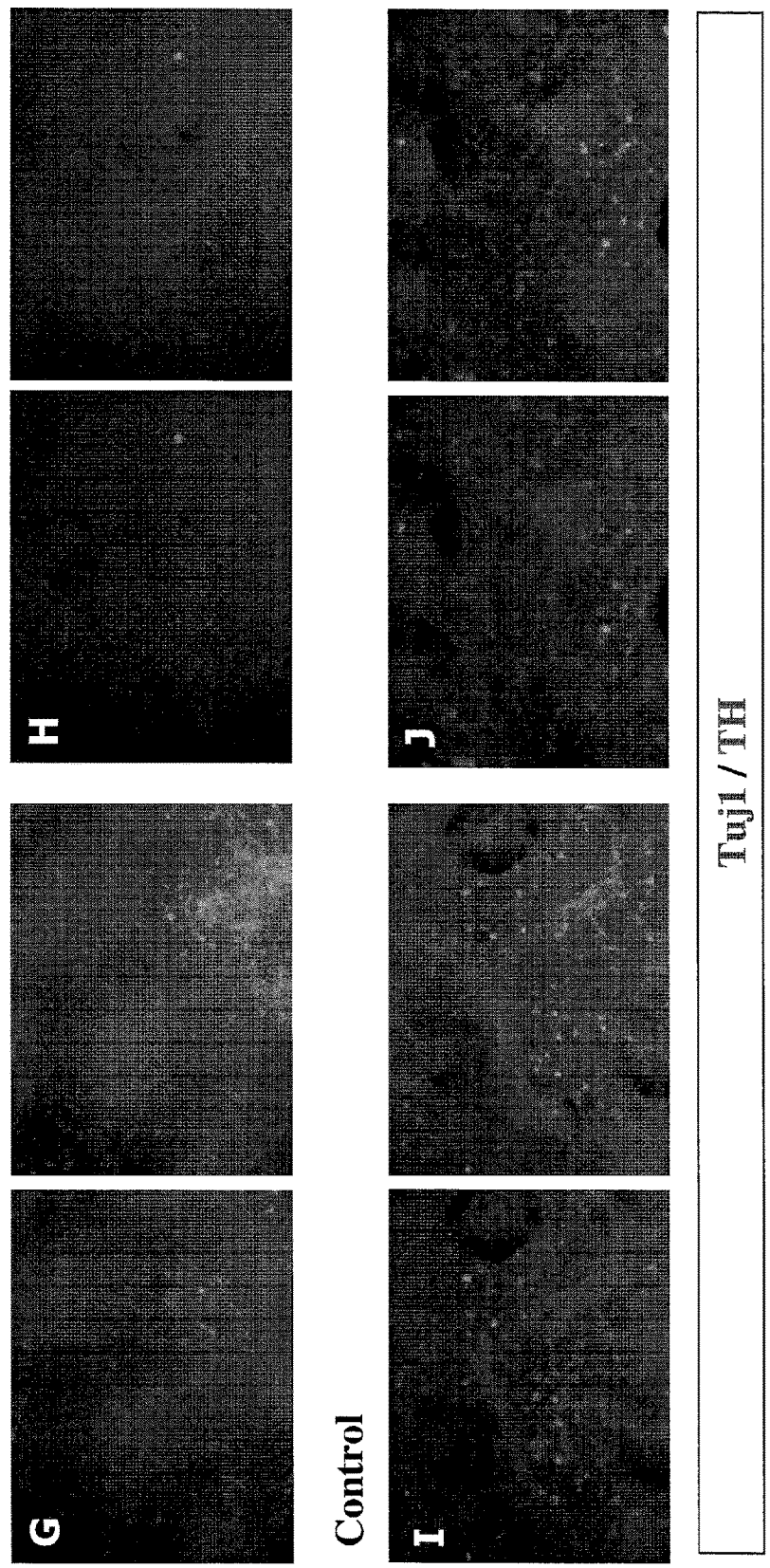
Figures 3, 24:
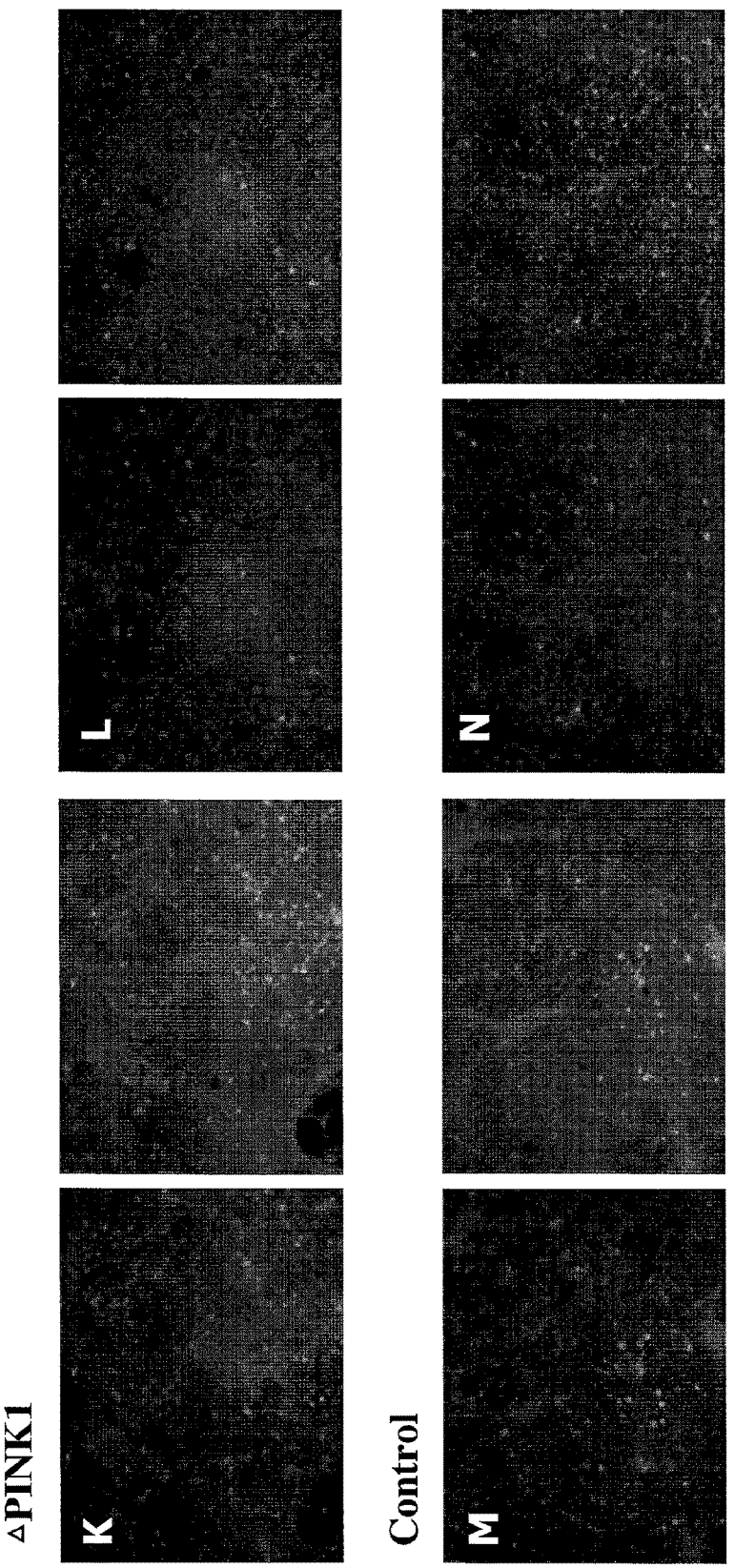

FIG. 24 shows an exemplary DA neurons derived from PINK1 mutant PD-iPSC are more vulnerable to toxic stimulation. PD-iPSC derived TH+ DA neurons derived via the floor-plate based protocols of the present inventions were more vulnerable to toxin challenge (valinomycin: mitochondria ionophore, 5 uM, 48 hr) than control-iPSC derived cells. In contrast, TH+ neurons derived via the classic MS5 based protocol did not show differential vulnerability between PD- versus control-derived cells. A-F) Representative TH immunocytochemistry at day 60 of differentiation: Normal condition (no toxin treatment) for both PD- and control-iPSC derived cells obtained via floor-plate based protocol (A, PD-iPSC derived cells shown), nearly complete degeneration of TH+ DA neurons in PD-iPSC following toxin treatment (B), partially degenerated TH+ DA neurons from control-iPSC(C), Normal condition both of PD- and control-iPSC derived cultures obtained via MS5 based protocol (D, PD-iPSC derived cells shown), TH+ neurons following toxin challenge in PD-iPSC (E), and control-iPSC derived cultures (F) obtained via MS5 protocol. G-H) low power images of immunocytochemistry for Tuj1 (red) and TH (green) by floor-plate based protocol at day 60 of differentiation: PD-iPSC of normal (G), versus toxin challenge (H) conditions and control iPSC of normal (I), versus toxin challenge (J) conditions. K-N) low power images of immunocytochemistry for Tuj1 (red) and TH (green) by MS5 based protocol at day 60 of differentiation: PD-iPSC of normal (K), versus toxin challenge (L) conditions and control iPSC of normal (M), versus toxin challenge (N) conditions.

Figure 25:
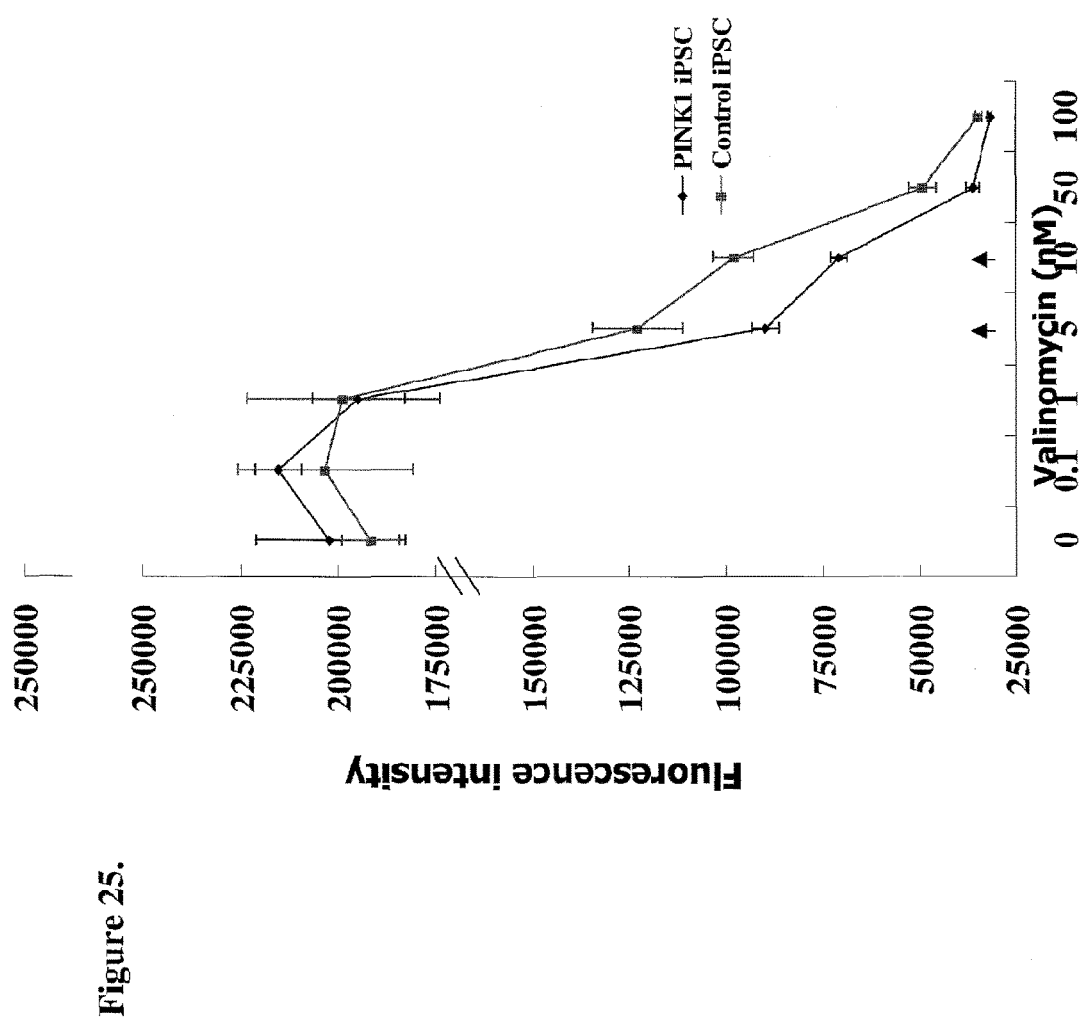

FIG. 25 shows an exemplary quantification of cell viability-dose response assay for toxin challenge. Cell viability assay with alamar-blue after 48 hrs of valinomycin treatment showed differential cell survival in a specific dose range for toxin challenge (5 and 10 uM) when comparing PD-iPSC and control iPSC (day 60 of floor-plate based differentiation of the present inventions). Note: this assay tests for overall cell death while the most dramatic effects were observed specifically in DA neurons (see FIG. 14). Therefore, alamar blue based quantification will likely underestimate the extent of the differential effect observed on DA neuron lineages.

Figure 26:
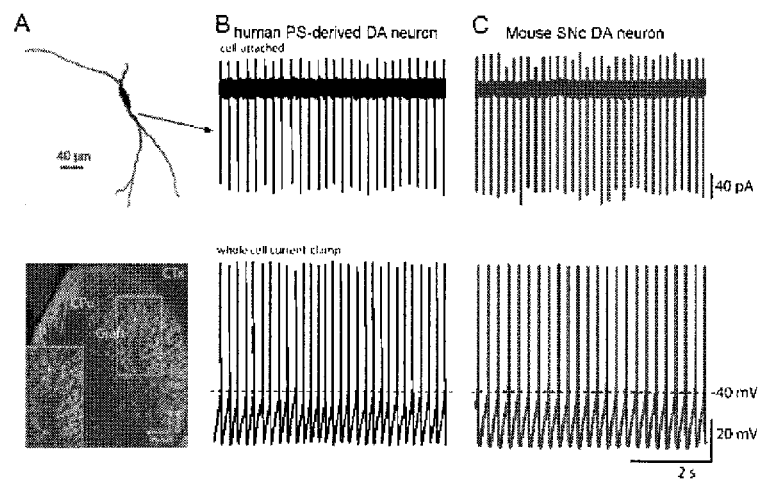

FIG. 26 shows exemplary grafted human DA neurons derived from pluripotent stem cells have electrophysiological features typical of those seen in mouse substantia nigra pars compacta (SNpc). A) Top-Reconstruction of a pace-making neuron in the graft region. Bottom-photomicrograph of a brain slice taken from the rat into which the hES-derived neurons were injected 9 months prior; the graft is outlined; a higher magnification image is shown inset at the bottom. The slice was processed for tyrosine hydroxylase, see white areas. B). Top-cell-attached patch recording from a putative DA neuron in the graft; Bottom-whole cell recording from the same cell. Recordings were made in the presence of glutamate and GABA receptor antagonists (50 μM AP5, 10 μM CNQX and 10 μM GABAzine) to eliminate synaptic input. These recordings demonstrate that the PS-derived neurons were autonomous pacemakers with normal intrasomatic voltage trajectories. Another neuron recorded in graft had similar properties. C) For comparison, cell-attached and whole cell recordings from a dopaminergic neuron in SNpc of an adult mouse are shown. Abbreviations (CTx=cortex, STr=striatum, SNpc=substantia nigra pars compacta, DA=dopaminergic).

Figure 27:
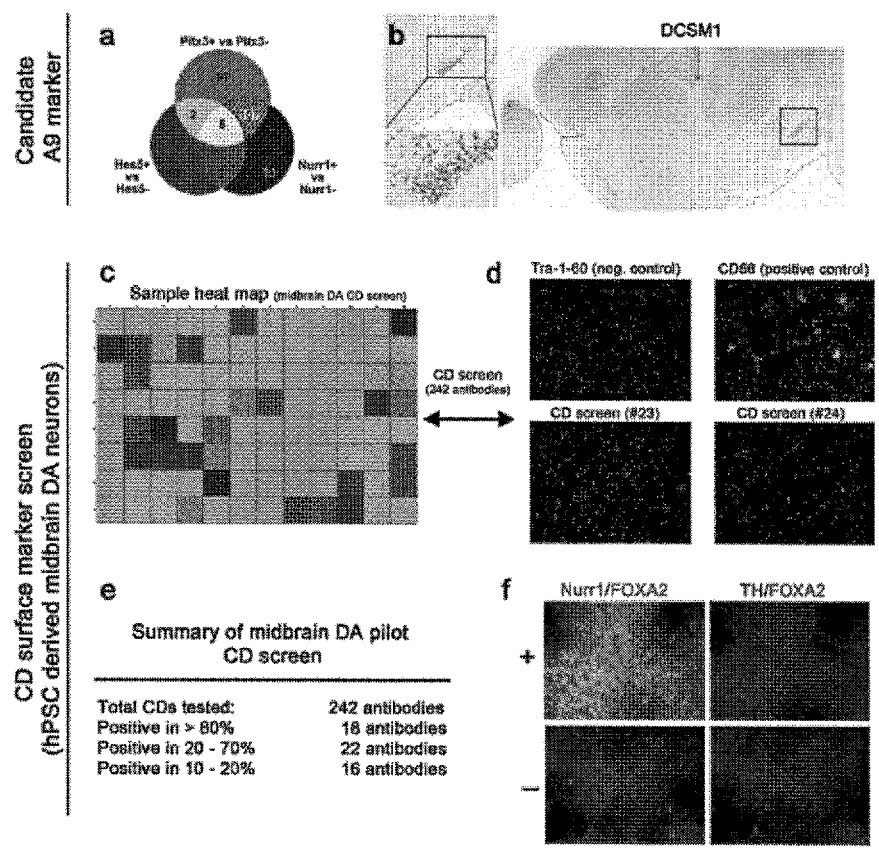

FIG. 27 shows an exemplary A9 candidate surface marker and CD-screen in hPSCs. a) Venn Diagram of transcriptome data from FACS purified mouse ESC derived mDA neurons. Among the 107 genes shared between PITX3 and Nurr1 the majority were known markers of midbrain DA neurons as well as novel markers were confirmed expressed within the ventral midbrain: b) One of those markers was DCSM1, a putative surface marker that appears to be enriched within the A9 region, based on mRNA in situ expression data (Allen Brain Atlas, Lein, E. S. et al., Genome-wide atlas of gene expression in the adult mouse brain, Nature 445: 168-176 (2007)). c-f) CD screen: c) representative 96 well plate (1 out of 3×96 plates used to screen complete CD panel). Dark wells label CD markers that are highly expressed in hESC DA neurons at day 25. e) Summary of the CD screening results in hESC derived DA neurons. f) One exemplary marker, CD142, a surface marker enriching specifically for DA neurons at the Nurr1+ stage was as found following FACS mediated isolation of CD142+ versus CD142− cells and analysis at day 7 post sort.

Figure 28:
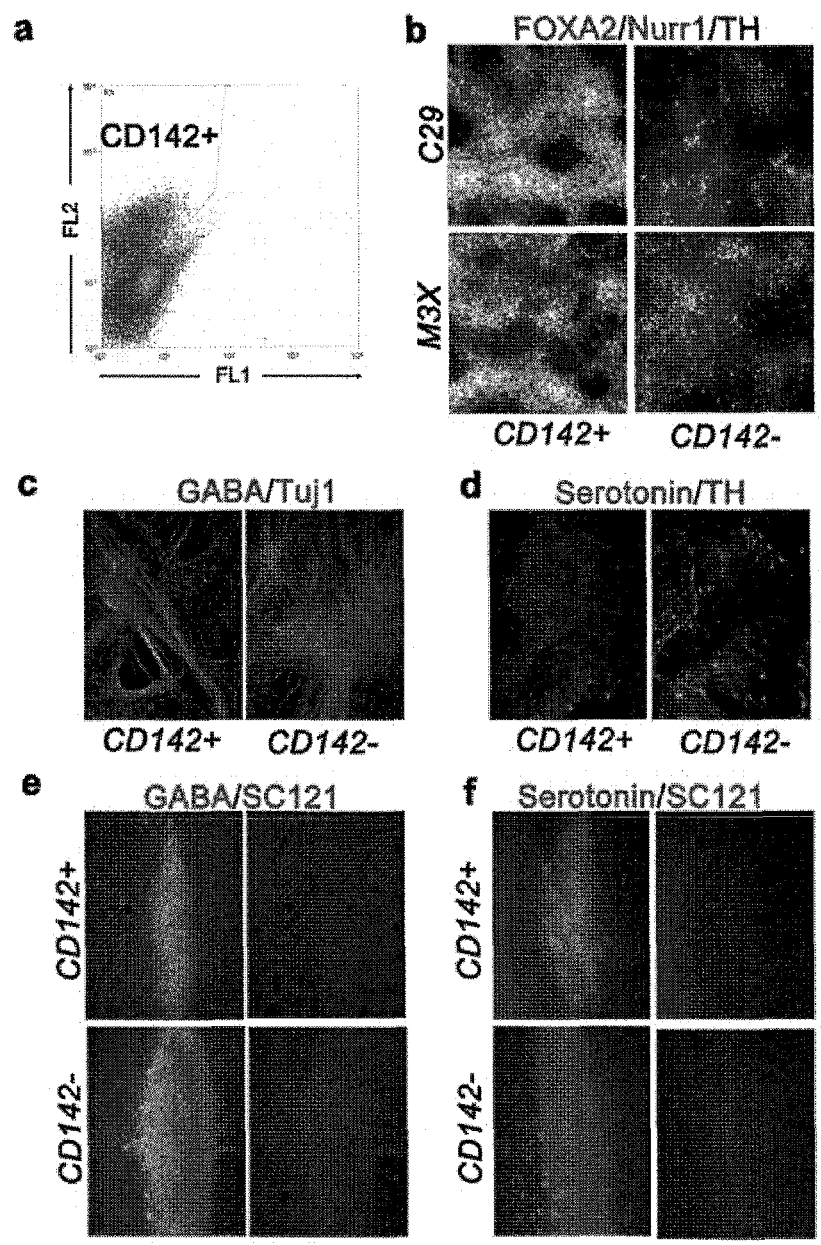

FIG. 28 shows exemplary CD142 enriched for Nurr1+ midbrain DA neuron stage and depletes for GABA and Serotonergic neurons. a) Flow cytometry showed representative CD142 expression on day 25 of differentiation. b) CD142 enriched for Nurr1+ stage among FOXA2/TH midbrain DA neurons in hESCs (e.g. WA09; FIG. 27f) and hiPSC lines tested (C29, and M3X represent two human iPSC lines at day 25 of differentiation). c, d) CD142 depletes GABAergic and Serotonergic contaminants following day 25 sorting and in vitro culture for 3 weeks. e, f) CD142 depletes GABAergic and Serotonergic neurons in vivo 3 months after transplantation. Cells were sorted for CD142 at day 25. Note: CD142 cells also enriched for TH and AADC.

Figure 29:
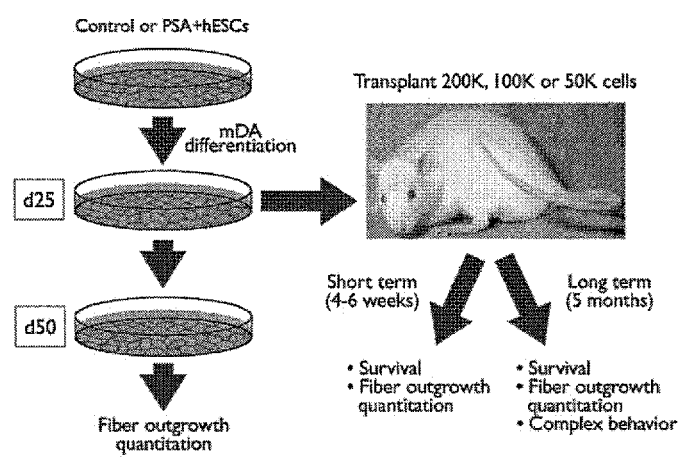

FIG. 29 shows an exemplary contemplated experimental use of PSA. PST-expressing and PSTnm exposed hESC derived DA neurons will be assessed in vitro for impact on DA phenotype and fiber outgrowth. In vivo studies in 6OHDA rat model will be tested for whether lower numbers of DA neurons with forced PSA expression can match behavioral recovery of standard grafts, and whether forced PSA expression in hESC-derived DA neurons is capable of inducing recover in assays of complex motor function.

Figure 30:
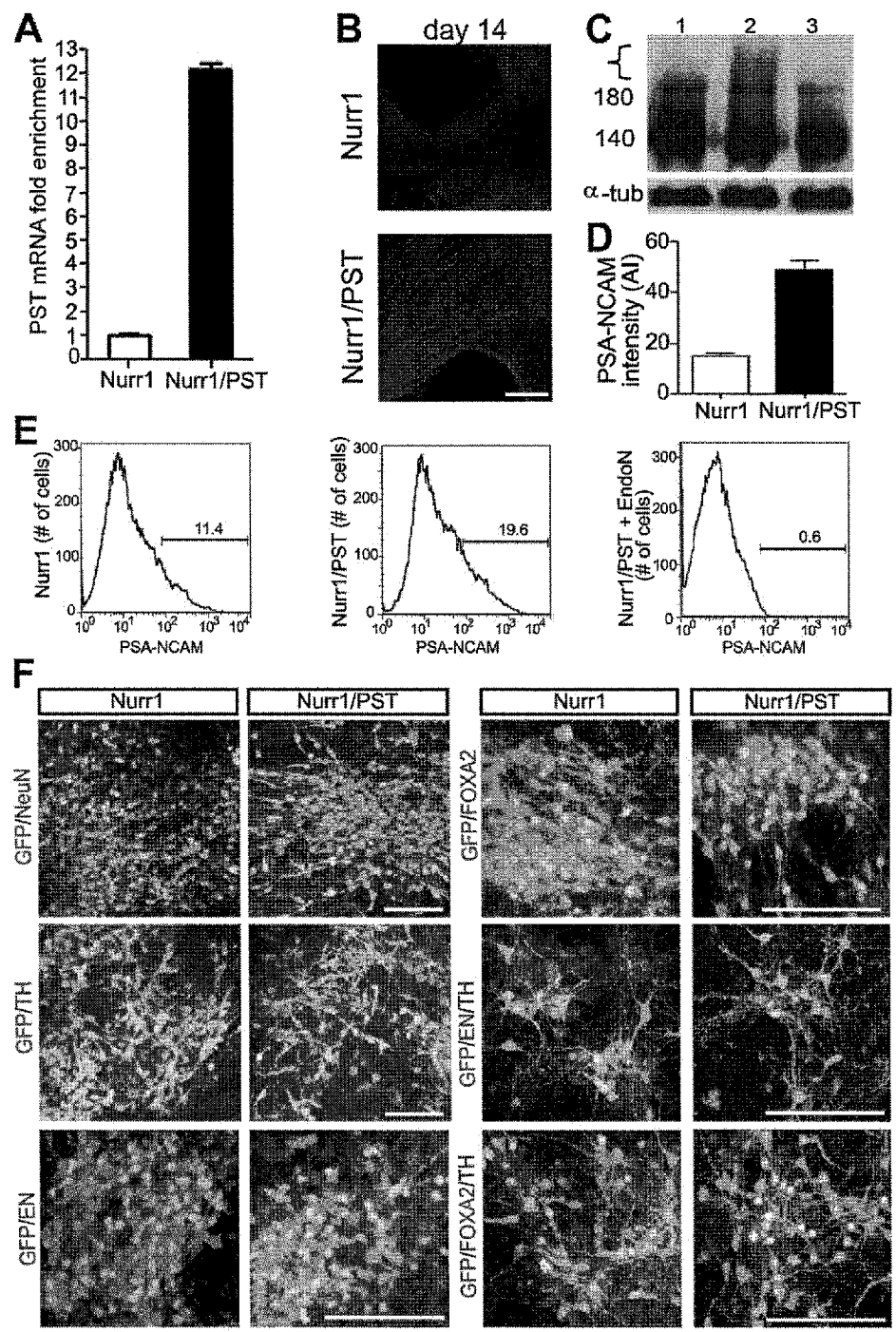

FIG. 30 shows an exemplary use of PST. Overexpression (mouse PST) resulted in increased levels of PSA-NCAM in differentiating mouse ES cells. (A) Quantification of PST mRNA by qPCR in control cells (Nurr1) and in cells overexpressing PST (Nurr1/PST). Data is expressed as the fold enrichment of PST levels in Nurr1/PST versus Nurr1 cells. (B) PSA immunostaining in DA neuron cultures at day 14 of differentiation shows increased levels of PSA in Nurr1/PST cells (Scale bar: 100 μm). (C) Western Blot for NCAM in differentiated cells. Nurr1/PST cells (lane 2) shows increased levels of the polysialylated form of NCAM (smear, brackets) compared to control (lane 1). PSA is removed from NCAM after endoN treatment (lane 3). (D) Quantification of the intensity of the PSA smear expressed in arbitrary units. (E) PSA FACS analysis at day 14 of differentiation. Treatment of cells with 20 units of endoN, 24 hours before the end of differentiation, abolished the PST effect. (F) Representative photomicrographs comparing Nurr1 and Nurr1/PST differentiated cells for GFP immunofluorescence and DA markers. Cells sorted for GFP and re-plated still retained the DA phenotype (post sort). Scale bars: 100 μm.

Figure 31:
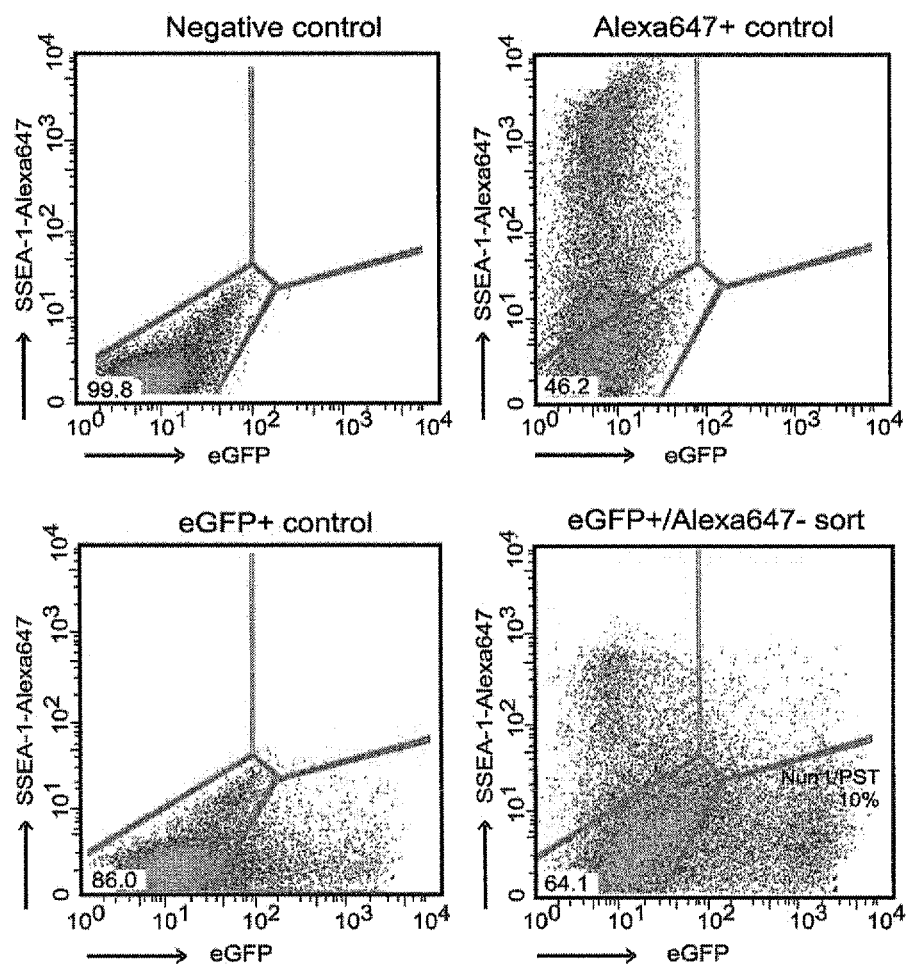

FIG. 31 shows an exemplary FACS analysis of ES-derived DA neurons. Flow cytometry-based isolation of GFP+ and SSEA-1− cells. As double negative and GFP negative controls, J1 mouse ES-cells were used. Around 5 to 10% of cells were sorted positively.

Figure 32:
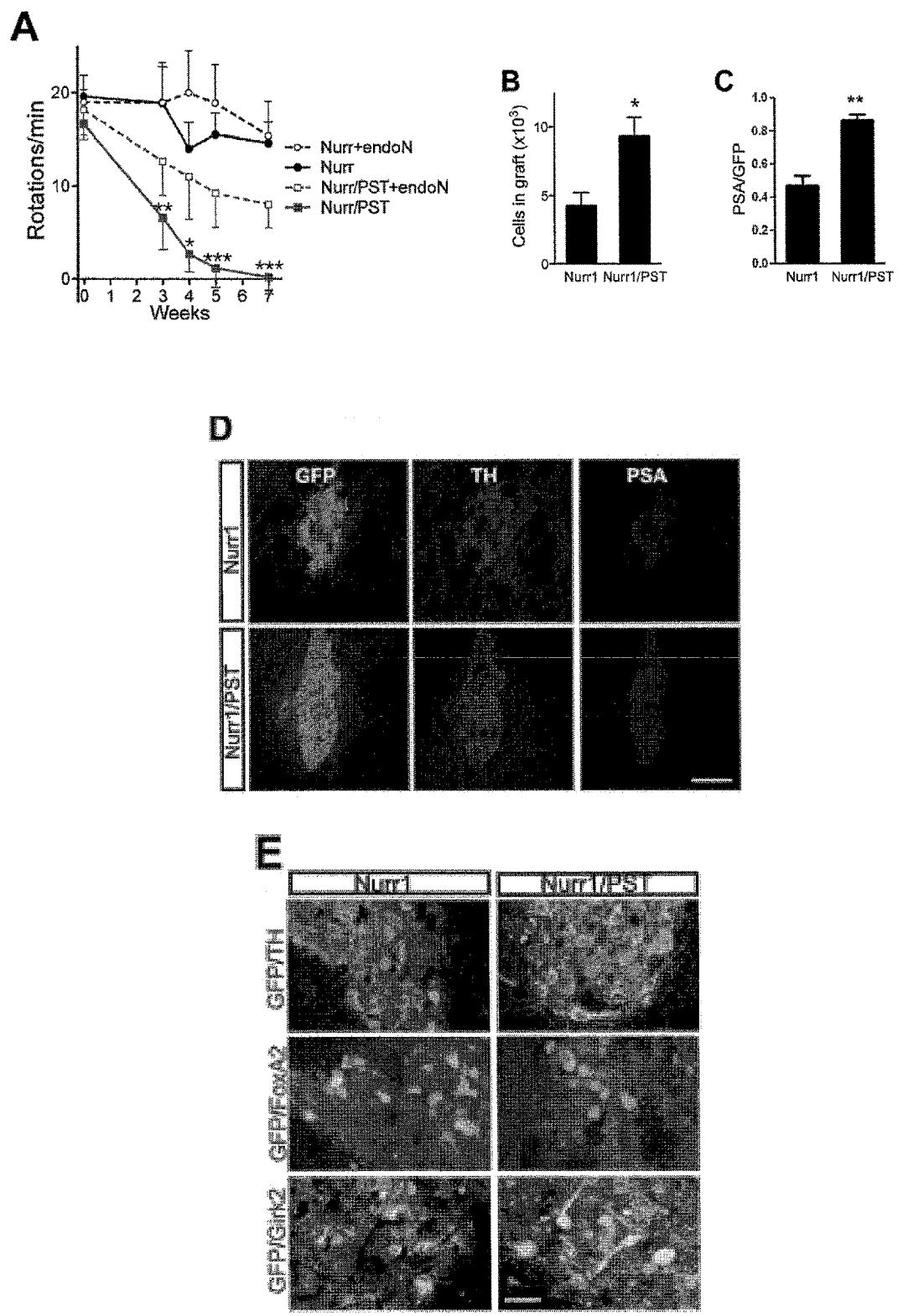

FIG. 32 shows exemplary Nurr1/PST grafts were more effective at inducing behavioral recovery in 6OHDA mouse model. Nurr1::GFP cells were differentiated and sorted at day 14 for GFP+/SSEA-1− population. Cells treated with endoN were cultured for 12 hours before sorting with 20 units of the enzyme. 55,000 cells were grafted in 1 ml of N2 media with BDNF and AA. (A) Animals scored for amphetamine-induced rotation (rotations/min during 20 min) for 3 weeks prior to grafting, then for 7 weeks after. Nurr1/PST cells significantly improve the outcome as compared to Nurr1 controls (2-way-ANOVA: $p<0.01$, with Bonferroni post-test: $*p<0.05$, $p<0.01$, $*p<0.001$; 6 animals/group). Removal of PSA by endoN abolishes the PST effect ($p=0.26$). (B) There were more GFP+ cells in the PST graft at endpoint than in control ($p<0.05$, t-test). (C) Ratio of PSA/GFP immunofluorescence at the core. $**p<0.01$. Student's t test (n=5/graft type). (D) GFP, TH and PSA immunofluorescence. Scale bar: 200 μm. (E) Grafted cells express DA markers. Individual z-planes of confocal micrographs are shown. Scale bar: 20 μm. Values are means+/−SEM.

Figure 33:
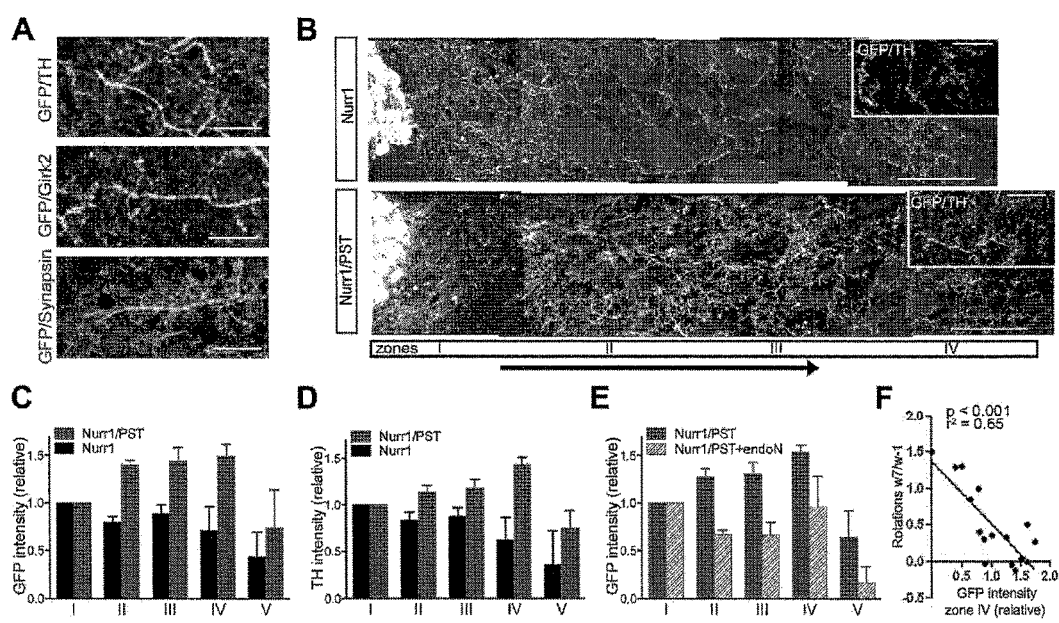

FIG. 33 shows exemplary PSA augmentation that increased host striatum innervation by ES-derived DA neurons. PSA-NCAM overexpression increased process outgrowth. (A) Representative photomicrographs of GFP/TH+, GFP/Girk2+ and GFP/synapsin+ processes in controls. Staining in Nurr1/PST samples was similar. Scale bar: 20 μm. (B) Representative z-stack projections showing GFP+ processes extending out of both Nurr1 and Nurr1/PST grafts. There are more GFP+ processes extending out of the Nurr1/PST graft (scale bar: 50 μm). Insets show GFP+/TH+ processes in same sections. Arrow: direction of growth. (C-E) Quantification of the intensity of GFP+ (C, E) and TH+ (D) processes at different distances from the graft site normalized to the intensity nearest to the injection site (areas were divided into five zones of ~100 μm apart. Normalization is relative to zone I; Two-way ANOVA, $p<0.01$ for both GFP and TH data, n=5/cell type; values are means+/−SEM). Nurr1/PST grafts grew more neurites into host striatum, which was partly suppressed (E) by endoN treatment. (F) Animal recovery correlated with the degree of process outgrowth. The graph shows the correlation (linear regression analyses) between the intensity of GFP+ neurites in zone IV and animal recovery for untreated and endoN-treated Nurr1 and Nurr1/PST grafted animals. Each value represents one animal ($r^2=0.65$, $p<0.001$, n=17).

Figure 34:
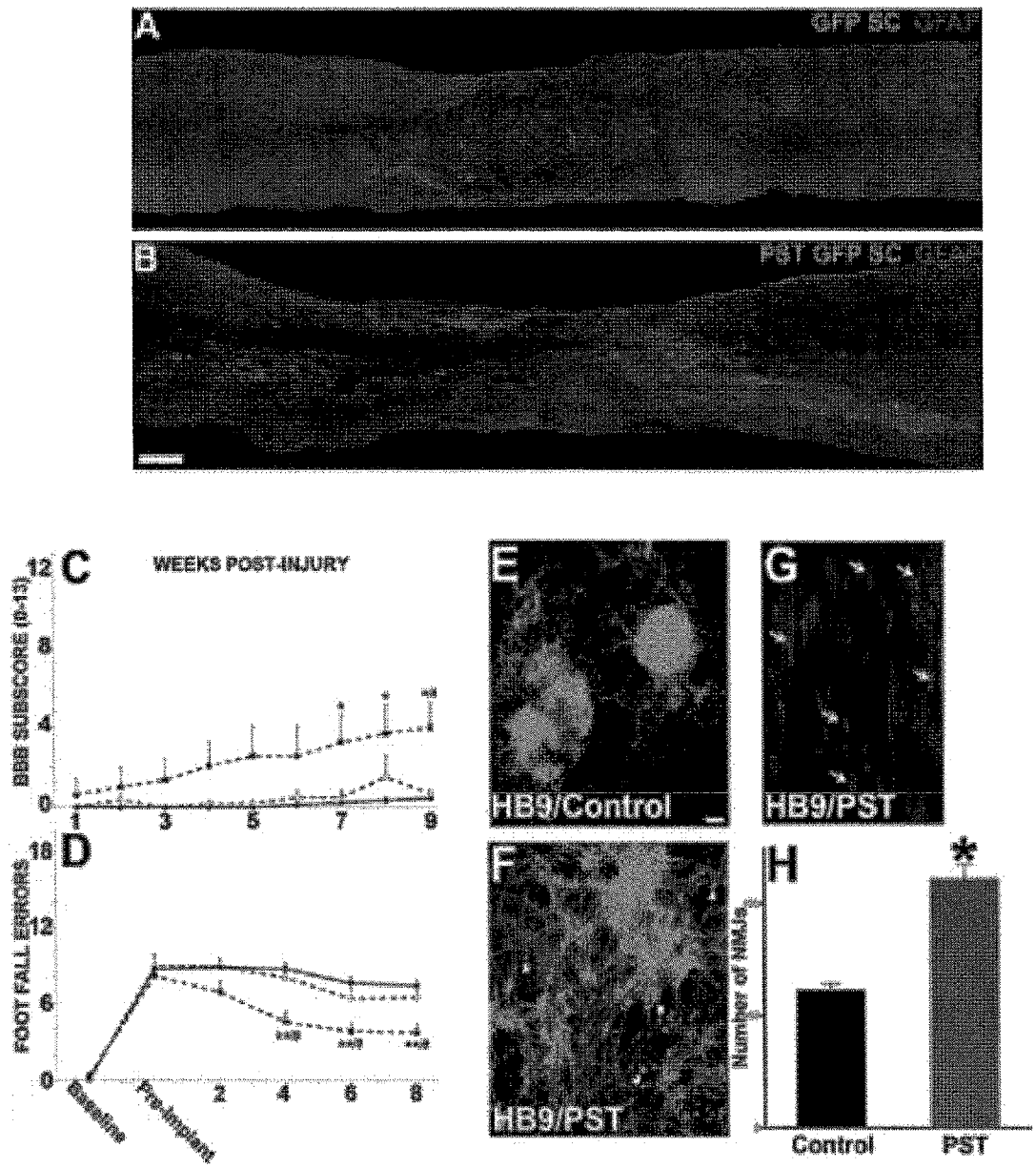

FIG. 34 shows an exemplary use of PST in methods associated with spinal cord injury and for expression on motoneurons. In control spinal cord, grafted GFP Schwann cells (SCs) are restricted to the lesion site by host scar tissue (A), whereas PST-modified SCs readily migrate considerable distances (B). This PSA engineering resulted in improvement in locomotion, BBB subscore; upper line in (C) shown vs lower line control) and hindlimb dexterity (gridwalk test; lower line in (D) vs upper line controls). E, H): differentiation of HB9::GFP mouse ESCs into motoneurons in which PST introduction increases fiber sprouting and cell migration (arrowheads) in vitro (E, F). Grafting of these PST-cells into sciatic nerve results in better target innervation as shown by the numbers of neuromuscular junctions (arrows) in the EDL muscle (G, H).

Figure 35:
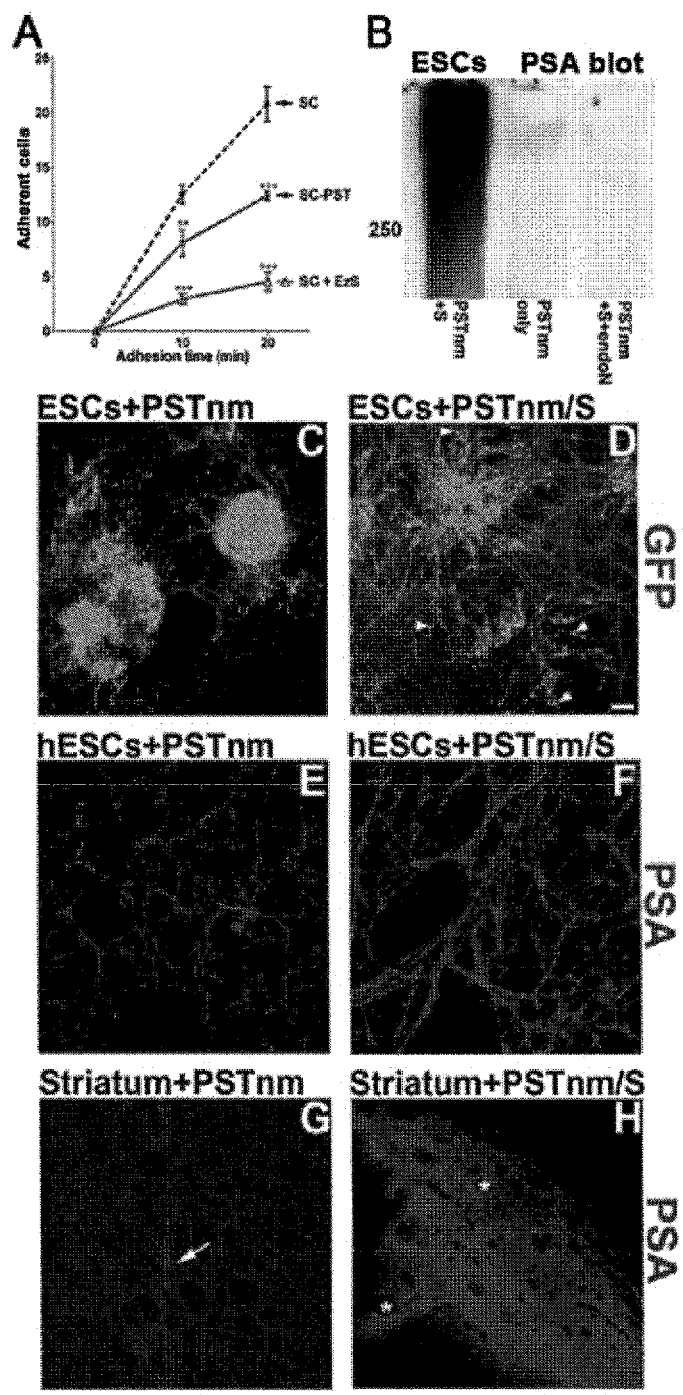

FIG. 35 shows an exemplary use of PSTnm enzyme. (A) PSTnm-produced PSA inhibits adhesion of Schwann cells in suspension to a Schwann cell monolayer even more effectively (red line-lowest line) than PSA produced by forced PST expression (green line-middle line). (B) PSA immunoblotting in ESC-derived HB9 motoneurons shows that control samples treated with PSTnm have undetectable levels of PSA. Incubation with PSTnm+CMP-sialic acid substrate produces a large PSA band, which is removed with endoN treatment. (C, D) Similar to effects obtained with the PST gene, polysialylation of these cells by PSTnm and substrate during differentiation enhances neurite outgrowth and cell migration (arrowheads). (E) PSA immunostaining of day-30 hESC-derived DA neurons. (F) This staining is significantly increased after treatment with PSTnm and substrate. (G) In vivo injection of PSTnm alone has no effect, while its co-administration with substrate (H) produces large amounts of PSA expression in mouse striatum.

DESCRIPTION OF THE INVENTION

The present invention relates to the field of stem cell biology, in particular the lineage specific differentiation of pluripotent or multipotent stem cells, which can include, but is not limited to, human embryonic stem cells (hESC) in addition to nonembryonic human induced pluripotent stem cells (hiPSC), somatic stem cells, stem cells from patients with a disease, or any other cell capable of lineage specific differentiation. Specifically described are methods to direct the lineage specific differentiation of hESC and/or hiPSC into floor plate midbrain progenitor cells and then further into large populations of midbrain fate FOXA2+LMX1A+ TH+ dopamine (DA) neurons using novel culture conditions. The midbrain fate FOXA2+LMX1A+TH+ dopamine (DA) neurons made using the methods of the present invention are further contemplated for various uses including, but not limited to, use in in vitro drug discovery assays, neurology research, and as a therapeutic to reverse disease of, or damage to, a lack of dopamine neurons in a patient. Further, compositions and methods are provided for differentiating midbrain fate FOXA2+LMX1A+TH+ dopamine (DA) neurons from human pluripotent stem cells for use in disease modeling, in particular Parkinson's disease.

The present inventions relate to characteristics of Parkinson's disease (PD) including the selective degeneration of midbrain dopamine (mDA) neurons in patients' brains. Because PD symptoms are primarily due to the selective loss of DA neurons in the substantia nigra of the ventral midbrain, PD is considered one of the diseases most suitable for cell replacement therapeutic strategies for treatment. Thus many attempts were made to transplant cells into patients' brains in order to replace the loss of function of the midbrain dopamine (mDA) neurons. However these experiments were unsuccessful and currently symptomatic treatments used on patients have a wide variability of success. Therefore, new treatments are needed for patients with PD in order to slow the loss of neuronal function.

Human pluripotent stem cells (hPSCs) are a source of cells for applications in regenerative medicine. Directed differentiation of hPSCs into specialized cells such as spinal motoneurons (Li, et al. *Nat. Biotechnol.* 23, 215-221 (2005), herein incorporated by reference) or midbrain dopamine (DA) like neurons resulting from differentiation by methods other then the methods of the present invention. The inventors' discovered as described herein that previous dopamine (DA) neurons (i.e. In Perrier, et al *Proc Natl Acad Sci USA* 101, 12543-8 (2004), herein incorporated by reference) referred to herein as dopamine (DA)-like neurons are not authentic midbrain dopamine (DA) neurons of the present inventions (see FIGS. 3, 10, 13 and 16). Therefore, the inventors labeled the floor-plate derived dopamine producing neurons made by methods described herein, i.e. dopamine producing neurons of the present inventions as "authentic" because unlike dopamine producing neurons made by published methods, when "authentic" dopamine producing neurons of the present inventions are transplanted into rodents and primates they reverse Parkinson-like neurological conditions with less interference from neural overgrowth and teratoma formation. Also, unlike previous methods of making dopamine producing neurons, "authentic" dopamine producing neurons of the present inventions are produced at higher percentages from starting populations and retain engrafting capability for several months in culture.

Thus, methods for making authentic midbrain DA neurons were discovered by using the differentiation methods described herein. However, the effective use of hPSCs for cell therapy has lagged far behind cell culture advances. While mouse PSC-derived DA neurons have shown efficacy in models of Parkinson's Disease (PD) (Tabar, et al. *Nature Med.* 14, 379-381 (2008); Wernig, et al. *Proc. Natl. Acad. Sci. U.S.A* 105, 5856-5861 (2008), all of which are herein incorporated by reference), DA neurons derived from human PSCs generally display poor in vivo performance (Lindvall and Kokaia, *J. Clin. Invest* 120, 29-40 (2010), herein incorporated by reference). In addition to not compensating for the endogenous loss of neuronal function, there are serious safety concerns when hPSC derived neurons are used for transplantation and are related to their potential for teratoma formation or neural overgrowth (Roy, et al. Nature Med. 12, 1259-1268 (2006); Elkabetz, et al. *Genes Dev.* 22, 152-165 (2008), herein incorporated by reference).

Another possible source of cells for transplantation are DA neurons derived from human ESCs. Previous attempts using these cells as a starting cell population to make differentiated cells that appeared to be DA like-midbrain neurons derived from human embryonic stem cells (hESCs) that were transplanted into rodent PD models resulted in poor in vivo survival of the transplants after transplantation. This failure was contemplated to most likely be due to incomplete midbrain DA neuron differentiation in vitro resulting in cells that appeared to be midbrain DA neurons but were not capable of engraftment to replace lost neuron function. In fact, the inventors show herein that DA-like neurons previously made in their laboratories and described in publications were not the same cell type nor had similar functions or engraftment capabilities as the floor-plate midbrain DA neuronal cells of the present inventions, see, FIGS. 16 and 17 for examples. Therefore the inventors also discovered that in order for cells to undergo directed differentiation in the laboratory to produce cell populations containing large numbers of properly functioning neurons, the cells needed to go through the specific developmental stages in order to become a suitable replacement cell population for cell based replacement therapies. The inventors also discovered that, at least for obtaining the engraftable DA neurons of the present inventions, certain developmental stages must be present, such as the FOX2A/LIM1A+ Day 11 intermediates. If such developmental stages are not present, the inventors' discovered that resulting DA-like neurons do not have the same functional capabilities as the midbrain DA neurons of the present inventions that were derived from FOX2A/LIM1A+ Day 11 intermediates.

In contrast to previous observations, novel culture techniques related to floor plate cell induction-based strategies for the derivation of human DA neurons that efficiently engraft in vivo are described herein. Thus past failures in obtaining cell populations comprising primarily committed DA neurons of the present inventions (i.e. FOXA2+ and LMX1A+ DA neurons capable of efficient engrafting) were contemplated to be the reason that engraftment of the DA like neurons failed, i.e. due to incomplete specification of the DA like cells. Previous hypothesis were that transplant failure was due to specific vulnerability of the cells, i.e. DA like cultured neurons were unable to survive the stress of transplantation. As described herein, midbrain FOXA2+/LMX1A+ floor plate precursors were derived from hPSCs in 11 days following exposure to small molecule activators of sonic hedgehog (SHH) and canonical WNT signaling. These Day 11 cells, double positive for FOXA2+ and LMX1A+, are contacted with additional small molecules to induce further differentiation into engraftable midbrain DA neurons, positive for TH+FOXA2+ and LMX1A+, by day 25. These mature floor-plate midbrain DA neurons can be maintained in vitro for several months. Extensive in vitro molecular profiling, biochemical and electrophysiological data defined developmental progression and confirmed identity of hPSC-derived midbrain DA neurons. In vivo survival and function was demonstrated in PD animal models in three host species. Long-term engraftment in 6-OHDA-lesioned mouse and rats demonstrates robust survival of midbrain DA neurons, complete restoration of amphetamine-induced rotation behavior and improvements in tests of forelimb use and akinesia. Finally, scalability is demonstrated by transplantation into Parkinsonian monkeys. Excellent DA neuron survival, function and lack of neural overgrowth in the three animal models tested indicate promise for the development of cell based therapies in PD based on the compositions and methods of the present inventions.

Therefore the inventors' contemplate the main use of their discoveries as the capability to produce an unlimited supply of fully functional floor-plate derived midbrain DA neurons suitable for pre-clinical and clinical therapeutic applications. Specifically, the inventors' discovered a new protocol for the efficient differentiation of mDA neurons from at least pluripotent cell populations isolated from rodents and humans (human embryonic stem cell (hESC) and human induced pluripotent stem cells (hiPSCs)). Those studies included PINK1 mutant iPS cell lines derived from a human patient suffering from a genetic form of Parkinson's disease Seibler, et al., The Journal of Neuroscience, 2011, 31(16):5970-5976, herein incorporated by reference. Human stem cells populations (hESC or hiPSC) were differentiated into a midbrain phenotype, which after contacting with neuronal maturation molecules gave rise to more authentic engraftable DA neurons. This protocol was used to demonstrate high yields of hESC progeny by Day 11 of directed differentiation into a midbrain DA (mDA) neuronal phenotype which included expression of key transcription factors e.g.

TH, FoxA2 and LMX1A which upon further differentiation yielded additional key proteins e.g. TH. Transplantation of these hESC derived mDA neurons into immunocompromised rodent and primate hosts, unlike previous in vitro derived DA neurons, showed good in vivo survival of the grafted cells with functional restoration of behavioral deficits.

Advantages of using methods of the present inventions for producing DA neuronal cells over other methods are, in part, evident from the following information. The use of somatic stem cells and neural stem cells in other methods with the goal of generating authentic midbrain DA neurons that efficiently engraft in vivo have not been successful (for review see Kriks & Studer, Protocols for generating ES cell-derived dopamine neurons in Development and engineering of dopamine neurons (eds. Pasterkamp, et al.) (Landes Biosciences, 2008, herein incorporated by reference). Pluripotent stem cells such as ES cells were then used as sources for generating engraftable cells. Early studies in the 1990s using mouse ES cells demonstrated the feasibility of deriving specific lineages from pluripotent cells in vitro including neurons (Okabe, et al., Mech. Dev. 59:89-102 (1996); Bain, et al., Dev. Biol. 168v342-357 (1995), all of which are herein incorporated by reference). In fact, midbrain DA neurons were generated using a directed differentiation strategy (Lee, et al., Nat. Biotechnol. 18v675-679 (2000), herein incorporated by reference) based on developmental insights from early explants studies (Ye, et al., Cell 93:755-766 (1998), herein incorporated by reference). Other directed differentiation strategies were used for producing other neuron types such as somatic motoneurons (Wichterle, et al., Cell 110, 385-397 (2002), herein incorporated by reference). However, these efforts did not result in cell populations containing high percentages of midbrain DA neurons or cells capable of restoring neuronal function in vivo. In fact, the resulting population contained a mixture of cell types in addition to midbrain DA neurons. Even the inventors developed other methods of making midbrain DA neurons, in part, see below, however these cell populations were also mixtures of cell types and failed to restore neuronal function. In particular, human ES cells were differentiated into early neuroepithelial cells, termed neural rosettes, followed by induction of rosette stage cells into cells expressing midbrain DA neuron precursor and differentiated markers. Those cells went on to exhibit functional neuronal features by electrophysiology, in vitro DA release and the formation of TH-immunogold positive synaptic contacts (Perrier, et al. From the Cover: Derivation of midbrain dopamine neurons from human embryonic stem cells. Proc Natl Acad Sci USA 101, 12543-8 (2004), herein incorporated by reference). However, despite these promising in vitro data, transplantation of the cells in 6OHDA lesioned murine hosts resulted in a very small number of surviving dopaminergic neurons. This was a surprising negative result given strong evidence of in vivo functionality of mouse ES derived DA neurons (Barberi, et al., Nat. Biotechnol. 21:1200-1207 (2003); Tabar, et al. Nature Med. 14:379-381 (2008); Bjorklund, et al. Proc. Natl. Acad. Sci. U.S.A. 99:2344-2349 (2002); Kim, et al. Nature 418:50-56 (2002), all of which are herein incorporated by reference), robust in vitro functional features of human ES derived DA neurons (Perrier, et al., From the Cover: Derivation of midbrain dopamine neurons from human embryonic stem cells. Proc Natl Acad Sci USA 101:12543-8 (2004), herein incorporated by reference) and clear evidence that human fetal DA neurons can survive as striatal xenografts (Brundin, et al. Exp. Brain Res. 70:192-208 (1988); Bjorklund, et al., Neuronal replacement by intracerebral neural implants in animal models of neurodegenerative disease. Raven. Press., New. York. 455-492 (1988), all of which are herein incorporated by reference). For nearly 8 years after initial failed attempts of grafting human ES cell derived DA neurons there was very little progress in the field. Some limited improvements were observed using primate pluripotent stem cell sources (Sanchez-Pernaute, et al. Long-term survival of dopamine neurons derived from parthenogenetic primate embryonic stem cells (Cyno1) in rat and primate striatum. Stem Cells 23:914-922 (2005), herein incorporated by reference), cells pretreated with FGF20 or Wnt5A or human ES cells differentiated in the presence of factors secreted from immortalized midbrain astrocytes (Roy, et al., Nature Med. 12:1259-1268 (2006), herein incorporated by reference). However, none of the previous strategies were success in producing an enriched population of DA neurons of the present inventions for use in engraftment procedures for restoring neuronal function in vivo.

I. Cell Culturing Methods for Inducing Neuronal Precursor (Lineage) Cells: Contacting Human Pluripotent Stem Cells with SB431542 and LDN-193189 Resulted in Differentiated Neural Lineage Cells.

The following example describes exemplary methods for providing cells of a neural lineage for use during development of the present inventions.

Dual SMAD inhibition was previously used as a rapid and highly effective method for inducing one type of neural lineage cells from hPSCs (Chambers, et al., *Nat Biotechnol* 27, (2009), herein incorporated by reference). These neural lineage cells induced by molecules, including Noggin, had a default pathway that allowed development into central nervous system cells, i.e. neural cell fate. Follow up studies reported the use of a small molecule dorsomorphin (DM) instead of Noggin that, at least in part, resulted in similar but not the same differentiated cells with major differences in consistency of cultures (Kim, et al., Robust enhancement of neural differentiation from human ES and iPS cells regardless of their innate difference in differentiation propensity. *Stem Cell Rev* 6, 270-281, (2010); Zhou, et al., High-Efficiency Induction of Neural Conversion in hESCs and hiPSCs with a Single Chemical Inhibitor of TGF-beta Superfamily Receptors. *Stem Cells,* 504, (2010), herein incorporated by reference).

The inventors observed that cells generated using Noggin, despite showing the same developmental stage as LDN treated cells, express the vast majority of the same markers, and are capable of a similar developmental potential to make various neural lineages, but also showed differences, such as being more anterior on an anterior-posterior axis (i.e. more forebrain, more cells express FOXG1, and the like) compared to neural cells induced using LDN. Thus, although LDN was used in place of Noggin to inhibit BMP among other signaling pathways, Noggin and LDN may have other types of activities which are different than inhibition of BMP.

In part due to the high expense of using Noggin, the inventors contemplated that the use of a BMP inhibitor might be able to substitute for Noggin in differentiating cells of neural cell fate. Therefore, a small molecule BMP inhibitor, LDN-193189, (Yu, et al., *Nat Med* 14, 1363-1369, (2008), herein incorporated by reference) was used and found during the development of the present inventions to replace Noggin, in combination with SB431542, for generating primitive neuroectoderm from hPSCs, cells that have neural cell fate, i.e. CNS cells (FIG. 2A). This combination treatment was termed LSB for the combination of these two inhibitors LDN-193189 and SB431542.

In general, cell differentiation was initiated by treatment of high confluency monolayer hES or hiPS with dual inhibition of SMAD signaling. A preferred embodiment utilizes a percentage confluency of 50%-400%, with a most preferred embodiment of 70%-80% confluency. It will be obvious to one skilled in the art that the initial plating density required to achieve a preferred confluency of the present invention will be dependent on cell type, size, plating efficiency, survival, adhesion and other parameters which can be determined empirically without undue experimentation on the part of the skilled artisan. Dual inhibition of SMAD can be achieved with a variety of compounds including Noggin, SB431542, LDN-193189, Dorsomorphin, or other molecules that block TGFβ, BMP, and Activin/Nodal signaling. A preferred embodiment utilizes the composition comprising SB431542 and LDN-193189 (collectively, LSB) at a concentration of 0.1 µM-250 µM, or more preferable 1-25 µM, or most preferable 10 µM of SB431542 and 10-5000 nM, or most preferably 100-500 nM of LDN-193189.

II. Derivation of DA Neurons from hESCs Through Rosette Cell Intermediates and Results of Transplant Studies that Used these DA-Like Neurons.

The inventors previous used several other directed differentiation methods that resulted in cell populations containing DA-like neurons. These DA-like neurons were used in transplantation studies that resulted in concerns on the further use of these cells for therapeutic applications. For examples, procedures described in Perrier et al., 2004 and Fasano et al., 2010, including MS5 neural induction, resulted in rosette cell formation and were used to make Day 11 precursors, see FIGS. 2, 16 and 17 for examples, that were further used to derive DA-like neurons. These neurons resulted from a low percentage of the precursor cells in the resulting Day 11 cell populations. Transplantation studies that used these neurons showed poor post transplant viability and loss of the DA-like neuronal phenotype in addition to observations of post transplantation development of inappropriate neural types along with loss of growth control, which led to development of teratomas. See FIGS. 16 and 17.

Specifically, at P0 hESCs were contacted with molecules for beginning neural induction of Oct4+ cells into rosette cells using MS5 feeder cells (Perrier et al., 2004). At the P1 stage Rosette cells were expanded by contacting cells with additional molecules for differentiating cells into cells at stage P2 with specific expression patterns including Pax2+/En1+ DA progenitor cells and were further differentiated into TH+/En1+ DA neurons. These cells were used for engraftment in 6OHDA lesioned rats, immuno suppressed with Cyclosporin A. Those transplantation studies showed poor in vivo viability, loss of the TH+ phenotype, concerns about further growth into unwanted, possibly lethal, cells, i.e. teratomas, and growth of cells into inappropriate neural types that would cause additional medical problems for the patient.

There were very small numbers of surviving TH+ neuron at 4.5 moths after transplantation (<50 TH+ cells/animal) in grafts from rosette derived DA neuron precursors FIG. 16A. However, in contrast to TH+ cells, GFP marked cells (GFP was driven by a ubiquitous promomoter) did survive quite well after transplantation. This suggests that most surviving cells following transplantation were neural cells of non-DA neuron identity (16B). Few graft-derived cells (hNA+ (green) co-express TH (red) again suggesting that most grafted human cells adopt a non-DA neuron phenotype FIG. 16C. Panels 16 D-E show that D-E, despite the very poor in vivo survival there was some (low and highly variable) improvement in a few behavioral assays such as amphetamine induced rotations (D), cylinder test and spontaneous rotations (E). Feeder-free neural induction was carried out as previously described (Chambers et al., 2009, herein incorporated by reference) but further modified to yield floor plate cells (Fasano et al., 2010, herein incorporated by reference).

In the modified Dual-SMAD inhibition method for differentiating pluripotent cells into floor plate cells, the inventors' previously discovered that high concentrations of SHH were required for FP induction by day 11. For example, in some embodiments, Sonic C25II was added at 200 ng/ml. In some experiments, DKK-1 (R&D; 100 ng/ml) FGF8 (R&D; 50 ng/ml), Wnt-1 (Peprotech; 50 ng/ml) and retinoic acid (R&D; 1 mM) were added, See FIG. 17. However none of the resulting cell populations at day 11 using previous methods, contained the high percentage of FOXA2+/LMX1A+midbrain floor-plate progenitor cells using methods of the present inventions.

III. Compounds for Use in Directed Differentiation: Screening Small Molecules Using Neuronal Lineage Cells of the Present Inventions Resulted in Compounds that Differentiated Cells into FOX2A+ and LIMX1A+Neuronal Cells by Day 11 of Culture.

The following example describes using exemplary cells from Section I for screening small molecule candidate compounds and determining whether their use would result in directed differentiation of a cell population containing a high percentage of midbrain floor plate neurons by Day 11 after the initial contact with the Dual-SMAD inhibitors. The results of this screen initially showed that a SHH activating molecule together with activation of FGF8 and Wnt led to the efficient derivation of FOXA2+/LMX1A+positive midbrain floor plate cells from hESC by day 11 of differentiation. The inventors show results herein of exemplary experiments that defined which molecules were necessary and the optimal time of contacting in order to derive the desired FOXA2+/LMX1A+positive cell population at Day 11.

Recent mouse genetic studies demonstrated an important role for the transcription factor FOXA2 in midbrain DA neuron development and survival. A unique feature of the developing midbrain is the co-expression of the floor plate marker FOXA2 and the roof plate marker LMX1A. Normally, floor plate and roof plate cells are located at distinct positions in the CNS (ventral versus dorsal) with diametrically opposed patterning requirements for their induction. Derivation of region-specific floor plate precursors from hESCs using a modified Dual-SMAD inhibition protocol was recently described. Canonical Wnt signaling was important for both roof plate function and midbrain DA neuron development.

A. CHIR99021 (CHIR) Induced a High Yield of Midbrain DA Neuron Precursor Fate by Day 11 of Culture.

Figure 5:
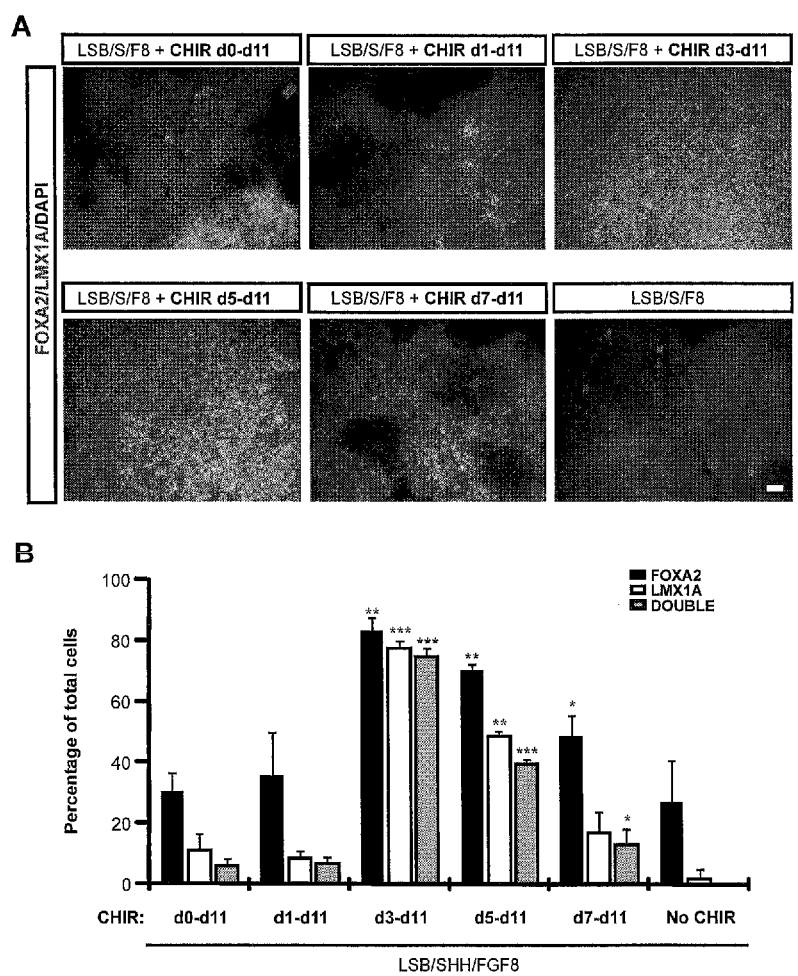
FIG. 5 shows an exemplary timing of CHIR99021 exposure determines induction of FOXA2/LMX1A midbrain floor plate precursors. a) Immunocytochemical analysis of FOXA2 (red)/LMX1A (green) at day 11 of differentiation following LSB/S/F8 treatment alone or in combination with CHIR starting at the various time points indicated. b) Quantification of the percentage of FOXA2+, LMX1A+ and double labeled cells at day 11 of differentiation following differential onset of CHIR exposure as described in (a). Significance levels for individual markers are presented as compared to no CHIR condition: ANOVA; Dunnett test: * $p<0.001$;  $p<0.01$; $p<0.05$). Scale bars correspond to 50 μm.
Figure 6:
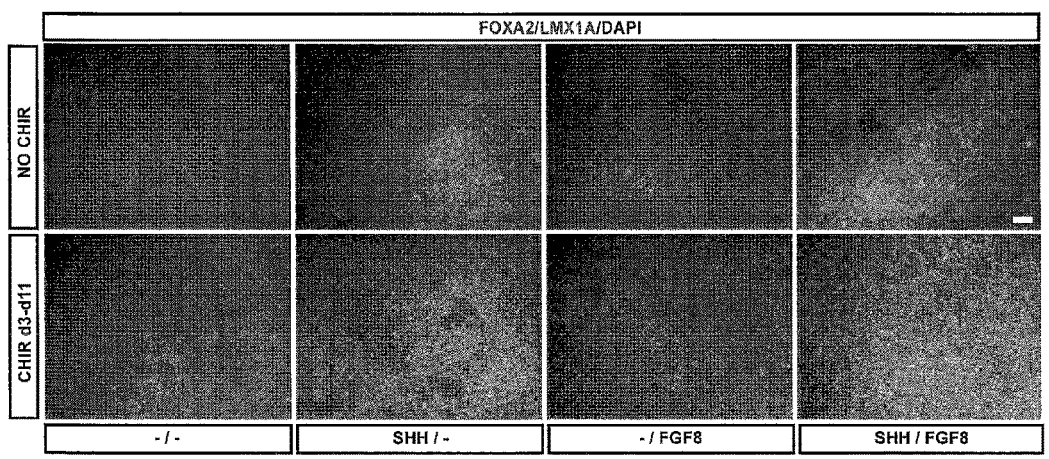
FIG. 6 shows an exemplary FGF8 exposure does not play a major role in the induction of FOXA2/LMX1A midbrain floor plate precursors. Representative images of FOXA2 (red)/LMX1A (green) expression by immunocytochemistry at day 11 of differentiation. Cells were exposed to LSB/CHIR in the presence or absence of SHH (purmorphamine+ SHH C25II) and FGF8. Scale bars correspond to 50 μm.
Figure 7:
FIG. 7 shows an exemplary exposure to high dose of SHH and/or a smoothened small molecule agonist (purmorphamine) is required for efficient midbrain floor plate induction in the presence of CHIR99021. Representative images of FOXA2 (red)/LMX1A (green) immunocytochemistry at day 11 of differentiation. Cells were treated with LSB/F8/CHIR in the presence of various concentrations of SHH (SHH-C25II) and smoothened agonist purmorphamine Scale bars correspond to 50 μm.

As described herein, exposure to CHIR99021 (CHIR), a potent GSK3β inhibitor known to strongly activate WNT signaling, induced LMX1A in FOXA2+ floor plate precursors (FIG. 1a). CHIR was more potent than recombinant Wnt3A or Wnt1 at inducing LMX1A expression. The efficiency of LMX1A induction was dependent on the timing of CHIR exposure with a maximum effect at day 3-11 (FIG. 5). CHIR induced co-expression of FOXA2/LMX1A, while other factors such as FGF8 had only marginal effects (FIG. 6). Induction of FOXA2/LMX1A co-expression required strong activation of SHH signaling using purmorphamine, a small molecule agonist, alone or in combination with recombinant SHH (FIG. 7).

Treatment with SHH agonists (purmorphamine+SHH) and FGF8 (S/F8) in the absence of CHIR99021 showed significantly lower expression of FOXA2 by day 11 and complete lack of LMX1A expression (FIG. 1a,b). Dual-SMAD inhibition (exposure to LDN-193189+ SB431542="LSB") did not yield FOXA2-expressing cells, but did yield a subset of LMX1A+ cells (FIG. 1a,b). The anterior marker OTX2 was robustly induced in LSB and LSB/S/F8/CHIR treated cultures, but not under LSB/S/F8 conditions (FIG. 1a,c). Systematic comparisons of the three culture conditions (FIG. 1d) were performed using global temporal gene expression profiling. Hierarchical clustering of differentially expressed genes segregated the three treatment conditions by day 11 of differentiation (FIG. 8a). FOXA1, FOXA2 and several other SHH downstream targets including PTCH1 were amongst the most differentially regulated transcripts in LSB/S/F8/CHIR versus LSB treatment sets (FIG. 1e). Expression of LMX1A, NGN2, and DDC indicated establishment of midbrain DA neuron precursor fate already by day 11 (FIG. 1e,f). In contrast, LSB cultures were enriched for dorsal forebrain precursor markers such as HES5, PAX6, LHX2, and EMX2. Direct comparison of LSB/S/F8/CHIR versus LSB/S/F8 treatment (FIG. 1f) confirmed selective enrichment for midbrain DA precursor markers in LSB/S/F8/CHIR group and suggested hypothalamic precursor identity in LSB/S/F8 treated cultures based on the differential expression of RAX1, SIX3, and SIX6 (see also POMC, OTP expression in FIG. 2d below). The full list of differentially expressed transcripts Tables 1, 2 and gene ontology analysis FIG. 8b (DAVID; http://david.abcc.ncifcrf.gov) confirmed enrichment for canonical WNT signaling upon CHIR treatment. Raw data are not yet available at GEO worldwideweb.ncbi.nlm.nih.gov/geo/ accession#: [TBD]). Comparative temporal analysis of gene expression for midbrain DA precursor markers (FIG. 1g) versus markers of anterior and ventral non-DA neuron fates (FIG. 1h) partitioned the three induction conditions into: i) LSB: dorsal forebrain; ii) LSB/S/F8: ventral/hypothalamic and iii) LSB/S/F8/CHIR: midbrain DA precursor identity.

Figure 18:
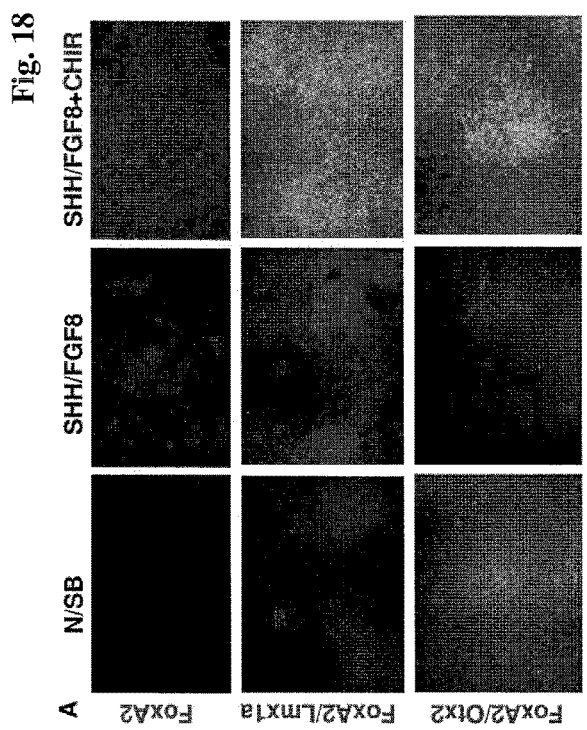
FIG. 18 shows an exemplary protocol for derivation of floor plate cells showing high levels of midbrain characteristics as compared to the low or absent levels in cells made from the procedures used in FIGS. 16 and 17. A: Midbrain floor plate induction in cell populations contacted with high levels of SHH, FGF8 and CHIR resulted in FoxA2 co-expression with midbrain markers LMX1A and Otx2 expression at day 11 of differentiation in contrast to cells contacted with molecules described in two other procedures as shown in FIGS. 16 and 17 (N/SB and SHH/FGF8, respectively). B: Global gene expression analysis at day 11 comparing the three groups of cells contacted with molecules from each of the three procedures including the third procedure of the present inventions (LDN/SB, SHH/FGF8, LSB/SHH/FGF8/CHIR) Chart B shows specifically the genes that are common among the three treatment conditions versus those genes that are unique to each individual condition. Chart B is a preliminary analysis used for the microarray results presented in FIG. 1. C: mRNA levels of midbrain markers FoxA2, LMX1A, are highly enriched in LSB/SHH/FGF8/CHIR-treated group compared to SHH/FGF-treated group.
Figure 19:
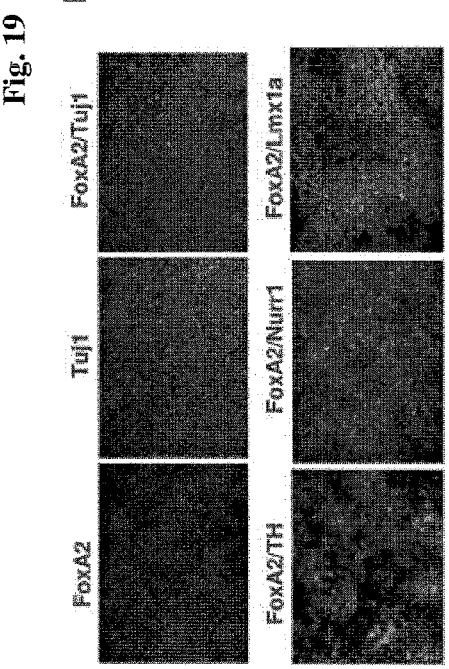
FIG. 19 shows an exemplary in vitro characterization of dopamine neurons derived from the midbrain region of the floor plate. A: Co-labeling of FoxA2+ neurons with mDA neuron markers TH, Nurr1 and LMX1A at d25 of differentiation. B: mRNA expression levels by QRT-PCR of mDA neuron markers as well as other midbrain cell types in LDN/SB+SHH/FGF8+SHH/FGF8+CHIR treated groups.

Cells resulting from the protocol derived during the development of the present inventions were compared to cells derived by previous methods. See, FIGS. 2 and 18 for an exemplary visual comparison to the SHH/FGF8+CHIR treated cells of the present inventions. FIG. 19A shows examples of FOXA2/Tuj1 double labeled cells following LSB/S/F8/CHIR treatment (upper panels) and FOXA2 co-labeling with TH, Mull and LMX1A (lower panels). Those marker combinations are diagnostic for early stage midbrain DA neuron precursors. FIG. 19B shows gene expression data (for comparison to FIG. 2E) for key dopamine neuron precursor markers.

In general Materials And Methods Used Herein Are Described: Human ESC(H9, H1) and iPSC lines (2C6 and SeV6) were subjected to a modified Dual SMAD-inhibition (Chambers, et al. *Nat. Biotechnol.* 27:275-280 (2009), herein incorporated by reference) based floor plate induction (Fasano, et al., *Cell Stem Cell* 6:336-347 (2010), herein incorporated by reference) protocol. Exposure to SHH C25II, Purmorphamine, FGF8 and CHIR99021 were optimized for midbrain floor plate and yield of novel populations of DA neuron (see FIG. 1d). Following floor plate induction, further maturation (days 11-25 or longer than 25 days in culture up to at least 100 days in culture) was carried out in differentiation medium based on Neurobasal/B27 in the presence of DA neuron survival and maturation factors (Perrier, et al. *Proc Natl Acad Sci USA* 101:12543-8 (2004), herein incorporated by reference) such as AA, BDNF, GDNF, TGFβ3 and dbcAMP (see full methods for details). The resulting DA neuron populations were subjected to extensive phenotypic characterization via immunocytochemistry, qRT-PCR, global gene expression profiling, HPLC analysis for the detection of dopamine and in vitro electrophysiological recordings. In vivo studies were performed in hemiparkinsonian rodents (mouse or rats injected with the 6OHDA toxin on one side of the animal's brain. The studies were carried out in adult NOD-SCID IL2Rgc mice (Jackson labs) and adult Sprague Dawley rats Taconic Farms, that received 6-hydroxydopamine lesions by stereotactic injections of the toxin as described previously as well as two adult rhesus monkeys that were treated with unilateral carotid injections of MPTP.

DA neurons were injected stereotactically in the striata of the animals ($150 \times 10^3$ cells in mice, $250 \times 10^3$ cells in rats) and a total of $7.5 \times 10^6$ cells (distributed in 6 tracts; 3 on each side of brain) in monkeys. Behavioral assays were performed at monthly intervals post-grafting, including amphetamine mediated rotational analysis as well as a test for focal akinesia ("stepping test") and limb use (cylinder test). Rats and mice were sacrificed at 18-20 weeks and the primates at 1 month post grafting. Characterization of the grafts was performed via stereological analyses of cell number and graft volumes as well as a comprehensive phenotypic characterization via immunohistochemistry.

*Culture of undifferentiated human ES cells.* hESC lines H9 (WA-09, XX, passages 27-55 from when 10/2009), H1 (WA-01, XY, passages 30-40 from when 6/2010) and iPS cell lines 2C6 (Kim, et al. *Cell Stem Cell* 8:695-706 (2011), herein incorporated by reference) (XY, passages 20-30) and SeV6 (XY, passages 20-30; derived from MRC-5 embryonic fibroblasts using non-integrating 4 factor Sendai vector system (Ban, et al. Proc. Natl. Acad. Sci. U.S.A (2011) 108(34):14234-14239:10.1073/pnas.1103509108, herein incorporated by reference) were maintained on mouse embryonic fibroblasts at plating concentrations estimated ranging from $0.5 \times 10^3$ per cm$^2$ to $100 \times 10^3$ per cm$^2$ based upon human ES cells which tend to cell cluster. (MEF, Global Stem, Rockville, Md.) in an optimal 20% knockout serum replacement (KSR, Invitrogen, Carlsbad, Calif.)-containing human ES cell medium (as described previously (Kim, et al. *Cell Stem Cell* 8:695-706 (2011), herein incorporated by reference). The use of knockout serum replacement may range from 0% to 40%.

Neural Induction.

For floor plate-based midbrain dopamine neuron induction, a modified version of the dual-SMAD inhibition (Chambers, et al. *Nat. Biotechnol.* 27:275-280 (2009), herein incorporated by reference) and floor plate induction (Fasano, et al. *Cell Stem Cell* 6:336-347 (2010), herein incorporated by reference) protocol was used based on timed exposure to LDN-193189 (100 nM (ranging in concentration from 0.5-50 μM, Stemgent, Cambridge, Mass.), SB431542 (10 μM (ranging in concentration from 0.5-50 μM, Tocris, Ellisville, Mich.), SHH C25II (100 ng/ml (ranging in concentration from 10-2000 ng/ml, R&D, Minneapolis, Minn.), Purmorphamine (2 μM (ranging in concentration from 10-500 ng/ml, Stemgent), FGF8 (100 ng/ml (ranging in concentration from 10-500 ng/ml, R&D) and CHIR99021 (CHIR; 3 μM (ranging in concentration from 0.1-10 μM, Stemgent).

For the floor plate induction protocol "SHH" treatment refers to exposure, i.e. contact, of cells to a combination of SHH C25II 100 ng/ml+Purmorphamine (2 µM). Cells were plated (35–40×10³ cells/cm²) and cultured for 11 days on matrigel or geltrex (used as purchased) (BD, Franklin Lakes, N.J.) in Knockout serum replacement medium (KSR) containing DMEM, 15% knockout serum replacement, 2 mM L-glutamine and 10-µM (ranging in concentration from 1-25 µM β-mercaptoethanol. KSR medium was gradually shifted to N2 medium starting on day 5 of differentiation, by mixing in ratios of 75% (KSR):25% (N2) on day 5-6, 50% (KSR):50% (N2) day 7-8 and 25% (KSR):75% (N2) on day 9-10, as described previously (Chambers, et al. *Nat. Biotechnol.* 27:275-280 (2009), herein incorporated by reference). On day 11, media was changed to Neurobasal medium/B27medium (1:50 dilution)/L-Glut (effective ranges 0.2-2 mM)) containing medium (NB/B27; Invitrogen) supplemented with CHIR (until day 13) and with BDNF (brain-derived neurotrophic factor, 20 ng/ml ranging from 5 to 100; R&D), ascorbic acid (AA; 0.2 mM (ranging in concentration from 0.01-1 mM), Sigma, St Louis, Mich.), GDNF (glial cell line-derived neurotrophic factor, 20 ng/ml (ranging in concentration from 1-200 ng/ml); R&D), TGFβ3 (transforming growth factor type β3, 1 ng/ml (ranging in concentration from 0.1-25 ng/ml); R&D), dibutyryl cAMP (0.5 mM (ranging in concentration from 0.05-2 mM); Sigma), and DAPT (10 nM (ranging in concentration from 0.5-50 nM); Tocris,) for 9 days. On day 20, cells were dissociated using Accutase® (Innovative Cell Technology, San Diego, Calif.) and replated under high cell density conditions (for example from 300-400 k cells/cm²) on dishes pre-coated with poly-ornithine (PO); 15 µg/ml (ranging in concentration from 1-50 µg/ml)/Laminin (1 µg/ml) (ranging in concentration from 0.1-10 µg/ml)/Fibronectin (2 µg/ml (ranging in concentration from 0.1-20 µg/ml) in differentiation medium (NB/B27+BDNF, AA, GDNF, dbcAMP (ranging in concentration as described herein), TGFβ3 and DAPT (ranging in concentration as described herein) until the desired maturation stage for a given experiment.

For rosette-based DA neuron induction previously described protocols were followed in part (Perrier, et al. *Proc Natl Acad Sci USA* 101:12543-8 (2004), herein incorporated by reference) with at least one exception where dual-SMAD inhibition was used to accelerate the initial neural induction step. In brief, hESCs were induced towards neural fate by coculture with irradiated MS5 cells in KSR supplemented with SB431542 and Noggin (250 ng/ml (ranging in concentration from 10-1000 ng/ml); R&D), from day 2-8 and SHH+FGF8 from day 6-11 of differentiation. After 11 days in KSR, neural rosettes were manually isolated and cultured (P1 stage) in N2 medium supplemented with SHH, FGF8, BDNF and AA as described previously (Perrier, et al. *Proc Natl Acad Sci USA* 101:12543-8 (2004), herein incorporated by reference). After 5-7 days in P1 stage, rosettes were again harvested mechanically and triturated following incubation in Ca²/Mg²-free Hanks' balanced salt solution (HBSS) for 1 h and replated on polyornithine (PO)/Laminin/Fibronectin coated plates. Patterning with SHH/FGF8 was continued for 7 days at P2 stage followed by final differentiation in the presence of BDNF, AA, GDNF, TGFb3 and dbcAMP as described above until the desired maturation stage for a given experiment (typically 5-7 days for transplantation studies or 32 days for in vitro functional studies).

Gene Expression Analyses.

Total RNA was extracted during differentiation at days: 0, 1, 3, 5, 7, 9, 11, 13 and 25 from each condition of control LSB, LSB/SHH/FGF8 and LSB/SHH/FGF8/CHIR using the RNeasy kit (Qiagen, Valencia, Calif.). For microarray analysis, total RNA was processed by the MSKCC Genomic core facility and hybridized on Illumina Human ref-12 bead arrays according to the specifications of the manufacturer. Comparisons were performed among each days and conditions using the LIMMA package from Bioconductor (worldwideweb.bioconductor.org). Genes found to have an adjusted P-value<0.05 and a fold change greater than two were considered significant. Some of the descriptive microarray data analyses and presentation was performed using a commercially available software package (Partek Genomics Suite (version 6.10.0915)). For qRT-PCR analyses, total RNA at day 25 of each condition was reverse transcribed (Quantitech, Qiagen) and amplified material was detected using commercially available Taqman gene expression assays (Applied Biosystems, Carlsbad, Calif.) with the data normalized to HPRT. Each data point represents 9 technical replicates from 3 independent biological samples. Raw data of microarray studies are not yet available at GEO worldwideweb.ncbi.nlm.nih.gov/geo).

Animal Surgery.

Rodent and monkey procedures were performed following NIH guidelines, and were approved by the local Institutional Animal Care and Use Committee (IACUC), the Institutional Biosafety Committee (IBC) as well as the Embryonic Stem Cell Research Committee (ESCRO).

Mice.

NOD-SCID IL2Rgc null mice (20-35 g in weight; Jackson Laboratory, Bar Harbor, Me.) were anesthetized with Ketamine (90 mg/kg; Akorn, Decatur, Ill.) and Xylazine (4 mg/kg Fort Dodge, Iowa). 6-hydroxydopamine (ranging in concentration from 1-20 µg) 6-OHDA (Sigma-Aldrich) was injected stereotactically into the striatum at the following coordinates (in millimeters): AP, 0.5 (from bregma; a skull suture used as reference for stereotactic surgery); ML, −2.0; DV, −3.0 (from dura a membrane covering the brain used for reference). Mice with successful lesions (an average of >6 rotations/minutes) were selected for transplantation. A total of 150×10³ cells were injected in a volume of 1.5 µl into the striatum at the following coordinates (in mm): AP, 0.5; ML, −1.8; DV, 3.2. The mice were sacrificed 18 weeks post transplantation.

Rats.

Adult female Sprague-Dawley (Taconic, Hudson, N.Y.) rats (180-230 g) were anesthetized with Ketamine (90 mg/kg) and xylazine (4 mg/kg) during surgical procedures. Unilateral, medial forebrain bundle lesions of the nigro-striatal pathway were established by stereotaxic injection of 6-OHDA (3.6 mg/ml in 0.2% ascorbic acid and 0.9% saline, Sigma) at two sites (Studer, et al. *Nature Neurosci.* 1:290-295 (1998), herein incorporated by reference). Rats were selected for transplantation if amphetamine-induced rotation exceeded 6 rotations/min by 6-8 weeks post injection. 250× 10³ cells were transplanted into the striatum of each animal (Coordinates: AP+1.0 mm, ML −2.5 mm and V−4.7 mm; toothbar set at −2.5). Control rats received PBS instead. The surgical procedures were described previously (Studer, et al. *Nature Neurosci.* 1:290-295 (1998), herein incorporated by reference). Daily intraperitoneal injections of cyclosporine 15 mg/kg (Bedford Labs, Bedford, Ohio) were started 24 hours prior to cell grafting and continued until sacrifice, 20 weeks following cell grafting. Primates. Two adult (17-18 yr old; 10-12 kg; female) rhesus monkeys were rendered hemiparkinsonian via carotid MPTP administration followed by weekly I.V. MPTP administration to create a bilateral parkinsonian syndrome (Kordower, et al. *Science* 290:767-773 (2000), herein incorporated by reference).

Both animals displayed parkinsonian symptoms consistent with a moderately-severe lesion based on behavioral analysis including crooked posture, dragging of leg and symptoms of rigor (inflexibility of movement), neglect (motor awareness to lateralized stimulus) and bradykinesia (slow movement initiation). These parameters can be assessed in monkeys using a modified Parkinsonian clinical rating scale (CRS). On the day of transplantation surgery, animals were tranquilized with ketamine (3.0 mg/kg, IM) and dexdomitor (0.02-0.04 mg/kg IM), intubated to maintain a stable airway and anesthetized with isoflurane. They were then placed into a stereotaxic frame for surgery. Both rhesus monkeys underwent a single surgery with three intracranial injections of human floor plate-derived DA cultures based on stereotaxic coordinates (Paxinos, et al. *The Rhesus Monkey Brain in Stereotaxic Coordinates* (Academic Press, 2000), herein incorporated by reference). Bilateral injections of cells (10 ul/injection; 125,000 cell/ul were performed at three sites (1-posterior caudate, 2-pre-commissural putamen and overlying white matter) for a total volume of 30 µl per hemisphere. An infusion pump attached to a stereotaxic micromanipulator was utilized to deliver the cells at a rate of 1 µl/min though a 50 µl Hamilton syringe with 28 G needle. After the injections were completed, the needle was left in place for an additional 2-5 minutes to allow the infusate to diffuse off the needle tip before slowly retracting the syringe. Immediately following surgery, the animals received analgesics (buprenex, 0.01 mg/kg IM, BID for 72 hours post surgery; meloxicam, 0.1 mg/kg SQ, SID for 72 hours post surgery) as well as an antibiotic (cephazolin, 25 mg/kg IM, BID) until 72-hours post-surgery. The animals received cyclosporine A (Neoral, Sandimmune) orally (30 mg/kg tapered to 15 mg/kg) once daily beginning 48-hrs prior to surgery until sacrifice, one month following transplantation.

Behavioral Assays.

Amphetamine-induced rotations (mice and rats) and the stepping test (rat) were carried out before transplantation and 4, 8, 12, 18 weeks after transplantation. Rotation behavior in mice was recorded 10 min after i.p. injection of d-amphetamine (10 mg/kg, Sigma) and recorded for 30 minutes. Rotation behavior in rats was recorded 40 min after i.p. injection of d-amphetamine (5 mg/kg) and automatically assessed by the TSE VideoMot2 system (Germany). The data were presented as the average number of rotations per minute. The stepping test was modified from Blume, et al. *Exp. Neurol.* 219:208-211 (2009) and Crawley, et al. *What's Wrong With My Mouse: Behavioral Phenotyping of Transgenic and Knockout Mice* (Wiley-Liss, 2000), all of which are herein incorporated by reference. In brief, each rat was placed on a flat surface; its hind legs were lifted by gently holding up the tail to allow only the forepaws to touch the table. The experimenter pulled the rat backwards 1 meter at a steady pace. Adjusting step numbers from both contralateral and ipsilateral forepaws were counted. Data was presented as the percentage of contralateral/(contralateral+ipsilateral) adjusting steps. The cylinder test was performed by placing each animal in a glass cylinder and counting the number of ipsilateral versus contralateral paw touches (out of 20 touches) to the wall of the cylinder as described previously (Tabar, et al. *Nature Med.* 14:379-381 (2008), herein incorporated by reference). Tissue Processing for rodents and primates are described below.

Mice and Rats:

Animals (mice and rats) received overdoses of Pentobarbital intraperitoneally (50 mg/kg) to induce deep anesthesia and were perfused in 4% paraformaldehyde (PFA). Brains were extracted, post-fixed in 4% PFA then soaked in 30% sucrose solutions for 2-5 days. They were sectioned on a cryostat after embedding in O.C.T. compound (Sakura-Finetek, Torrance, Calif.).

Primates:

Animals were sacrificed under deep anesthesia with ketamine (10 mg/kg, Intramuscular (IM)) and pentobarbital (25 mg/kg, intravenous (IV)) via cardiac perfusion with heparinized 0.9% saline followed by fresh cold 4% PFA fixative (pH7.4). Immediately following primary fixation, brains were removed from the skull and post-fixed in 4% PFA, free-floating, for 24-36 hrs. They were then rinsed and re-suspended in 10% sucrose on a slow shaker at 4° C., and allowed to "sink". The process was then repeated in 20% sucrose followed by 30% sucrose. Whole brains were cut coronally into 40 µm serial sections on a frozen sledge microtome and stored free-floating in cryopreservative medium at –20° Celcius.

Immunohistochemistry:

Cells were fixed in 4% PFA and blocked with 1% bovine serum albumin (BSA) with 0.3% Triton. Brain tissue sections were washed in cold PBS and processed similarly. Primary antibodies were diluted in 1-5% BSA or Normal Goat Serum and incubated according to manufacturer recommendations. A comprehensive list of antibodies and sources is provided as Table 6. Appropriate Alexa488, Alexa555 and Alexa647-conjugated secondary antibodies (Molecular Probes, Carlsbad, Calif.) were used with 4',6-diamidino-2-phenylindole (DAPI) nuclear counterstain (Thermo Fisher, Rockford, Ill.). For some analyses biotinylated secondary antibodies were used followed by visualization via DAB (3,3'-Diaminobenzidine) chromogen.

HPLC Analysis.

Reversed-phase HPLC with electrochemical detection for measuring levels of dopamine, Homovanillic acid (HVA) and DOPAC (3,4-Dihydroxy-Phenylacetic Acid) was performed as described previously (Roy, et al. *Nature Med.* 12:1259-1268 (2006); Studer, et al. *Brain Res. Bull.* 41:143-150 (1996), all of which are herein incorporated by reference). Culture samples were collected in perchloric acid at day 65 of differentiation. For some experiments DA was measured directly in the medium using the same detection system but following aluminum extraction of dopamine and its metabolites using a commercially available kit as described previously (Studer, et al. *Brain Res. Bull.* 41:143-150 (1996), herein incorporated by reference).

Electrophysiological Recordings:

Cultures were transferred to a recording chamber on an upright microscope equipped with a 40× water-immersion objective (Eclipse E600FN; Nikon); cultures were perfused with saline containing in mM: 125 NaCl, 2.5 KCl, 25 NaHCO$_3$, 1.25 NaH$_2$PO$_4$, 2 CaCl, 1 MgCl$_2$, and 25 glucose (34° C.; saturated with 95% O$_2$-5% CO$_2$; pH 7.4; 298 mOsm/L). The saline flow rate was 2-3 ml/min running through an in-line heater (SH-27B with TC-324B controller; Warner Instruments). Neurons were visualized by video microscopy with a cooled-CCD digital camera (CoolSNAP ES$^2$, Photometrics, Roper Scientific, Tucson, Ariz.). Cells selected for electrophysiological recordings had neuron-like shapes with fine branching neurites. Somatic whole-cell patch-clamp recordings in current clamp configuration were performed with a MultiClamp 700B amplifier (Molecular Devices). Signals were filtered at 1-4 kHz and digitized at 5-20 kHz with a Digidata 1440A (Molecular Devices). Recording patch electrodes were fabricated from filamented borosilicate glass (Sutter Instruments) pulled on a Flaming-Brown puller (P-97, Sutter Instruments) and had resistances of 4-6 MΩ in the bath. Electrodes were filled with internal solution containing in mM: 135 K-MeSO$_4$, 5 KCl, 5 HEPES, 0.25 EGTA, 10 phosphocroeatine-di(tris), 2 ATP-Mg, and 0.5 GTP-Na (pH 7.3, osmolarity adjusted to 290-300 mOsm/L). The amplifier bridge circuit was adjusted to compensate for electrode resistance and monitored. Electrode capacitance was compensated. When series resistance increased >20% during the recording, the data were discarded because increased resistance suggested a partial technical failure during recordings.

Cell Counts and Stereological Analyses.

Figure 1:
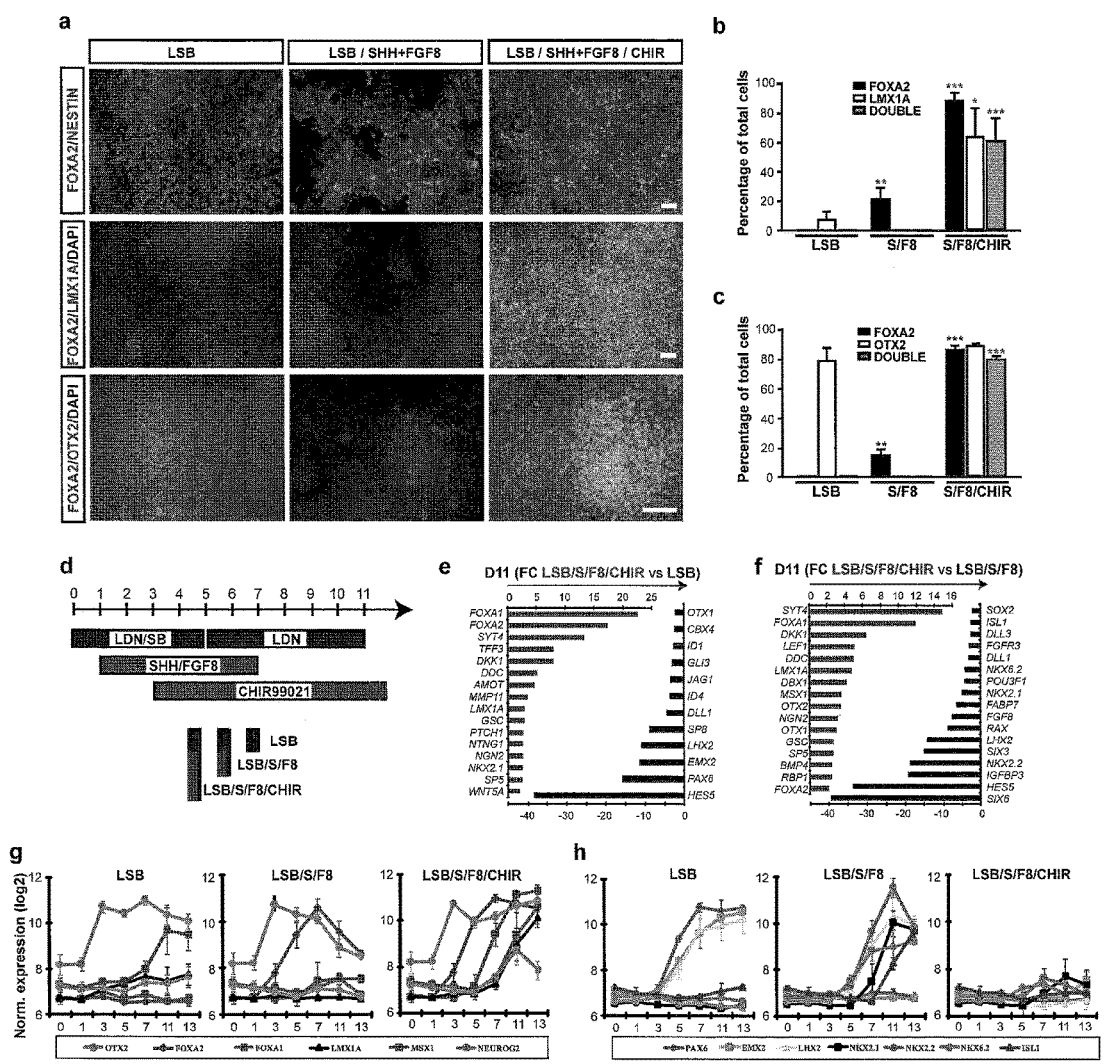
FIG. 1 shows exemplary induction and neurogenic conversion of human ES cell-derived midbrain floor plate precursors dependent on CHIR990221 addition. a) Immunocytochemical analysis at day 11 of differentiation for FOXA2 (red), NESTIN (green, upper panels), LMX1A (green, middle panels) and OTX2 (green, lower panels) expression. b,c) Quantification of the data presented in (a). Data are from three independent experiments carried out each in triplicates (mean±SEM). Significance levels for individual markers are presented as compared to LSB only treatment: ANOVA; Dunnett test: * $p<0.001$;  $p<0.01$; $p<0.05$). d) Schematic illustration of the culture conditions used for the three treatment conditions. e,f) Lists of selected differentially expressed genes at day 11 comparing LSB/S/F8/CHIR conditions with either LSB (e) or LSB/S/F8 (f). g,h) Temporal gene expression analysis of selected markers characteristic of midbrain DA precursor identity (g), forebrain and ventral non-DA precursor identity (h). Scale bars correspond to 50 μm.
Figure 2:
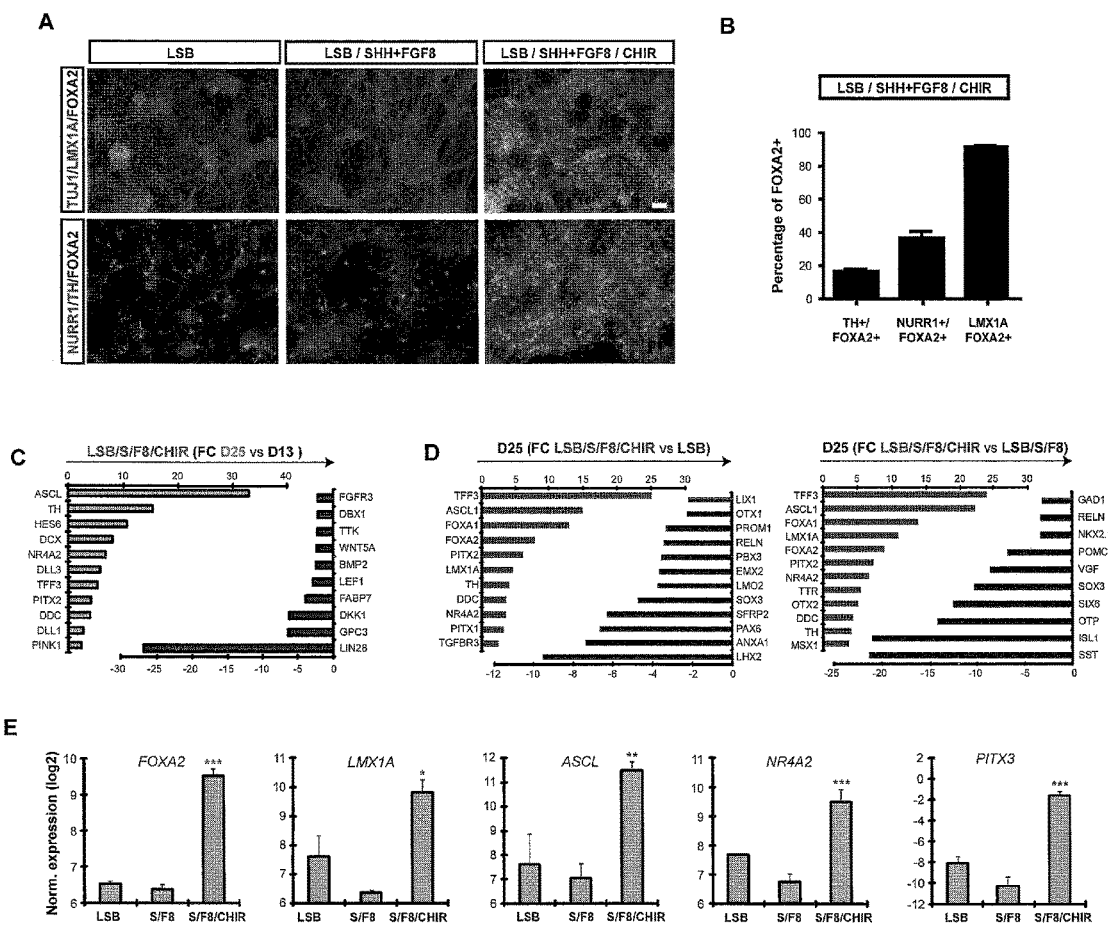
FIG. 2 shows an exemplary immunocytochemical and molecular analysis of midbrain DA neuron fate in LSB/S/F8/CHIR treated versus LSB/S/F8 (ventral/hypothalamic) and LSB (dorsal forebrain) fates. a) Immunocytochemical analysis at day 25 for expression of FOXA2 (blue) in combination with Tuj1 (red)/LMX1A (green) (upper panels) and NURR1 (red)/TH (green) (lower panels). b) Quantitative co-expression analysis in LSB/S/F8/CHIR treated cultures. Data are from three independent experiments carried out each in triplicates (mean±SEM). c,d) Global gene expression analysis was performed at day 25 (triplicate samples for all three conditions). Selected lists of the most differentially expressed genes comparing day 13 versus day 25 in the LSB/S/F8/CHIR condition (c) and comparing LSB/S/F8/CHIR treatment versus LSB (d, left panel) and LSB/S/F8 (d, right panel). e) Normalized differential gene expression analysis for key midbrain DA neuron markers. Significance levels for individual markers are presented as compared to LSB only treatment: ANOVA; Dunnett test: * $p<0.001$;  $p<0.01$; $p<0.05$). Scale bars correspond to 50 μm.
Figure 11:
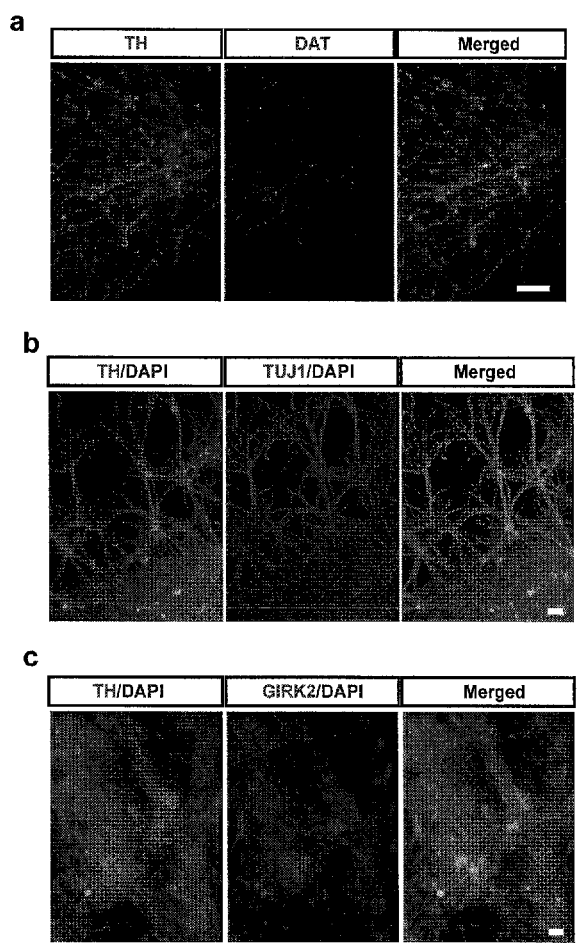
FIG. 11 shows an exemplary in vitro maturation of floor plate-derived DA neuron cultures. a) Immunocytochemical analysis of floor plate-derived TH neurons (green) for DAT expression (red; day 80). b) Extensive Tuj1+ (red) fiber tracts were observed by day 60 of differentiation extending over distances of >2 mm. c) At day 80 of differentiation, co-expression of GIRK2 (red) in TH+ neurons (green). Scale bars correspond to 20 µm in (a) 100 µm in (b) and 20 µm in (c).

The percentages of marker positive cells at the floor plate (day 11) FIG. 1, midbrain dopamine neuron precursor (day 25), FIG. 2 and mature DA neuron stages (day 50 or later) FIGS. 3 and 11, were determined in samples derived from at least 3 independent experiments each. Images for quantification were selected in a uniform random manner and each image was scored first for the number of DAPI-positive nuclei, followed by counting the number of cells expressing the marker of interest. Data are presented as mean±SEM. Quantification of human cells (identified with anti-hNA) and TH+ neurons within grafts was performed on every tenth section where a graft was identifiable. Cell counts and graft volume was determined using the optical fractionator's probe and the Cavalieri estimator using the Stereo Investigator software (MBF bioscience, Vermont) as described previously in Tabar, et al. *Nat. Biotechnol.* 23:601-606 (2005), herein incorporated by reference. Data are presented as estimated total cell number and total graft volume+/− standard error of means (SEM).

The following formulations describe exemplary cell culture medium for use in developing embodiments of the present inventions.

hESC medium for maintenance (1 liter): 800 mL DMEM/F12, 200 mL of Knockout Serum Replacement, 5 mL of 200 mM L-Glutamine, 5 mL of Pen/Strep, 10 mL of 10 mM MEM minimum non-essential amino 15 acids solution, 55 µM of 13-mercaptoethanol, and bFGF (final concentration is 4 ng/mL).

KSR medium for hESC differentiation (1 liter): 820 mL of Knock out DMEM, 150 mL of Knock out Serum Replacement, 10 mL of 200 mM L-Glutamine, 10 mL of Pen/Strep, 10 mL of 10 mM MEM, and 55 µM of 13-mercaptoethanol.

N2 medium for hESC differentiation (1 liter): 985 ml dist. H$_2$0 with DMEM/F12 powder, 1.55 g of glucose (Sigma, cat. no. G7021), 2.00 g of sodium bicarbonate (Sigma, cat. no. S5761), putrescine (100 uL aliquot of 1.61 g dissolved in 100 mL of distilled water; Sigma, cat. no. P5780), progesterone (20 uL aliquot of 0.032 g dissolved in 100 mL 100% ethanol; Sigma, cat. no. P8783), sodium selenite (60 uL aliquot of 0.5 mM solution in distilled water; Bioshop Canada, cat. no. SEL888), and 100 mg of transferrin (Celliance/Millipore, cat. no. 4452-01), and 25 mg of insulin (Sigma, cat. no. I6634) in 10 mL of 5 mM NaOH.

Dulbecco's Modification of Eagles Medium (DMEM), with 10% FBS for preparing PMEF ((primary mouse embryo fibroblast (PMEF)) feeder cells) (1 liter): 885 mL of DMEM, 100 mL of FBS, 10 mL of Pen/Strep, and 5 mL of L-Glutamine.

Alpha Minimum Essential Medium (MEM) with 10% FBS for preparing MS-5 feeder cell medium (1 liter): 890 mL of Alpha MEM, 100 mL of FBS, 10 mL of Pen/Strep Gelatin solution (500 ml): Dissolve 0.5 g of gelatin in 500 ml of warm (50-60° C.) Milli-Q water. Cool to room temperature.

In general, the following is a brief summary for exemplary methods of monitoring the production of mature DA neurons for use in grafting (see, also, conditions shown in Table 7. Day 13 is a midbrain floor plate stage, characterized by co-expression of FOXA2/LMX1A. In addition to expression of FOXA2 and LMX1A, a loss of OCT4 expression and lack of induction of forebrain markers PAX6 and FOXG1 is found. Day 25 is the midbrain DA neuron precursor stage, characterized by the continuous expression of FOXA2/LMX1A and expression of the neuronal (TUJ1) and DA markers (NURR1, TH). Proliferating, Ki67+ cells and the number of PAX6 and FOXG1 forebrain neural precursors are monitored, where these markers are not desired. For unbiased and rapid quantification of immunofluorescence data, an Operetta (Perkin Elmer) High Content Microscope was used for measurements. qRT-PCR assays was also used for each marker to confirm immunofluorescence data. In some embodiments, cell lines (cultures) passing these preliminary in vitro tests, are used for engraftment, see, Table 7. In some embodiments, mature DA neurons were cryopreserved without serum at day 25 (ranging from day 20-day 25) in culture medium +7% DMSO (ranging from 3%-12%) until thawed for use in engraftment. In some embodiments, cell samples are stored in liquid nitrogen. In some embodiments, cells are stored in low temperature freezers. In other embodiments, cryoprotectants such as myoinositol, polyvinyl alcohol, serum replacement, caspase inhibition compounds, are contemplated for use in addition to DMSO. After thawing, cells are tested for viability, marker expression, etc., prior for use in grafting. In some embodiments, thawed cells were tested for maintenance of function in long-term in vitro and in vivo assays for monitoring freezing and storage conditions.

B. Studies to Identify Additional Factors for the Generation of Functional DA Neurons.

Additional "drop out" and "add in" experiments for tissue culture components are contemplated for use in producing cells of the present inventions. For example, FGF8 was shown that although its use resulted in cells of the present inventions, it was not required for production of these cells. These experiments will be extended to additional reagents, such as those listed in Table 8, as additives to cell cultures along with the four "core" molecules that resulted in DA neuronal cells of the present inventions, i.e. i) Alk4/5/7 ("TGFβ-)inhibitor (SB431542), ii) Alk2/3 ("BMP")-inhibitor (LDN-193189), iii) Smoothened ("SHH")-agonist (Purmorphamine), and iv) GSK3β-inhibitor (CHIR99021).

As described herein, the use of SB431542 and LDN193189 showed efficient neural conversion of pluripotent stem cells while the addition of Purmorphamine and CHIR99021 to these cells demonstrated midbrain floor plate induction. Other chemicals and recombinant proteins were or can be used to provide long-term trophic support and/or accelerate differentiation. Some of these compounds will be used in further tests in order to define their roles in cell differentiation described herein.

For these experiments, performance of other compounds will be compared to exemplary limits for DA neuron differentiation (Table 7) versus the use of the 4 core-factors (Table 8).

These type of experiments are contemplated to define the minimal number of factors needed for producing authentic DA neuronal cells of the present inventions.

C. Embodiments for Establishing Dose Response Curves for Potential Proliferating Contaminants (Pluripotent hESCs, Neural Rosettes).

During the development of the present inventions, no teratomas or excessive overgrowths were observed within the grafts up to at least 5 months survival in vivo. In order to monitor safety for longer term studies in order to reflect contemplated longitivity of grafts in humans, a cell number threshold is contemplated for determining a clinically relevant contamination limit of problematic cell types, such as undifferentiated hESCs which may develop into teratomas or primitive neuroectodermal precursors capable of significant proliferation. Therefore, some embodiments are contemplated for further enrichment of dopaminergic neurons in cells for use in grafts, i.e. depleting contaminating cell types prior to engraftment, see, Table 7 for exemplary limits.

The following describes exemplary standardized set of additional in assays for validating enhancement strategies. For hESCs, a pre-determined mix of undifferentiated (Oct4+/Nanog+) cells with hES derived DA neurons will be used to monitor clinical symptoms suggestive of mass effect and/or animal death in animal experiments. A dose response of one hES cell per 10,000 hESC-derived DA cells, 1/5000, 1/1000 and 1/100 will be performed. Cells will be injected intra-striatally and the animals will receive immunosuppression. Rats will be monitored closely and will be sacrificed upon manifestation of neurological symptoms or at a maximum of 6 months. The brains will be analyzed for graft volumes and composition as described herein. The cell ratios will adjusted until a clear in vivo threshold is established for the emergence of teratomas. For determining contaminating levels of primitive neuroectodermal precursors, a similar strategy will be followed. The presence of early neural precursors have a significant potential for proliferation and broad differentiation into central nervous system as well as peripheral nervous system (PNS) fates. Graft analysis will consist of IHC for rosette cells (PLZF expression), their CNS progeny (neural precursors expressing Nestin/Sox2 or forebrain precursors, expressing FoxG1) as well as graft volumes and a proliferation index (% Ki67+ of total surviving cells).

IV. Parkinson's Disease.

Parkinson's disease (PD) is the second most common neurodegenerative disorder and is estimated to affect 4.1-4.6 million patients world-wide, a number predicted to more than double by 2030. It is the second most common neurodegenerative disorder after Alzheimer's disease, affecting approximately 1 million patients in the US with 60,000 new patients diagnosed each year. The disease has a major socioeconomic impact causing significant morbidity and mortality, and the combined direct and indirect costs of PD, including health care cost and lost income, is estimated to be approximately $25 billion per year in the US alone. Currently there is no cure for Parkinson's disease (PD), an age-related, progressive and disabling disorder. PD is characterized pathologically by a selective loss of midbrain DA neurons in the substantia nigra. A fundamental characteristic of PD is therefore progressive, severe and irreversible loss of midbrain dopamine (DA) neurons resulting in ultimately disabling motor dysfunction. While pharmacological, exercise-based, gene- and surgical therapies have been developed for PD, none of those approaches are yet able to restore proper DA neuron function. Long-term control of motor symptoms in patients often remains suboptimal, and while recognizing the importance progressive non-dopamine responsive motor and non-motor symptoms, the fundamental issue of long term dopamine-responsive symptom control remains an area of critical therapeutic need. Widespread pathology is recognized in PD, affecting both central and peripheral nervous systems, the cardinal features of PD (bradykinesia, rigidity, and tremor partially) are fundamentally related to DA neuronal cell loss and are dopamine-responsive. Thus PD is contemplated for treatment using neuronal cell replacement due to the rather selective loss of midbrain DA neurons that is responsible for most motor symptoms of the disease. a healthy human brain harbors approximately one million DA neurons. Therefore, in one embodiment, DA neuron replacement is contemplated to require a relatively small number of surviving cells as compared to most other disorders in the CNS.

One challenge in developing a cell based therapy for PD was the identification of an appropriate cell source for use in neuronal replacement. This search has been going on for more than 30 years, with many potential sources for DA neuron replacement were proposed (Kriks, Protocols for generating ES cell-derived dopamine neurons in Development and engineering of dopamine neurons (eds. Pasterkamp, R. J., Smidt, & Burbach) (Landes Biosciences, 2008; Fitzpatrick, et al., Antioxid. Redox. Signal. 11:2189-2208 (2009)). In the past, several of those sources have progressed to early stage clinical trials including catecholaminergic cells from the adrenal medulla Madrazo, et al., N. Engl. J. Med. 316, 831-834 (1987), carotid body transplants (Arjona, et al., Neurosurgery 53: 321-328 (2003)), or encapsulated retinal pigment epithelial cells (Spheramine trial Bakay, et al., Front Biosci. 9, 592-602 (2004). However, those trials mostly failed to show clinical efficacy and resulted in poor long-term survival and low DA release from the grafted cells. Another approach was the transplantation of fetal midbrain DA neurons performed in over 300 patients worldwide (Brundin, et al., Prog. Brain Res. 184, 265-294 (2010); Lindvall, & Kokaia, J. Clin. Invest 120:29-40 (2010). Therapy using human fetal tissue in these patients demonstrated evidence of DA neuron survival and in vivo DA release up to 10 or 20 years after transplantation in some patients. However, in many patients, fetal tissue transplantation fails to replace DA neuronal function. Further, fetal tissue transplantation is plagued by multiple challenges including low quantity and quality of donor tissue, ethical and practical issues surrounding tissue acquisition, and the poorly defined heterogeneous nature of transplanted cells, which are some of the factors contributing to the variable clinical outcomes. Examples of fetal transplantation are described in; Mendez, et al. Nature Med. (2008)); Kordower, et al. N. Engl. J. Med. 332:1118-1124 (1995); Piccini, et al. Nature Neuroscience 2:1137-1140 (1999). However, the clinical results were mixed with some positive data in early, open-label studies (Lindvall, et al. Science 247:574-577 (1990); Widner, et al. N. Engl. J. Med. 327:1556-1563 (1992); Brundin, et al. Brain 123:1380-1390 (2000); Freed, et al. N. Engl. J. Med. 327:1549-1555 (1992); Freeman, et al. Bilateral fetal nigral transplantation into the postcommissural putamen in Parkinson's disease. Ann Neurol 38:379-388 (1995). However modest results were found in two larger, NIH-sponsored, placebo-controlled clinical trials in the US (Freed, et al. N. Engl. J. Med. 344, 710-719 (2001); Olanow, et al. Ann. Neurol. 54:403-414 (2003)). There are many hypotheses as to the limited efficacy observed in the human fetal grafting trials including that fetal grafting may not provide a sufficient number of cells at the correct developmental stage for an optimal therapeutic benefit. Furthermore, fetal tissue is quite poorly defined by cell type and variable with regard to the stage and quality of each tissue sample Bjorklund, et al. Lancet Neurol. 2, 437-445 (2003). Another contributing factor may be a low-level inflammatory host response to the graft (Bjorklund, et al. Lancet Neurol. 2, 437-445 (2003)).

In contrast, a stem cell-derived cell source or other type of consistent cell type for use in providing cells for transplantation is contemplated to overcome many of the challenges associated with fetal tissue grafting and could offer an unlimited source of DA neurons at the optimum stage for transplantation. After nearly 20 years of attempts using various potential stem cell sources, the inventors' succeeded in obtaining authentic human midbrain DA neurons from pluripotent stem cells capable of reversing neurological defects in murine animals and primates. This novel differentiation strategy was highly efficient and led to robust in vivo engraftment of the cells, induction of functional recovery in PD models of disease, and lack of adverse events such as inappropriate cell proliferation as supported by preclinical data. FDA approval for a human ES cell based strategy for treating PD is contemplated because the FDA approved testing other human ES cell derivatives in spinal cord injury (Strauss, Nat. Biotechnol. 28:989-990 (2010) and macular degeneration (Schwartz, et al. Lancet 379:713-720 (2012)).

Additional embodiments including "enhancement" strategies to control cell purity promote axonal fiber outgrowth and include novel safety/regulatory features in grafting strategies are contemplated. For example, in some embodiments, a method of cell purification demonstrated starting from a simple surface marker screen against a cell type of interest, (such as CD142) towards a meaningful enrichment strategy for a specific neuron type. In some embodiments, this method is contemplated for use in providing cells for use in humans. Further, in other embodiments, engineered expression of PSA-NCAM is contemplated for enhancing axonal outgrowth for use in neural repair in vivo. Such applications include promotion of long-distance axonal growth for treating motoneuron disease, Huntington's disease or other disorders primarily affecting projection neurons. Additional embodiments are contemplated for a GMP qualified pluripotent cell source, and the like. Because the engraftment methods described herein, require a small number of DA neurons and are based upon relatively simple, cost-effective small molecule methods developed for DA neuron induction, it is contemplated that DA neuron replacement therapy would be at a reasonable cost on a per patient basis.

One potential biological limitation of the transplantation approach in PD is the fact that neuronal degeneration in PD proceeds to affect many cell types other than midbrain dopamine neurons, particularly at later stages of the disease. In fact in a long term study, non-DA responsive symptoms predominate in late PD, leading to dysphagia, falls, dementia and other significant morbidities. However, some non-motor symptoms are contemplated to benefit from restoring dopaminergic function. Furthermore, it is contemplated that the use of hESC derived DA neurons at early stages of the disease would prevent some of the secondary PD symptoms, including the degeneration of the dopamine receptive populations of the striatum. However, even in the absence of impacting the non-DA responsive symptoms of the disease, the long-term functional dopaminergic restoration of the striatum would be a major achievement for treating this currently incurable disorder. In the case of Parkinson's disease there are several alternative therapies available including drug-based strategies and surgical approaches such as deep brain stimulation. In some embodiments, efficacy of recovery is contemplated to be comparable to or beyond the levels achieved with alternative therapies. In other embodiments, use of this mature DA neuron cell engraftment therapy is contemplated to be particularly beneficial for a particular subset of patients. In other embodiments, use of this mature DA neuron cell engraftment therapy is contemplated for use in addition to existing drug and surgical type approaches. One major benefit of using mature DA neuron cell engraftment therapy of the present inventions is the unique neurorestorative nature post engraftment, i.e. long term recovery of neuronal function that is contemplated for use in patients for progressive removal of drug therapy. Cell transplantation is contemplated to affect a different spectrum of DA-related symptoms than those responding to drugs or other therapy. Thus in one embodiment, mature DA neuron transplantation is contemplated for use with DBS. In another embodiment, mature DA neuron is contemplated for use with therapy.

A) Parkinson's Disease and Current Therapies.

Great progress was made in the identification of rare genetic changes contributing to familial forms of PD. However, for the majority of PD cases the contribution of any potential genetic predisposition remains unclear. Traditional therapeutic strategies in PD are limited by the fact that at the onset of clinical symptoms 30-70% of all DA neurons in the substantia nigra have irreversibly degenerated. One therapeutic option is the pharmacological replacement of DA neuron deficiency using the DA precursor L-Dopa. However, despite the dramatic initial response of some PD patients to L-Dopa therapy, long-term clinical outcome remains poor and severe side effects of L-Dopa therapy, including motor fluctuations and dyskinesias, occur frequently in late-stage disease. Pulsatile delivery of L-dopa has a major role in development of these later stage motor complications therefore a "smoother" more physiologic delivery of dopamine, i.e. such as from engrafted cells of the present inventions, would therefore be highly desirable. In addition to pharmacological strategies, there are several surgical treatment options. These include the ablation or functional inactivation of cells within the basal ganglia via pallidotomy or deep brain stimulation by targeting the subthalamic nucleus or globus pallidus pars interna. While these surgical options are alternatives for some patients, they provide symptomatic relief from the disease but do not restore normal DA function. Furthermore surgical and non-surgical side effects have been reported, including hardware malfunction, infections, stroke, hemorrhage and the like. Other treatment options include the delivery of growth factors such as GDNF or Neurturin using direct intra-parenchymal infusion or viral expression by gene therapy. While initial open label studies in PD showed promising results for GDNF subsequent controlled trials in a larger set of patients failed to confirm any benefit and raised potential safety concerns due to the production of anti-GDNF antibodies in a subset of patients. AAV-based delivery of Neurturin, a molecule related to GDNF, also failed to show any significant clinical benefit in a large placebo-controlled, multicenter trial. Early data from a Phase 2 trial of AAV-borne glutamic acid decarboxylase (GAD) injections into the subthalamic nucleus were recently reported (Lancet Neurology, April 2011) however, the clinical benefits were modest at best in this study. While efforts on neurotrophic factor-based- or alternative neuroprotective strategies might bring temporary relief to patients, none of them can bring back/replace DA neurons already lost due to the disease, the main goal a cell replacement therapy.

B) Cell Therapy in PD.

Clinical symptoms become apparent in PD after 70-80% of striatal dopamine and about 50% of nigral dopamine neurons are lost. However, midbrain dopamine neurons developed by 8.5 weeks post conception with little evidence of dopamine neuron replacement throughout the remainder of life. Therefore, dopamine neurons by time of disease onset are many decades old without a natural mechanism to replace these cells, thus cell transplantation may be needed to replace those cells in the brains of PD patients. DA neuron replacement in PD was done in the 1980s based on the use of adrenal medulla derived chromaffin cells. Those hormone producing cells were shown to switch neurotransmitter phenotype from adrenalin to DA when placed ectopically into the CNS. While several hundred PD patients were grafted worldwide using this approach, it became clear over time that grafted cells survive very poorly with a transient effect at best. Therefore, this approach was quickly abandoned for clinical use. In contrast, the use of fetal midbrain tissue grafting was based on more extensive preclinical studies in rodent models that demonstrated robust long-term engraftment and functional improvement across a panel of DA related behavioral assays. Encouraged by those preclinical data, fetal grafting proceeded at multiple centers in the late 1980s and early 1990s. Those studies showed clear evidence that functional long-term engraftment with increased DA release in the grafted area as measured by Fluorodopa PET and subsequent histological studies in some patients that died due to unrelated causes. However, the use of fetal graft raised two potential problems with cell-based therapeutic approaches. First, an unexpected problem of fetal grafts was the induction of graft-induced dyskinesias (GID) in about 15% of patients. While the mechanism of GID remains controversial, recent evidence indicated that serotonergic neurons were capable of inappropriate storage and release of DA. Another potential mechanism suggested to explain GID was the uneven distribution of DA neurons, i.e. causing hot spots of DA release. In contrast, during the development of the present inventions, methods for detecting and reducing Serotonergic neurons were discovered which would reduce the incidence of GID. Further, injection of mature DA neurons would provide an even distribution of mature neurons including extending dopaminergic fiber terminals within the host striatum. Another problem with fetal grafting treatment was (and is) limited availability of fetal midbrain tissue at the appropriate developmental stage. An alternative strategy was tried clinically to address the issue of limited supply by using fetal pig derived DA neurons. However, DA neuron survival in those xenografts was poor and the overall approach was abandoned. A recent trial using retinal pigmented epithelium also failed to show any benefits. In contrast, the use of human ES cells as sources of transplant cells is contemplated to provide an unlimited source of cells for making dopamine neurons for use in transplantation.

V. Compounds and Culture Methods were Discovered for Directed Differentiation of FOXA2+ and LMX1A+Positive Neuronal Precursor Cells into Midbrain DA (mDA) Neurons of the Present Inventions.

The inventors' discovered during the development of the present inventions that timing of CHIR99021 exposure determines induction of FOXA2/LMX1A midbrain floor plate precursors. Therefore the inventors tested for immunocytochemical analysis of FOXA2/LMX1A at day 11 of differentiation following LSB/S/F8 (i.e. treating cells with LSB, S, i.e. SHH, and FGF8 (F8) treatment alone or in combination with CHIR starting at various timepoints: d(day)0-d11, d1-d11, d3-d11, d5-d11, d7-d11 compared to duplicate cultures of cells with no CHIR treatment. Then quantification of the percentage of FOXA2+, LMX1A+ and double labeled cells were determined at day 11 of differentiation following differential onset of CHIR exposure as described in the immunocytochemical analysis.

A. CHIR99021 (C) is a Factor for Inducing FOXA2+/LMX1A+ Cells by Day 11 from LSB Cultured Cells Contacted with an Activator of Hedgehog and Purmorphamine.

The following example describes using exemplary methods for testing the efficacy of each compound for inducing directed neuronal differentiation of mDA neurons.

This example describes the discovery of small molecules and contact timing for providing directed differentiation of FOXA2+LMX1A+DA neurons of the present inventions. The following is a brief summary of some of the experimental discoveries described herein: Treatment of Dual-SMAD inhibited cells with SHH agonists (purmorphamine+SHH) and FGF8 (S/F8) in the absence of CHIR99021 showed significantly lower expression of FOXA2 by day 11 and complete lack of LMX1A expression (FIG. 1a,b). The anterior marker OTX2 was robustly induced in LSB and LSB/S/F8/CHIR treated cultures, but not under LSB/S/F8 conditions (FIG. 1a,c).

A cell population containing pluripotent cells was chosen by the inventors for a starting population and plated at Day 0. Cell are grown to near confluency prior to differentiation (between 60-100% confluence). These cells were contacted with Dual SMAD inhibitors (i.e. exposure to LDN-193189+SB431542="LSB") on Day 0. The inventors followed a cell population with regular feedings containing fresh LSB until Day 11 and discovered that some remaining cells were LMX1A+ but did not express FOXA2 (FIG. 1a,b). The inventors plated duplicate starting cell populations then tested for cell types (i.e. gene/protein expression patterns) after contacting with mixtures containing any of the following SHH agonists (purmorphamine+SHH) and FGF8 (S/F8) contacting the cells with different exposure regimens, i.e. contacting cells at Day 0, or Day 1, or Day 2, etc. for specific amounts of time, i.e. 24 hours, 48 hours, etc. Three primary exemplary culture conditions tested were 1) cells contacted with LDN/SB (LSB) on Day 0 then contacted with fresh LSB until Day 5, on Day 5 cells were contacted with fresh LDN without SB until Day 11, 2) cells contacted with LDN/SB (LSB) on Day 0 then contacted with fresh LSB until Day 5, on Day 5 cells were contacted with fresh LDN without SB until Day 11 while during this time cells were additionally contacted with fresh purmorphamine, SHH and FGF8 until Day 7 and 3) cells contacted with LDN/SB (LSB) on Day 0 then contacted with fresh LSB until Day 5, on Day 5 cells were contacted with fresh LDN without SB until Day 11 while during this time cells were additionally contacted with fresh purmorphamine, SHH and FGF8 until Day 7 while additionally contacted with fresh CHIR starting on Day 3 of culture until Day 11 with several variations of these primary conditions in order to determine optimal yield of cell types.

B. In Vitro Characterization of FOXA2+/LMX1A+ Cells Derived from the Midbrain Region of the Floor Plate in Comparison to DA Precursor Cells Generated with Other Techniques.

Systematic comparisons of the three culture conditions (FIG. 1d) were performed using global temporal gene expression profiling. Hierarchical clustering of differentially expressed genes segregated the three treatment conditions by day 11 of differentiation (FIG. 8a). FOXA1, FOXA2 and several other SHH downstream targets including PTCH1 were amongst the most differentially regulated transcripts in LSB/S/F8/CHIR versus LSB treatment sets (FIG. 1e). Expression of LMX1A, NGN2, and DDC indicated establishment of midbrain DA neuron precursor fate already by day 11 (FIG. 1e,f). In contrast, LSB cultures were enriched for dorsal forebrain precursor markers such as HES5, PAX6, LHX2, and EMX2. Direct comparison of LSB/S/F8/CHIR versus LSB/S/F8 treatment (FIG. 1f) confirmed selective enrichment for midbrain DA precursor markers in LSB/S/

F8/CHIR group and suggested hypothalamic precursor identity in LSB/S/F8 treated cultures based on the differential expression of RAX1, SIX3, and SIX6 (see also POMC, OTP expression in FIG. 2d below). An exemplary list of differentially expressed transcripts are shown, i.e. Tables 1, 2 and gene ontology analysis for Day 11, FIG. 8b (DAVID; http://david.abcc.ncifcrf.gov) confirmed enrichment for canonical WNT signaling upon CHIR treatment. Raw data are not yet available at GEO worldwideweb.ncbi.nlm.nih.gov/geo/ accession#: [TBD]). Comparative temporal analysis of gene expression for midbrain DA precursor markers (FIG. 1g) versus markers of anterior and ventral non-DA neuron fates (FIG. 1h) partitioned the three induction conditions into: i) LSB: dorsal forebrain; ii) LSB/S/F8: ventral/hypothalamic and iii) LSB/S/F8/CHIR: midbrain DA precursor identity.

VI. Further Differentiation of FOXA2+/LMX1A+Day 11 Cells into Midbrain DA Neurons by Day 25 and Maintained Up to Day 65.

For further differentiation, precursor FOXA2+/LMX1A+ cells were maintained in a medium promoting neuronal maturation (BAGCT, see Example I). For comparison two other techniques were used to generate DA neuronal precursor cells. The following types of comparisons were made between the populations of differentiated cells resulting from previous methods and methods of the present inventions: A) Immunocytochemical analysis at day 50 of differentiation for TH in combination with LMX1A, FOXA2 and NURR1, B) Quantification of TH+, FOXA2+, LMX1+, and NURR1+ cells out of total cells comparing rosette-derived versus floor plate-derived (LSB/S/F8/CHIR) cultures. C) Quantification of the percentages of serotonin+ (5-HT), and GABA+ neuronal subtypes (non-DA neuron contaminants) at day 50 in floor plate and rosette-derived DA neuron cultures. And D) HPLC analysis for measuring dopamine and metabolites: Comparison of the DA, DOPAC and HVA levels between floor plate versus rosette-derived cultures.

By day 25, three precursor cell populations yielded Tuj1+ neurons (FIG. 2a) and cells expressing TH, the rate-limiting enzyme in the synthesis of DA. However, LSB/S/F8/CHIR treatment yielded TH+ cells that co-expressed LMX1A and FOXA2 and displayed strong induction of the nuclear receptor NURR1 (NR4A2) (FIG. 2a,b). Comparing gene expression in day 13 versus day 25 cultures confirmed robust induction of other postmitotic DA neuron markers (FIG. 2c). Characterizing DA neuron identity at day 25 in comparison to LSB and LSB/S/F8 treated cultures confirmed enrichment for known midbrain DA neuron transcripts and identified multiple novel candidate markers (FIG. 2d, Tables 3-5, FIG. 8b). For example, the transcript most highly enriched in LSB/S/F8/CHIR (midbrain DA group) was TTF3, a gene not previously associated with midbrain DA neuron development, but highly expressed in the human substantia nigra (FIG. 8c; Allen Brain Atlas: http://human.brain-map.org).

Figure 9:
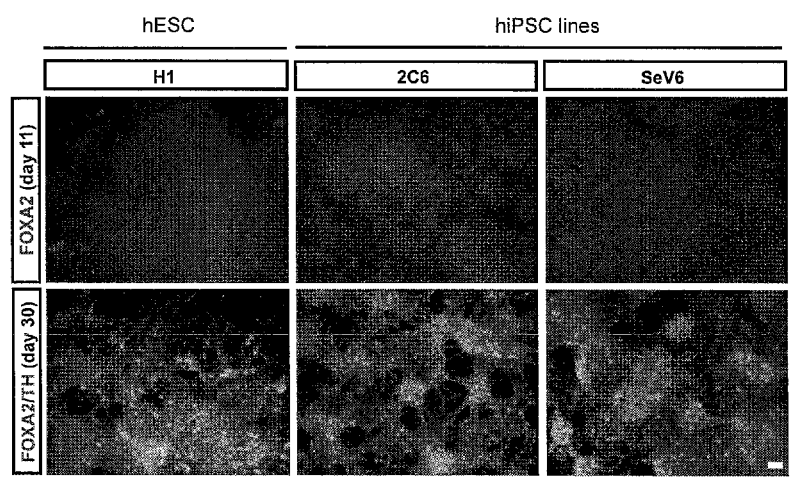
FIG. 9 shows an exemplary differentiation protocol for floor plate induction and midbrain DA neuron development in representative independent hESC and hiPSC lines. Data from the hESC line H1 and the hiPSC lines 2C6 (from a sporadic PD patient) and SeV6 (Sendai-based, integration-free) are presented. The floor plate based protocol described in FIG. 1d and FIG. 10, was used followed by analysis of FOXA2 (red) expression at day 11 and TH (green)/FOXA2 (red) at day 25 of differentiation.

Similar data were obtained for EBF-1, EBF-3 (FIG. 8c) as well as TTR, a known transcriptional target of FOXA2 in the liver. The data obtained during the development of the present inventions indicated enrichment of several PITX genes in midbrain DA precursor cells. PITX3, a classic marker of midbrain DA neurons, was also robustly expressed at day 25 of differentiation (FIG. 2e). Finally, both midbrain floor plate and DA neuron induction could be readily reproduced in independent hESC and hiPSC lines (FIG. 9). The data demonstrated herein showed that the LSB/S/F8/CHIR protocol as opposed to other tested protocols yields cells expressing a marker profile matching midbrain DA neuron fate.

Figure 10:
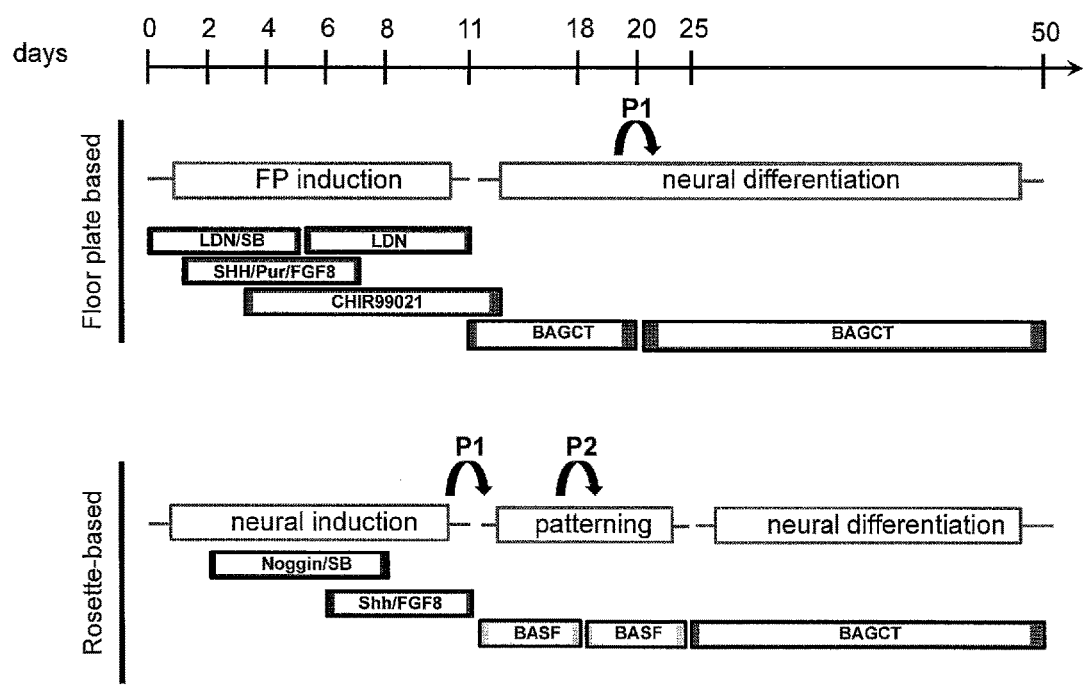
FIG. 10 shows an exemplary schematic summary of the differentiation conditions used for floor plate-derived and rosette-derived DA neuron cultures. Both protocols used dual-SMAD inhibition to accelerate neural fate acquisition. LDN was used for BMP inhibition in the floor plate protocol while the traditional noggin induction was used for rosette cultures. The abbreviations are: LDN: LDN-193189, SB: SB431542, SHH (purmorphamine+SHH C25II), FGF8: FGF8, BAGCT: BDNF+ascorbic acid+GDNF+dbcAMP+TGFβ3. SHH/FGF8 in the rosette protocol used SHH C25I alone in the absence of purmorphamine following the initial recommendation for patterning of rosette-derived DA neuron cultures. Note: Purmorphamine treatment at rosette stage shows toxicity at concentration suitable for patterning floor plate cells. BASF: BDNF+ascorbic acid+SHH/FGF8.

In vitro and in vivo properties of floor plate-derived DA neurons were compared to DA-like neurons obtained via a neural rosette intermediate (FIGS. 10 and 16). Patterning of neural rosettes represents the currently most widely used strategy for deriving DA neurons from hPSCs. Both floor plate- and rosette-based protocols were efficient at generating TH+ neurons capable of long-term in vitro survival (day 50 of differentiation; FIG. 3-1a). However, the percentage of TH+ cells was significantly higher in floor plate-derived cultures (FIG. 3-1b). While TH+ cells in both protocols displayed co-expression of NURR1, floor plate-derived DA neurons co-expressed FOXA2 and LMX1A (FIG. 3-1a,b and 3-2).

Figures 1, 3:
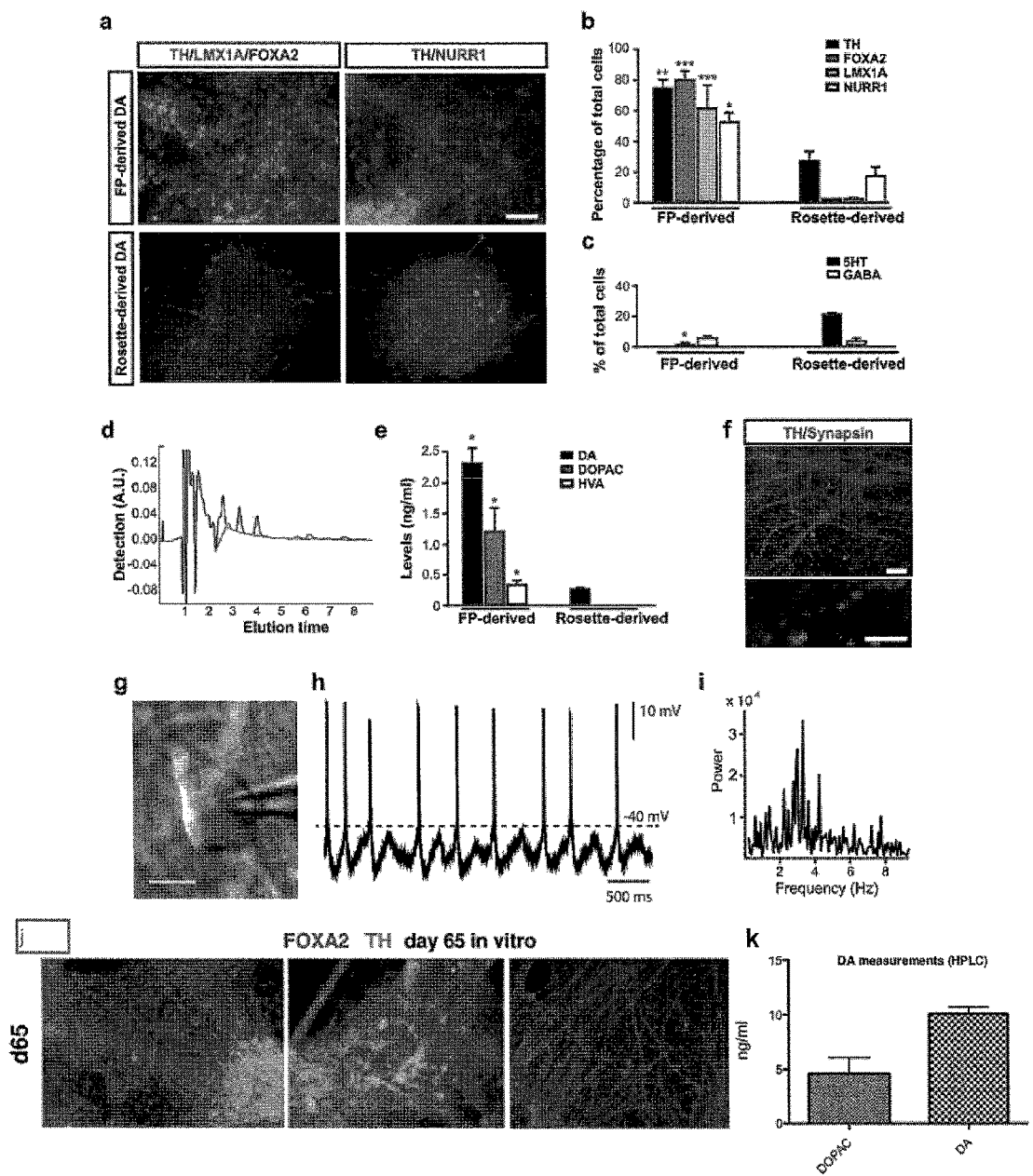
Figures 2, 3:
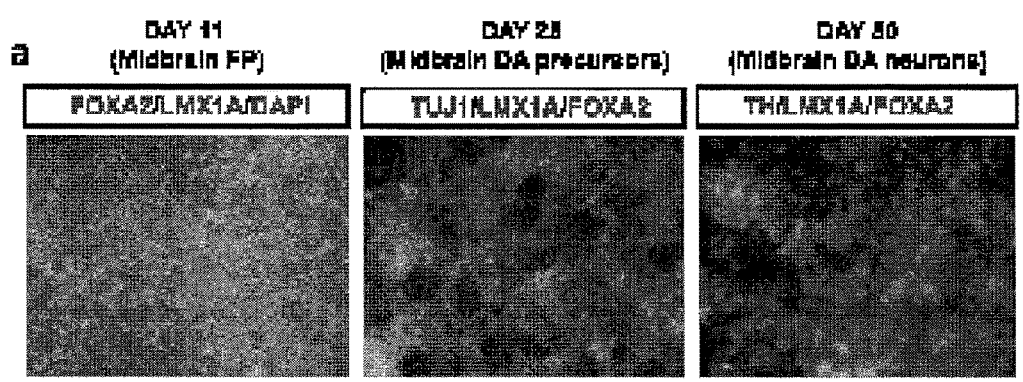

Few GABA and serotonin (5-HT)-positive neurons were observed (FIG. 3-1c). DA, and its metabolites DOPAC and HVA, were present in cultures generated with either protocol, but DA levels were approximately 8 times higher in floor plate cultures (FIG. 3-1d,e). Midbrain DA neurons exhibited extensive fiber outgrowth and robust expression of mature neuronal markers including synapsin, dopamine transporter (DAT), and G-protein coupled, inwardly rectifying potassium channel (Kir3.2, also called GIRK2, expressed in substantia nigra pars compacta (SNpc) DA neurons) (FIG. 3-1f, FIG. 11). SNpc DA neurons in vivo exhibit an electrophysiological phenotype that differentiates them from most other neurons in the brain. In particular, they spike spontaneously at a slow (1-3 Hz) rate. Moreover, this slow spiking is accompanied by a slow, sub-threshold oscillatory potential. After 2-3 weeks in vitro, these same physiological features are displayed by SNpc DA neurons cultured from early postnatal mice. The DA neurons differentiated from hESCs consistently (4/4 tests) displayed this distinctive physiological phenotype (FIG. 3-1g-i).

Maintenance of mDA neurons in vitro at d65 showed TH positive neurons are still expressing FoxA2 and extend long fibers typical for mDA neurons. FIG. 3-1j. DA release measurement by HPLC showed d65 old TH+ neurons are functional in vitro FIG. 3-1k.

In summary, neurogenic conversion of midbrain floor plate precursors and the development of an optimized floor plate midbrain DA neuron differentiation protocol is described herein. Floor plate derived DA neurons were obtained from human ES cells following small molecule based activation of SHH and canonical WNT signaling during early differentiation stages (FIG. 3-2). These hES cells progressed from a FOXA2/LMX1A double positive midbrain floor plate stage, to Tuj1+ immature neurons with co-expression of FOXA2/LMX1A then to mature DA neurons (FIG. 3-2a,b) with robust DA release and electrophysiological properties characteristic of substantia nigra pars compacta (SNpc; A9-type) midbrain DA neurons, including autonomous pacemaking activity (FIG. 3-2c). Surprisingly, this was a highly efficient process with more than half of cells in the culture dish adopting mature midbrain marker profile (see FIG. 3-2b).

VII. Characterization of Floor Plate-Derived Midbrain Dopamine Neurons In Vivo as Engrafted Neurons.

Figure 4:
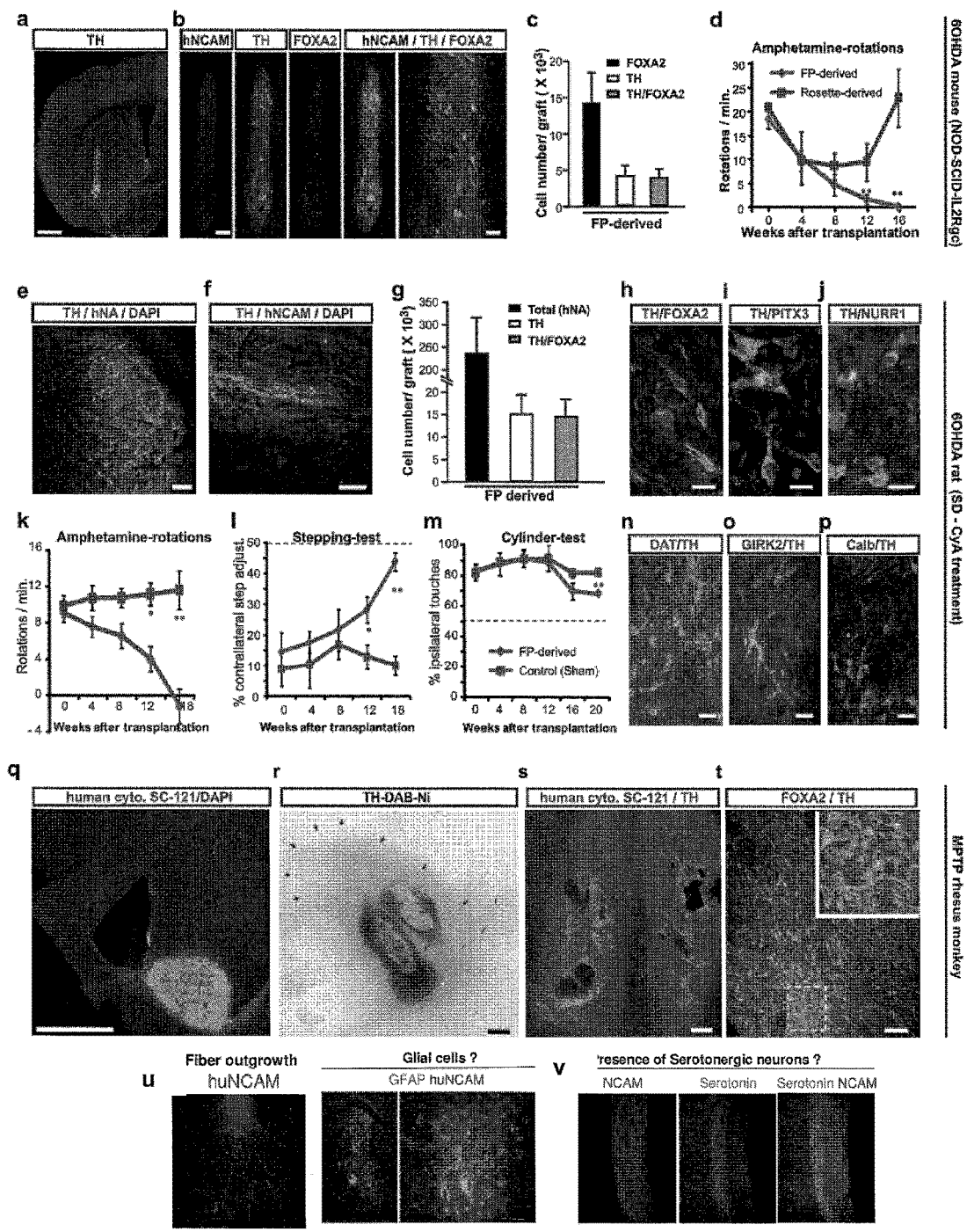
FIG. 4 shows an exemplary in vivo survival and function of floor plate-derived human DA neurons in mouse, rat and monkey PD model host brain. a-d) Transplantation of floor plate-derived DA neurons in 6-OHDA lesioned adult mice (NOD-SCID IL2Rgc null strain). a) TH expression and graft morphology at 4.5 months after transplantation. b) Expression of human specific marker (hNCAM, blue), TH (green), and FOXA2 (red). c) Quantification of FOXA2+, TH+ and double-labeled cells in floor plate-derived grafts (mean±SEM, n=4 at 4.5 months post grafting). d) Amphetamine-induced rotation analysis in floor plate-derived (blue) versus rosette-derived (green) grafts. Scale bars correspond to 500 μm in (a), 100 μm in (b) and 40 μm in (4c). e-p) Transplantation of floor plate-derived DA neurons into 6-OHDA lesioned adult rats. Immunohistochemical analysis for co-expression of TH (green) and the human specific markers (red) hNA. e) and hNCAM (4f). g) Stereological quantification of the number of total (hNA+) cells, TH+ cells and TH+ cells co-expressing FOXA2. The average graft volume was 2.6+/−0.6 mm$^3$). h-j) High power images showing co-expression of TH (green) with midbrain specific transcription factors FOXA2, PITX3 and NURR1 (red). k-m) Behavioral analysis of animals treated with floor plate-derived DA neuron grafts versus sham-treated animals. k) Amphetamine-induced rotational asymmetry. l) stepping test: measuring forelimb akinesia in affected versus non-affected side. m) Cylinder test: measuring ipsilateral versus contra-lateral paw preference upon rearing. Grafted animals showed significant improvement in at least three tests ($p<0.01$ at 4.5-5 month; n=4-6 each). n-p) Immunohistochemical analysis for TH (green) and co-expression (red) with DAT (n), GIRK2 (o) and calbindin (p). Significance levels (panels d, k, l, m) are: ** $p<0.01$; $p<0.05$). Scale bars correspond to 200 μm in (e), 50 μm in (f), 20 μm in (h-j) and 40 μm in (n-p). q-t) Transplantation of floor plate-derived DA neurons into adult 1-methyl-4-phenyl-1,2,3,6-tetrahydropyridine (MPTP) lesioned rhesus monkey. q) Overview of representative graft site at 1 month after transplantation marked by expression of human specific cytoplasm marker SC-121 (green). r) TH expression in graft with a surrounding halo of TH+ fibers (arrows). s) Analysis of co-expression of SC-121 (red) with TH (green) in graft core. t) Co-expression analysis of FOXA2 (red) in TH+ neurons (green). Scale bars correspond to 2 mm for (q), 500 μm for (r), 200 μm for (s), and 50 μm for (t). u) graft derived fiber outgrowth (huNCAM+) into the host striatum. v) Graft-derived cells do not differentiate into glial cell. However, grafts contained a few serotonergic fibers in addition to the TH+ cell population.
Figure 12:
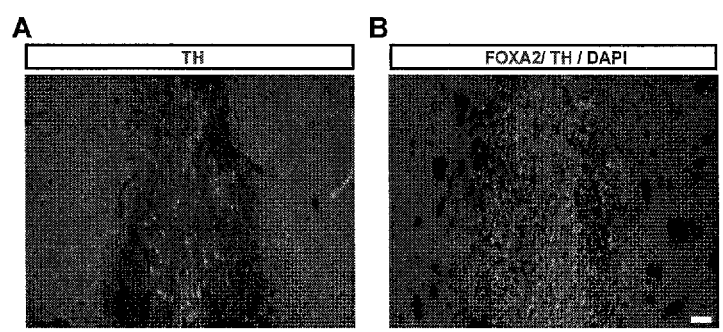
FIG. 12 shows an exemplary immunohistochemical analysis of short-term (6 weeks) in vivo survival studies in adult intact (unlesioned) mouse striatum (NOD-SCID IL2Rgc null strain). Analysis of floor plate derived grafts (day 25 cells; 150×10$^3$ cells/animal). a) Representative image of graft core showing TH+ cells surrounded by TH+ host fibers. An average of 6,200 TH+ cells (n=3) were present in the graft at 6 weeks after transplantation. b) FOXA2 expressing cells (red) were only found in the graft but not in the surrounding host striatum demonstrating graft origin and midbrain identity of the cells. Nearly all TH+ neurons (green) co-expressed FOXA2 (red). However, a considerable proportion of FOXA2+ cells did not co-express TH suggesting that these cells have not yet acquired a mature DA phenotype or represent another FOXA2+ neuronal population negative for DA neuron markers. Scale bars correspond to 50 µm.
Figure 13:
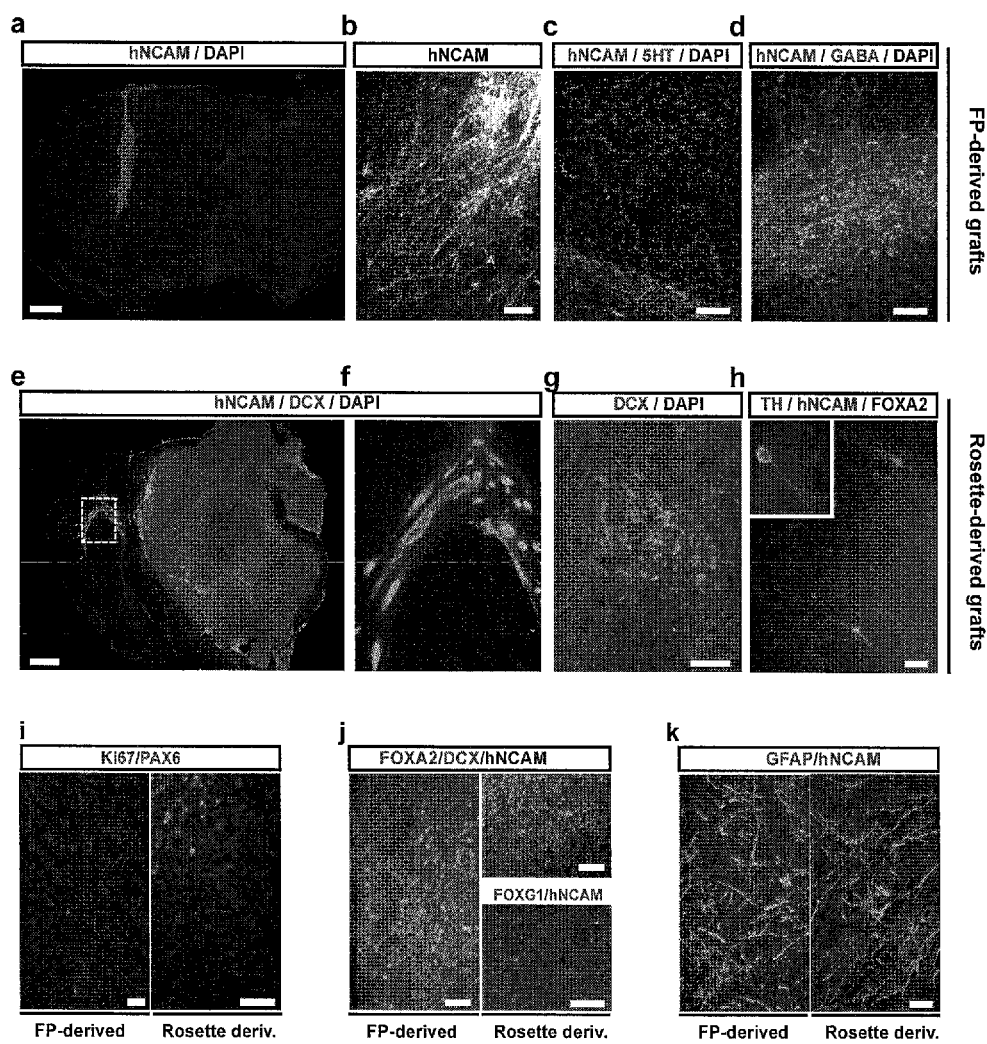
FIG. 13 shows an exemplary histological analysis of long-term (4.5 months) grafted 6-OHDA lesioned mice (NOD-SCID IL2Rgc null strain) comparing behavior of floor plate- versus rosette-derived grafts. Analysis of floor plate-derived grafts. a) Example of one of the largest floor plate-derived grafts. The graft retains a well circumscribed hNCAM+ (red) cytoarchitecture. b) Robust hNCAM+ fiber outgrowth was observed at graft periphery. c) Serotonergic (5-HT+) fibers (green) in graft are largely negative for hNCAM (red) suggesting host origin. d) GABAergic neurons and fibers (green) in graft. Analysis of rosette-derived grafts: e) Neural overgrowth with compression of host brain tissue. The majority of cells were positive for both NCAM (red) and DCX (green) suggesting neuronal fate. f) NCAM+/DCX+ fibers extended to the non-transplanted contra-lateral side of the brain. g) Within the graft core multiple DCX+ clusters were observed. h) Few TH+ cells (green) and fibers were observed at graft periphery and nearly all rosette-derived TH+ cells in vivo were negative for FOXA2 (blue). Immunohistochemical analysis of floor plate-derived versus rosette-derived grafts at 4.5 months. Representative images are presented for expression of the proliferation marker Ki67 (red) and the neural precursor marker PAX6 (green) (i), expression of FOXA2/DCX (j), FOXG1/hNCAM (j, inset), and the astrocytes marker GFAP (green) (k). Scale bars correspond to 500 µm in (a), 50 µm in (b-d), to 500 µm in (e), 50 µm in (g-h), 50 µm in (i), 40 µm in (j) and 20 µm in (k).

The following example describes using exemplary methods of the present inventions for use in therapeutic cell replacement. One major challenge in the field is the ability to generate hPSC-derived midbrain DA neurons that functionally engraft in vivo without the risk of neural overgrowth or inappropriate differentiation into non-midbrain neurons or develop teratomas. Based on fetal tissue transplantation studies, the inventors' contemplated that the time of cell cycle exit, marked by expression of NURR1, may be a suitable stage for grafting (approximately day 25 of differentiation, FIG. 2). Initial studies using day 25 cells in non-lesioned adult mice showed robust survival of hPSC-derived FOXA2+/TH+ neurons at 6 weeks after transplantation (FIG. 12). Survival of FOXA2+/TH+ cells long-term in Parkinsonian hosts without resulting in neural overgrowth was tested. To this end, 6-hydroxy-dopamine (6-OHDA) lesions (Tabar, et al. Nature Med. 14:379-381 (2008), herein incorporated by reference) were made in NOD-SCID IL2Rgc null mice, a strain that efficiently supports xenograft survival with particular sensitivity for exposing rare tumorigenic cells (Quintana, et al. Efficient tumour formation by single human melanoma cells. *Nature* 456:593-598 (2008), herein incorporated by reference). Both floor plate- and rosette-derived DA neuron cultures were grafted (150×10$^3$ cells/animal) without prior purification in order to reveal potential contaminating cells with high proliferative potential. Four and a half months after transplantation floor plate-derived DA neuron grafts showed a well-defined graft core composed of TH+ cells co-expressing FOXA2 and the human specific marker hNCAM (FIG. 4a-c). Functional analysis showed a complete rescue of amphetamine-induced rotation behavior. In contrast, rosette-derived neuronal grafts showed few TH+ neurons, did not produce a significant reduction in rotation behavior (FIG. 4d) and displayed massive neural overgrowth (graft volume>20 mm$^3$; FIG. 13). Extensive overgrowth of rosette-derived neuronal cells used in grafting as reported herein was comparable to previous work with rosette-derived DA grafts from the inventors' group (Kim, et al miR-371-3 Expression Predicts Neural Differentiation Propensity in Human Pluripotent Stem Cells. Cell Stem Cell 8:695-706 (2011), herein incorporated by reference) and others (Hargus, et al. *Proceedings of the National Academy of Sciences of the United States of America* 107:15921-15926 (2010), herein incorporated by reference). The overgrowth was likely due to the longer survival periods (4.5 months versus 6 weeks), lack of FACS purification prior to transplantation and choice of NOD-SCID IL2Rgc null host. The number of proliferating Ki67+ cells was minimal in floor plate-derived grafts (<1% of total cells), while rosette-derived grafts retained pockets of proliferating neural precursors. Neural overgrowth is thought to be caused by primitive anterior neuroectodermal cells within the graft (Elkabetz, et al. *Genes Dev.* 22:152-165 (2008); Aubry, et al. *Proc. Natl. Acad. Sci. U.S.A.* 105:16707-16712 (2008), herein incorporated by reference). This hypothesis was supported by the expression of the forebrain marker FOXG1 in rosette- but not floor plate-derived grafts. A small percentage of astroglial cells were present in both floor plate- and rosette-derived grafts, though most GFAP+ cells were negative for human markers indicating host origin (FIG. 13).

Results in NOD-SCID IL2Rgc null mice described herein demonstrated robust long-term survival of FOXA2+/TH+ neurons, complete reversal of amphetamine-induced rotation behavior and lack of any signs of neural overgrowth. However, some of these outcomes could be attributable to the specific use of NOD-SCID IL2Rgc null mice. To test this hypothesis, floor plate-derived DA neuron cultures (250×10$^3$ cells) were transplanted in adult 6-OHDA lesioned rats immunosuppressed pharmacologically using cyclosporine A. Five months after transplantation graft survival was robust (FIG. 4e-h) with an average of more than 15,000 TH+ cells co-expressing FOXA2 (FIG. 4g), and human nuclear antigen (hNA) (FIG. 4e); TH+/hNCAM+ fibers emanated from the graft core into the surrounding host striatum (FIG. 4f). In addition to FOXA2, TH+ cells expressed midbrain DA neuron markers PITX3 and NURR1 (FIG. 4h-j). Behavioral analyses showed complete rescue of amphetamine-induced rotational asymmetry, in contrast to sham-grafted animals that did not show improvements (FIG. 4k). Grafted animals also showed improvements in the stepping test (FIG. 4l) measuring forelimb akinesia and in the cylinder test (FIG. 4m), assays that do not depend on pharmacological stimulation of the DA system. The late onset of recovery (approximately 3-4 months after transplantation) is expected for human DA neurons and depends on the rate of in vivo maturation such as the levels of DAT expression (FIG. 4n). The presence of TH+ cells expressing Kir3.2 channels (GIRK2) or calbindin indicate that both SNpc (A9) and ventral tegmental area (A10) DA neurons are present in the graft (FIG. 4o,p).

Figure 14:
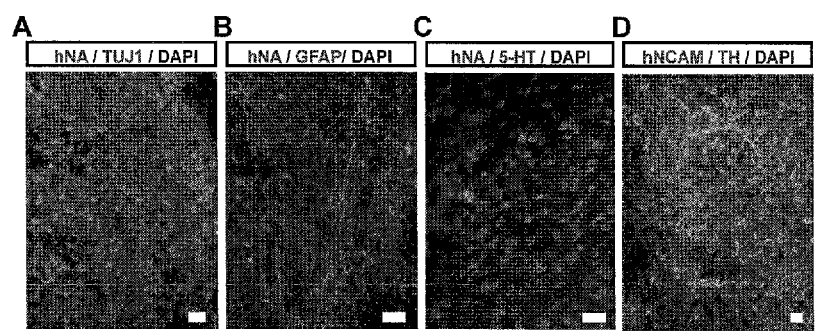
FIG. 14 shows an exemplary histological analysis of long-term (5 months) grafted 6-OHDA lesioned SD rats. a) The large majority of hNA+ (red) cells expressed Tuj1 (green) indicating neuronal fate identity. b) GFAP+ fibers (green) within the graft did not co-express hNA (red) suggesting host origin. c) A few human serotonergic (5-HT+) cell bodies (green) were observed while most serotonergic fibers were host-derived similar to the data in mouse host (FIG. 13C). d) Additional example of TH+ neurons (green) within graft characterized for expression of hNCAM (red) to confirm human identity of cells in host brain. Scale bars correspond to 25 µm in panels.

As in mice (FIG. 13), serotonergic and GABAergic cells were rare (<1% of total cells) in rat cells, as were the mostly host-derived GFAP+ glial cells (7% of total cells; FIG. 14). While few serotonin+ neurons were detected in the graft, hNCAM-negative cells were observed that were likely host-derived serotonergic fibers (FIG. 14).

Engraftment of floor-plate derived DA neurons in mice, rats, and monkeys demonstrated the surprising recovery of neuronal function in rodent and primate species. Short-term (6 weeks) survival assays were extended for surprisingly long-term survival for up to 5 months after transplantation into the mouse striatum of 6OHDA lesioned and immuno-compromised host mice. In fact, a direct comparison of a traditional, rosette-based method of making DA neurons (Perrier, et al. Proc Natl Acad Sci USA 101, 12543-8 (2004)) compared to the novel floor plate based DA neuron differentiation protocol described herein, showed that floor plate derived DA neurons were capable of long-term DA neuron engraftment while rosette-based neurons were not (FIG. 4a-c).

In particular, a robust induction of behavioral recovery in amphetamine-induced rotations in 6-OH lesioned mice transplanted with floor-plate (fp)-derived (blue line) neurons and rosette-derived (red line) DA neurons (FIG. 4d) showed that fp derived neurons had higher recovery rates. Mice grafted with floor-plate derived DA neurons showed almost complete recovery in amphetamine scores. Animals grafted with rosette-derived DA neurons showed less behavioral improvement and some over time reversed to initial high rotation numbers.

Robust graft function was also found in the 6OHDA lesioned rat model. The rat, unlike the PD mouse, allows for more complex behavioral assays and addresses DA neuron survival in a xenografting setting following pharmacological immunosuppression (a therapy more closely mimicking human grafting protocols). Excellent graft survival, evidence of DA fiber outgrowth and maintenance of midbrain specific transcription factor expression confirmed long-term survival of floor-plated derived neurons expressing authentic midbrain DA neuron markers (FIG. 4e-j). A battery of functional assays showed significant improvement in both drug induced (amphetamine-induced rotations) and in spontaneous behavioral tests (cylinder and stepping test).

The results demonstrated herein showed excellent graft survival and behavioral outcome in two independent murine models. However, the number of DA neurons required in a mouse or rat brain represents a small fraction of the larger number of cells needed for engrafting in primates and humans. To test the scalability of this protocol, performed pilot grafting studies were done in two adult MPTP lesioned rhesus monkeys.

Additionally, it was not initially known whether the methods and cells described herein would also restore neuronal function in a primate, information which might be used in support of enablement for use of these methods and cells in humans. Thus, an initial set of studies was performed in at least 2 monkeys to test short-term (4-6 weeks) in vivo survival and maintenance of midbrain DA neuron phenotype in the primate brain. Those studies described herein, showed robust survival of TH/FOXA2 positive midbrain DA neurons and evidence of re-innervation of the host striatum (FIG. 4q-t). Grafting larger numbers of cells, similar to those estimated in the number range required for future human grafting studies, resulted in robust midbrain DA neuron survival. In addition to these short-term data, a set of longer-term studies in rhesus monkeys was done evaluating 3 month-survival of cells and an optimized immunosuppression regimen of CellCept, Prograf, and Prednisone daily (used as triple therapy in combination). Surprisingly, robust 3 month survival of human ES derived midbrain DA neurons in the primate brain was discovered along with a greatly reduced inflammatory host reaction to the grafts compared to the strong host microglia response observed in the initial grafting study (see, FIG. 15).

Specifically, methods relating to the monkey studies included, batches of 50×10$^6$ transplantable DA neuron precursors were obtained by day 25 of differentiation using the floor plate-based protocol. Classic dose was 3 mg MPTP-HCL injected into the carotid artery (range 0.5-5 mg). This was followed by systemic injection of MPTP 0.2 mg/kg IV of MPTP. Cells were injected at three locations (posterior caudate and pre-commissural putamen) on each side of the brain (6 tracts in total, 1.25×10$^6$ cells/tract), and the animals were immunosuppressed with cyclosporine-A. One side of the brain was injected with DA precursors from a GFP expressing subclone of H9, while the other side was engrafted with cells derived from unmarked H9 cells. Results showing engraftment of neurons in rhesus monkeys with continued FOX2A expression and TH production are shown in FIG. 4q-t. One month after transplantation, robust survival of midbrain DA neurons was observed based on expression of GFP (FIG. 15) and the human specific cytoplasmic marker (SC-121) (FIG. 4q). Each graft core was surrounded by a halo of TH+ fibers extending up to 3 mm into the host (FIG. 4r). The graft cores were composed of TH+ neurons co-expressing SC-121 (FIG. 4s) and FOXA2 (FIG. 4t). SC-121 and GFP negative areas within the graft contained Iba1+ host microglia (FIG. 15) indicating incomplete immunosuppression.

In summary, engraftment of novel DA neuronal cell population in primates, i.e. adult MPTP (3 mg of MPTP-HCL (1-methyl-4-phenyl-1,2,3,6-tetrahydropyridine; ranging in concentration from 0.5-5 mg MPTP-HCl) lesioned rhesus monkeys containing a severe >95% loss of endogenous midbrain DA neurons. MPTP exposure caused observable changes and symptoms similar to Parkinson's disease in humans.

In summary, a novel floor plate-based hPSC differentiation protocol was discovered that faithfully recapitulates midbrain DA neuron development. Access to cells with the cardinal features of midbrain DA neurons will enable a broad range of biomedical applications such as basic developmental studies, high-throughput drug discovery and PD-iPSC based disease modeling. Importantly, this study finally established a means of obtaining a scalable source of FOXA2+/TH+ neurons for neural transplantation—a major step on the road towards considering a cell based therapy for PD.

Furthermore, derivation of authentic midbrain DA neurons from hESCs showed excellent in vivo performance (see FIG. 4), and DA neuron yield, at the time of grafting (approximately 40% mature neurons in the population at Day 25-30 of differentiation, that exceeded the percentages obtained following dissection of human fetal ventral midbrain tissue (typically approximately 10%) (Sauer, et al., Restor. Neurol. Neurosci. 2:123-135 (1991)).

The following are brief descriptions of materials and methods for use in evaluating two main parameters after engraftment: duration of survival and extent of behavioral assessments. For short term studies e.g. aiming at confirming cell survival or phenotypic composition, behavioral assessments are contemplated and the animals will be tested about 4-8 weeks post grafting for survival. Long-term studies will include behavioral assessment post grafting and animal survival for at least 5 months following grafting. When analyzing enhancement strategies, such as PSA-NCAM modifications, behavioral assessment are contemplated to include more complex parameters such as the staircase test for skilled forelimb use.

Exemplary protocols for assessment of in vivo performance has at least four main components and includes the following: i—Lesion Induction, ii—Core Behavioral Analysis, iii Grafting, and iv—Tissue Analysis. Although these procedures were used on rats, in some embodiments these procedures may be use on other species.

i—Lesion Induction.

Unilateral injections of 6-hydroxydopamine (6-OHDA) in the median forebrain bundle (MFB) is one standard approach for induction of Parkinson-like symptoms in rats. 6-OHDA is a neurotoxin that gets retrogradely transported via the nigrostriatal pathway in the MFB back to the substantia nigra whereby it results in neuronal cell death via impairment of mitochondrial respiratory enzymes. Targeted neurons include the A9 dopaminergic neurons within the substantia nigra compacta (SNC) as well as the A10 neurons in the ventral tegmental area. This lesion model is widely studied and accepted as an excellent pre-clinical model for the study of the neurochemical and behavioral consequences of advanced PD as it results in extensive unilateral depletion of dopamine within the caudate-putamen complex (CPU). The behavioral consequences are also well described and include spontaneous and drug-induced rotations as well as impairment in limb use (see below). Bilateral models of Parkinsonism may better mimic human disease but they result in adipsia and aphagia in rats.

The procedure was performed in anesthetized animals (Ketamine/xylazine) via stereotactic injection in 2 sites along the median forebrain bundle. The efficiency of complete lesion induction is highly dependent on the experience of the operator and during development of the present inventions ranged from 60-80%. The animals were allowed to recover and then subjected to a battery of behavioral tests starting 2 weeks after surgery.

ii—Core Behavioral Analysis.

Behavioral analysis is initiated 2 weeks following surgery and continues after transplantation until the animal is sacrificed. Its purpose is 1) to establish that the lesion is stable and complete and that the animal has not exhibited spontaneous reversal of the symptoms, a phenomenon that has been shown in partially lesioned animals, 2) to demonstrate the impact of transplantation of dopamine neurons on established behavioral parameters.

a—Rotational Behavior.

Rats are observed for spontaneous rotations and for D-amphetamine-induced (ipsilateral) rotations (10 mg/kg). A threshold of >6 rotations per min is required as an indicator for a significant lesion. Apomorphine-induced rotations can also be analyzed but positive results are contemplated to require >80-90% depletion of dopamine innervation in the caudate-putamen and are less consistent in MFB lesions, in comparison to CPU lesions. Three sets of data are obtained at 2 week intervals and averaged. Rats with a rotation score of <6 are not included in the studies.

b—Stepping Test.

This is a test for forelimb akinesia. A rat is held with one hand by the experimenter fixing the hindlimbs (slightly raising the torso) and with the other hand fixing the forelimb that is not to be monitored. In this way the other forepaw has to bear the weight. The rat is moved slowly sideways in both forehand and backhand positions. The number of adjusting steps for both directions and both paws are counted.

c—Cylinder Test.

This is a test for forelimb use asymmetry. The rat is placed in a transparent cylinder. During a time period of 5 min the rearing behavior of the rat is scored. The behavior is analyzed during rearing and landing. The percentage of simultaneous and asymmetric use of the paws during these movements is determined. This can be carried out via a computerized video monitoring system. Negative results on these tests were known to correlate with dopamine depletion and results were shown to be improved following restorative grafting as described herein.

iii—Grafting.

Animals receive stereotactic injections of dopamine neurons into the striatum, at 3 weeks following the Parkinsonism-inducing lesions, and if behavioral testing confirms an adequate lesion. The coordinates for injection are widely established. Following grafting, the same set of behavioral tests is performed bimonthly for variable durations (on average 5 months are required to achieve stable behavioral recovery).

iv—Tissue Analysis.

Animals are euthanized and perfused. The brains are sectioned and processed for immunohistochemistry and stereological analysis. Antibodies include TH, FoxA2, Pitx3, Nurr1, Lmx1a, Girk2, DAT for dopamine neuron identity and function; 5-HT to identify Serotonergic neurons; Human NCAM or human nuclear antigen for human identity; Nestin, Sox2 for neural precursors; Ki-67 for proliferation; Oct4, Nanog for pluripotency markers; alpha-fetoprotein; myosin; cytokeratin for multi-lineage markers to rule out teratomas formation. Quantitative parameters include graft volumes (Cavalieri estimator), total cell counts and dopaminergic cell counts (using TH/FoxA2 double labeling neurons) and Proliferative index (% Ki67+). Antibodies listed are commercially available and used during the development of the present inventions.

In some embodiments, Sprague-Dawley (SD) rats are contemplated for use in order to better model the human situation. SD rats will receive daily intraperitoneal injections of cyclosporine (15 mg/kg) starting one day prior to grafting until sacrifice. With long term injections of the aqueous from of cyclosporine (Neoral, an oral solution used in humans) there was negligible morbidity.

In some embodiments, exemplary methods for scaling up mDA neuron cultures are provided, see, Table 9. In particular embodiments, such methods are contemplated for use in producing GMP level cultures for clinical use.

Assessment Parameters.

In vivo testing was contemplated for use in short term and long-term methods of graft effectiveness. Results obtained during the development of the present inventions showed tissue characterization identical in both cases, with an expectation of increased proportion of TH+ cells in long term survivors, due to differentiation of grafted precursors.

On average when 15,000 TH+/FoxA2+ neurons per 250,000 cells were transplanted the animals survived 5 months post grafting. Significantly less double labeled cells survived and counted in short survivals. Thus contemplated in vivo yields, as shown in Table 9 are conservative estimates. Exemplary parameters used to assess a Pass/Fail status for graft composition results are shown in Table 10.

In long-term grafts, behavioral assessment is an essential component of the performance of hES line products. Guidelines that define loss of function and recovery were best described for the amphetamine rotations whereby a robust graft should normalize the behavior and occasionally result in contralateral movement due to DA imbalance. The limits listed in Table 11 are exemplary guidelines as determined during the development of the present inventions.

In some embodiments, cell sources for use in differentiation methods of the present inventions include but are not limited to WA09, ACT (M09), Bio-Time and Roslin cell lines. In some embodiments, cell sources for use in differentiation methods of the present inventions include but are not limited to GMP grade lines. In some embodiments, cell sources for use in differentiation methods of the present inventions include but are not limited to production of mature DA neurons for use in short term engraftment survival analysis. In some embodiments, cell sources for use in differentiation methods of the present inventions include but are not limited to production of mature DA neurons for use in engraftment experiments that include behavioral assessments. Controls will consist of the Research Grade WA09 and a sham saline group. Statistical analyses will use ANOVA with the Dunnett post-hoc test.

A. Complex Behavioral Assays for Assessment of Degree of Striatal Reinnervation.

Standard behavioral tests (as described herein) exhibited a direct correlation with the number of surviving dopamine neurons within the graft. In rats treated with mature DA neuronal cells of the present inventions, behavior tests show maximum recovery with an estimate of about 30% DA neuron recovery which is required to reduce amphetamine-induced rotations. Thus, once a threshold for survival of DA neurons in the host is reached (an estimate of 800-1200 DA neurons in the rat model), it may be difficult to distinguish behavioral differences reflecting enhancement strategies. A microtransplantation approach was described that results in placement of multiple small grafts throughout the striatum, as opposed to large grafts. While controlling for the total number of DA cells transplanted, differences were observed in behavioral outcomes when comparing 2 groups: Rats with multiple small grafts exhibited earlier and more extensive behavioral recovery in drug-induced rotations and the stepping tests when compared to animals with a single large graft and the same number of DA neurons and the same amount of dopamine release. Surprisingly, there was a distinct difference in forelimb skilled use, whereby animals with small widely distributed grafts exhibited improvement while rats bearing standard grafts did not. Skilled forelimb use is considered a task that requires spatial and temporal control over DA release, and thus proper connectivity between the grafted neurons and the host striatum. Thus in some embodiments, use of mature DA neurons of the present inventions in engraftment procedures resulted in the recovery of forelimb use. Accordingly in some embodiments, mature DA neurons of the present inventions are administered to one location of the striatum. In other embodiments, mature DA neurons of the present inventions are administered to at least 2 or more locations within the striatum.

B. Skilled Forelimb Use (or the Staircase) Test.

The forelimb test analyzes forelimb reaching and grasping and was performed pre- and post-lesion and post-transplantation. Animals were food deprived for 48 hours prior to the test, and tested daily for 5 days pre-lesion then twice after lesion at 3 week interval. Following grafting, the test is repeated 2 more times, at months 3 and 5. Animals were placed in a plexiglass chamber equipped with a double staircase. Food pellets are placed on 5 steps bilaterally for pre-graft testing, and unilaterally (on the affected limb side, contralateral to the rotation) after grafting. The animals are tested over a set time frame (e.g. 10 minutes) and the numbers and ratio of pellets that were eaten (successful reach) and the pellets that were taken were calculated and compared to the individual animal's pre-lesion performance. There were several variations of this test involving the number of iterations and the timing of the test.

VIII. Differentiated Cells by Using Methods Described Herein Showed Electrophysiology Responses Similar to DA Cells In Situ.

The following example describes using exemplary methods of the present inventions for determining the functional capability of midbrain DA neurons resulting from differentiation by methods described herein. Substantia nigra pars compacta (SNpc) DA neurons in vivo exhibit an electrophysiological phenotype that differentiates them from most other neurons in the brain. In particular, they spike spontaneously at a slow (1-3 Hz) rate. Moreover, this slow spiking is accompanied by a slow, sub-threshold oscillatory potential. After 2-3 weeks in vitro, these same physiological features are displayed by SNpc DA neurons cultured from early postnatal mice. In order to determine whether the mDA neurons of the present inventions showed a comparable electrophysiological phenotype, the mDA neurons of the present inventions were tested for their electrical response signature. Midbrain DA neurons of the present inventions on day 80-100 of culture were tested by single cell recording. These mDA neurons differentiated from hESCs consistently (4/4 tests) displayed this distinctive physiological phenotype by showing specific autonomous spiking behavior and oscillatory membrane potential changes (FIG. 3g-i). This behavior is known as autonomous pacemaking activity and a specific property of midbrain DA neurons and in particular the subtype of midbrain dopamine neurons most relevant for Parkinson's disease (substantia nigra type midbrain DA neurons).

Electrophysiological measurements are contemplated for use in acute slice preparations, i.e. from biopsies of engrafted areas. In one embodiment, A9- versus A10 type graft-derived DA neurons will be identified in vivo based on testing for the autonomouse pacemaking activity that is specific to A9-type dopamine neurons that are most affected in PD. In other words, A10 type neurons do not have pacemaking activity Conditions were established for the in vivo recording of human pluripotent stem cell derived DA neurons in acute slice preparations, see, FIG. 26. Specifically, grafted human DA neurons derived from pluripotent stem cells were measured for and discovered to have electrophysiological features typical of those seen in mouse substantia nigra pars compacta (SNpc), FIG. 26A where the top view shows reconstruction of a pacemaking neuron in the graft region. Bottom shows an exemplary photomicrograph of a brain slice taken from the rat into which the hES-derived neurons were injected 9 months prior; the graft is outlined; a higher magnification image is shown inset at the bottom. The slice was processed for tyrosine hydroxylase which shows up as white, FIG. 26B. Further, the top view shows an exemplary cell-attached patch recording from a putative DA neuron in the graft; Bottom shows an exemplary whole cell recording from the same cell. Recordings were made in the presence of glutamate and GABA receptor antagonists (50 µM AP5, 10 µM CNQX and 10 µM GABAzine) to eliminate synaptic input. These recordings demonstrated that the PS-derived neurons were autonomous pacemakers with normal intrasomatic voltage trajectories. Another neuron recorded in a graft sample had similar properties, FIG. 26C. For comparison, cell-attached and whole cell recordings from a dopaminergic neuron in SNpc of an adult mouse are shown. Abbreviations (CTx=cortex, STr=striatum, SNpc=substantia nigra pars compacta, DA=dopaminergic). This data shows in vivo functional studies in grafted rat striatum months after transplantation. Thus in some embodiments, in vivo functional studies on grafted tissue demonstrates recovery of substantia nigra pars compacta (SNpc).

IX. Directed Differentiation of PINK1 Mutant Genetic PD-iPS Cells (PINK1 Mutation) into DA Neurons Revealed Parkinson-Like Abnormalities in the Mature DA Neurons.

This example described the discovery that large populations of midbrain DA neurons developed with characteristics of a PD patient's neurons when a PD patient's cell line, i.e. PINK1 mutant PD-iPSC cell, obtained in a manner that did not result in the destruction of an embryo, were used as the cell population for obtaining FOXA2/LIM1XA/TH+ DA neurons of the present inventions.

In one embodiment, the inventors' contemplate isolating a starting cell population from a patient for use in the methods of making authentic DA neurons in vitro, where the patient has a symptom of Parkinson's disease (PD), for the potential advantage of using the treated cells in in vitro tests for 1) observing differentiation or functional abnormalities compared to authentic DA neurons from humans not having a neurological symptom, then 2) using an observed abnormality for developing a therapeutic treatment for reversing that abnormality and 3) treating the patient with the therapeutic treatment for reducing, i.e. reversing, a symptom of Parkinson's disease.

In one embodiment, the inventors' contemplate isolating a starting cell population from the same patient for deriving authentic DA neurons for use in transplantation treatment, where the patient has a symptom of Parkinson's disease (PD), for the potential advantage of reducing immunological rejection, i.e. transplantation rejection. In other embodiments, reduction of transplantation rejection is contemplated by using a beginning cell source isolated from a human whose Major Histocompatibility Antigens (MHC) match (ie. Twin) or a human having an acceptable MHC tissue match for transplantation (such as a relative to the patient or an unrelated human expressing overlapping MHC molecules.

A. Directed Differentiation Showed that Genetic PD-iPS Cells PINK1 Cells Contained the Capability to Develop into Midbrain Like DA Neurons.

Figure 20:
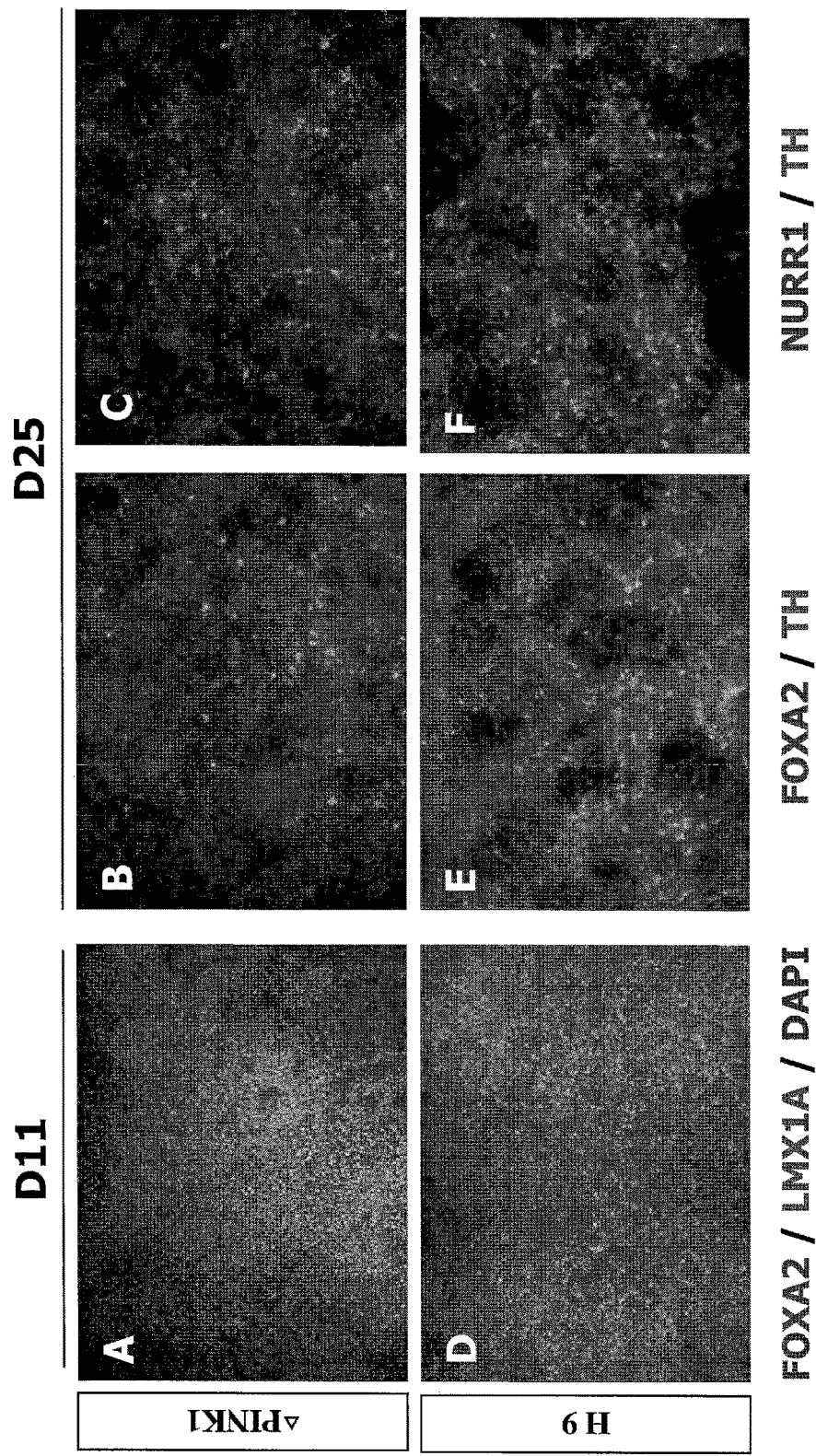
FIG. 20 shows an exemplary comparable differentiation potential towards midbrain DA neuron fate of PINK1 mutant PD-iPS cells versus wild-type hES (or iPS) cells. PINK1 Q456X mutant PD-iPSC line was differentiated using the novel floor-plate based midbrain DA neurons methods of the present inventions yielding midbrain differentiation profiles comparable to those obtained from H9 line. A-C) Immunocytochemical analysis of PINK1 mutant PD-iPSC line at day 11 of differentiation (midbrain precursor stage) for FOXA2 (red), LMX1A (green) and DAPI (blue) (A), day 25 of differentiation (early postmitotic DA neuronal stage) for FOXA2 (red) and TH (green) (B) and for NURR1 (red) and TH (green) (C). D-F) Same set of immunocytochemical analyses performed using H9 derived cells at day 11 of differentiation for FOXA2 (red), LMX1A (green) and DAPI (blue) (D), at day 25 of differentiation for FOXA2 (red) and TH (green) (E) and for NURR1 (red) and TH (green) (F).

See, FIGS. 20-25. A PINK1 Q456X mutant PD-iPSC line was differentiated using the novel floor-plate based midbrain DA neuron protocol (method) described herein which yielded midbrain DA neurons that expressed differentiation profiles comparable to those obtained from the novel floor-plate based midbrain DA neuron protocol differentiated H9 line. (FIG. 20). This example described the discovery that large populations of midbrain DA neurons developed with characteristics of a PD patient's neurons when a PD patient's cell line, i.e. PINK1 mutant PD-iPSC cell, obtained in a manner that did not result in the destruction of an embryo, were used as the cell population for obtaining FOXA2/LIM1XA/TH+ DA neurons of the present inventions.

PINK1 Q456X mutant PD-iPSC line was differentiated using the novel floor-plate based midbrain DA neuron protocol (method) of the present inventions which yielded midbrain differentiation profiles comparable to those obtained from the iPSC H9 line. A-C) Immunocytochemical analysis of PINK1 mutant PD-iPSC line at day 11 of differentiation (midbrain precursor stage) for FOXA2 (red), LMX1A (green) and DAPI (blue) (A), day 25 of differentiation (early postmitotic DA neuronal stage) for FOXA2 (red) and TH (green) (B) and for NURR1 (red) and TH (green) (C). D-F) Same set of immunocytochemical analyses performed using H9 derived cells at day 11 of differentiation for FOXA2 (red), LMX1A (green) and DAPI (blue) (D), at day 25 of differentiation for FOXA2 (red) and TH (green) (E) and for NURR1 (red) and TH (green) (F).

B. Genetic PD-iPSC Expressed a PD Like Phenotype of Protein Aggregation. FIGS. 21-24.

Figure 21:
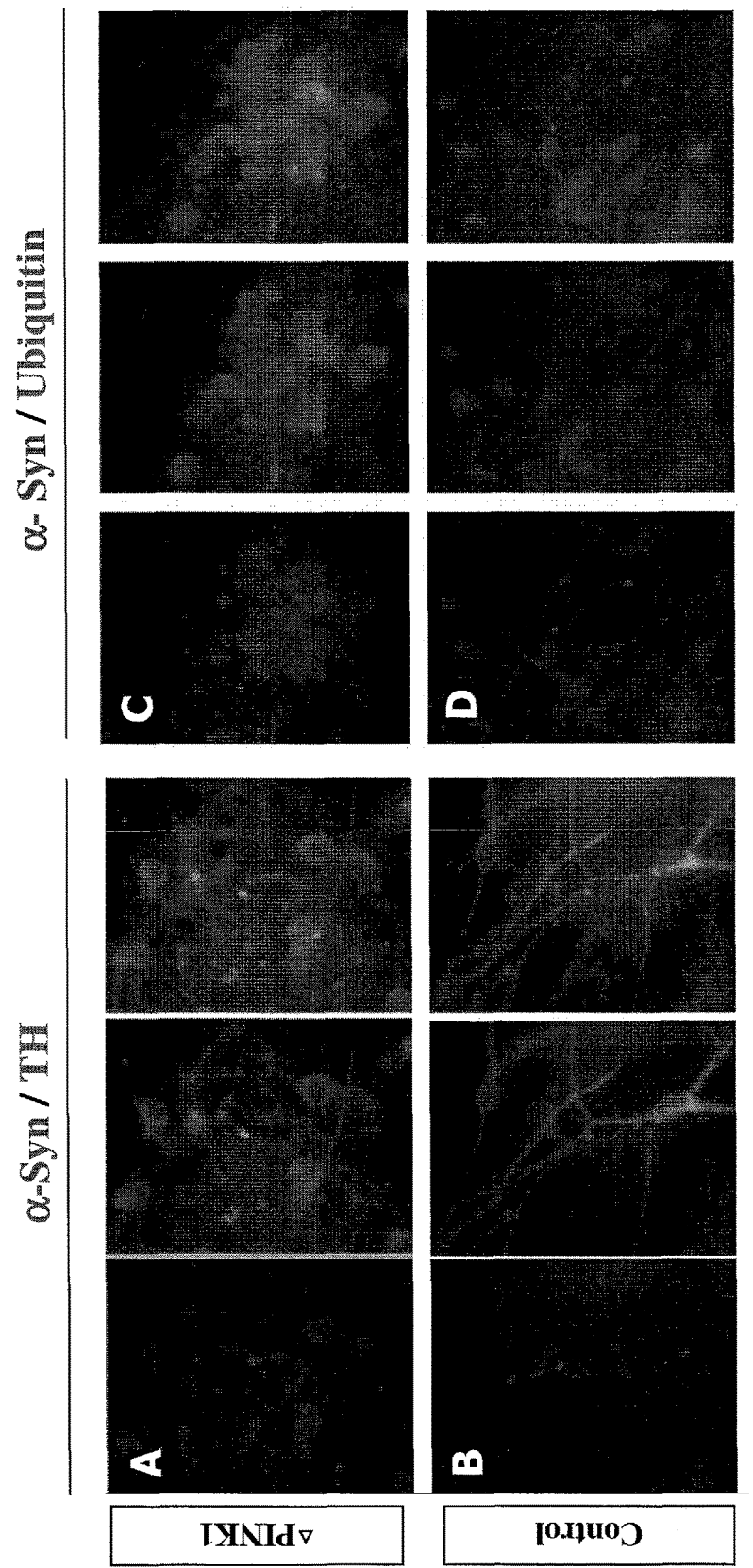
FIG. 21 shows an exemplary PINK1 mutant PD-iPSC showed PD like phenotype of protein aggregation following long-term differentiation and maturation in vitro. At day 55 of differentiation, PINK1 mutant PD-iPSC showed evidence of α-synuclein (a major component of Lewy body formation in PD patients) expression in cytosol of TH+ DA neurons. The cells also showed high expression of ubiquitin (a classical Lewy body marker). In contrast, DA neurons derived from control iPS line showed expression of normal synaptic (as opposed to cytosolic) α-synuclein expression and very low levels of ubiquitin. A, B) Immunocytochemical analysis of PINK1 mutant PD-iPSC line at day 55 of differentiation for α-synuclein (LB509, red), TH (green) and merged image (A) and α-synuclein (red) and Ubiquitin (green) (B). C, D) Immunocytochemical analysis of control-iPSC line at day 55 of differentiation for α-synuclein (red) and TH (green) (C) and α-synuclein (red) and Ubiquitin (green) (D).

The inventors discovered that PINK1 mutant PD-iPSC showed evidence of α-synuclein (major component of Lewy body on PD patience) expression in cytosol of TH+ DA neurons at day 55 of differentiation using the novel floor-plate based midbrain DA neuron induction protocol, (FIG. 21 a-b). A, B) Immunocytochemical analysis of PINK1 mutant PD-iPSC line at day 55 of differentiation for α-synuclein (LB509, red), TH (green) and merged image (A) and α-synuclein (red) and ubiquitin (green) (B). These α-synuclein positive cells also showed high expression of ubiquitin (classical Lewy body marker). In contrast, DA neurons derived from control iPS line showed expression of normal synaptic (as opposed to cytosolic) α-synuclein expression and very low levels of Ubiquitin (FIG. 21c-d). C, D) Immunocytochemical analysis of control-iPSC line at day 55 of differentiation for α-synuclein (red) and TH (green) (C) and α-synuclein (red) and ubiquitin (green) (D).

C. Expression of Aggregated Form of α-Synuclein.

Figure 22:
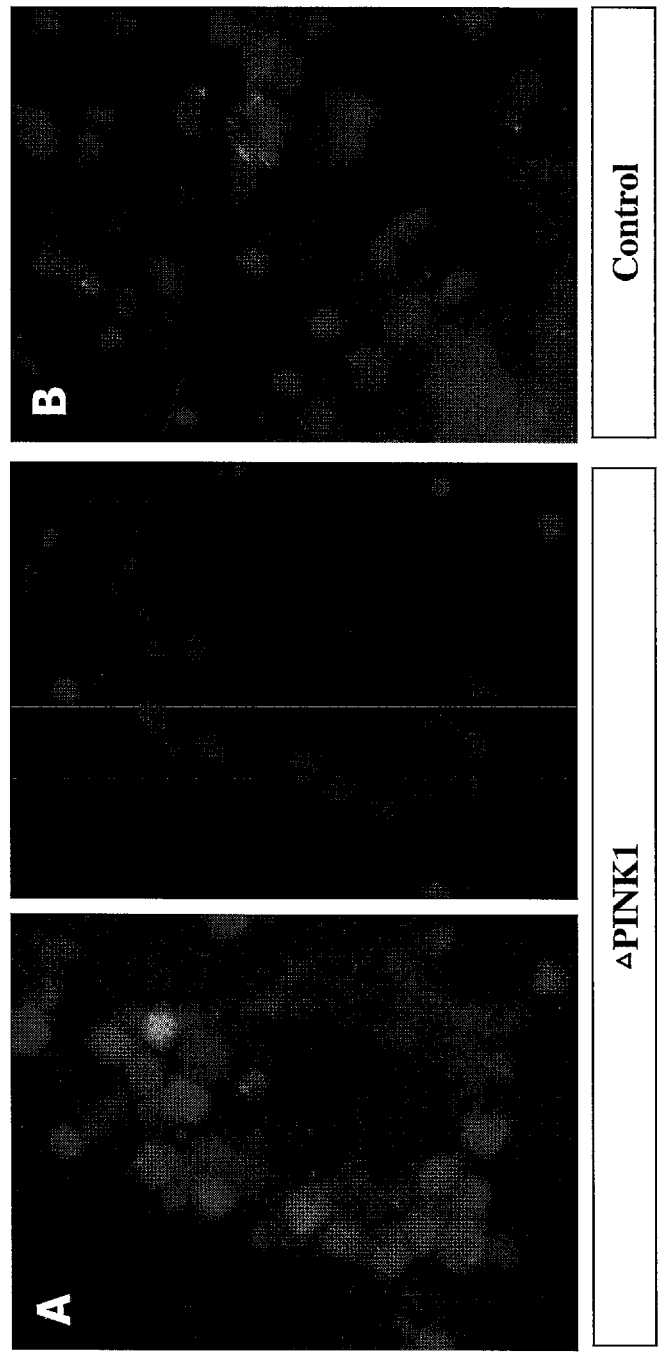
FIG. 22 shows an exemplary expression of aggregated form of α-synuclein. In the PD patient brain, dimerized insoluble forms of a-synuclein lead to aggregation in Lewy body. The dimerized form of α-synuclein shows phospholylation of Serine 129 on α-synuclein. PINK1 mutant PD-iPSC derived cells showed strong expression for Ser129 phosphorylated α-synuclein in contrast to control-iPSC derived cells that showed very low levels of expression. A, B) Immunocytochemical analysis for Ser129 phosphorylated α-synuclein (green) and DAPI (blue) in PINK1 mutant PD-iPSC derived cells at day 55 of differentiation (A) and matched control-iPSC derived cells (B).
Figure 23:
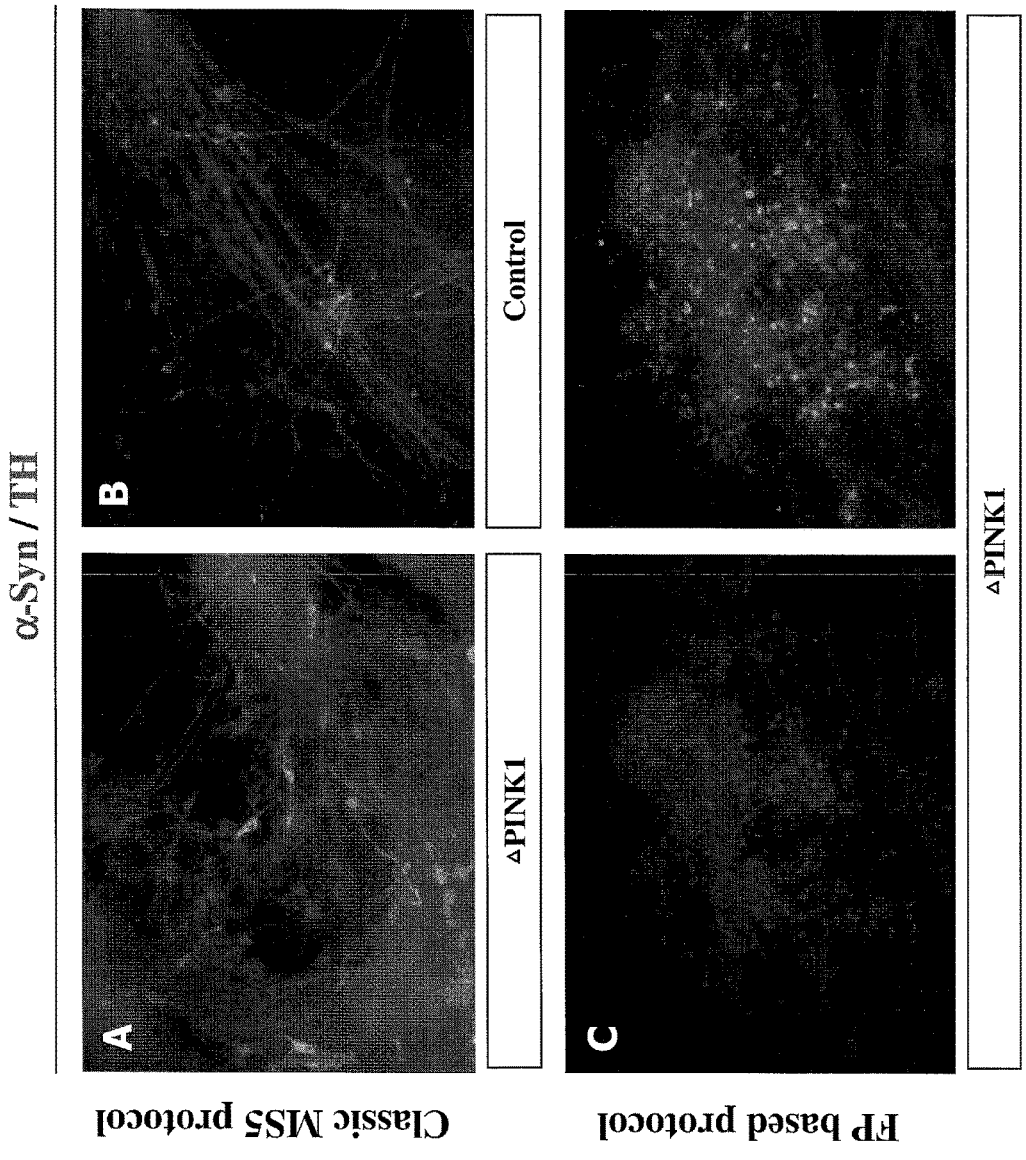
FIG. 23 shows exemplary differences in α-synuclein expression patterns are observed depending of differentiation protocol. The inventors' show that 'authentic' midbrain DA neurons have PD specific vulnerability and corresponding, specific in vitro phenotypes. DA neurons obtained using the classical MS5 stromal feeder based differentiation protocol (Perrier et al., PNAS 2004, herein incorporated by reference) can yield large numbers of TH+ neurons. However, based on the data of the present inventions, the TH+ cells resulting from differentiation by the classical MS5 stromal feeder protocol are not authentic midbrain DA neurons. In cultures differentiated via the MS5 protocol, there were many α-synuclein positive cells. However, those cells did not co-express TH. Moreover, there was no difference in expression patterns between PD-iPSC and control-iPSC when using the MS5 differentiation strategy. These data indicate that α-synuclein is also expressed in other non-DA cell types and that such non-DA α-synuclein is unchanged in disease versus control-iPSC derived cells—particularly when using standard MS5 differentiation protocols. Finally, the new floor plate based differentiation protocol of the present inventions yields large number of TH+ cells co-expressing α-synuclein. Those TH+ cells express α-synuclein in a cytosolic expression pattern. A, B) Immunocytochemical analysis for α-synuclein (LB509, red), TH (green) of PINK1 mutant PD-iPSC line at day 60 of MS5 based differentiation (A) and control-iPSC (B). C) Immunocytochemical analysis of PINK1 mutant PD-iPSC line at day 55 of floor-plate based differentiation for α-synuclein (red), TH (green).

In the PD patient brain, dimerized insoluble form of a-synuclein leads to aggregation in Lewy body. The dimerized form of α-synuclein shows phospholylation of Serine 129 on α-synuclein. At the same day of differentiation, PINK1 mutant PD-iPSC derived cells showed strong expression for Ser129 phosphorylated α-synuclein in contrast to control-iPSC derived cells that showed very low levels of expression (FIG. 22).

PINK1 mutant PD-iPSC derived cells showed strong expression for Ser129 phosphorylated α-synuclein in contrast to control-iPSC derived cells that showed very low levels of expression. A, B) Immunocytochemical analysis for Ser129 phosphorylated α-synuclein (green) and DAPI (blue) in PINK1 mutant PD-iPSC derived cells at day 55 of differentiation (A) and matched control-iPSC derived cells (B).

D. Differences in α-Synuclein Expression Patterns are Observed Depending of Differentiation Protocol.

The inventors contemplated that floor-plate derived "authentic" midbrain DA neurons showed PD specific vulnerability and corresponding, specific, in vitro phenotypes. DA neurons obtained using the classical MS5 stromal feeder based differentiation protocol (Perrier et al., PNAS 2004, herein incorporated by reference) yielded large numbers of TH+ neurons. However, based on data obtained during the development of the present inventions, the inventors showed that MS5 based TH+ cells were not authentic floorplate derived midbrain DA neurons. In cultures differentiated via the MS5 protocol, there were many α-synuclein positive cells. However, those cells did not co-express TH. Moreover, there was no difference in expression patterns between PD-iPSC and control-iPSC when using the MS5 differentiation strategy (FIG. 23a-b). These data indicate that α-synuclein is also expressed in other non-DA cell types and that such non-DA α-synuclein is unchanged in disease versus control-iPSC derived cells—particularly when using standard MS5 differentiation protocols. These are the DA-like rosette derived neurons reported in publications (e.g. Perrier PNAS 2004). Those MS5 based TH+ (=DA-like) cells are used for comparison in FIGS. 3, 10, 13 and 16. These data indicate that α-synuclein is also expressed in other non-DA cell types and that such non-DA α-synuclein is unchanged in disease versus control-iPSC derived cells—particularly when using standard MS5 differentiation protocols. Finally, the new floor plate based differentiation protocol described herein, yields large number of TH+ cells co-expressing α-synuclein. Those TH+ cells express α-synuclein in a cytosolic expression pattern. FIG. 24A, B) Immunocytochemical analysis for α-synuclein (LB509, red), TH (green) of PINK1 mutant PD-iPSC line at day 60 of MS5 based differentiation (A) and control-iPSC (B). C) Immunocytochemical analysis of PINK1 mutant PD-iPSC line at day 55 of floor-plate based differentiation for α-synuclein (red), TH (green).

E. DA Neurons Derived from Genetic PD-iPS Cells are More Vulnerable to Toxic Stimulation. FIG. 24-25.

PD-iPSC derived TH+ DA neurons derived via floor-plate based protocol were more vulnerable to toxin challenge (valinomycin: mitochondria ionophore, 5 uM (ranging in concentration from 1-10 uM), 48 hr) than control-iPSC derived cells. In contrast, TH+ neurons derived via the classic MS5 based protocol did not show differential vulnerability between PD- versus control-derived cells (FIG. 24). Entire cell viability assay with alamar-blue after 48 hrs of valinomycin treatment also showed differential cell survival in a specific dose range for toxin challenge (5 and 10 uM) when comparing PD-iPSC and control iPSC (FIG. 25). Normal condition both of PD- and control-iPSC derived cultures obtained via MS5 based protocol (D, PD-iPSC derived cells shown), TH+ neurons following toxin challenge in PD-iPSC (E), and control-iPSC derived cultures (F) obtained via MS5 protocol. G-H) low power images of immunocytochemistry for Tuj1 (red) and TH (green) by floor-plate based protocol at day 60 of differentiation: PD-iPSC of normal (G), versus toxin challenge (H) conditions and control iPSC of normal (I), versus toxin challenge (J) conditions. K-N) low power images of immunocytochemistry for Tuj1 (red) and TH (green) by MS5 based protocol at day 60 of differentiation: PD-iPSC of normal (K), versus toxin challenge (L) conditions and control iPSC of normal (M), versus toxin challenge (N) conditions. F.

Exemplary Quantification of Cell Viability—Dose Response Assay for Toxin Challenge.

Cell viability assay with alamar-blue after 48 hrs of valinomycin treatment showed differential cell survival in a specific dose range for toxin challenge (5 and 10 uM) when comparing PD-iPSC and control iPSC (day 60 of floor-plate based differentiation). Note: this assay tests for overall cell death while the most dramatic effects were observed specifically in DA neurons (see FIG. 14). Therefore, alamar blue based quantification will likely underestimate the extent of the differential effect observed on DA neuron lineages.

X. Contemplated Large Scale Culture Using Compositions and Methods of the Present Inventions for Providing Exemplary mDA Neurons.

The descriptions herein show exemplary methods and uses for large-scale production of mDA neuronal cells resulting from differentiation by compositions and methods described herein. The scalable generation (i.e. methods contemplated to be successful for generating mDA neuronal cells from cultures containing a relatively small number of cells) were shown to yield cell populations capable of transplantable mDA neurons at Day 25. In particular for PINK iPSC cells. See, Table 9).

XI. Methods to Enrich for Midbrain DA Neurons.

Several methods were developed and tested prior to and during the development of the present inventions with the goal of enriching cell populations for midbrain DA neuron precursors by overcoming problems such as by depleting contaminating cell populations, including but not limited to contaminating pluripotent stem cells. Initial studies were performed using primary embryonic mouse neurons, embryonic rat neurons and mouse ESC derived populations. In addition to having goals of increasing neural populations for use in DA neuron enrichment, the mouse ESCs studies included developing procedures for preventing teratoma formation which was problematic in previous procedures. These strategies included negative selection for cell surface markers expressed on pluripotent cells (such as SSEA1) along with positive selection of cells expressing neural marker (NCAM). Using mouse cells, several genetic reporter strategies were proposed for use in identifying enrichment for neural cells in DA neuron transplantation paradigms (for example, identifying cells with expression of SOX1, Corin/Lmx1a, Ngn2, TH, Pitx or DAT). Functional testing was performed in primary cells from Ngn2-reporter mice (Thomposon et al., Exp Neurol. 198(1):183-98 (2006)) and from Lmx1A-reporter mice also sorted for Corin (Jönsson, Exp Neurol. 219(1):341-54 (2009). For mouse ESC derived populations studies were performed using SOX1 (Barraud et al., Eur J. Neurosci. 2005 22(7):1555-69), TH (Kelly et al., Minerva Endocrinol. 1991 16(4):203-6), Pitx3 (Hedlund et al., Stem Cells. 2008 26(6):1526-36) and DAT (Zhou et al., Stem Cells. 2009 27(12):2952-61) mouse ESC reporter lines. Additionally, during the development of the present inventions, the inventors performed a comprehensive transplantation study directly comparing the in vivo performance of three purified mouse ESC-derived populations representing sequential stages of DA neuron development: Midbrain precursors (Hes5::GFP), early postmitotic cells (Nurr1::GFP), and mature DA neurons (Pitx3::YFP). Those studies identified Nurr1-expressing DA developmental as particularly suitable for grafting and demonstrated that purified DA neurons are capable of efficient engraftment in vivo. Furthermore, these results were used for selection of cells at day 25 of differentiation (onset of Nurr1 expression) for use in grafting hESC-DA neurons into mouse, rat and rhesus monkey models of PD.

During development of the present inventions production of authentic midbrain DA neurons from hESCs showed excellent in vivo performance (see FIG. 4), and the use of protocols described herein resulted in a DA neuron yield, at the time of grafting of approximately 40%. This percentage exceeded the percentages DA neurons obtained following dissection of human fetal ventral midbrain tissue (typically approximately 10%) Thus use of a hESC-based source of DA neurons as described herein is contemplated for even further improvements in purity when using cell purification strategies. Additionally, genetic reporter lines were developed for use with hESC similar to those used in mouse studies, including a human cell line as a Nurr1::GFP line. However, the use of genetic reporters may be problematic for translational use in humans because GFP is immunogenic in humans thus not suitable for human use. Furthermore, FACS sorting may be problematic for establishing clinical grade DA neuron master cell banks (i.e. developing frozen stocks of human DA neurons for use in transplantation) given the length of time that would be required for sorting batches of the approximately $10^9$ cells required for each transplant in addition to potentially high costs and lower cell yield after recovery from storage.

In contrast to genetic reporter systems and FACS based cell isolation, the inventors contemplated isolation of DA neurons based on surface marker expression using alternative strategies for cell separation techniques contemplated for use in PD patients. For example magnetic bead sorting (e.g. CliniMACS® system) was widely used in FDA-approved, cell-based applications and allowed for rapid and cost-effective isolation of up to $10^{10}$ cells under GMP-compliant conditions, i.e. conditions approved for isolating cells for use in humans. Thus in some embodiments, magnetic bead sorting is contemplated for enrichment of mature DA neurons, for example, using CD142 attached to magnetic beads for enriching Nurr1+ neurons for use in grafts.

XII. Identifying Cell Surface Markers for Use in Methods of Providing Mature DA Neurons.

Cell surface marker expression data collected during the development of the present inventions showed identification of several novel cell surface markers expressed on midbrain DA neurons. Specifically, markers for further identifying cells, such as specific cells that would mature into DA neurons, mature DA neurons of the present inventions and A9 cells, were found. Two main strategies were used to identify such surface markers: first, an unbiased gene expression screen in genetic reporter lines (FIG. 27a) showed several candidate markers, including CD142 and a marker termed DCSM1, that was selectively expressed in midbrain DA neurons and appeared to specifically mark A9-type DA neurons (FIG. 27b. A second strategy was the use of a CD cell surface marker screen in hESC derived DA neurons which tested for 242 commercially available antibodies in 96 well format (FIG. 27c,d). The results of such an exemplary screen (FIG. 27e) led to the identification of at least 5 validated markers enriched in midbrain DA neurons including CD142, a marker that selectively marked a Nurr1+ DA neuron stage (FIG. 27f), in addition to, CD63, CD99, and DCSM1.

Specifically, as illustrated in FIG. 27, a CD surface marker screen for WA09-derived DA neurons at day 25 of differentiation tested for up to 242 individual antibodies. These results were compared to duplicate screens of a broad range of other WA09 derived neural cell types (e.g. hESC-derived HB9::GFP+ motoneurons, hESC derived cortical neurons, hESC derived Nkx2.1::GFP+ ventral forebrain precursors, and several other hESC derived neuron types. The resulting database of surface marker expression profile was then used to select candidate CD markers selectively enriched in any given subtype such as midbrain DA neurons (FIG. 27). One of the markers discovered associated with hESC DA neuron differentiation was CD142. CD142 selection of cells enriched specifically for hESC derived DA neurons at Nurr1+ stage while depleting other neuron subtypes. In some embodiments, CD142 is expressed before Nurr1+. In some embodiments, a midbrain DA neuronal cell population sorted for CD142 has Nurr1+ and Nurr1− cells. In some embodiments, a midbrain DA neuronal cell population sorted for CD142 has Nurr1− cells. In some embodiments, cultured Nurr1−CD142+ sorted midbrain DA neuronal cell population begin expressing Nurr1 (i.e. become Nurr1+) in up to two days after sorting.

In addition to CD142, CD63 and CD99 were markers enriched on hESC derived DA neurons. Thus is some embodiments, DA neuronal cultures are enriched for DA neurons by sorting or selecting from markers including but not limited to CD142, CD63, CD99, DCSM1, Nurr1+, etc. CD142 typically marks approximately 30% of the total cell population at day 25 of differentiation (FIG. 28a). Selectivity of CD142 for Nurr1+ DA neuron stage was confirmed in multiple independent hESC and hiPSC lines (FIG. 28b). Importantly, in addition to enriching for DA neurons, CD142 selectively depletes other neuron subtypes such as GABA and Serotonergic neurons. (FIG. 28c-f). In vivo studies were performed that demonstrated the ability of CD142 to give rise to high purity DA neuron grafts without detectable contaminating GABA and Serotonergic neurons. Serotonergic neurons are a cell type that has been implicated in human fetal tissue grafting as the potential source of graft-induced dyskinesias. Although grafting methods described herein using unpurified cells already resulted in few Serotonergic neurons, the use of CD142 should further reduce this risk.

A. Markers for Identifying A9 Type Mature mDA Neurons.

A9 derived vs. A10 derived DA neurons were found to have distinct in vitro and in vivo functional properties and innervations patterns specific to their role in mesostriatal versus mesolimbic function. During the development of the present inventions the inventors discovered that the authentic mDA neurons produced by methods of the present inventions (FIG. 4) gave rise to neurons with having more A9 than A10 characteristics. In particular, authentic mDA neurons that were TH+ at least in part expressed Girk2, a marker used to define A9 type DA neurons. Additionally many mature DA neurons exhibited autonomous pacemaking activity that is a functional feature present in A9 but not A10 type DA neurons. However, some TH+ cells generated in vitro were not of A9 identity. Thus the inventors contemplated enrichment procedures such as those described herein, for providing purified populations of human A9 type authentic mDA neurons (versus A10) neurons. As described herein, the inventors discovered at least two markers unique to A9 type neurons and at least two markers at unique to at least A10 type neurons. Thus in some embodiments, A9 type neurons are identified by (Girk2, Aldh1) versus A10 (Calbindin, Otx2) markers.

B. Defining a Marker Set that Enhanced Yield of Midbrain DA Neuron with an A9 Subtype.

At least two strategies were contemplated for defining A9 specific surface markers: Candidate markers were obtained from a gene expression screen, such as described herein, and candidate CD-antibodies from a surface marker screen, as described herein. Populations In another method, global transcriptome analysis in purified populations of mouse ESC derived mDA neurons at distinct stages of differentiation (using BAC transgenic technology; see FIG. 27a,b). Surface markers were discovered in a surface marker profile on DA neurons derived from WA09 RCB with the following exemplary methods. RCB WA09-derived DA neurons at day 25 of differentiation were dissociated and replated onto 96 well plates, followed by exposure to the 242 CD antibodies and data analysis using the Operetta high content scanner. Amount of DA-enrichment was tested for at least 5 additional antibodies which bound to CD markers identified in these screens (for examples, CD142, CD63 and CD99). Candidate CD-positive versus CD-negative cells were assessed using the DA QC assays, including expression of FOXA2/TH and TH/Nurr1 (see, Table 7). In some embodiments, global gene expression profiles are contemplated for comparison of unsorted to CD142+ cells. In some embodiments, cells sorted/separated expression a desired marker were used in short-term and long-term in vivo studies as described herein. Among the DA neurons specific markers identified in these studies was a surface marker gene that was termed DCSM1 (DA cell surface marker 1). Based on in situ expression data, expression in the ventral midbrain but more surprisingly found expression to be at least partially A9 selective, both in the developing and adult mouse brain (FIG. 27) and in the human adult brain. Numerous cells expressing DCSM1 expression in hESC derived DA neurons were observed. In vitro assays for A9 vs A10 identity included long-term differentiation of marker+ cells (day 50 and day 75 of differentiation) and analysis of i) expression for A9, (Girk2, Aldh1) versus A10 (Calbindin, Otx2) markers in mature neurons, (ii) differential axon guidance responses to Netrin-1 and Sema3 and, (iii) A9 enriched neurons were assessed by electrophysiology tests. A9 DA neurons exhibited specific functional features as described herein for hESC derived A9 neurons. In vivo studies were performed for cells expressing DCSM1 and other markers in order to confirm i) A9 marker expression (Girk2, Aldh1) versus A10 (Calbindin, Otx2), ii) graft DA fiber outgrowth and iii) electrophysiological A9 properties in slice preparation of the grafted cells (see FIG. 26).

XIII. Use of Polysialic Acid (PSA) and Polysialyltransferase (PST) Enzyme.

Graft integration and extent of DA fiber outgrowth are challenges in grafting methods including the fetal grafting studies in PD patients. One problem encountered with graft tissues and cells is limited fiber outgrowth from these grafts when treating patients. This problem is particularly critical in humans since patient recovery requires extensive striatal reinnervation. In previous methods, achieving adequate reinnervation after a tissue graft required multiple injections of cell deposits across the striatum. Each injection can cause striatal damage and inflammation along with other surgical risk. Such risks include the injury of a blood vessel during cell injection that could potentially induce a stroke or seizures in the patient. PSA is a natural cell surface sialic acid homopolymer (i.e. alpha 2,8-linked sialic acid) that has been identified as a posttranslational modification (through the action of polysialyltransferase (PST) enzyme) of other cell surface molecules, such as (polysialylated) neural cell adhesion molecule (NCAM), NCAM (CD56), and the like. PSA appeared to function in regulating plasticity of some cell behaviors that required changes in cell-cell interactions, including cell migration and axon outgrowth. While highly expressed in the embryo, PSA was down regulated in adult tissues with the exception of localized regions of the CNS that maintain structural and physiological plasticity (such as hippocampus, suprachiasmatic nucleus, SVZ). Thus in some embodiments, polysialic acid (PSA) was contemplated for use in promoting fiber outgrowth of engrafted cells. Examples of PSA use in other cell types are described in WO 2006/042105 herein incorporated by reference in its entirety. In some embodiments, the inventors contemplate the use of authentic DA neurons in combination with PSA as described herein.

A. Increased PSA in DA Neurons for Use in PD Patients.

Major challenges remain for providing methods and cells based upon previous results from the use of small animal models, including limited survival of transplanted cells and poor fiber innervation of host tissue. The impact of these limitations is contemplated to be more severe in the larger human striatum, and thus increased survival and innervation is necessary for effective clinical application of ES-derived DA neurons. Improved fiber outgrowth and graft integration in animal models, including the use of at least one, up to several injections is contemplated to represent reductions in risk associated with multiple injections or poor distribution of DA neurons in vivo.

Regulation of cell interactions by polysialic acid (PSA) is one of the factors that promoted cell distribution, axon outgrowth and target innervation during vertebrate development, see, for example, Rutishauser, Polysialic acid in the plasticity of the developing and adult vertebrate nervous system. Nat Rev Neurosci 9, 26-35 (2008). PSA was a carbohydrate polymer attached to the neural cell adhesion molecule (NCAM), that attenuated cell-cell interactions, and thereby promoted tissue plasticity. In a glial scar, enhanced expression of PSA in the adult brain promoted the migration of neuronal precursors from the subventricular zone into the cortex, and improved axonal growth (El et al. Use of polysialic acid in repair of the central nervous system. Proc Natl Acad Sci USA 103, 16989-16994 (2006). As described herein, engineered increased PSA expression on purified mouse ES-derived DA neurons resulted in improved graft cell counts, extensive DA neuron fiber outgrowth into host striatum and surprisingly, enhanced behavioral recovery in Parkinsonian mice. Further, genetic engineering of ESC-derived DA neurons for increased cell surface PSA levels concurrently increased in vivo survival and fiber outgrowth into host striatum. One exemplary embodiment is shown in FIG. 29 for using a mammalian PST gene, i.e. mouse or human. Another exemplary embodiment shown in FIG. 29 shows the use of bacterial PST, i.e. PSTnm. Specifically, as described herein, increased PSA on cells used for mature DA neuron based cell therapy is contemplated for use in the treatment of PD.

B. Use of Mouse PST for Increased PSA Expression.

In vivo results demonstrated increased neuritic extensions and a significant reversal of amphetamine-induced rotations in 6-OHDA mice that received mouse PST-cell modified grafts while equal numbers cells that were not PST modified failed to achieve the same (FIG. 33). Moreover, improved DA fiber innervation was observed to correlate with enhanced behavioral outcome in a PD mouse model, such as when small (injection of approximately 50,000 cells) PSA positive cell-grafts were made they provided graft integration and fiber outgrowth that were approximately 70% of the areas covered compared to the use of larger (100,000 or more cells) comparative grafts. A side-by-side comparison of PSA-enhanced versus control treated ES-derived DA neuron grafts showed behavioral recovery in the PSA group (when grafts were based on transplantation of 55,000 cells each) but not observed in control cells. Transplantation of 100,000 ES derived DA neurons in the mouse brain showed behavioral recovery in both PSA-treated and control-treated ES-derived DA neurons suggesting that grafts derived from 100,000 cells are sufficient to reinnervate the mouse brain without PSA enhancement. Thus in another embodiment, engineered expression of PSA expression on the surface of authentic DA neurons is contemplated for use in procedures for treatment of patients with PD. When PSA was induced on neuronal cells of the present inventions it was identical to the PSA polymer that occurred naturally in brain cells thus unlike the use of other cell surface molecules for engineering therapeutic cell types, cells engineered for PSA expression are contemplated to have little antigenicity in vivo when used on cells for engraftment procedures in humans. Moreover, high PSA levels on engrafted cells, either endogenouse neural precursors (Battista et al., J. Neurosci. 30(11): 3995-4003 (2010)), Schwann cells (Ghosh et al., Glia. 60(6):979-92 (2012)) and ES-derived DA neurons of the present inventions did not cause detectable side-effects when used in a variety of adult rodent model. The engineered expression of PSA to effective levels involved the action of a single polysialyltransferase (PST) enzyme whose sole product is this unique glycopolymer. Surprisingly, the amount of expressed protein and nature of the enzymatic product was remarkably constant and closely resembled the PSA found naturally in embryonic tissues.

As described herein, engineered PSA expression is contemplated on neuronal cells for use in engraftment procedures. In particular, PSA is contemplated for use in preparing cells for therapeutic use by overcoming problems encountered when using other types of induced cell surface marker expression. Further, the use of PSA expression was reproducible in protocols that cross vertebrate species (such as using mouse PST genes expressed in human cells) because its acceptors are also consistent in structure across species and are found on the majority of cell surfaces. Engineering PST genes into hESCs to increase PSA on DA neurons. A gene encoding the human polysialyl-transferase (hPST) was introduced into a hESC line (WA01) using a lentiviral vector (pLenty, Invitrogen) and as described herein. Twenty selected clones were expanded and analyzed for PST expression. PST-expressing hESC clones were differentiated to ensure that PST was not silenced in DA neurons. Quantification of PSA-NCAM at different stages of differentiation (day 0, 11, 25, and 50) was done using FACS analysis and immunofluorescence (Operetta). Positive clones were subjected to the suite of DA neuron QC parameters outlined in Table 7. At least 3 clones that retain high, uniform levels of PSA-NCAM during differentiation and perform well in the QC parameters (Table 7) will advance to assessment of the neurite outgrowth in PST-overexpressing hESC-derived DA neurons Selected control and PST-overexpressing hESC clones were differentiated into DA neurons using the standard protocol described herein, followed by cell fixation and analysis at days 25 and 50. The number and length of TH-positive fibers in such cultures were quantified with the Operetta High Content Microscope. The Neurite Analysis module in Harmony software 3.0 quantified neurite number and length, with or without PST, and the data was statistically analyzed using a two-way ANOVA. PST-overexpressing and control hESC clones that advance from in vitro studies above, were differentiated again into DA neurons and transplanted into a rat model of PD. Short-term grafts (4-6 weeks) to determine survival, PSA-NCAM expression and neurite outgrowth were done. For each clone that passed short-term in vivo parameters were subjected to long-term grafting studies. For those studies animals received half or a quarter of the standard ($200 \times 10^3$) dose of cells. These studies were to address whether increased PSA leads to increased long-term survival after transplantation (5 months), and whether smaller DA neuron numbers are capable of matching or outperforming the functional capacity of non-PST grafts transplanted at standard cell doses (FIG. 27).

In addition, complex behavioral assays sensitive to the extent of striatal reinnervation were monitored to further distinguish the functional potential of PST-versus control DA neuron grafts. The animals were sacrificed following completion of behavioral assays, and fiber outgrowth was quantitated using human specific antibodies NCAM and SC121 and antibodies against TH (see also FIG. 29). The intensity and spread of the hNCAM+, SC121+ and TH+ graft was measured, as well as the percentage of human cells co-expressing DA neuron markers (TH, FOXA2) and PSA. The density of NCAM/TH+ halo of neurites emanating from the graft were quantified at different distances. Data was compared among groups using a two-way ANOVA with a Bonferroni post-hoc test. In addition, sections were examined for qualitative changes (e.g. branching, thickness, graft distribution and shape). In addition, some grafts will be processed for slice electrophysiological evaluation (see FIG. 26) in terms of A9 phenotype, synapse formation with host striatum, as well as innervation by endogenous afferents.

The following example shows enhancement of polysialic acid expression that improved the function of ES-derived dopamine neuron grafts in Parkinsonian mice.

ES cells expressing GFP under control of Nurr1 promoter (Nurr1::GFP ES cells) were stably transduced with a lentiviral vector ubiquitously expressing polysialyltransferase (PST). Transduced cells showed a dramatic increase in PST mRNA as compared to controls (FIG. 30A). Expression of PST was observed to be sufficient for PSA synthesis on NCAM. Accordingly, PSA-NCAM expression was greatly increased in PST-modified cells at day 14 of DA neuron differentiation (FIG. 30B-E). Both the endogenous and induced cell surface PSA on ES-derived DA neurons could be removed (FIG. 30E) by a phage endoneuraminidase (endoN) that specifically cleaved PSA's unique alpha-2,8-linked sialic acid polymers. Surprisingly, PST transduction was not observed to affect expression of neuronal or midbrain markers in the GFP-purified DA neurons (FIG. 30F).

Other studies in 6OHDA-lesioned hemiparkinsonian mice showed that transplantation of approximately 100,000 ES-derived DA neuron precursors is required to produce robust functional recovery, as measured by the amphetamine-enhanced rotation test. In the present studies, sought to graft a sub-optimal number of cells in order to be able to assess augmentation by enhanced PSA expression. In order to transplant highly enriched DA neuron populations that are depleted for contaminating pluripotent cells, FACS-purified cultures at day 14 of differentiation for expression of Nurr1-driven GFP and for the absence of SSEA-1 expression (FIG. 31). Without PST overexpression, a reduction of the minimally effective graft size by half (55,000 Nurr1+ DA cells) failed to produce detectable behavioral recovery. By contrast, with enhanced PSA expression, the same number of Nurr1/PST DA neurons resulted in a significant correction of the PD behavioral impairment (p<0.01; two-way ANOVA), with complete recovery approximately 5 weeks after surgery (FIG. 32A). PSA removal prior to transplantation by incubation with endoN indicated the specificity of PSA's enhancement, in that the endoN treatment partially reversed the functional restitution obtained with Nurr1/PST (FIG. 32A).

To examine the characteristics of the grafted cells, animals were processed for immunohistochemistry two months after transplantation. There was a difference in the number of surviving Nurr1+ neurons, in that animals grafted with the PST-transduced line had on average twice as many GFP+ cells as animals grafted with control cells (9,300+/−1,400 vs. 4,230+/−1010 GFP+ cells per graft in PST versus control samples respectively; FIG. 32B, p<0.05, Student's t test). Furthermore, Nurr1/PST grafts also displayed higher levels of PSA expression in vivo (FIG. 32C,D). However, the proportions of cells expressing the midbrain DA markers TH and FoxA2 within the graft core were comparable for the Nurr1 and Nurr1/PST cells (TH: 62.0%+/−8.0 vs. 51.3%+/−7.0 p=0.33; FoxA2: 63.2%+/−8.6 vs. 55.4%+/−2.0, p=0.3, respectively; FIG. 32E).

Neuronal processes that emerged from the Nurr1 and Nurr1/PST cells showed comparable levels of TH, Girk2 (G-protein-coupled, inwardly rectifying potassium channel) and synapsin (FIG. 33A). Unlike other studies with transplanted Schwann cells (Ghosh, et al. Glia 60, 979-992 (2012)), enhanced PSA expression had little effect on migration of DA cells from the grafting site. However, there were clear changes in neurite outgrowth. As shown in FIG. 33B, there were more DA neuronal processes emerging from Nurr1/PST cells as compared to Nurr1+ controls. When the intensity of GFP and TH immunofluorescence was quantified in five successive 100 μm zones away from the transplant, Nurr1/PST grafts displayed a much higher relative density of processes (FIG. 33C,D; p<0.01 for both GFP and TH, two-way ANOVA). In quantifying this effect, normalized the relative density of processes to the density observed in the most proximal zone immediate to the graft core. Such normalization was required to compensate for the larger number of surviving cells in the Nurr1/PST grafts and to confirm a specific effect of PSA on neurite outgrowth. Specificity was also demonstrated when cell surface PSA was removed by endoN treatment prior to grafting. Thus pre-treatment with endoN reduced distal fiber outgrowth back to control levels (FIG. 33E).

These discoveries showed that at least some of the effects of PSA on graft function resulted from enhanced fiber innervation of striatum. Accordingly, there was a strong correlation between graft function and the relative extent of GFP-positive fiber outgrowth for example into zone IV (FIG. 33F; p<0.001, r2=0.65, n=17). Surprisingly, the fiber outgrowth/behavioral relationship was consistent for experimental groups (control, PSA enhanced, and endoN-treated), indicating that graft-host innervation was a parameter for behavior recovery in the mouse Parkinsonian model. Several factors contributed mechanistically to increased fiber outgrowth, such as enhanced penetration of the zone of reactive glia encapsulating the graft core, increased sprouting ability, improved outgrowth into the surrounding host tissue (e.g. easier growth cone translocation), and prevention of premature connections with host tissue in proximity to the graft core. The exemplary mechanisms are consistent with PSA's role in facilitating process outgrowth during normal development and in the adult nervous system.

The experiments described herein demonstrated the use of engineered PSA in DA neuron grafting which provided superior results compared to grafts from other types of cells. Data clearly indicated that PSA enhancement provided a significant augmentation of the ability of grafted DA neurons to innervate host striatum and attenuate PD functional deficits. Therefore clinical translation is contemplated comprising DA neurons of the present inventions for providing cells prior to transplantation. In some embodiments, the cells will be genetically manipulated for expressing PSA. In some embodiments, PST may be delivered directly to the cells via exposure to the purified enzyme and substrate, in vitro, prior to transplantation. In some embodiments, PSA strategy for human translation in PD grafting is contemplated to minimize the need for multiple injections and thereby reduce the surgical risks resulting from these multiple injections.

In other embodiments, this technology is contemplated for use on other cell types and species, for example, augmenting the migration of grafted Schwann cells in creating a bridge (for example, cell-cell communication) for regrowth of axons at the site of spinal cord injury.

The following are exemplary materials and methods used in this example.

Animals: Six-week old 129S3/SvImJ mice (Jackson Laboratory) were kept under controlled temperature with food and water available ad libitum. Experimental procedures were performed according to NIH and institutional animal use guidelines and approved by the local Institutional Animal Care and Use Committee (IACUC) and the Institutional Biosafety Committee (IBC).

6OHDA injection and amphetamine-induced test: Animals were anesthetized with sodium pentobarbital (10 mg/kg) and injected in the right striatum with 2 µl of 6OHDA (4 µg/µl in saline, 0.5% ascorbic acid). The injections were performed with a Hamilton syringe at coordinates: 0.5 mm posterior, 1.8 mm lateral relative to bregma and 2.5 mm ventral to brain surface. Before the surgery animals received a single i.p. injection of desipramine (25 mg/Kg, Sigma). Two weeks after surgery animals were scored in the amphetamine-induced rotation test. They were placed on 30 cm diameter clear plastic cylinders for half an hour after which they received a single i.p. injection of amphetamine (10 mg/Kg, Sigma). After 20 min, the number of ipsilateral/contralateral rotations was scored during another 20 min. Animals were scored once a week for seven weeks then deeply anesthetized and perfused through the heart with PBS and 4% paraformaldehyde in 0.1 M phosphate buffer (PB, pH 7.4). Brains were removed and post-fixed overnight at 4° C. in 4% paraformaldehyde then vibratome sliced (Pelco-101, Ted Pella) in 40 µm-thick sagittal sections.

Cell differentiation and transplantation: A Nurr1::GFP BAC transgenic BAC mouse ES reporter cell line (i.e., GFP expression is driven by Nurr1 promoter) 5 was transduced with a lentivirus (pLenti, Invitrogen) containing the mouse PST gene under control of the CMV promoter. ES cells were propagated on mitomycin C-treated MEFs (StemCell Technologies) in DMEM (Invitrogen), 10% FBS (HyClone) supplemented with 1,400 units/ml LIF (ESGRO; Invitrogen), 2 mM L-glutamine, 1 mM β-mercaptoethanol, 100 U/ml penicillin and 100 µg/ml streptomycin (Invitrogen). DA differentiation was induced according to Barberi et al., Nat Biotechnol 21, 1200-1207 (2003), with modifications. Briefly, cells were differentiated on MS5 feeder cells in gelatin-coated dishes (10,000 cells/10 cm dish) and cultured for four days on serum replacement media (SRM). At day 4, Sonic hedgehog (SHH, 200 ng/ml) and FGF8 (100 ng/ml) were added. At day 7 of differentiation, the media was changed to N2 supplemented with SHH, FGF8 and bFGF (10 ng/ml). At day 11, terminal differentiation was induced by withdrawal of SHH, FGF8 and bFGF and the addition of ascorbic acid (AA, 200 µM) and BDNF (20 ng/ml).

Cells were harvested at day 14-15 with accutase treatment for 45 min, washed once with N2 and incubated with AlexaFluor-647 conjugated anti-SSEA-1 antibody (BD Pharmingen) for 25 min. Cells were washed once with N2, resuspended in HEPES buffer with 0.1% BSA. DAPI was added to assess viability. FACS was performed with a MoFlo cell sorter and the population of interest was sorted for GFP fluorescence (Nurr1). The population positive for AlexaFluor-647 (SSEA-1) was negatively sorted. For GFP negative control, naïve J1 mouse ES-cells were used at the same differentiation stage.

Nurr1::GFP sorted cells were analyzed for viability and resuspended in N2 with BDN and AA to a final concentration of 55,000 cells/µl One µl was injected into the lesioned mouse striatum with a 50 µm tipped fine glass capillary at coordinates: 0.3 mm posterior, 1.5 mm lateral from bregma and 2.2 mm ventral to the brain surface. An aliquot of the cell suspension was re-plated in matrigel-coated 6 mm dishes for further characterization.

For immunofluorescence analysis, cells were fixed with paraformaldehyde for 10 min at 40 C, washed twice with PBS, blocked with 5% BSA (0.1% Triton X-100 in PBS) and incubated with primary antibodies for 2 hrs at room temperature: rabbit anti-GFP (1:1000, Invitrogen), mouse IgM anti-PSA (1:2000, 5A5), mouse anti-NeuN (1:800, Chemicon), mouse anti-TH (1:1000, Sigma), goat anti-FoxA2 (1:800, Santa Cruz), goat anti-Engrailed (1:800, Santa Cruz). Cells were then incubated with Cy-conjugated secondary antibodies (1:1000, Jackson).

EndoN treatment: To remove PSA from NCAM, the night before harvesting, cells were treated with 20 units of endoN, a phage enzyme that specifically removes PSA 7-9. Cells were then harvested and injected as described before but were resuspended in N2 with BDNF and AA and 5 units of endoN. We previously assessed that the injection of the same amount of endoN alone into lesioned mice did not improve animal behavior.

PST mRNA and PSA-NCAM analysis in vitro: For Western blot analysis, cells were treated with WB buffer (PBS with 1% NP40, 150 mM NaCl, 1 mM EDTA, and 1× protease/phosphatase inhibitors added immediately before extraction, at pH of 7.4) and sonicated twice for 5 sec, centrifuged and resuspended in Laemli buffer (LB). Aliquots without LB were saved for protein determination. Equal amounts of protein were loaded into 6% sodium dodecyl sulfate-polyacrylamide gel electrophoresis gel (BioRad). Proteins were transferred by electrophoresis onto polyvinylidene membranes (Millipore). The membranes were blocked for 1-6 hr in 0.1% Triton X-100 TBS (TBS-T) with 5% non-fat dry milk and incubated overnight with anti-NCAM antibody (1:10,000, Santa Cruz) in TBS-T with 5% milk. Blots were then incubated with peroxidase-conjugated secondary antibody (1:10,000, Jackson) and detected with ECL detection method (Amersham Pharmacia Biotech). Protein levels were quantified using ImageJ software.

For qRT-PCR analysis, total RNA was extracted with Trizol (Sigma), reverse-transcribed (Qiagen) and amplified with 10 µl of 2×SYBR reaction mixture and 0.2 µM of forward and reverse primers to a final volume of 20 µl. For PSA-NCAM FACS analysis, cells were harvested with accutase treatment for 45 min, washed once and incubated with mouse IgM anti-PSA (1:250, 5A5) for 25 min on ice, washed once with N2 media and incubated with Cy3-conjugated anti-mouse-IgM (1:250, Jackson) for another 25 mM on ice. Cells were washed once with N2 and resuspended with 0.1% BSA with 7AAD and analyzed in a FACS Calibur cell sorter. As control, no primary antibody was added.

Immunohistological and stereological procedures: Free floating coronal sections were blocked in 0.1% Triton X-100, 5% donkey serum in PBS for 30 mM at room temperature and incubated 48 hrs at 4° C. with different antibodies: rabbit anti-GFP (1:300), chicken anti-GFP (1:200, Chemicon), mouse anti-TH (1:200), mouse IgM anti-PSA (1:1000), mouse anti-NeuN (1:400), goat anti-FoxA2 (1:300), rabbit anti-Girk2 (1:300, Alomone Labs), mouse anti-synapsin (1:200, BD Transduction Laboratories). Sections were then washed and incubated with secondary antibodies: Cy2, Cy3 and Cy5-conjugated donkey antibodies (1:400, Jackson). For PSA a Cy5-conjugated donkey anti-IgM was used (1:500 Jackson). Incubations were performed for 2 hrs at room temperature. Sections were washed twice in PBS and mounted in Mowiol (Calbiochem).

One-in-three coronal sections of the brain were analyzed for each immunolabeling. Digital images were collected by a Zeiss LSM 510 laser scanning confocal microscope with three lasers (Argon 488, HeNe 543 and HeNe 633) with a c-Apochromat 40× objective (water-immersion). The number GFP+ and TH+ cells was counted in one-in-three sections encompassing the whole brain under a 40× objective, and the total number of cells/graft estimated. Double-labeled cells were analyzed in single optical planes through the entire z-axis.

For the analysis of the percentage of GFP/TH+ and GFP/FoxA2+ labeled cells, 100 GFP+ cells were analyzed for each marker. For process outgrowth analysis, confocal z-scans were performed at 0.8 μm intervals through the entire z-axis (20-40 μm) with a pinhole of 1 μm under a 40× objective. Sections were scanned from the injection site laterally until no processes were observed. 3-D projections encompassing the whole scanned area were sequentially matched. For GFP and TH intensity analysis, the entire scanned area was divided into five successive 100 μm zones away from the transplant and the intensities were measured using ImageJ software. Data were normalized to the intensity in the zone nearest the graft (zone I) to control for any potential differences in graft size.

Statistical analysis: Data are presented as the mean standard error of the mean (SEM). Comparisons were performed using Student's t test or two-way analysis of variance (ANOVA) followed by Bonferroni post-hoc test. Linear regression analysis was performed and quantified using the Pearson correlation.

C. Over-Expression of the Human PST Gene (Polysialyl Transferase).

Lesioned animal groups received one of 3 doses of wild type cells or cells expressing PST or pretreated with PST enzyme. They were processed for behavioral testing following the paradigms discussed in Table 11 (amphetamine rotations, cylinder test, stepping test). The doses chosen (for examples, 200 k, 100 k, 50 k cells) were used successfully in mice such that resulting neurons showed results as described herein for mouse PST genes.

D. Direct Administration of Purified PST Enzyme to Cells.

In other words, a nontransgenic method of PSA induction. Pre-treatment of cells with the PST enzyme which results in polysialylation and increased expression of surface PSA. Although mammalian PSTs are low abundance membrane proteins that operate in the Golgi, the purified *Neisseria meningitides* α-2,8-polysialyltransferase (PSTnm) operated in an extracellular environment when using a commercially available non-toxic substrate (i.e. CMP-sialic acid) and produced a polymer chemically identical to mammalian PSA. As one example, an active fragment of this enzyme was effective for adding PSA to therapeutic proteins in vitro to augment in vivo pharmacokinetics. In the presence of CMP sialic acid, PSA was synthesized by PSTnm directly on surfaces of a wide variety of cell types in vitro, including mouse and human ESCs (FIG. 35A-E). The direct injection of PSTnm and substrate in vivo triggers increased PSA accumulation on cell surfaces in adult brain regions, including cerebral cortex, striatum and spinal cord (FIG. 35GH). PSA produced by PSTnm was degraded by endoN (FIG. 35B) which removed induced PSA, demonstrating that PSTnm-produced PSA has functional properties comparable to endogenous PSA (FIG. 35A,C, D). PSA expression via PSTnm occurred in less than an hour which overcame the slow PST transgene induction. Expression persisted for several weeks in vivo after which PSA markers were reduced thus overcoming side effects from prolonged induction of a PST transgene. Therefore the use of in vitro cell exposure to PSTnm+substrate is contemplated as a simple, alternative strategy for triggering increased PSA levels in hESC derived DA neurons and other cell types for use in engraftment procedures. In part, this alternative approach for translation, i.e. use in human engraftment procedures, has the advantages of being non-invasive nature, i.e. avoiding the use of transgenic methods, GMP-grade reagents are used in these procedures for meeting clinical use protocols, and having a transient nature of biochemically-generated PSA expression matching the expected time frame for DA fibers leaving the graft core and entering the host brain, necessary for avoiding some dangerous side effects of using cells engineered for engraftment.

The following example shows enzymatic engineering of PSA on hESC-derived DA neurons using the purified bacterial polysialyltransferase, PSTnm, to enhance transplant efficacy.

Although effective, PST gene transfection necessitated genetic modifications of hESCs with limited control over the duration of polysialylation. This example describes the discovery that external PSTnm induced PSA, instead of gene delivery, (see, FIG. 35). In FIG. 35A, PST treated Schwann cells (SC) (green line-middle line) had increased adhesion time while PSTnm-produced PSA inhibited adhesion. In particular, (A) PSTnm-produced PSA inhibits adhesion of Schwann cells in suspension to a Schwann cell monolayer even more effectively (red line-lowest line) than PSA produced by forced PST expression (green line-middle line). (B) PSA immunoblotting in ESC-derived HB9 motoneurons shows that control samples treated with PSTnm alone had undetectable levels of PSA. Incubation with PSTnm+CMP-sialic acid substrate produces a large PSA band, which is removed with endoN treatment. (C, D) Similar to effects obtained with the PST gene, polysialylation of these cells by PSTnm and substrate during differentiation enhances neurite outgrowth and cell migration (arrowheads). (E) PSA immunostaining of day-30 hESC-derived DA neurons. (F) This staining is significantly increased after treatment with PSTnm and substrate. (G) In vivo injection of PSTnm alone has no effect, while its co-administration with substrate (H) produces large amounts of PSA expression in mouse striatum.

Thus mature DA neurons externally treated with PSTnm is contemplated for use in the producing cells for engraftment. Both mammalian PST and PSTnm produced chemically identical chains of PSA. Increased PSA on hESC-derived DA neurons (FIG. 35F) should persist for several weeks, sufficient for DA fibers to exit graft core. Because PSTnm is removed prior to grafting, immunogenicity to this enzyme contaminating the grafted cells should not be factor.

PSTnm was produced from an engineered fragment with enhanced solubility and activity characteristics (Willis et al., Characterization of the alpha-2,8-polysialyltransferase from *Neisseria meningitidis* with synthetic acceptors, and the development of a self-priming polysialyltransferase fusion enzyme. Glycobiology 18, 177-186 (2008)). Cultures of hESC were induced to differentiate into DA neurons before PSTnm exposure, exposure to substrate or both. Cultures were examined at different time-points of exposure (10 min to 6 hrs) by quantitative immunofluorescence (Operetta) and western blotting to determine the speed and levels of polysialylation. Thus, Day 25 differentiated hESC-derived DA neurons will be incubated with the optimum concentrations of PSTnm and substrate using the conditions described herein. PSA+mDA neurons will be transplanted in short- and long-term assays as described herein and in FIG. 29.

E. Applications for Spinal Cord Injury.

Several studies aimed towards the eventual use in human patients and strategies described herein, showed broad potential of these procedures including PST-gene delivery by injecting lentiviral vectors expressing PST directly into the CNS to promote axon regeneration and endogenous progenitor migration. One such strategy for use in human procedures targets spinal cord injury. In one type of spinal cord regeneration procedure, Schwann cell grafts were used as part of the therapy for rebuilding cellular bridges for use in in vivo axon regeneration. However, patient recovery of locomotor function, including fine muscle control, resisted any therapeutic intervention. As shown herein, enhancing PSA expression on Schwann cells used for engraftment resulted in enhancement of Schwann cell migration and axonal growth which further resulted in dramatic effects on increasing locomotor function (FIG. 30A-D). Thus in some embodiments, increasing PSA expression on Schwann cells in vitro is contemplated for use in engraftment procedures in humans having spinal cord injury. Another strategy for use of engineered expression of PSA by increased expression of PST genes in human procedures involved HB9 ESC-derived motoneurons, where introduction of the PST gene in these neurons via lentiviral vector based gene expression resulted in a dramatic increase in the outgrowth of axons both in culture and after grafting in mice for repairing a mechanically induced sciatic nerve injury. The latter resulted in an improved and specific targeting of muscle tissue (FIG. 30E-H). Thus in another embodiment, engineered expression of PSA expression on the surface of ESC-derived motoneurons for use in restoring function of the sciatic nerve.

IVX. Increased Safety of DA Neuron Grafts.

Contemplated embodiments for further reducing health risks to patients for use in methods of producing cells of the present inventions are described below.

Although the cells produced by methods described herein demonstrated characteristics for reduced risks to patients when used for engraftment, additional embodiments are contemplated to further reduce the possibility of risk to the health of patients receiving engrafted cells. One of several concerns for hESC-based cell therapy procedures is the possibility of introducing contaminating undifferentiated cells that resisted differentiation which under post engraftment conditions develop into cells that cause harm to the patient. In the case of a pluripotent cell, one harmful result is teratoma formation that endangers the patient's life. Teratoma formation using hESC derived cells was reported following short-term neural differentiation protocols based on spontaneous cell differentiation. However, the inventors' use of human ES derived neural cell types, unlike their mouse ESC-derived counterparts, rarely resulted in teratoma formation following appropriate neural differentiation strategies as described in the current invention (i.e. monolayer culture, dual-SMAD-inhibition protocol and growth in cytokines that do not promote proliferation). In fact after analyzing several hundred animals with human cell grafts, using a variety of neural differentiation strategies over the last 10 years, teratoma formation was not observed. Furthermore, teratomas were not observed in PD transplantation procedures of the present inventions using human cells for grafts. The difference between the use of human vs. mouse cells for engraftment procedures for use in humans is contemplated to be related to the different stage of pluripotency captured in human versus mouse ESCs, whereby human cells are thought to match the properties of a pluripotent stage described as Epi-SCs, unlike mouse ESCs which may be at a different developmental stage.

However, at least one of the problems using cells from previous transplantation studies was the continued risk of neural overgrowth that is substantial in Perrier et al., PNAS 2004 and similar protocols which are surprisingly absent when using mature DA neurons and transplantation methods of the present inventions. Further, another problem found in engraftment tests in previous studies was the formation of hESC derived neuroepithelial structures (i.e. neural rosette-type) that continue to proliferate in vivo. This in vivo expansion of grafted neuroepithelial cells was observed in various neural transplantation paradigms including hESC derived DA neuron transplantation studies in rodent Parkinson's and Huntington's disease models. Those "neural rosette-type" proliferating cells represented non-transformed primary cells with a high intrinsic growth potential which resulted in large grafts composed of ectopic, mostly cortical-type tissue in grafted animals. As described herein, several strategies were used to eliminate contaminating pluripotent or neuroepithelial cells at the time of grafting (e.g. selection for SSEA-4 (pluripotent marker) or Forse-1 (neuroepithelial marker). These strategies were partially successful when using rosette-based differentiation strategies and neural overgrowth was still observed in a subset of grafts sorted for Forse1 or sorted negatively for SSEA-4. Surprisingly, with the development of this floor plate-based rather than rosette-based DA neuron differentiation procedures, the issue of neuroepithelial overgrowth was overcome. Rarely observed were graft-derived, proliferating cells within functional hESC floor plate-derived DA neuron grafts.

Based upon the adverse results of other engraftment procedures, another safety concern for using DA neuronal grafting into humans are side effects of the therapy such as the occurrence of graft-induced dyskinesia (GID) observed in about 15% of patients receiving fetal tissue in transplantation trials. However, as discussed herein, the nearly complete absence of graft derived Serotonergic cells, along with the use of a more consistent cell source with the possibility of further depleting unwanted cell types (see, text associated with FIG. 28), and the possibility of controlling in vivo DA fiber distribution (see, FIG. 29; i.e. preventing "hot spots" of neuronal clusters secreting L-Dopa and other compounds) are major advantages of using the methods of the present inventions over other methods for providing cells for use in engraftment procedures. Thus use of the methods of the present inventions is contemplated to minimize risk to patients.

VX. Use of Human ESCs for Clinical Translation.

In preferred embodiments, human ESCs are contemplated for use in methods for making and using cells for engraftment procedures in humans, in other words, cell therapy for the treatment of PD. In particular, human ESCs have numerous advantages over using human iPSCs in methods of the present inventions, such as, for one example, for use in providing engraftable midbrain DA neurons for use as a PD cell therapy. In particular, the use of induced pluripotent stem cells (iPSCs) as a cell source for DA neuron derivation has several advantages, such as providing a genetically matched cell source for each patient. However, a number of recent studies have created uncertainty regarding the safety and full genetic compatibility of iPSCs. Reprogrammed cells have been shown to harbor potentially dangerous genetic and epigenetic abnormalities that are undesirable for clinical utility. Furthermore, work in mouse iPSCs showed that iPSC derived cells are not fully immunocompatible which is the main argument to support their use in human transplantation. Furthermore, there are no FDA-approved procedures using iPSCs for engraftment. Finally, it would be impractical and cost-prohibitive to envisage the generation of GMP-compliant and fully QC-controlled cell banks for each individual patient. In comparison, the genetic stability of hiPSCs compared to hESCs was intensively studied. Although hESCs were observed to acquire mutations over time in culture the timing and rate of such mutations appeared to differ from hiPSCs, where hESCs were generally considered more genetically stable than iPSCs, for examples, see, Hussein, et al., Nature 471, 58-62 (2011); Mayshar, et al. Cell Stem Cell 7, 521-531 (2010); Lister, et al. Nature 471, 68-73 (2011); Laurent, et al. Cell Stem Cell 8, 106-118 (2011). Additionally, standard operating procedures were devised for several hESC lines that satisfied the rigorous safety tests required by the FDA for cellular and gene therapy products. The FDA has approved two groups in the United States to advance hESC-based cellular therapies to clinical use. For example, Geron Corporation entered a Phase I trial with hESC-derived oligodendrocyte precursor cells (GRNOPC1), and Advanced Cell Technology (ACT), Inc. has two current Phase I/II trials using hESC-derived retinal pigmented epithelial cells to treat Stargardt's Macular Dystrophy (trial NCT01345006) and Advanced Dry Age Related Macular Degeneration (trial NCT01344993).

Finally, the fact that both of the FDA-approved, hESC-based clinical trials target nervous system disorders show advantages of using hESC-based methods for providing engraftment material for treating nervous system diseases and injuries. The nervous system is considered an immuno-privileged site since foreign tissue (allografts) elicits weak immune responses when compared to the same graft placed into the periphery. In fact, after twenty-five years of transplanting fetal cells into human brains, it was found that some allogenic neurons survived for up to 16 years in the human brain with transient immunosuppression. Therefore it appears that identical antigenic matching between a cell source and the graft recipient is not essential. Thus hESCs are contemplated as a universal, allogenic source of DA neurons for treating PD in addition to other nervous system diseases, disorders and injuries. Patients receiving cells of the present inventions are contemplated to have a clinical diagnosis of PD. Authentic DA neurons grafts are contemplated for use in early intervention and moderate-to-severe PD, including patients in whom there is insufficient symptomatic control with available medications, such as levodopa, adjunctive medication, etc. In some embodiments, patients contemplated to receive neuron grafts have subtle signs in early PD (e.g. by the use of neuroimaging for detecting dopaminergic deficits, FDG-PET, and signs of dyskinesias, etc. Dyskinesia as measured by the Unified Dyskinesia Rating scale (UDysRS) (Goetz, et al., Mov Disord. 23, 2398-2403 (2008)) is contemplated for use in monitoring patients before and after engraftment. Patients may also have "scans without evidence of dopaminergic deficits" (SWEDDS), some of whom may have dystonia or essential tremor. Brain MRI would be done in order to identify patients with other (non dopa) contributory factors to Parkinsonism. In some embodiments, patients would have a positive response to levodopa. Determining pre- and post-transplantation parameters and endpoints for subject monitoring, such as motor evaluation, non-motor evaluation, quality of life, and also the use of neuroimaging and other biomarkers. Motor function: The UPDRS and newly-validated MDS-UPDRS (Goetz, et al., Mov Disord. 23, 2129-2170 (2008)) are widely used for measuring PD motor symptoms. However, other tests including 10 m walk or 6 minute walk tests, timed up and go, functional gait assessment, functional reach, and others are contemplated for more patient-oriented outcome measures. Patients would be tested in the "off" state, as well as "on", and rating scales would be included for "off" time (for example following Movement Disorder Society recommendations based upon clinimetric properties of validated wearing off scales (Antonini, et al. Mov Disord. 26, 2169-2175 (2011)) and dyskinesia rating scales (for example UdysRS (Goetz, et al., Mov Disord. 23, 2398-2403 (2008)). Videotaping standardized patient examinations in both "on" and "off" states is contemplated. Non-motor function: Measures will primarily target cognitive, psychiatric outcomes and dysautonomia in addition to addressing cognition, depression, anxiety, apathy, sleep, fatigue, psychosis, and other non-motor symptoms before and after engraftment. Quality of life: PD-specific questionnaires (PD-QUALIF) and/or well-validated quality of life scales such as the SF-36 are contemplated to monitor patient outcomes.

Neuroimaging and other biomarkers: Functional imaging was widely used in surgical PD trials. While dopamine-based imaging (such as FDOPA-PET) is contemplated for use in examining graft maintenance, neuroimaging techniques using other ligands are contemplated for use including imaging-based markers, for example targeting inflammation, and of non-imaging systemic markers as exploratory data collection. Imaging would find use in pre-operative planning, e.g. extent and location of DA depletion within the basal ganglia and incorporation of PET data in tailoring surgical planning for each patient. Location of graft placement and number of cell deposits. In some embodiments, the putamen (Freed, et al. N. Engl. J. Med. 344, 710-719 (2001); Lindvall, et al. Prog. Brain Res. 82, 729-734 (1990) and postcommissural putamen (Olanow, et al. Ann. Neurol. 54, 403-414 (2003)) are sites of cell engraftment (administration). In some embodiments, multiple placements via different surgical tracks are contemplated. MRI with a Clearpoint system which provides real time imaging and visualization of the trajectory path and targeting accuracy is contemplated for monitoring the engrafted cells. This system is used in placement of Deep Brain Stimulation electrodes in PD patients. Cell number and Composition of the graft. Fetal trials were performed with essentially unknown number of DA neurons since they used fetal graft material with numerous cell types. Based upon data provided herein, an estimated 100,000-200,000 surviving TH+ neurons are contemplated for recovery of DA neuronal function.

Immunosuppression. In some embodiments, immunosuppression of grafted patients is contemplated, at least 6 months up to the lifetime of a patient. In some embodiments, patients will not be immunosuppressed for purposes of having engrafted tissue.

TABLE 1

Gene expression array data of significantly up-regulated and down-regulated genes at differentiation day 11 in SHH/FGF8/Chir treated Floor-plate based population over control LSB treated population.

| Column # | Column ID | Fold-Change | p-value |
|---|---|---|---|
| 7304 | FOXA1 | 22.5512 | 5.03E−16 |
| 7305 | FOXA2 | 17.3328 | 5.70E−17 |
| 31270 | SPON1 | 16.4393 | 2.14E−14 |
| 31684 | SYT4 | 13.2693 | 9.61E−12 |

TABLE 1-continued

Gene expression array data of significantly up-regulated and down-regulated genes at differentiation day 11 in SHH/FGF8/Chir treated Floor-plate based population over control LSB treated population.

| Column # | Column ID | Fold-Change | p-value |
|---|---|---|---|
| 4334 | COL22A1 | 8.54042 | 2.05E-17 |
| 6616 | FBLN1 | 8.24162 | 4.97E-18 |
| 32035 | TFF3 | 8.01805 | 1.08E-13 |
| 5324 | DKK1 | 7.95664 | 1.19E-09 |
| 3244 | CAPN6 | 7.58928 | 1.77E-08 |
| 2544 | C20ORF56 | 7.58575 | 6.71E-15 |
| 27591 | PKDCC | 7.42271 | 2.02E-11 |
| 23584 | LOC91461 | 5.43556 | 9.86E-09 |
| 5037 | DDC | 5.19301 | 2.09E-08 |
| 13598 | LDB2 | 4.76303 | 2.92E-09 |
| 723 | AMOT | 4.58838 | 5.68E-08 |
| 4978 | DBX1 | 4.40946 | 2.36E-09 |
| 31138 | SOX8 | 4.32227 | 9.29E-08 |
| 30193 | SILV | 4.3198 | 2.52E-07 |
| 30148 | SHISA2 | 4.31109 | 1.60E-07 |
| 31509 | STK39 | 3.65624 | 2.90E-06 |
| 27661 | PLCL2 | 3.63607 | 6.81E-11 |
| 24425 | MGST1 | 3.59223 | 2.48E-11 |
| 32945 | TSPAN7 | 3.57361 | 7.36E-07 |
| 29082 | RHOU | 3.51768 | 5.89E-06 |
| 9283 | HS.19193 | 3.49663 | 6.24E-13 |
| 5478 | DOCK10 | 3.43476 | 8.18E-07 |
| 25094 | MMP11 | 3.40705 | 2.13E-08 |
| 29975 | SERPINF1 | 3.36169 | 1.97E-10 |
| 29042 | RGS4 | 3.33544 | 7.01E-06 |
| 926 | APCDD1 | 3.33059 | 3.47E-10 |
| 12640 | IRX3 | 3.32454 | 1.65E-05 |
| 26837 | OSBPL10 | 3.3051 | 9.55E-07 |
| 32086 | THBS4 | 3.29135 | 9.77E-07 |
| 14581 | LOC100130506 | 3.1293 | 5.81E-09 |
| 4931 | DAB2 | 3.02851 | 4.80E-09 |
| 12642 | IRX5 | 2.95938 | 2.73E-08 |
| 13774 | LMX1A | 2.81057 | 1.42E-06 |
| 31516 | STOM | 2.76317 | 2.01E-07 |
| 26374 | ODZ4 | 2.75644 | 3.06E-06 |
| 8210 | GSC | 2.75053 | 3.47E-07 |
| 26170 | NRCAM | 2.71264 | 1.82E-08 |
| 28414 | PTCH1 | 2.63379 | 2.99E-08 |
| 31578 | SULF2 | 2.59351 | 1.42E-07 |
| 7366 | FREM1 | 2.5697 | 2.25E-07 |
| 13743 | LITAF | 2.55681 | 3.65E-08 |
| 26236 | NTNG1 | 2.55383 | 1.78E-07 |
| 25869 | NEUROG2 | 2.55012 | 5.05E-06 |
| 26132 | NPY | 2.54575 | 4.48E-06 |
| 25967 | NKX2-1 | 2.52195 | 0.00023 |
| 27101 | PCDH18 | 2.46481 | 1.69E-05 |
| 32557 | TNFRSF19 | 2.45297 | 4.06E-08 |
| 5759 | EFEMP1 | 2.44308 | 7.78E-09 |
| 31148 | SP5 | 2.43459 | 5.34E-06 |
| 28069 | PQLC3 | 2.42685 | 2.59E-05 |
| 30313 | SLC20A2 | 2.40457 | 1.24E-06 |
| 30743 | SNHG4 | 2.35277 | 8.69E-08 |
| 27607 | PKP2 | 2.34734 | 5.34E-05 |
| 25520 | MYL4 | 2.3327 | 3.93E-08 |
| 26128 | NPTX2 | 2.29568 | 1.08E-05 |
| 26006 | NMD3 | 2.29039 | 3.18E-05 |
| 16924 | LOC391019 | 2.28656 | 1.25E-05 |
| 19975 | LOC646966 | 2.26444 | 6.23E-05 |
| 29894 | SEMA6A | 2.25036 | 0.000844 |
| 6161 | EYA2 | 2.23175 | 0.00024 |
| 26105 | NPFFR2 | 2.23095 | 7.31E-05 |
| 4818 | CXXC4 | 2.23047 | 1.66E-05 |
| 2764 | C4ORF14 | 2.22128 | 5.73E-06 |
| 18269 | LOC642989 | 2.22053 | 0.000735 |
| 13059 | KIAA1324L | 2.21906 | 4.75E-05 |
| 23663 | LRIG3 | 2.21159 | 4.38E-07 |
| 6196 | FABP5L2 | 2.19875 | 3.09E-05 |
| 29347 | RPL13A | 2.19362 | 0.000122 |
| 12446 | IL1RAPL1 | 2.19134 | 1.75E-05 |
| 28455 | PTN | 2.18577 | 9.36E-05 |
| 30746 | SNHG7 | 2.18224 | 4.35E-07 |
| 28788 | RASL12 | 2.16856 | 1.39E-05 |
| 17150 | LOC401074 | 2.16782 | 1.07E-06 |
| 30283 | SLC16A3 | 2.16541 | 6.06E-05 |
| 15378 | LOC100133008 | 2.16461 | 3.15E-05 |
| 32180 | TLE6 | 2.16433 | 6.35E-07 |
| 12887 | KCNQ1OT1 | 2.1641 | 2.97E-06 |
| 31210 | SPATS2L | 2.16393 | 0.000597 |
| 4241 | CMTM8 | 2.16297 | 0.000392 |
| 30933 | SNORD25 | 2.15953 | 0.000363 |
| 2803 | C5ORF13 | 2.15734 | 3.94E-05 |
| 32131 | TIGA1 | 2.15335 | 1.80E-05 |
| 1667 | BMP7 | 2.14281 | 0.000497 |
| 20837 | LOC649946 | 2.14098 | 8.39E-05 |
| 25756 | NCRNA00219 | 2.12543 | 6.42E-07 |
| 8003 | GPM6B | 2.08967 | 3.45E-05 |
| 5650 | DYM | 2.08942 | 0.000179 |
| 29606 | S1PR3 | 2.08344 | 0.000479 |
| 27681 | PLEKHA5 | 2.08285 | 0.000217 |
| 11495 | HS.570308 | 2.08044 | 1.67E-06 |
| 26232 | NTN1 | 2.06755 | 2.49E-08 |
| 12635 | IRS1 | 2.06435 | 0.000109 |
| 20404 | LOC648343 | 2.05497 | 0.000791 |
| 29352 | RPL15 | 2.05205 | 2.82E-06 |
| 33800 | WNT5A | 2.03874 | 1.08E-06 |
| 30481 | SLC38A4 | 2.03653 | 1.13E-06 |
| 12059 | HS.7093 | 2.01993 | 2.66E-06 |
| 22500 | LOC728126 | 2.0183 | 1.16E-06 |
| 16095 | LOC136143 | 2.01775 | 5.71E-05 |
| 12718 | ITPR3 | 2.01384 | 1.67E-05 |
| 4004 | CHN2 | 2.00649 | 7.18E-06 |
| 32162 | TIPARP | 2.00538 | 0.000633 |
| 482 | ADSS | 2.00282 | 0.000136 |
| 2196 | C17ORF45 | 2.00241 | 6.15E-05 |
| 3447 | CCDC51 | -2.00054 | 0.000177 |
| 5945 | ENC1 | -2.0038 | 0.000468 |
| 27915 | POU3F2 | -2.00877 | 2.04E-07 |
| 23143 | LOC729779 | -2.01527 | 0.000972 |
| 23972 | MAP1LC3A | -2.01892 | 3.37E-06 |
| 7611 | GAS6 | -2.02463 | 9.63E-08 |
| 17062 | LOC399959 | -2.02793 | 2.39E-05 |
| 29519 | RSPO3 | -2.03762 | 1.61E-05 |
| 29038 | RGS20 | -2.04076 | 3.60E-09 |
| 19157 | LOC644936 | -2.04097 | 0.000128 |
| 30502 | SLC3A2 | -2.04467 | 5.58E-05 |
| 33508 | VCAM1 | -2.05421 | 2.51E-06 |
| 490 | AFAP1L2 | -2.05673 | 8.23E-07 |
| 23275 | LOC730167 | -2.06009 | 0.000652 |
| 29215 | RNF175 | -2.06406 | 6.81E-05 |
| 5923 | EMILIN2 | -2.06713 | 2.81E-06 |
| 34367 | ZNF462 | -2.07292 | 1.63E-05 |
| 26244 | NUAK1 | -2.0732 | 0.000172 |
| 25818 | NEBL | -2.07351 | 1.55E-06 |
| 29624 | SALL3 | -2.0787 | 2.15E-06 |
| 33491 | VANGL2 | -2.08497 | 0.000402 |
| 30581 | SLC7A8 | -2.08722 | 1.40E-08 |
| 875 | ANXA3 | -2.08727 | 0.000227 |
| 34075 | ZFP36L1 | -2.08803 | 5.08E-05 |
| 15637 | LOC100133760 | -2.09319 | 8.14E-05 |
| 1227 | ASNS | -2.10169 | 8.03E-05 |
| 33804 | WNT7B | -2.1052 | 3.00E-08 |
| 24064 | MARS | -2.107 | 0.000146 |
| 33725 | WDR72 | -2.11201 | 0.000617 |
| 31295 | SPRY1 | -2.12339 | 2.43E-05 |
| 7495 | GABARAPL1 | -2.12367 | 1.70E-05 |
| 4331 | COL1A2 | -2.12521 | 1.97E-05 |
| 6821 | FILIP1 | -2.1288 | 0.00026 |
| 24246 | METRN | -2.13118 | 1.99E-05 |
| 12056 | HS.66187 | -2.13789 | 2.97E-05 |
| 28438 | PTGIS | -2.14246 | 7.36E-06 |
| 12980 | KIAA0367 | -2.15304 | 1.92E-05 |
| 1575 | BCMO1 | -2.16946 | 7.40E-05 |
| 25473 | MXRA5 | -2.17542 | 3.63E-06 |
| 32537 | TNFAIP1 | -2.17984 | 7.66E-06 |
| 34064 | ZFHX4 | -2.23036 | 0.00046 |
| 28787 | RASL11B | -2.23056 | 0.000115 |

TABLE 1-continued

Gene expression array data of significantly up-regulated and down-regulated genes at differentiation day 11 in SHH/FGF8/Chir treated Floor-plate based population over control LSB treated population.

| Column # | Column ID | Fold-Change | p-value |
|---|---|---|---|
| 5632 | DUSP6 | −2.23366 | 0.000732 |
| 3149 | CACHD1 | −2.23514 | 5.39E−05 |
| 3221 | CAMKV | −2.25983 | 5.01E−08 |
| 7248 | FLNC | −2.26856 | 1.13E−05 |
| 28307 | PRSS8 | −2.28456 | 1.35E−05 |
| 12662 | ISYNA1 | −2.29255 | 1.40E−05 |
| 7524 | GADD45A | −2.2962 | 7.46E−07 |
| 5921 | EMID2 | −2.29995 | 1.55E−05 |
| 941 | APLP1 | −2.31453 | 2.03E−07 |
| 30576 | SLC7A5 | −2.32091 | 0.000757 |
| 7474 | FZD3 | −2.32644 | 6.13E−06 |
| 5940 | EMX2OS | −2.3303 | 2.65E−07 |
| 1259 | ATF3 | −2.34034 | 2.59E−06 |
| 33806 | WNT8B | −2.34155 | 3.96E−08 |
| 31388 | SST | −2.34663 | 1.83E−06 |
| 3188 | CALCB | −2.34833 | 3.49E−06 |
| 1075 | ARHGEF6 | −2.35421 | 1.54E−08 |
| 26885 | OTX1 | −2.35607 | 0.00023 |
| 26393 | OLFM3 | −2.35759 | 2.32E−07 |
| 33087 | TUBB2A | −2.36013 | 0.000777 |
| 31747 | TAGLN | −2.36809 | 2.16E−05 |
| 5372 | DMRTA1 | −2.36884 | 5.28E−08 |
| 3614 | CD200R1 | −2.37345 | 1.25E−14 |
| 17147 | LOC401056 | −2.37854 | 8.57E−10 |
| 33801 | WNT5B | −2.3794 | 3.01E−08 |
| 28590 | RAB11FIP1 | −2.40833 | 6.65E−07 |
| 23362 | LOC730525 | −2.41129 | 1.59E−06 |
| 27658 | PLCH1 | −2.4212 | 3.31E−07 |
| 7000 | FLJ32310 | −2.42179 | 5.77E−06 |
| 3339 | CBX4 | −2.43314 | 1.13E−07 |
| 6073 | ERRFI1 | −2.44539 | 1.44E−05 |
| 32521 | TMSB15A | −2.45505 | 1.31E−05 |
| 13242 | KLHL14 | −2.51767 | 2.71E−11 |
| 30201 | SIPA1L2 | −2.52018 | 3.67E−06 |
| 32760 | TRIB1 | −2.52274 | 1.73E−06 |
| 13641 | LFNG | −2.53204 | 5.33E−07 |
| 12285 | IER3 | −2.54594 | 1.65E−07 |
| 28506 | PTPRZ1 | −2.55447 | 1.62E−06 |
| 1608 | BEX2 | −2.56331 | 0.000109 |
| 32179 | TLE4 | −2.56513 | 0.000135 |
| 10888 | HS.551307 | −2.56708 | 0.000405 |
| 683 | ALPK2 | −2.57443 | 2.83E−06 |
| 32551 | TNFRSF12A | −2.59274 | 4.02E−06 |
| 32610 | TNRC9 | −2.59782 | 3.23E−07 |
| 777 | ANKRD1 | −2.61554 | 3.15E−05 |
| 13622 | LEMD1 | −2.62351 | 2.97E−05 |
| 26777 | OR7E156P | −2.64884 | 3.51E−07 |
| 24377 | MGC39900 | −2.66479 | 1.46E−05 |
| 12267 | ID1 | −2.66562 | 6.68E−07 |
| 27726 | PLP1 | −2.69279 | 9.13E−07 |
| 4350 | COL4A6 | −2.69704 | 1.17E−07 |
| 4320 | COL11A1 | −2.71039 | 1.79E−09 |
| 3127 | CA2 | −2.71276 | 2.35E−08 |
| 26151 | NR2E1 | −2.72059 | 4.25E−14 |
| 31267 | SPOCK1 | −2.7283 | 3.38E−05 |
| 13744 | LIX1 | −2.73818 | 9.34E−06 |
| 32038 | TFPI | −2.77685 | 6.23E−05 |
| 32776 | TRIM24 | −2.79151 | 8.73E−08 |
| 32756 | TRH | −2.79963 | 3.98E−07 |
| 32652 | TOX3 | −2.81075 | 9.35E−06 |
| 2405 | C1ORF21 | −2.81457 | 9.49E−09 |
| 5371 | DMRT3 | −2.82614 | 4.28E−09 |
| 32381 | TMEM2 | −2.83489 | 1.83E−05 |
| 2437 | C1ORF61 | −2.85324 | 3.53E−09 |
| 2868 | C6ORF141 | −2.8569 | 6.05E−06 |
| 1178 | ARX | −2.87861 | 0.000122 |
| 26245 | NUAK2 | −2.95666 | 4.14E−08 |
| 33796 | WNT2B | −2.96258 | 1.15E−10 |
| 28507 | PTRF | −2.97439 | 2.07E−07 |
| 7662 | GCNT1 | −2.98108 | 1.49E−06 |
| 5930 | EMP1 | −2.9918 | 1.11E−06 |
| 31844 | TBC1D9 | −3.00324 | 2.53E−09 |
| 4352 | COL5A2 | −3.02084 | 1.26E−07 |
| 4699 | CTNNA2 | −3.04046 | 6.91E−09 |
| 2516 | C20ORF177 | −3.04277 | 4.86E−08 |
| 3518 | CCL2 | −3.04332 | 9.50E−11 |
| 34315 | ZNF385B | −3.05084 | 5.56E−07 |
| 12058 | HS.7023 | −3.0642 | 3.72E−08 |
| 23661 | LRIG1 | −3.07681 | 3.30E−07 |
| 7813 | GLI3 | −3.07936 | 1.22E−08 |
| 31513 | STMN2 | −3.09098 | 4.93E−06 |
| 30023 | SFRP1 | −3.09686 | 1.13E−06 |
| 1128 | ARMCX2 | −3.09746 | 2.91E−06 |
| 4689 | CTGF | −3.11416 | 4.47E−08 |
| 6365 | FAM181A | −3.1422 | 2.56E−09 |
| 4121 | CLDN1 | −3.15492 | 1.93E−06 |
| 627 | ALDH1A1 | −3.15745 | 1.18E−12 |
| 629 | ALDH1A3 | −3.17887 | 4.46E−13 |
| 33501 | VAT1L | −3.18253 | 1.21E−06 |
| 4912 | CYR61 | −3.18856 | 3.58E−07 |
| 12781 | KANK4 | −3.20054 | 7.99E−12 |
| 3067 | C9ORF171 | −3.24146 | 3.73E−11 |
| 12363 | IGFBP3 | −3.34999 | 1.02E−06 |
| 4533 | CRIP1 | −3.45501 | 6.62E−08 |
| 3740 | CDH11 | −3.48609 | 2.23E−08 |
| 816 | ANKRD38 | −3.48622 | 6.93E−12 |
| 12730 | JAG1 | −3.58463 | 3.83E−08 |
| 12271 | ID4 | −3.72402 | 1.78E−12 |
| 810 | ANKRD34B | −3.76606 | 1.15E−11 |
| 12850 | KCNJ13 | −3.81092 | 2.16E−09 |
| 6112 | ETV5 | −3.81591 | 4.37E−10 |
| 9265 | HS.181245 | −3.86611 | 1.24E−09 |
| 633 | ALDH2 | −3.87108 | 1.97E−09 |
| 26180 | NRIP3 | −3.92066 | 6.08E−08 |
| 30413 | SLC2A1 | −4.11899 | 1.18E−05 |
| 5479 | DOCK11 | −4.35251 | 5.67E−09 |
| 25658 | NAV1 | −4.35259 | 1.02E−10 |
| 5349 | DLL1 | −4.47474 | 1.58E−07 |
| 34418 | ZNF533 | −4.49025 | 1.16E−09 |
| 327 | ACTC1 | −4.63509 | 7.37E−09 |
| 1037 | ARHGAP15 | −4.67561 | 9.89E−10 |
| 31132 | SOX3 | −4.72958 | 7.45E−09 |
| 26153 | NR2F1 | −4.73849 | 1.53E−09 |
| 3129 | CA4 | −4.7904 | 3.00E−09 |
| 33071 | TTYH1 | −4.79045 | 8.94E−14 |
| 5766 | EFHD1 | −4.86615 | 1.16E−09 |
| 867 | ANXA1 | −4.95401 | 1.41E−08 |
| 8500 | HES4 | −5.24189 | 1.63E−11 |
| 4299 | CNTNAP2 | −6.14001 | 2.94E−08 |
| 23947 | MAMDC2 | −6.36522 | 2.23E−10 |
| 7605 | GAS1 | −6.38074 | 2.63E−11 |
| 31151 | SP8 | −8.88965 | 4.42E−20 |
| 30024 | SFRP2 | −9.73482 | 4.24E−14 |
| 13677 | LHX2 | −10.9076 | 6.16E−11 |
| 5939 | EMX2 | −11.5085 | 1.34E−19 |
| 21068 | LOC650757 | −12.1496 | 7.71E−20 |
| 27068 | PAX6 | −15.7636 | 2.24E−22 |
| 5554 | DRD4 | −17.3929 | 3.17E−16 |
| 26065 | NOS2A | −20.0139 | 2.83E−16 |
| 1501 | BARHL1 | −20.6077 | 2.59E−14 |
| 26064 | NOS2 | −25.1751 | 7.45E−17 |
| 8501 | HES5 | −38.4549 | 8.90E−22 |

TABLE 2

Gene expression array data of significantly up-regulated and down-regulated genes at differentiation day 11 in SHH/FGF8/Chir treated Floor-plate based population over SHH/FGF8 only treated population.

| Column # | Probeset ID | Fold-Change | p-value |
|---|---|---|---|
| 31575 | SYT4 | 14.8775 | 3.24E-12 |
| 7195 | FOXA1 | 11.8929 | 2.65E-13 |
| 4225 | COL22A1 | 8.26361 | 3.21E-17 |
| 5215 | DKK1 | 6.39507 | 1.32E-08 |
| 7956 | GPR177 | 5.98201 | 5.65E-12 |
| 13508 | LEF1 | 5.07514 | 2.45E-11 |
| 2435 | C20ORF56 | 5.02955 | 2.71E-12 |
| 4928 | DDC | 5.0147 | 3.23E-08 |
| 11952 | HS.71947 | 4.81098 | 5.13E-09 |
| 13665 | LMX1A | 4.7485 | 3.59E-10 |
| 12427 | INHBE | 4.72434 | 3.41E-07 |
| 32562 | TPBG | 4.63162 | 1.44E-09 |
| 1152 | ATF5 | 4.48583 | 0.000153048 |
| 5369 | DOCK10 | 4.23427 | 4.29E-08 |
| 31414 | STOX1 | 4.20695 | 3.94E-10 |
| 4869 | DBX1 | 4.17519 | 5.31E-09 |
| 31977 | THBS4 | 4.13195 | 3.66E-08 |
| 2694 | C5ORF13 | 4.0095 | 7.84E-10 |
| 31469 | SULF2 | 3.83814 | 8.51E-11 |
| 31468 | SULF1 | 3.81974 | 3.96E-07 |
| 34285 | ZNF503 | 3.81092 | 2.76E-08 |
| 12531 | IRX3 | 3.73598 | 3.93E-06 |
| 4935 | DDIT4 | 3.73152 | 3.78E-05 |
| 31369 | STC2 | 3.70632 | 8.48E-08 |
| 27482 | PKDCC | 3.69823 | 2.20E-07 |
| 4257 | COLEC12 | 3.6503 | 5.20E-06 |
| 31926 | TFF3 | 3.62059 | 1.12E-08 |
| 25244 | MSX1 | 3.60243 | 0.000146141 |
| 23475 | LOC91461 | 3.58231 | 2.08E-06 |
| 26777 | OTX2 | 3.47814 | 3.97E-09 |
| 13489 | LDB2 | 3.44124 | 3.22E-07 |
| 13657 | LMO3 | 3.29197 | 2.61E-12 |
| 817 | APCDD1 | 3.21277 | 6.95E-10 |
| 4822 | DAB2 | 3.18324 | 1.84E-09 |
| 25760 | NEUROG2 | 3.16851 | 1.30E-07 |
| 31101 | SPATS2L | 3.15744 | 2.80E-06 |
| 1311 | AXIN2 | 3.13274 | 1.80E-06 |
| 32448 | TNFRSF19 | 3.11104 | 2.48E-10 |
| 4934 | DDIT3 | 3.08248 | 4.83E-05 |
| 26776 | OTX1 | 3.05293 | 6.14E-06 |
| 28360 | PTPN13 | 3.03567 | 5.18E-06 |
| 994 | ARL4A | 2.98803 | 1.45E-07 |
| 26728 | OSBPL10 | 2.94508 | 5.19E-06 |
| 32836 | TSPAN7 | 2.86094 | 1.65E-05 |
| 5665 | EFNB2 | 2.78085 | 0.000222563 |
| 8101 | GSC | 2.75066 | 3.46E-07 |
| 6426 | FAM84B | 2.74213 | 7.89E-07 |
| 29866 | SERPINF1 | 2.73192 | 1.26E-08 |
| 924 | ARHGAP10 | 2.72522 | 3.36E-07 |
| 31039 | SP5 | 2.68162 | 9.57E-07 |
| 28210 | PSAT1 | 2.64735 | 9.82E-06 |
| 28933 | RGS4 | 2.6312 | 0.000148375 |
| 13547 | LGI1 | 2.61567 | 1.30E-06 |
| 7369 | FZD7 | 2.61404 | 2.46E-06 |
| 25351 | MUSTN1 | 2.55841 | 4.85E-07 |
| 25411 | MYL4 | 2.55345 | 4.77E-09 |
| 28424 | PVRL3 | 2.55083 | 1.04E-07 |
| 299 | ADAMTS9 | 2.53131 | 2.88E-08 |
| 1555 | BMP4 | 2.52708 | 9.40E-05 |
| 31161 | SPON1 | 2.5133 | 0.000145864 |
| 26265 | ODZ4 | 2.50312 | 1.46E-05 |
| 33730 | XBP1 | 2.50164 | 1.72E-06 |
| 28766 | RBP1 | 2.49237 | 6.12E-05 |
| 12533 | IRX5 | 2.48929 | 7.43E-07 |
| 1118 | ASNS | 2.47416 | 4.50E-06 |
| 2770 | C6ORF160 | 2.40219 | 3.58E-05 |
| 12337 | IL1RAPL1 | 2.40145 | 3.15E-06 |
| 12526 | IRS1 | 2.3994 | 7.70E-06 |
| 7221 | FOXJ1 | 2.39492 | 8.89E-05 |
| 28647 | RARB | 2.37013 | 9.11E-09 |
| 14472 | LOC100130506 | 2.36331 | 1.36E-06 |
| 3979 | CITED2 | 2.36201 | 2.92E-05 |
| 31430 | STT3B | 2.34069 | 1.29E-05 |
| 26023 | NPY | 2.3346 | 1.98E-05 |
| 6052 | EYA2 | 2.3192 | 0.000136915 |
| 26991 | PCDH17 | 2.31776 | 8.71E-05 |
| 26127 | NTNG1 | 2.31615 | 1.30E-06 |
| 373 | ADSS | 2.29099 | 1.20E-05 |
| 6120 | FAM107A | 2.26256 | 0.000677009 |
| 28387 | PTPRM | 2.25934 | 1.41E-05 |
| 31572 | SYT17 | 2.257 | 7.10E-05 |
| 7143 | FLRT2 | 2.24042 | 1.35E-07 |
| 32372 | TMEM88 | 2.2394 | 4.55E-05 |
| 27552 | PLCL2 | 2.23488 | 1.24E-06 |
| 5681 | EGLN3 | 2.23059 | 0.000841858 |
| 3837 | CHAC1 | 2.22744 | 2.61E-05 |
| 26045 | NR2F2 | 2.21836 | 1.71E-05 |
| 7196 | FOXA2 | 2.21691 | 8.01E-05 |
| 12950 | KIAA1324L | 2.18683 | 6.09E-05 |
| 3667 | CDK6 | 2.1717 | 0.00076066 |
| 9540 | HS.36053 | 2.15618 | 5.44E-07 |
| 19012 | LOC644860 | 2.15508 | 7.00E-06 |
| 4366 | CPNE8 | 2.15418 | 9.80E-06 |
| 4936 | DDIT4L | 2.14147 | 0.000195501 |
| 29691 | SDCBP | 2.13721 | 3.10E-05 |
| 7144 | FLRT3 | 2.11969 | 0.00033768 |
| 5851 | ENPP2 | 2.10048 | 0.000485738 |
| 1558 | BMP7 | 2.0876 | 0.000718573 |
| 23514 | LPAR4 | 2.08062 | 1.96E-06 |
| 23554 | LRIG3 | 2.07935 | 1.81E-06 |
| 5964 | ERRFI1 | 2.07249 | 0.000220066 |
| 3623 | CDCA7 | 2.07177 | 0.000280326 |
| 30635 | SNHG5 | 2.0594 | 4.95E-06 |
| 32620 | TRAM2 | 2.04784 | 0.000111169 |
| 12809 | KCTD6 | 2.04602 | 0.000114945 |
| 28901 | RGL1 | 2.04043 | 0.000167278 |
| 30628 | SNHG1 | 2.03706 | 0.000252445 |
| 27947 | PPPDE1 | 2.02017 | 2.69E-05 |
| 5434 | DPYSL3 | -2.00257 | 0.000139976 |
| 23863 | MAP1LC3A | -2.00377 | 4.01E-06 |
| 24226 | MGC18216 | -2.01184 | 0.000204988 |
| 4818 | D4S234E | -2.01244 | 8.77E-05 |
| 4825 | DACH2 | -2.01277 | 8.71E-07 |
| 4386 | CPXM2 | -2.02106 | 2.02E-05 |
| 32224 | TMEM169 | -2.02651 | 0.000222019 |
| 151 | ACBD7 | -2.03074 | 6.94E-05 |
| 8643 | HOOK1 | -2.03984 | 1.85E-05 |
| 4278 | COPG2IT1 | -2.04004 | 8.62E-07 |
| 32981 | TUBB3 | -2.04044 | 0.000989413 |
| 5887 | EPHA1 | -2.05082 | 1.41E-06 |
| 28929 | RGS20 | -2.06283 | 2.60E-09 |
| 28068 | PRKCH | -2.06869 | 4.13E-06 |
| 33539 | WBP2 | -2.0692 | 0.000157614 |
| 23711 | LY6E | -2.07026 | 8.93E-05 |
| 29803 | SEPP1 | -2.08034 | 2.48E-05 |
| 12713 | KCND2 | -2.08768 | 1.63E-08 |
| 34309 | ZNF533 | -2.08871 | 0.000231468 |
| 14009 | LOC100129034 | -2.09106 | 4.54E-07 |
| 25915 | NMU | -2.09244 | 0.000184692 |
| 24132 | MEST | -2.09269 | 2.92E-06 |
| 2715 | C5ORF41 | -2.09563 | 1.42E-05 |
| 27778 | PON2 | -2.09758 | 1.79E-05 |
| 24105 | MEG3 | -2.10214 | 5.69E-07 |
| 31812 | TCF7L2 | -2.10261 | 0.000153698 |
| 33783 | YBX2 | -2.1118 | 6.90E-06 |
| 28329 | PTGIS | -2.11465 | 9.61E-06 |
| 6694 | FHDC1 | -2.11553 | 8.86E-06 |
| 24175 | MFNG | -2.11579 | 2.95E-05 |
| 6640 | FEZ1 | -2.11631 | 2.58E-06 |
| 2407 | C20ORF177 | -2.12232 | 3.62E-05 |
| 26783 | OVOL2 | -2.12627 | 4.13E-06 |
| 28883 | RFTN2 | -2.13498 | 7.25E-08 |
| 19038 | LOC644919 | -2.13675 | 2.95E-06 |
| 30004 | SH3BP4 | -2.13785 | 0.000314453 |
| 31020 | SOX2 | -2.14642 | 0.000107169 |
| 16268 | LOC284422 | -2.16056 | 1.07E-05 |

TABLE 2-continued

Gene expression array data of significantly up-regulated and down-regulated genes at differentiation day 11 in SHH/FGF8/Chir treated Floor-plate based population over SHH/FGF8 only treated population.

| Column # | Probeset ID | Fold-Change | p-value |
|---|---|---|---|
| 4819 | DAAM1 | −2.16701 | 3.85E−05 |
| 32404 | TMPRSS2 | −2.1693 | 6.26E−07 |
| 26668 | OR7E156P | −2.17193 | 1.53E−05 |
| 12609 | ITPR3 | −2.18226 | 3.09E−06 |
| 6372 | FAM65B | −2.18271 | 1.37E−06 |
| 12635 | JARID2 | −2.18541 | 4.46E−05 |
| 25024 | MOBKL2B | −2.19737 | 5.45E−05 |
| 31567 | SYT13 | −2.19832 | 2.30E−05 |
| 25658 | NDRG1 | −2.20101 | 5.25E−07 |
| 24318 | MGST3 | −2.20252 | 3.24E−07 |
| 2147 | C18ORF26 | −2.2117 | 2.55E−06 |
| 31010 | SOSTDC1 | −2.21381 | 2.23E−08 |
| 4662 | CXCL14 | −2.21955 | 1.81E−08 |
| 33161 | UCA1 | −2.21966 | 2.19E−05 |
| 12176 | IER3 | −2.21992 | 2.75E−06 |
| 7171 | FNBP1 | −2.23104 | 1.98E−05 |
| 12199 | IFITM3 | −2.23167 | 4.22E−06 |
| 25635 | NCRNA00153 | −2.24173 | 2.01E−05 |
| 27531 | PLAC9 | −2.24346 | 9.11E−08 |
| 25743 | NES | −2.2469 | 3.16E−06 |
| 31405 | STMN3 | −2.25856 | 0.000796798 |
| 7536 | GCA | −2.27697 | 1.34E−05 |
| 12275 | IGSF3 | −2.28535 | 4.08E−06 |
| 17038 | LOC401056 | −2.2854 | 2.45E−09 |
| 4533 | CSRP2 | −2.28899 | 0.000244001 |
| 31606 | TACSTD1 | −2.28933 | 0.000115538 |
| 29372 | RRAGD | −2.29258 | 0.000537359 |
| 5884 | EPCAM | −2.29475 | 0.00099285 |
| 28398 | PTRF | −2.29476 | 1.92E−05 |
| 12672 | KANK4 | −2.29735 | 1.73E−08 |
| 3505 | CD200R1 | −2.30795 | 3.06E−14 |
| 33264 | UPK2 | −2.30847 | 1.37E−10 |
| 24978 | MMD | −2.317 | 1.46E−05 |
| 6002 | ETV4 | −2.32842 | 6.04E−09 |
| 27655 | PMP22 | −2.33585 | 4.94E−12 |
| 5657 | EFHD1 | −2.33997 | 7.47E−05 |
| 31186 | SPRY1 | −2.34859 | 3.56E−06 |
| 3631 | CDH11 | −2.35006 | 1.77E−05 |
| 29555 | SAT1 | −2.35602 | 2.21E−06 |
| 33268 | UPP1 | −2.36162 | 5.38E−08 |
| 1968 | C14ORF4 | −2.36739 | 2.59E−06 |
| 9512 | HS.34447 | −2.37168 | 7.49E−08 |
| 16243 | LOC283953 | −2.38022 | 4.57E−07 |
| 3203 | CAV2 | −2.38208 | 1.09E−11 |
| 26223 | NYNRIN | −2.40311 | 1.90E−05 |
| 22623 | LOC728715 | −2.41353 | 0.000504831 |
| 25084 | MPPED2 | −2.42024 | 6.42E−10 |
| 13403 | LAMC2 | −2.42245 | 5.32E−10 |
| 25083 | MPPED1 | −2.42332 | 3.73E−14 |
| 13402 | LAMC1 | −2.43845 | 7.40E−05 |
| 15722 | LOC100134265 | −2.44777 | 4.60E−06 |
| 5836 | ENC1 | −2.45175 | 1.84E−05 |
| 244 | ACVR2A | −2.46307 | 1.87E−06 |
| 33616 | WDR72 | −2.46656 | 6.61E−05 |
| 28509 | RAB31 | −2.47199 | 1.57E−06 |
| 3629 | CDH1 | −2.4799 | 3.05E−06 |
| 28905 | RGMA | −2.50113 | 4.45E−06 |
| 29475 | S100A11 | −2.50568 | 3.24E−06 |
| 8259 | HAPLN1 | −2.50809 | 7.14E−07 |
| 3942 | CHST7 | −2.51075 | 9.78E−08 |
| 12543 | ISL1 | −2.51716 | 2.76E−10 |
| 28305 | PTCH1 | −2.52418 | 7.32E−08 |
| 32541 | TOX | −2.5288 | 5.34E−09 |
| 6067 | F2RL1 | −2.54309 | 2.36E−08 |
| 32334 | TMEM54 | −2.57701 | 2.04E−06 |
| 3436 | CCND1 | −2.58061 | 6.72E−05 |
| 707 | ANKRD38 | −2.58621 | 4.12E−09 |
| 5241 | DLL3 | −2.5911 | 8.77E−08 |
| 33424 | VGF | −2.59836 | 0.000406676 |
| 23253 | LOC730525 | −2.61609 | 3.32E−07 |
| 31368 | STC1 | −2.63136 | 1.20E−05 |
| 31910 | TFAP2C | −2.63773 | 4.72E−08 |
| 25012 | MN1 | −2.6469 | 8.33E−08 |
| 28419 | PVALB | −2.67012 | 1.23E−10 |
| 6960 | FLJ37644 | −2.67066 | 1.78E−12 |
| 7417 | GADD45G | −2.68804 | 2.14E−06 |
| 4709 | CXXC4 | −2.68958 | 5.39E−07 |
| 8050 | GRHL3 | −2.73097 | 4.15E−11 |
| 23990 | MBIP | −2.73995 | 9.29E−07 |
| 5418 | DPPA4 | −2.75778 | 5.66E−08 |
| 32212 | TMEM158 | −2.77503 | 9.30E−06 |
| 5896 | EPHB1 | −2.77518 | 2.29E−06 |
| 31404 | STMN2 | −2.79651 | 2.03E−05 |
| 12454 | INSM1 | −2.81526 | 1.15E−09 |
| 13142 | KLHL24 | −2.81638 | 2.31E−07 |
| 9856 | HS.475334 | −2.82304 | 1.09E−05 |
| 33125 | UBL3 | −2.85607 | 2.77E−08 |
| 13655 | LMO1 | −2.90621 | 4.10E−06 |
| 6003 | ETV5 | −2.90987 | 5.54E−08 |
| 966 | ARHGEF6 | −2.92751 | 9.82E−11 |
| 31187 | SPRY2 | −2.94814 | 6.74E−09 |
| 28501 | RAB25 | −2.97139 | 5.77E−07 |
| 4675 | CXCR7 | −2.9864 | 6.13E−07 |
| 32652 | TRIB2 | −2.99455 | 8.47E−08 |
| 28397 | PTPRZ1 | −3.02099 | 8.00E−08 |
| 31158 | SPOCK1 | −3.02198 | 8.12E−06 |
| 25849 | NKD2 | −3.02555 | 4.12E−11 |
| 25471 | MYT1 | −3.03712 | 6.21E−09 |
| 6856 | FLJ25404 | −3.03813 | 1.95E−08 |
| 30304 | SLC2A1 | −3.05478 | 0.000275534 |
| 12256 | IGFBP5 | −3.06686 | 2.00E−06 |
| 23779 | MAF | −3.07491 | 2.81E−08 |
| 28198 | PRSS8 | −3.08336 | 6.31E−08 |
| 9923 | HS.509165 | −3.09539 | 2.57E−07 |
| 4243 | COL5A2 | −3.10066 | 8.01E−08 |
| 3112 | CAMKV | −3.10668 | 3.37E−11 |
| 29915 | SFRP2 | −3.13051 | 3.42E−07 |
| 13092 | KIT | −3.13441 | 8.27E−12 |
| 6684 | FGFR3 | −3.13726 | 7.73E−09 |
| 8646 | HOPX | −3.15424 | 1.07E−14 |
| 29497 | S1PR3 | −3.15587 | 8.43E−07 |
| 33399 | VCAM1 | −3.15952 | 2.02E−10 |
| 5240 | DLL1 | −3.18075 | 1.28E−05 |
| 28112 | PRODH | −3.18595 | 2.33E−07 |
| 23200 | LOC730278 | −3.27115 | 1.92E−07 |
| 1202 | ATP1B2 | −3.29446 | 2.34E−08 |
| 6720 | FJX1 | −3.3039 | 6.85E−07 |
| 3609 | CDC42EP4 | −3.33348 | 2.25E−09 |
| 12198 | IFITM2 | −3.35237 | 3.41E−11 |
| 3679 | CDKN1C | −3.37225 | 1.15E−09 |
| 3202 | CAV1 | −3.37517 | 5.73E−13 |
| 31171 | SPRED1 | −3.42954 | 3.76E−08 |
| 30010 | SH3GL3 | −3.43813 | 3.73E−11 |
| 8335 | HDC | −3.45787 | 1.51E−12 |
| 8391 | HES4 | −3.49495 | 1.00E−08 |
| 33335 | USP44 | −3.50303 | 6.22E−11 |
| 1101 | ASCL1 | −3.54534 | 1.26E−11 |
| 29945 | SFTA3 | −3.5611 | 1.59E−07 |
| 13619 | LIPA | −3.56979 | 1.34E−08 |
| 27178 | PDPN | −3.72978 | 5.33E−12 |
| 7370 | FZD8 | −3.74383 | 7.14E−09 |
| 3647 | CDH3 | −3.80687 | 3.54E−09 |
| 2759 | C6ORF141 | −3.94476 | 5.10E−06 |
| 13595 | LIMCH1 | −3.94759 | 2.52E−11 |
| 13513 | LEMD1 | −3.98954 | 6.68E−08 |
| 5961 | ERP27 | −4.02755 | 8.38E−13 |
| 29666 | SCRG1 | −4.03799 | 1.96E−17 |
| 7286 | FRZB | −4.04927 | 2.19E−05 |
| 12977 | KIAA1598 | −4.04996 | 4.12E−09 |
| 2380 | C20ORF100 | −4.16273 | 2.94E−12 |
| 25866 | NKX6-2 | −4.17171 | 1.46E−10 |
| 31030 | SOX9 | −4.21749 | 9.69E−10 |
| 27805 | POU3F1 | −4.22404 | 1.53E−11 |
| 7879 | GPC4 | −4.23918 | 8.64E−08 |
| 17977 | LOC642590 | −4.36113 | 1.29E−10 |
| 19608 | LOC646347 | −4.53146 | 1.77E−08 |

TABLE 2-continued

Gene expression array data of significantly up-regulated and down-regulated genes at differentiation day 11 in SHH/FGF8/Chir treated Floor-plate based population over SHH/FGF8 only treated population.

| Column # | Probeset ID | Fold-Change | p-value |
|---|---|---|---|
| 5238 | DLK1 | −4.62809 | 8.12E−05 |
| 8401 | HEY1 | −4.68961 | 2.52E−12 |
| 30592 | SMS | −4.74656 | 5.18E−12 |
| 29914 | SFRP1 | −4.84227 | 1.53E−09 |
| 13376 | L1TD1 | −4.85832 | 6.96E−08 |
| 7984 | GPR56 | −4.87971 | 1.88E−13 |
| 7367 | FZD5 | −5.00247 | 2.43E−11 |
| 25858 | NKX2-1 | −5.06868 | 2.84E−08 |
| 7801 | GNG8 | −5.39693 | 2.22E−13 |
| 9156 | HS.181245 | −5.99308 | 1.43E−12 |
| 32962 | TTYH1 | −6.33607 | 1.00E−15 |
| 5523 | DUSP6 | −6.34711 | 8.15E−10 |
| 6091 | FABP7 | −6.56016 | 2.28E−09 |
| 5248 | DLX5 | −6.56829 | 8.74E−13 |
| 12754 | KCNK12 | −6.912 | 1.07E−12 |
| 30165 | SLC15A3 | −7.17663 | 1.60E−19 |
| 6675 | FGF8 | −7.58196 | 1.32E−18 |
| 31023 | SOX3 | −7.63996 | 1.53E−11 |
| 8395 | HESX1 | −8.28818 | 3.36E−10 |
| 28692 | RAX | −8.87763 | 6.24E−12 |
| 20959 | LOC650757 | −9.74543 | 1.18E−18 |
| 14470 | LOC100130502 | −10.333 | 1.53E−10 |
| 13568 | LHX2 | −14.1638 | 4.81E−12 |
| 30111 | SIX3 | −15.019 | 8.24E−13 |
| 12197 | IFITM1 | −16.4704 | 9.16E−16 |
| 25859 | NKX2-2 | −18.6642 | 7.93E−20 |
| 12254 | IGFBP3 | −19.1294 | 8.81E−16 |
| 8392 | HES5 | −33.7356 | 2.69E−21 |
| 30114 | SIX6 | −39.4411 | 2.59E−18 |

TABLE 3

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 1209 | ASCL1 | 33.085 | 1.60E−09 |
| 3978 | CHGA | 28.1727 | 4.44E−13 |
| 31604 | STMN2 | 20.9978 | 1.47E−08 |
| 32159 | TH | 15.2965 | 2.12E−08 |
| 31606 | STMN4 | 15.2102 | 3.72E−09 |
| 7685 | GAP43 | 12.5729 | 5.42E−09 |
| 4926 | D4S234E | 10.7914 | 4.91E−08 |
| 8593 | HES6 | 10.6527 | 2.94E−09 |
| 4342 | COL3A1 | 10.0606 | 3.86E−06 |
| 12149 | HS.7023 | 9.60731 | 3.97E−08 |
| 5691 | EBF3 | 9.28771 | 5.13E−11 |
| 29820 | SCG2 | 9.22584 | 1.02E−06 |
| 12655 | INSM2 | 9.01409 | 3.73E−12 |
| 27988 | POSTN | 8.79262 | 1.09E−10 |
| 28590 | PTPRO | 8.70512 | 3.13E−10 |
| 30386 | SLC17A6 | 8.22904 | 2.02E−06 |
| 31767 | SYT13 | 8.1735 | 3.63E−07 |
| 30390 | SLC18A1 | 8.15448 | 6.47E−15 |
| 5689 | EBF1 | 8.05344 | 2.30E−06 |
| 5029 | DCX | 8.00552 | 8.30E−08 |
| 2470 | C1QL1 | 7.47022 | 8.68E−10 |
| 12609 | INA | 6.92121 | 5.72E−07 |
| 26250 | NR4A2 | 6.75723 | 1.27E−13 |
| 29624 | RTN1 | 6.6247 | 6.52E−07 |
| 9374 | HS.19193 | 6.58382 | 1.95E−08 |
| 436 | ADCYAP1 | 6.49154 | 9.75E−11 |
| 1607 | BEX2 | 6.33986 | 8.93E−09 |
| 34098 | ZCCHC12 | 6.19663 | 9.95E−07 |
| 7056 | FLJ25404 | 6.19296 | 2.14E−06 |
| 31605 | STMN3 | 6.17605 | 8.77E−07 |
| 7997 | GNG3 | 6.1196 | 1.26E−06 |

TABLE 3-continued

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 25922 | NEFM | 6.11347 | 2.51E−04 |
| 12359 | ID2 | 6.07844 | 1.32E−06 |
| 29017 | REEP1 | 6.04393 | 2.25E−06 |
| 30810 | SNAP25 | 6.03677 | 3.62E−06 |
| 25671 | MYT1 | 5.86419 | 8.19E−06 |
| 33297 | UBE2J1 | 5.76887 | 6.22E−08 |
| 5349 | DLL3 | 5.76451 | 4.92E−08 |
| 29133 | RGS4 | 5.69761 | 1.87E−06 |
| 28123 | PPP2R2B | 5.56067 | 2.80E−08 |
| 27287 | PCSK1N | 5.43156 | 3.22E−09 |
| 32126 | TFF3 | 5.26964 | 3.17E−08 |
| 27288 | PCSK2 | 5.22877 | 9.14E−10 |
| 4533 | CRIP2 | 5.18375 | 8.40E−08 |
| 12506 | IL13RA2 | 5.1246 | 1.31E−06 |
| 32417 | TMEM163 | 5.01765 | 7.55E−09 |
| 30813 | SNAP91 | 4.92061 | 4.28E−05 |
| 13260 | KIF5C | 4.86241 | 2.93E−06 |
| 15798 | LOC100133923 | 4.83074 | 3.74E−07 |
| 32412 | TMEM158 | 4.76646 | 4.81E−06 |
| 3770 | CDK5R1 | 4.75524 | 1.18E−05 |
| 5739 | EEF1A2 | 4.75232 | 9.53E−05 |
| 32697 | TNRC4 | 4.75179 | 1.29E−05 |
| 5455 | DNER | 4.71709 | 1.52E−05 |
| 6700 | FAT3 | 4.68785 | 1.91E−06 |
| 6197 | ETS2 | 4.67343 | 1.08E−10 |
| 25753 | NBEA | 4.65265 | 6.99E−07 |
| 12944 | KCNJ16 | 4.53077 | 3.54E−12 |
| 3979 | CHGB | 4.52218 | 7.76E−05 |
| 25562 | MXD4 | 4.445 | 7.25E−07 |
| 3941 | CGNL1 | 4.44195 | 7.24E−06 |
| 26499 | ONECUT2 | 4.37403 | 2.39E−07 |
| 2867 | C6ORF141 | 4.35252 | 2.58E−10 |
| 12362 | ID4 | 4.32183 | 6.05E−05 |
| 26011 | NHLH2 | 4.31928 | 5.91E−05 |
| 2035 | C14ORF132 | 4.31666 | 9.46E−07 |
| 9428 | HS.204481 | 4.29602 | 1.66E−09 |
| 8288 | GRM8 | 4.17846 | 1.62E−06 |
| 7617 | GADD45G | 4.17663 | 2.21E−06 |
| 4298 | CNTNAP2 | 4.13552 | 4.10E−05 |
| 1408 | AUTS2 | 4.13111 | 2.79E−05 |
| 23822 | LRRC4C | 4.11703 | 1.27E−09 |
| 31454 | SRRM4 | 4.11574 | 8.04E−07 |
| 4003 | CHN2 | 4.09589 | 3.30E−07 |
| 27665 | PITX2 | 4.08382 | 1.94E−11 |
| 13296 | KLC1 | 4.0528 | 4.19E−06 |
| 27773 | PLEKHA6 | 4.0464 | 2.57E−07 |
| 25618 | MYLIP | 3.99268 | 2.96E−06 |
| 5036 | DDC | 3.96553 | 8.46E−05 |
| 33181 | TUBB3 | 3.93922 | 1.52E−04 |
| 24522 | MIAT | 3.93906 | 9.87E−05 |
| 27411 | PEG10 | 3.9374 | 3.48E−05 |
| 32343 | TMEFF2 | 3.92112 | 6.49E−07 |
| 29821 | SCG3 | 3.92108 | 6.47E−06 |
| 31759 | SYP | 3.89869 | 2.51E−04 |
| 9425 | HS.202577 | 3.89053 | 2.85E−07 |
| 33943 | XKR4 | 3.87043 | 1.49E−06 |
| 33178 | TUBB2A | 3.86265 | 6.11E−05 |
| 12654 | INSM1 | 3.84646 | 5.59E−05 |
| 13236 | KIF1A | 3.84543 | 3.27E−05 |
| 25721 | NAPB | 3.81995 | 3.50E−05 |
| 31765 | SYT11 | 3.77827 | 1.14E−05 |
| 5877 | ELAVL3 | 3.70028 | 9.69E−05 |
| 13858 | LMO4 | 3.69359 | 2.09E−06 |
| 4103 | CLASP2 | 3.64468 | 1.79E−05 |
| 2956 | C7ORF41 | 3.63616 | 5.69E−05 |
| 33362 | UCHL1 | 3.61003 | 5.64E−05 |
| 29645 | RUNDC3A | 3.54448 | 8.42E−05 |
| 24063 | MAP1LC3A | 3.53736 | 4.36E−06 |
| 5944 | ENC1 | 3.51677 | 0.000141473 |
| 28730 | RAB40B | 3.48084 | 4.57E−07 |
| 25162 | MLLT11 | 3.4633 | 3.13E−05 |
| 7469 | FRMD4A | 3.46181 | 7.40E−06 |
| 13070 | KIAA0363 | 3.43032 | 6.39E−05 |

TABLE 3-continued

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 13342 | KLHL24 | 3.41191 | 3.34E-05 |
| 7988 | GNB3 | 3.38669 | 3.31E-09 |
| 31840 | TAGLN3 | 3.36355 | 1.67E-03 |
| 12147 | HS.66187 | 3.34592 | 0.000125172 |
| 4549 | CRMP1 | 3.32015 | 2.42E-04 |
| 23453 | LOC730525 | 3.31501 | 1.64E-03 |
| 31514 | ST6GALNAC5 | 3.29449 | 1.19E-05 |
| 27054 | PAFAH1B1 | 3.25816 | 1.30E-04 |
| 32432 | TMEM170B | 3.25165 | 2.44E-05 |
| 27686 | PKIA | 3.24255 | 4.29E-05 |
| 1748 | BSN | 3.2101 | 0.000169219 |
| 6213 | EVL | 3.17682 | 3.36E-05 |
| 34217 | ZMIZ1 | 3.16249 | 3.29E-04 |
| 16419 | LOC283514 | 3.15057 | 4.57E-06 |
| 32081 | TERF2IP | 3.13818 | 3.43E-05 |
| 4932 | DACH1 | 3.11457 | 7.79E-06 |
| 5424 | DNAJC19 | 3.09946 | 1.64E-09 |
| 8093 | GPM6A | 3.07619 | 1.59E-03 |
| 15034 | LOC100131718 | 3.0686 | 4.01E-05 |
| 8706 | HIST1H4K | 3.06394 | 1.84E-06 |
| 28238 | PRICKLE2 | 3.06341 | 1.98E-06 |
| 31429 | SRGAP3 | 3.0575 | 7.84E-06 |
| 13760 | LHFP | 3.04812 | 0.000126565 |
| 3181 | CADPS | 3.03806 | 6.60E-06 |
| 3186 | CALCA | 3.03372 | 3.13E-08 |
| 1672 | BMPR2 | 3.03171 | 9.26E-06 |
| 25861 | NDRG4 | 3.00851 | 0.000239868 |
| 2265 | C18ORF8 | 2.99462 | 9.07E-06 |
| 4698 | CTNNA2 | 2.962 | 6.07E-05 |
| 1606 | BEX1 | 2.96088 | 5.37E-05 |
| 32769 | TPH1 | 2.96087 | 2.88E-07 |
| 31986 | TCEAL7 | 2.95947 | 3.43E-05 |
| 3322 | CBLN2 | 2.95729 | 1.12E-04 |
| 29639 | RUFY3 | 2.95504 | 2.59E-05 |
| 3851 | CELSR3 | 2.9545 | 6.27E-04 |
| 3177 | CADM1 | 2.95335 | 1.81E-04 |
| 20895 | LOC649841 | 2.94392 | 2.21E-05 |
| 13713 | LEMD1 | 2.93152 | 9.17E-06 |
| 8184 | GPR56 | 2.93095 | 3.08E-04 |
| 31935 | TBC1D9 | 2.92862 | 6.60E-05 |
| 8046 | GOLSYN | 2.9099 | 2.80E-06 |
| 33004 | TSHZ1 | 2.90158 | 2.76E-07 |
| 5876 | ELAVL2 | 2.90115 | 0.00136166 |
| 12733 | IRX5 | 2.88659 | 1.21E-04 |
| 1254 | ATCAY | 2.86583 | 7.41E-04 |
| 31763 | SYT1 | 2.86449 | 1.02E-03 |
| 29193 | RIMBP2 | 2.84834 | 6.29E-06 |
| 28741 | RAB6B | 2.84821 | 0.000698361 |
| 27533 | PHF21B | 2.8457 | 6.44E-05 |
| 24135 | MAPT | 2.83633 | 5.22E-04 |
| 10116 | HS.505676 | 2.83499 | 1.50E-05 |
| 8712 | HIST2H2BE | 2.82687 | 0.000157254 |
| 24061 | MAP1B | 2.82235 | 0.000357426 |
| 13054 | KIAA0182 | 2.8162 | 2.66E-04 |
| 34044 | ZBTB20 | 2.81539 | 8.77E-08 |
| 29509 | RPRM | 2.81168 | 0.000475144 |
| 34007 | YPEL5 | 2.81061 | 1.16E-04 |
| 13609 | LANCL2 | 2.80004 | 8.07E-06 |
| 940 | APLP1 | 2.77078 | 2.57E-05 |
| 29849 | SCN3B | 2.76654 | 7.14E-05 |
| 29201 | RIMS3 | 2.76205 | 2.94E-04 |
| 27394 | PDZD4 | 2.75594 | 0.000212095 |
| 1364 | ATP6V1G2 | 2.75366 | 0.0012022 |
| 31778 | SYT7 | 2.74946 | 4.15E-05 |
| 32351 | TMEM106A | 2.73965 | 0.000217998 |
| 7717 | GATS | 2.72521 | 3.10E-05 |
| 506 | AGAP3 | 2.71696 | 2.07E-05 |
| 24141 | MARCH4 | 2.70769 | 8.96E-06 |
| 5348 | DLL1 | 2.7028 | 2.05E-04 |
| 6212 | EVI5L | 2.6886 | 6.79E-05 |
| 3196 | CALM1 | 2.68129 | 8.50E-05 |
| 31386 | SPRY1 | 2.67788 | 1.15E-03 |
| 33128 | TTR | 2.66999 | 2.76E-05 |
| 297 | ACPL2 | 2.66551 | 1.52E-06 |
| 5325 | DKK3 | 2.65119 | 5.63E-05 |
| 23853 | LRRN3 | 2.64615 | 1.37E-03 |
| 32615 | TMSL3 | 2.63733 | 4.56E-05 |
| 29822 | SCG5 | 2.63452 | 1.42E-04 |
| 32000 | TCF12 | 2.63327 | 1.80E-06 |
| 3497 | CCDC92 | 2.6296 | 2.23E-05 |
| 5610 | DUSP1 | 2.60841 | 1.78E-04 |
| 14524 | LOC100130053 | 2.60135 | 4.53E-04 |
| 26279 | NRSN1 | 2.59336 | 0.00111467 |
| 25711 | NANOS3 | 2.58916 | 4.15E-06 |
| 5543 | DPYSL4 | 2.58236 | 0.000223516 |
| 6231 | EXOC7 | 2.58163 | 4.89E-06 |
| 24134 | MAPRE3 | 2.57689 | 4.85E-05 |
| 9382 | HS.193784 | 2.57602 | 2.18E-06 |
| 1608 | BEX4 | 2.57251 | 9.83E-05 |
| 6514 | FAM36A | 2.56726 | 7.62E-05 |
| 13640 | LBH | 2.56551 | 1.34E-05 |
| 9920 | HS.437111 | 2.55902 | 4.44E-05 |
| 33904 | WSB2 | 2.55865 | 5.08E-04 |
| 9757 | HS.369017 | 2.55838 | 4.25E-05 |
| 18920 | LOC644250 | 2.55607 | 0.000475214 |
| 27311 | PDCD4 | 2.55148 | 0.000139052 |
| 7562 | FZD1 | 2.54808 | 2.48E-06 |
| 13191 | KIAA1688 | 2.54643 | 9.31E-05 |
| 4292 | CNTN2 | 2.53802 | 2.29E-04 |
| 32474 | TMEM200A | 2.53495 | 4.93E-07 |
| 6635 | FAM89B | 2.5341 | 1.64E-05 |
| 23500 | LOC730990 | 2.53197 | 3.94E-05 |
| 1375 | ATP9A | 2.52973 | 1.09E-04 |
| 8126 | GPR137C | 2.52944 | 0.000217768 |
| 19248 | LOC644936 | 2.52867 | 4.31E-04 |
| 4916 | CYTH2 | 2.5213 | 6.31E-06 |
| 20654 | LOC648921 | 2.51994 | 1.76E-03 |
| 2445 | C1ORF71 | 2.50491 | 9.78E-04 |
| 21820 | LOC652726 | 2.49851 | 5.58E-05 |
| 16100 | LOC100134868 | 2.49288 | 0.00076351 |
| 27105 | PAPSS2 | 2.49026 | 0.000148906 |
| 32246 | TIMP2 | 2.48501 | 3.26E-05 |
| 27648 | PIP5K2B | 2.48028 | 0.000236563 |
| 12214 | HSBP1 | 2.47723 | 1.82E-04 |
| 32754 | TP53INP2 | 2.47324 | 2.42E-05 |
| 29037 | REM2 | 2.46751 | 0.000170127 |
| 34742 | ZNF84 | 2.46625 | 2.39E-04 |
| 3872 | CENTA1 | 2.46106 | 3.74E-04 |
| 23918 | LY6H | 2.45793 | 0.000317539 |
| 29595 | RSBN1 | 2.45785 | 8.01E-04 |
| 1733 | BRP44L | 2.45488 | 5.07E-04 |
| 2751 | C3ORF70 | 2.45314 | 1.92E-06 |
| 12862 | JUN | 2.4481 | 4.37E-04 |
| 15357 | LOC100132727 | 2.44481 | 0.00058635 |
| 13224 | KIDINS220 | 2.43944 | 0.00068445 |
| 33183 | TUBB4Q | 2.43584 | 0.00171503 |
| 685 | ALPP | 2.43222 | 3.60E-05 |
| 14002 | LOC100128274 | 2.43042 | 1.90E-04 |
| 20699 | LOC649095 | 2.42655 | 0.00040167 |
| 7123 | FLJ35390 | 2.39837 | 0.00162187 |
| 16740 | LOC387856 | 2.39594 | 8.21E-04 |
| 7033 | FLJ22184 | 2.3897 | 4.07E-04 |
| 20602 | LOC648740 | 2.38616 | 8.38E-06 |
| 10392 | HS.538962 | 2.38583 | 0.000324449 |
| 31615 | STOX2 | 2.38135 | 4.42E-04 |
| 23592 | LOC731895 | 2.3779 | 0.000838915 |
| 32863 | TRIM2 | 2.37536 | 5.63E-04 |
| 30075 | SERTAD4 | 2.36897 | 0.000363024 |
| 26135 | NOL4 | 2.36463 | 0.000261492 |
| 27620 | PIK3R1 | 2.35977 | 1.01E-07 |
| 27073 | PAK3 | 2.34949 | 1.62E-04 |
| 27855 | PMP22 | 2.34705 | 7.89E-06 |
| 27636 | PINK1 | 2.34687 | 1.17E-05 |
| 3223 | CAMSAP1 | 2.34021 | 1.96E-04 |
| 9323 | HS.168950 | 2.33738 | 1.84E-04 |
| 17248 | LOC401115 | 2.33367 | 0.000151535 |

TABLE 3-continued

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 6270 | F3 | 2.32945 | 2.00E-08 |
| 2256 | C18ORF32 | 2.32914 | 4.41E-04 |
| 777 | ANKRD10 | 2.32837 | 2.48E-04 |
| 5372 | DMRTA2 | 2.32784 | 5.27E-06 |
| 6347 | FAM117B | 2.32504 | 9.42E-05 |
| 731 | AMY1A | 2.3232 | 0.000158787 |
| 7610 | GABRR1 | 2.31983 | 8.23E-08 |
| 1520 | BAZ2B | 2.30948 | 5.18E-04 |
| 7920 | GLRA2 | 2.30858 | 6.83E-05 |
| 10190 | HS.522924 | 2.30739 | 1.62E-03 |
| 7762 | GDAP1 | 2.30342 | 6.22E-05 |
| 31325 | SPHK2 | 2.29983 | 1.68E-04 |
| 31499 | ST18 | 2.2969 | 9.74E-04 |
| 15124 | LOC100131989 | 2.29335 | 1.57E-04 |
| 23665 | LOC88523 | 2.29171 | 0.000476299 |
| 30325 | SKP1 | 2.28675 | 1.76E-04 |
| 2743 | C3ORF58 | 2.28463 | 0.000119256 |
| 27566 | PHYHIPL | 2.28388 | 1.72E-03 |
| 27332 | PDE4D | 2.28016 | 3.70E-05 |
| 760 | ANK2 | 2.27803 | 3.84E-05 |
| 1101 | ARL3 | 2.26792 | 1.03E-03 |
| 25218 | MNX1 | 2.26631 | 4.41E-07 |
| 7255 | FLJ44048 | 2.26493 | 6.84E-06 |
| 30029 | SERINC1 | 2.26355 | 3.12E-04 |
| 34800 | ZSWIM6 | 2.2634 | 3.19E-04 |
| 13943 | LOC100128062 | 2.26302 | 0.000498795 |
| 18811 | LOC644033 | 2.2611 | 5.93E-04 |
| 20075 | LOC646996 | 2.25787 | 1.36E-04 |
| 7976 | GNAO1 | 2.25676 | 0.00121073 |
| 22799 | LOC728661 | 2.25642 | 0.000599836 |
| 979 | APPBP2 | 2.25324 | 6.41E-04 |
| 25716 | NAP1L3 | 2.24879 | 9.43E-04 |
| 14359 | LOC100129502 | 2.24469 | 1.52E-04 |
| 25580 | MYCBP2 | 2.24333 | 0.000445387 |
| 27083 | PAM | 2.23671 | 0.00170991 |
| 22583 | LOC728105 | 2.2358 | 0.000601193 |
| 29747 | SARM1 | 2.2285 | 5.83E-07 |
| 7602 | GABRB3 | 2.22682 | 4.00E-04 |
| 30261 | SIAH3 | 2.22476 | 1.89E-05 |
| 27664 | PITX1 | 2.22382 | 0.00102378 |
| 19467 | LOC645452 | 2.21703 | 0.000168591 |
| 6533 | FAM46A | 2.21591 | 1.24E-03 |
| 26308 | NT5C2 | 2.21285 | 0.00159191 |
| 1086 | ARID5B | 2.21184 | 0.000139405 |
| 494 | AFF3 | 2.21139 | 1.28E-03 |
| 29124 | RGS16 | 2.21012 | 2.33E-05 |
| 10056 | HS.475334 | 2.20669 | 1.41E-03 |
| 3738 | CDH10 | 2.20522 | 0.000389319 |
| 9819 | HS.388347 | 2.2022 | 2.82E-05 |
| 34703 | ZNF786 | 2.20193 | 1.65E-03 |
| 8705 | HIST1H4J | 2.19897 | 4.86E-06 |
| 9740 | HS.36053 | 2.19737 | 3.65E-05 |
| 651 | ALG13 | 2.19414 | 4.86E-05 |
| 33588 | VASH2 | 2.19373 | 0.000586609 |
| 28810 | RALGPS1 | 2.19311 | 0.000999046 |
| 5774 | EFNB3 | 2.191 | 0.000919096 |
| 1745 | BSCL2 | 2.18758 | 8.17E-04 |
| 29151 | RHBDL3 | 2.18758 | 4.86E-05 |
| 3740 | CDH12 | 2.18674 | 0.000112317 |
| 24064 | MAP1LC3B | 2.18347 | 2.00E-04 |
| 32539 | TMEM59 | 2.17758 | 1.77E-03 |
| 33171 | TUBA3E | 2.17556 | 2.58E-04 |
| 526 | AGPAT4 | 2.17042 | 1.95E-04 |
| 27832 | PLXNA1 | 2.16997 | 0.000477137 |
| 34219 | ZMPSTE24 | 2.16821 | 0.00130116 |
| 34669 | ZNF738 | 2.16494 | 0.00145642 |
| 28749 | RAB9B | 2.16376 | 1.41E-03 |
| 3350 | CCBE1 | 2.16311 | 2.69E-04 |
| 5875 | ELAVL1 | 2.15865 | 6.37E-04 |
| 13154 | KIAA1370 | 2.15727 | 5.07E-05 |
| 1356 | ATP6V1B2 | 2.15309 | 0.000839601 |
| 6457 | FAM181B | 2.15303 | 6.91E-04 |
| 25137 | MKL2 | 2.14461 | 0.000214816 |
| 27876 | PNMA1 | 2.14384 | 0.000290225 |
| 23806 | LRRC37B2 | 2.14195 | 4.81E-04 |
| 6851 | FGD3 | 2.139 | 1.84E-04 |
| 1746 | BSDC1 | 2.13842 | 0.000430355 |
| 27997 | POTEF | 2.13305 | 0.000655028 |
| 2969 | C7ORF55 | 2.12929 | 5.66E-05 |
| 29923 | SEC11C | 2.12843 | 8.11E-04 |
| 31488 | SSX2IP | 2.12215 | 5.19E-06 |
| 29277 | RNF128 | 2.12203 | 5.41E-06 |
| 30348 | SLC12A2 | 2.12048 | 0.000343525 |
| 8277 | GRK5 | 2.11347 | 0.000106085 |
| 8573 | HEPACAM2 | 2.11332 | 2.39E-09 |
| 1610 | BEXL1 | 2.10951 | 2.62E-04 |
| 4229 | CMIP | 2.10246 | 0.000705627 |
| 30224 | SHANK2 | 2.10164 | 0.000611099 |
| 23763 | LRP1B | 2.09999 | 4.76E-05 |
| 6724 | FBXL16 | 2.09975 | 8.65E-04 |
| 26092 | NLRP8 | 2.09701 | 0.00161834 |
| 17496 | LOC440704 | 2.09699 | 0.0015232 |
| 2543 | C20ORF56 | 2.09698 | 4.79E-07 |
| 32624 | TMX4 | 2.09279 | 8.41E-04 |
| 20006 | LOC646821 | 2.0917 | 5.47E-05 |
| 25809 | NCOA6 | 2.09025 | 1.61E-03 |
| 2811 | C5ORF28 | 2.08938 | 6.33E-04 |
| 3279 | CASD1 | 2.0821 | 6.10E-05 |
| 28256 | PRKAR1A | 2.08207 | 0.00119569 |
| 6208 | EVI1 | 2.07806 | 4.85E-05 |
| 6920 | FJX1 | 2.07539 | 1.80E-03 |
| 31199 | SORBS2 | 2.07266 | 7.37E-05 |
| 3968 | CHD6 | 2.06939 | 4.92E-05 |
| 34605 | ZNF652 | 2.06441 | 0.00172675 |
| 4838 | CYCS | 2.06436 | 1.39E-03 |
| 34025 | ZADH2 | 2.05857 | 3.02E-05 |
| 17246 | LOC401098 | 2.05589 | 1.58E-03 |
| 27462 | PFN2 | 2.05533 | 1.58E-03 |
| 27137 | PARP6 | 2.05441 | 5.65E-04 |
| 5651 | DYNC1I1 | 2.04874 | 0.000834135 |
| 7587 | GABARAPL2 | 2.04534 | 0.00165234 |
| 149 | AASDHPPT | 2.04017 | 7.58E-04 |
| 1970 | C12ORF51 | 2.038 | 0.000668525 |
| 31721 | SVOP | 2.03603 | 7.00E-04 |
| 1389 | ATXN1 | 2.03408 | 3.27E-05 |
| 20667 | LOC648980 | 2.03345 | 0.00062575 |
| 24523 | MIB1 | 2.03159 | 3.22E-04 |
| 31982 | TCEAL3 | 2.03073 | 0.00151379 |
| 12229 | HSD17B7 | 2.03003 | 1.50E-03 |
| 27402 | PDZRN4 | 2.02983 | 2.33E-05 |
| 6395 | FAM13B | 2.02944 | 3.18E-04 |
| 1349 | ATP6V0C | 2.02572 | 1.08E-03 |
| 12828 | JAKMIP2 | 2.01869 | 8.10E-04 |
| 34227 | ZMYND11 | 2.01687 | 0.00171037 |
| 31603 | STMN1 | 2.00603 | 0.000940483 |
| 29145 | RHBDD2 | 2.00523 | 6.87E-04 |
| 25808 | NCOA5 | 2.00244 | 0.000102715 |
| 30330 | SLAIN1 | 2.00203 | 1.00E-03 |
| 2195 | C17ORF45 | -2.00166 | 0.00119767 |
| 23469 | LOC730746 | -2.00168 | 1.67E-03 |
| 30825 | SND1 | -2.00433 | 0.00128091 |
| 19456 | LOC645436 | -2.00559 | 1.69E-03 |
| 6242 | EXOSC7 | -2.0060 | 0.000798232 |
| 17727 | LOC442232 | -2.00726 | 7.96E-05 |
| 28062 | PPIH | -2.00996 | 8.70E-04 |
| 23234 | LOC729779 | -2.01096 | 4.05E-04 |
| 33339 | TYK2 | -2.01275 | 0.000787726 |
| 27020 | P4HA2 | -2.01467 | 1.30E-03 |
| 4563 | CRTAP | -2.01592 | 2.86E-06 |
| 29147 | RHBDF1 | -2.01731 | 9.21E-04 |
| 18367 | LOC643007 | -2.01867 | 0.000867101 |
| 2331 | C1ORF106 | -2.02039 | 2.06E-04 |
| 1332 | ATP5G2 | -2.02135 | 0.00169599 |
| 25354 | MRPL45 | -2.02158 | 0.00179523 |
| 11023 | HS.552799 | -2.02363 | 1.41E-04 |
| 17333 | LOC402112 | -2.02644 | 0.00178903 |

TABLE 3-continued

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 4341 | COL2A1 | −2.03118 | 0.00112645 |
| 14518 | LOC100130009 | −2.03222 | 1.54E−05 |
| 23928 | LYN | −2.03236 | 0.000609191 |
| 20489 | LOC648294 | −2.0327 | 0.0004778 |
| 32244 | TIMM9 | −2.03469 | 0.0015035 |
| 29412 | RPA1 | −2.03493 | 1.70E−03 |
| 33756 | WDR12 | −2.03533 | 5.96E−04 |
| 25781 | NCAPD2 | −2.03535 | 0.00132141 |
| 19436 | LOC645385 | −2.03595 | 0.00151373 |
| 2095 | C14ORF93 | −2.04138 | 6.93E−06 |
| 33243 | TYRO3 | −2.04437 | 4.26E−04 |
| 13396 | KNTC1 | −2.04704 | 1.95E−05 |
| 19027 | LOC644464 | −2.051 | 0.000744833 |
| 1355 | ATP6V1B1 | −2.0528 | 0.000263628 |
| 32263 | TKT | −2.05643 | 0.000380042 |
| 1039 | ARHGAP19 | −2.05734 | 6.74E−05 |
| 4923 | CYYR1 | −2.05748 | 1.68E−05 |
| 30076 | SESN1 | −2.05841 | 2.09E−04 |
| 5054 | DDX10 | −2.06089 | 0.000505 |
| 12782 | ITGB3BP | −2.06492 | 6.73E−06 |
| 17492 | LOC440589 | −2.06666 | 4.64E−04 |
| 23246 | LOC729816 | −2.06873 | 0.000791801 |
| 24128 | MAPKAPK3 | −2.06933 | 0.00146997 |
| 12221 | HSD17B11 | −2.07106 | 2.25E−05 |
| 32916 | TRIM71 | −2.07489 | 2.28E−05 |
| 16186 | LOC136143 | −2.07533 | 4.81E−04 |
| 31614 | STOX1 | −2.07691 | 0.000191887 |
| 28717 | RAB38 | −2.07726 | 6.33E−04 |
| 21994 | LOC653156 | −2.07967 | 1.41E−03 |
| 29560 | RPSA | −2.08096 | 0.000379606 |
| 17241 | LOC401074 | −2.08141 | 6.58E−08 |
| 8588 | HES1 | −2.08285 | 0.000819562 |
| 29494 | RPLP1 | −2.08688 | 1.30E−03 |
| 6884 | FGFR3 | −2.09082 | 5.89E−06 |
| 4977 | DBX1 | −2.09957 | 0.000222703 |
| 29544 | RPS5 | −2.10042 | 0.00138553 |
| 29213 | RIPK2 | −2.10641 | 0.000218454 |
| 14423 | LOC100129685 | −2.1066 | 1.19E−03 |
| 27816 | PLOD3 | −2.10673 | 0.000954258 |
| 8805 | HNRNPA1 | −2.10967 | 1.74E−05 |
| 6898 | FHL3 | −2.1127 | 5.26E−05 |
| 18250 | LOC642741 | −2.1147 | 1.02E−03 |
| 32523 | TMEM45A | −2.1169 | 0.000464867 |
| 17691 | LOC441876 | −2.11785 | 1.02E−04 |
| 1488 | BAIAP2L1 | −2.11832 | 3.63E−05 |
| 4156 | CLEC2D | −2.11902 | 0.000733653 |
| 6966 | FLJ10986 | −2.12606 | 0.000420546 |
| 14281 | LOC100129237 | −2.12997 | 4.96E−04 |
| 16802 | LOC388556 | −2.13532 | 6.52E−04 |
| 25385 | MRPS30 | −2.13565 | 3.28E−04 |
| 18023 | LOC642250 | −2.13595 | 0.00107704 |
| 31129 | SNRPA | −2.13825 | 6.40E−04 |
| 3730 | CDCA5 | −2.14343 | 0.0016145 |
| 26121 | NOB1 | −2.14482 | 3.43E−06 |
| 3733 | CDCA8 | −2.14728 | 0.000158263 |
| 33839 | WDYHV1 | −2.14889 | 0.000901318 |
| 15213 | LOC100132299 | −2.14934 | 3.42E−05 |
| 23294 | LOC729964 | −2.14942 | 0.000145725 |
| 23388 | LOC730246 | −2.15222 | 5.52E−04 |
| 29474 | RPL36 | −2.15341 | 1.12E−03 |
| 20693 | LOC649076 | −2.15494 | 0.000533848 |
| 14136 | LOC100128771 | −2.15556 | 6.32E−05 |
| 29459 | RPL27 | −2.15569 | 8.13E−04 |
| 20894 | LOC649839 | −2.15637 | 0.000233819 |
| 5649 | DYM | −2.15657 | 5.43E−04 |
| 6676 | FANCG | −2.15913 | 2.75E−04 |
| 26223 | NPY | −2.15981 | 4.99E−04 |
| 22700 | LOC728428 | −2.16464 | 0.00122727 |
| 27540 | PHGDH | −2.17929 | 0.000926407 |
| 23875 | LSM4 | −2.18409 | 0.00036081 |
| 15295 | LOC100132528 | −2.18468 | 8.34E−04 |
| 14997 | LOC100131609 | −2.187 | 0.000875169 |
| 29442 | RPL14L | −2.18734 | 4.55E−04 |
| 16653 | LOC343184 | −2.19197 | 6.17E−05 |
| 5697 | EBPL | −2.19209 | 2.05E−05 |
| 2763 | C4ORF14 | −2.19304 | 0.00128088 |
| 4474 | CPNE8 | −2.19514 | 2.56E−04 |
| 17500 | LOC440737 | −2.19615 | 0.000989795 |
| 22974 | LOC729102 | −2.1963 | 0.000282713 |
| 21275 | LOC651149 | −2.19678 | 1.31E−03 |
| 17403 | LOC440055 | −2.19775 | 1.17E−03 |
| 29440 | RPL13L | −2.19817 | 2.16E−05 |
| 27368 | PDK3 | −2.20067 | 3.05E−04 |
| 31760 | SYPL1 | −2.20452 | 0.000128778 |
| 14389 | LOC100129585 | −2.20627 | 8.87E−05 |
| 29490 | RPL8 | −2.20725 | 1.35E−04 |
| 15083 | LOC100131866 | −2.20753 | 2.67E−05 |
| 2915 | C6ORF48 | −2.20788 | 0.000428494 |
| 19976 | LOC646766 | −2.21365 | 0.00033802 |
| 28801 | RAI14 | −2.21753 | 0.000675636 |
| 18557 | LOC643433 | −2.21779 | 0.000542767 |
| 16862 | LOC389141 | −2.21829 | 0.000459763 |
| 5715 | ECT2 | −2.21838 | 1.41E−03 |
| 29558 | RPS8 | −2.22068 | 0.00161471 |
| 19556 | LOC645691 | −2.22442 | 0.00107987 |
| 16693 | LOC347544 | −2.22526 | 0.000534957 |
| 23972 | MAD2L1 | −2.22823 | 0.000457464 |
| 18286 | LOC642817 | −2.23024 | 0.00054939 |
| 31588 | STK24 | −2.23459 | 3.03E−04 |
| 31024 | SNORD25 | −2.236 | 5.13E−05 |
| 1282 | ATIC | −2.24113 | 0.000182776 |
| 33110 | TTK | −2.24337 | 4.48E−04 |
| 23352 | LOC730107 | −2.24665 | 0.000445574 |
| 8727 | HJURP | −2.24769 | 2.63E−05 |
| 23237 | LOC729789 | −2.24864 | 3.21E−04 |
| 29503 | RPP40 | −2.25604 | 1.62E−04 |
| 17594 | LOC441246 | −2.25891 | 4.60E−04 |
| 17228 | LOC400963 | −2.26592 | 0.000542002 |
| 29521 | RPS18 | −2.26781 | 0.00151457 |
| 32392 | TMEM144 | −2.27099 | 5.66E−08 |
| 7652 | GALK1 | −2.27206 | 9.50E−04 |
| 27192 | PCDH18 | −2.27211 | 0.000113843 |
| 4297 | CNTNAP1 | −2.2794 | 2.43E−04 |
| 23041 | LOC729279 | −2.28142 | 5.88E−05 |
| 5840 | EIF3H | −2.28165 | 0.000193064 |
| 8828 | HNRPC | −2.28204 | 0.00128473 |
| 30493 | SLC27A3 | −2.29001 | 2.85E−04 |
| 5742 | EEF1D | −2.29339 | 0.000126152 |
| 30601 | SLC44A1 | −2.29419 | 0.000172089 |
| 3866 | CENPN | −2.2944 | 0.000143689 |
| 29449 | RPL22 | −2.29465 | 0.00105741 |
| 20804 | LOC649447 | −2.29999 | 0.000262246 |
| 28036 | PPAT | −2.3009 | 0.000393145 |
| 25509 | MTP18 | −2.30185 | 3.55E−05 |
| 3538 | CCNA2 | −2.30784 | 0.000412267 |
| 33891 | WNT5A | −2.3104 | 3.36E−04 |
| 28110 | PPP1R3C | −2.31108 | 3.02E−06 |
| 1659 | BMP2 | −2.32278 | 2.31E−05 |
| 18725 | LOC643863 | −2.32406 | 1.02E−05 |
| 359 | ADA | −2.3269 | 2.14E−05 |
| 13751 | LGMN | −2.32715 | 4.54E−05 |
| 12250 | HSP90AB1 | −2.32781 | 1.49E−03 |
| 5850 | EIF4B | −2.32818 | 1.13E−05 |
| 13724 | LEPREL1 | −2.32851 | 0.000169338 |
| 17534 | LOC440991 | −2.33062 | 1.54E−04 |
| 29559 | RPS9 | −2.33092 | 1.06E−04 |
| 3724 | CDC7 | −2.33576 | 0.000342965 |
| 27035 | PABPC4 | −2.33611 | 0.000164425 |
| 33241 | TYMS | −2.34068 | 0.00106577 |
| 30229 | SHC1 | −2.34608 | 0.00105777 |
| 21754 | LOC652624 | −2.34734 | 2.21E−04 |
| 5846 | EIF3M | −2.34987 | 0.00181367 |
| 15032 | LOC100131713 | −2.35114 | 0.000201749 |
| 29432 | RPL10A | −2.35345 | 0.00131867 |
| 24235 | MCM6 | −2.35636 | 0.00108431 |
| 19046 | LOC644511 | −2.36244 | 0.000514797 |

TABLE 3-continued

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 5044 | DDIT4L | -2.36718 | 0.000107365 |
| 545 | AHCY | -2.3677 | 0.000431822 |
| 18592 | LOC643531 | -2.37199 | 1.01E-03 |
| 5744 | EEF1G | -2.37611 | 0.000630065 |
| 5765 | EFHD1 | -2.38043 | 1.20E-03 |
| 32637 | TNFRSF10B | -2.38066 | 1.53E-05 |
| 26099 | NME1-NME2 | -2.38426 | 4.44E-05 |
| 22757 | LOC728564 | -2.38494 | 3.69E-04 |
| 8826 | HNRPA1P4 | -2.38609 | 3.87E-05 |
| 17458 | LOC440359 | -2.38691 | 5.63E-04 |
| 28560 | PTPN13 | -2.39211 | 0.000413752 |
| 15180 | LOC100132199 | -2.39337 | 2.68E-05 |
| 4955 | DARS | -2.39728 | 1.56E-03 |
| 1882 | C11ORF1 | -2.39828 | 2.51E-05 |
| 23282 | LOC729926 | -2.39973 | 7.65E-04 |
| 15041 | LOC100131735 | -2.40035 | 2.35E-05 |
| 22829 | LOC728732 | -2.40089 | 6.11E-05 |
| 3973 | CHEK1 | -2.40178 | 1.16E-06 |
| 600 | AKR1A1 | -2.40346 | 0.000695089 |
| 15586 | LOC100133372 | -2.40481 | 1.53E-04 |
| 31607 | STOM | -2.40533 | 3.40E-07 |
| 22710 | LOC728453 | -2.40686 | 0.0001068 |
| 29457 | RPL26 | -2.4112 | 0.000285349 |
| 29921 | SEC11A | -2.41182 | 0.00102718 |
| 16776 | LOC388275 | -2.41288 | 5.56E-06 |
| 29438 | RPL13A | -2.41592 | 0.000922424 |
| 3795 | CDKN3 | -2.41856 | 0.000112421 |
| 30404 | SLC20A2 | -2.41879 | 6.23E-06 |
| 32648 | TNFRSF19 | -2.42065 | 6.93E-05 |
| 31239 | SP5 | -2.42085 | 2.37E-09 |
| 23974 | MAD2L2 | -2.42585 | 0.000123115 |
| 12602 | IMPA2 | -2.42996 | 1.90E-06 |
| 17525 | LOC440927 | -2.43391 | 0.00119949 |
| 29414 | RPA3 | -2.43719 | 0.00177478 |
| 16156 | LOC127295 | -2.43999 | 5.06E-04 |
| 29565 | RPUSD3 | -2.44425 | 1.98E-07 |
| 16979 | LOC390578 | -2.44648 | 8.18E-08 |
| 15104 | LOC100131940 | -2.44655 | 2.19E-05 |
| 26103 | NME4 | -2.44757 | 0.00114224 |
| 8825 | HNRPA1L-2 | -2.45235 | 5.46E-04 |
| 1537 | BCAR3 | -2.45546 | 0.000368573 |
| 14206 | LOC100129028 | -2.45901 | 3.51E-04 |
| 16672 | LOC345041 | -2.46013 | 0.000101781 |
| 3125 | CA14 | -2.46417 | 0.000205741 |
| 32089 | TET1 | -2.46774 | 3.21E-05 |
| 12231 | HSD17B8 | -2.47022 | 0.000519001 |
| 4479 | CPS1 | -2.47967 | 2.21E-06 |
| 25464 | MTA3 | -2.48169 | 8.09E-05 |
| 5758 | EFEMP1 | -2.48833 | 1.42E-05 |
| 28160 | PQLC3 | -2.48845 | 0.000585543 |
| 30245 | SHMT2 | -2.48964 | 0.00117427 |
| 23103 | LOC729423 | -2.50041 | 6.49E-06 |
| 12741 | ISG20L1 | -2.50404 | 9.70E-05 |
| 29539 | RPS3 | -2.50954 | 0.000103446 |
| 22857 | LOC728791 | -2.5096 | 5.69E-06 |
| 23391 | LOC730255 | -2.50972 | 1.22E-03 |
| 24097 | MAP4K2 | -2.51767 | 5.17E-06 |
| 7686 | GAPDH | -2.51826 | 0.00128279 |
| 2433 | C1ORF57 | -2.51861 | 1.49E-03 |
| 2262 | C18ORF56 | -2.51885 | 0.000156088 |
| 1792 | BUB1 | -2.52119 | 9.50E-05 |
| 5831 | EIF2S3 | -2.52373 | 3.38E-04 |
| 29039 | RENBP | -2.53102 | 4.92E-07 |
| 29481 | RPL39L | -2.53153 | 0.00013954 |
| 17141 | LOC399804 | -2.5389 | 3.38E-05 |
| 34552 | ZNF581 | -2.54051 | 9.37E-05 |
| 1156 | ARRDC4 | -2.54054 | 2.88E-05 |
| 8789 | HMMR | -2.54277 | 8.17E-05 |
| 28953 | RBMX | -2.5493 | 5.57E-05 |
| 32179 | THEM2 | -2.55298 | 5.30E-04 |
| 13239 | KIF20A | -2.55316 | 1.13E-05 |
| 1403 | AURKA | -2.55681 | 5.93E-05 |
| 27066 | PAICS | -2.55763 | 0.00111653 |
| 5836 | EIF3D | -2.56061 | 6.72E-05 |
| 13252 | KIF2C | -2.56757 | 1.70E-06 |
| 14814 | LOC100130980 | -2.57639 | 4.33E-05 |
| 31821 | TAF1D | -2.57677 | 6.27E-06 |
| 27653 | PIR | -2.58392 | 2.26E-06 |
| 7564 | FZD2 | -2.58518 | 0.000146094 |
| 28778 | RAD51AP1 | -2.59104 | 5.06E-06 |
| 14695 | LOC100130562 | -2.59563 | 3.41E-05 |
| 8547 | HEATR1 | -2.59617 | 5.95E-07 |
| 22591 | LOC728126 | -2.59998 | 3.37E-05 |
| 29483 | RPL4 | -2.62451 | 7.56E-05 |
| 25783 | NCAPG | -2.62632 | 6.41E-05 |
| 20366 | LOC647856 | -2.6267 | 1.31E-05 |
| 29462 | RPL29 | -2.62809 | 4.36E-07 |
| 23274 | LOC729903 | -2.63121 | 4.28E-05 |
| 15975 | LOC100134393 | -2.6327 | 2.71E-04 |
| 9745 | HS.363526 | -2.6341 | 0.000643774 |
| 561 | AIF1L | -2.63663 | 1.37E-04 |
| 8597 | HEXB | -2.63709 | 1.51E-03 |
| 5993 | EPDR1 | -2.63912 | 0.00156376 |
| 7966 | GMPS | -2.64155 | 1.99E-04 |
| 27563 | PHYH | -2.64322 | 2.14E-05 |
| 4100 | CKS1B | -2.64512 | 1.68E-04 |
| 7898 | GLDC | -2.64809 | 0.00143371 |
| 5513 | DPH5 | -2.6481 | 2.11E-05 |
| 18914 | LOC644237 | -2.66097 | 0.0011589 |
| 20185 | LOC647285 | -2.66563 | 1.82E-04 |
| 22536 | LOC727984 | -2.67684 | 0.000223687 |
| 8625 | HIBADH | -2.68374 | 0.00144114 |
| 684 | ALPL | -2.69266 | 2.39E-06 |
| 17636 | LOC441506 | -2.70546 | 6.10E-05 |
| 30602 | SLC44A2 | -2.70757 | 1.24E-03 |
| 16741 | LOC387867 | -2.71424 | 2.45E-05 |
| 23060 | LOC729340 | -2.7157 | 0.000999351 |
| 27743 | PLCD1 | -2.72 | 1.14E-07 |
| 22597 | LOC728139 | -2.72434 | 4.77E-05 |
| 28530 | PTGR1 | -2.72675 | 7.39E-05 |
| 5741 | EEF1B2 | -2.7289 | 4.84E-05 |
| 18360 | LOC642989 | -2.73236 | 0.000921883 |
| 20058 | LOC646942 | -2.74335 | 5.41E-05 |
| 16737 | LOC387825 | -2.74954 | 5.93E-06 |
| 16236 | LOC148430 | -2.76485 | 2.32E-05 |
| 29441 | RPL14 | -2.76505 | 4.49E-06 |
| 31176 | SNX5 | -2.77426 | 4.41E-08 |
| 13592 | LAMA1 | -2.77535 | 2.89E-07 |
| 16814 | LOC388707 | -2.77694 | 1.99E-06 |
| 29179 | RHPN2 | -2.78226 | 0.00110049 |
| 23133 | LOC729500 | -2.78295 | 8.63E-06 |
| 2524 | C20ORF199 | -2.79683 | 8.26E-05 |
| 27370 | PDLIM1 | -2.79852 | 0.000250318 |
| 27030 | PABPC1 | -2.7998 | 0.000107149 |
| 7486 | FRZB | -2.81189 | 5.35E-04 |
| 17023 | LOC391075 | -2.82637 | 0.00139394 |
| 6705 | FBL | -2.8276 | 2.59E-05 |
| 13708 | LEF1 | -2.83207 | 1.15E-05 |
| 4101 | CKS2 | -2.83376 | 0.000537912 |
| 13438 | KRT19 | -2.83803 | 2.34E-05 |
| 28410 | PSAT1 | -2.8451 | 8.29E-07 |
| 33979 | YAP1 | -2.84569 | 0.00106156 |
| 29435 | RPL12 | -2.85091 | 4.23E-05 |
| 22553 | LOC728031 | -2.85482 | 8.14E-05 |
| 29524 | RPS2 | -2.85918 | 1.32E-05 |
| 23861 | LRTM1 | -2.85972 | 1.48E-12 |
| 26404 | NUSAP1 | -2.86459 | 9.00E-05 |
| 20473 | LOC648249 | -2.86802 | 4.01E-06 |
| 23319 | LOC730029 | -2.87607 | 3.58E-05 |
| 24516 | MGST1 | -2.87812 | 2.82E-06 |
| 349 | ACVR1 | -2.88477 | 0.000447642 |
| 30500 | SLC29A1 | -2.91375 | 2.94E-06 |
| 17086 | LOC391833 | -2.91531 | 4.06E-05 |
| 20614 | LOC648771 | -2.91567 | 7.23E-05 |
| 27493 | PGM1 | -2.92082 | 0.000287518 |
| 30836 | SNHG6 | -2.92725 | 2.13E-05 |

TABLE 3-continued

Gene expression array data of significantly up-regulated and down-regulated genes at differentiation day 25 over day 13 in SHH/FGF8/Chir treated Floor-plate based population.

| Column # | Column ID | Fold-Change | p-value |
|---|---|---|---|
| 20015 | LOC646849 | −2.95184 | 3.75E−05 |
| 16783 | LOC388339 | −2.95309 | 4.55E−05 |
| 3785 | CDKN1A | −2.95807 | 0.000310093 |
| 29436 | RPL12P6 | −2.97114 | 2.40E−06 |
| 5258 | DIMT1L | −2.97803 | 1.83E−06 |
| 15940 | LOC100134304 | −2.98223 | 4.08E−08 |
| 13733 | LGALS1 | −2.98473 | 0.00160731 |
| 27902 | PODXL | −3.00627 | 2.35E−08 |
| 16630 | LOC341315 | −3.02065 | 1.10E−04 |
| 481 | ADSS | −3.02244 | 4.06E−06 |
| 29557 | RPS7 | −3.06985 | 2.69E−06 |
| 1406 | AURKB | −3.07612 | 5.67E−07 |
| 23373 | LOC730187 | −3.08276 | 4.32E−06 |
| 25214 | MND1 | −3.08698 | 3.39E−07 |
| 14412 | LOC100129657 | −3.08986 | 0.00120608 |
| 33282 | UBE2C | −3.09218 | 4.69E−06 |
| 30114 | SFRP1 | −3.10477 | 0.000250519 |
| 17015 | LOC391019 | −3.10602 | 2.05E−05 |
| 28602 | PTTG1 | −3.11309 | 2.05E−05 |
| 17541 | LOC441013 | −3.11866 | 6.73E−07 |
| 20657 | LOC648931 | −3.12515 | 3.24E−09 |
| 31661 | SUCLG2 | −3.13505 | 5.75E−07 |
| 1559 | BCL2L12 | −3.13599 | 4.40E−07 |
| 32222 | TIGA1 | −3.13783 | 7.09E−05 |
| 7770 | GDF15 | −3.14204 | 1.42E−07 |
| 2878 | C6ORF160 | −3.15022 | 0.000111744 |
| 15382 | LOC100132795 | −3.21797 | 1.51E−05 |
| 4930 | DAB2 | −3.2203 | 2.91E−06 |
| 32933 | TRIP6 | −3.23132 | 1.32E−06 |
| 20091 | LOC647030 | −3.23731 | 4.86E−05 |
| 26048 | NKD1 | −3.24181 | 4.37E−06 |
| 6320 | FAM107A | −3.24905 | 0.000449795 |
| 16552 | LOC286444 | −3.25137 | 6.05E−06 |
| 26390 | NUP37 | −3.26236 | 3.70E−05 |
| 19783 | LOC646294 | −3.28211 | 1.06E−06 |
| 2210 | C17ORF61 | −3.28907 | 2.68E−05 |
| 19553 | LOC645688 | −3.29172 | 3.95E−06 |
| 25847 | NCRNA00219 | −3.29327 | 7.23E−05 |
| 28663 | QPRT | −3.29832 | 2.04E−05 |
| 31361 | SPON1 | −3.32269 | 5.27E−06 |
| 30835 | SNHG5 | −3.32459 | 0.000204237 |
| 4596 | CSDA | −3.3629 | 0.000363294 |
| 455 | ADM | −3.40482 | 4.11E−05 |
| 23228 | LOC729768 | −3.41997 | 2.20E−05 |
| 1753 | BST2 | −3.42742 | 1.17E−07 |
| 20685 | LOC649049 | −3.46913 | 1.63E−06 |
| 17292 | LOC401537 | −3.50501 | 3.79E−07 |
| 6707 | FBLN1 | −3.53279 | 3.88E−06 |
| 28241 | PRIM1 | −3.53892 | 1.17E−06 |
| 8754 | HLA-E | −3.54293 | 2.03E−07 |
| 643 | ALDOA | −3.55096 | 0.000184641 |
| 14422 | LOC100129681 | −3.55393 | 9.42E−07 |
| 8773 | HMGB2 | −3.56419 | 9.08E−05 |
| 32964 | TRPM4 | −3.5945 | 2.41E−06 |
| 12398 | IFITM2 | −3.59918 | 1.38E−03 |
| 32177 | THBS4 | −3.6116 | 6.59E−07 |
| 3540 | CCNB1IP1 | −3.62989 | 3.35E−08 |
| 5477 | DOCK10 | −3.64495 | 7.09E−07 |
| 28387 | PRSS23 | −3.67253 | 0.000258012 |
| 26369 | NUDT7 | −3.67565 | 7.62E−05 |
| 26207 | NPM3 | −3.69114 | 1.35E−06 |
| 23887 | LTA4H | −3.69913 | 6.82E−05 |
| 12399 | IFITM3 | −3.70541 | 0.000779898 |
| 8769 | HMGA1 | −3.72752 | 3.30E−08 |
| 323 | ACTA2 | −3.74071 | 1.75E−04 |
| 1530 | BBS9 | −3.7636 | 3.82E−07 |
| 7501 | FSTL1 | −3.80754 | 0.000136961 |
| 27805 | PLIN2 | −3.82123 | 4.77E−10 |
| 28975 | RBPMS2 | −3.82727 | 3.95E−06 |
| 23218 | LOC729742 | −3.84552 | 7.82E−07 |
| 13597 | LAMB1 | −3.85107 | 1.24E−07 |
| 6291 | FABP7 | −3.85422 | 0.000335025 |
| 12606 | IMPDH2 | −3.85952 | 4.79E−06 |
| 13834 | LITAF | −3.86 | 4.66E−05 |
| 3953 | CHCHD10 | −3.91295 | 4.20E−06 |
| 2439 | C1ORF64 | −3.9544 | 5.48E−10 |
| 8473 | HAUS4 | −3.96227 | 4.95E−12 |
| 925 | APCDD1 | −3.97854 | 6.09E−08 |
| 5952 | ENO3 | −4.00663 | 6.90E−09 |
| 27019 | P4HA1 | −4.01147 | 0.00032695 |
| 4724 | CTSL2 | −4.01208 | 1.47E−06 |
| 19348 | LOC645173 | −4.02454 | 2.71E−06 |
| 28605 | PTTG3P | −4.02805 | 3.37E−06 |
| 4239 | CMTM7 | −4.08386 | 7.09E−09 |
| 8089 | GPI | −4.08821 | 1.18E−05 |
| 1616 | BGN | −4.11601 | 0.000348095 |
| 23196 | LOC729679 | −4.2525 | 4.55E−08 |
| 3694 | CDC20 | −4.28351 | 3.38E−06 |
| 32729 | TOP2A | −4.29945 | 1.43E−06 |
| 30828 | SNHG1 | −4.38641 | 2.77E−06 |
| 3243 | CAPN6 | −4.44794 | 4.50E−07 |
| 30284 | SILV | −4.59486 | 1.80E−07 |
| 15342 | LOC100132673 | −4.69254 | 2.18E−07 |
| 29716 | SALL4 | −4.95909 | 2.66E−08 |
| 3541 | CCNB2 | −5.23718 | 4.33E−08 |
| 30511 | SLC2A3 | −5.39887 | 5.64E−07 |
| 13691 | LDHA | −5.76362 | 0.000569306 |
| 7500 | FST | −5.82949 | 8.74E−09 |
| 1543 | BCAT1 | −6.13131 | 3.52E−06 |
| 5323 | DKK1 | −6.17493 | 4.94E−08 |
| 4343 | COL4A1 | −6.21986 | 6.18E−07 |
| 8078 | GPC3 | −6.35513 | 0.000466041 |
| 4333 | COL22A1 | −6.371 | 1.87E−08 |
| 32774 | TPM2 | −6.8139 | 1.85E−08 |
| 2430 | C1ORF54 | −7.81915 | 1.70E−07 |
| 965 | APOE | −9.10671 | 6.03E−07 |
| 13804 | LIN28 | −26.8821 | 1.20E−13 |

TABLE 4

Gene expression array data of significantly up-regulated and down-regulated genes at differentiation day 25 in SHH/FGF8/Chir treated Floor-plate based population over control LSB treated population.

| Column # | Column ID | Fold-Change | p-value |
|---|---|---|---|
| 32126 | TFF3 | 25.0585 | 2.47E−14 |
| 1209 | ASCL1 | 14.9328 | 1.97E−07 |
| 7395 | FOXA1 | 12.9897 | 4.15E−14 |
| 29133 | RGS4 | 11.0181 | 6.65E−09 |
| 27988 | POSTN | 8.20403 | 2.16E−10 |
| 7396 | FOXA2 | 7.98132 | 1.60E−14 |
| 4342 | COL3A1 | 7.58625 | 2.49E−05 |
| 12731 | IRX3 | 7.42399 | 1.64E−06 |
| 9374 | HS.19193 | 7.27196 | 7.36E−09 |
| 3978 | CHGA | 7.14305 | 2.77E−08 |
| 2470 | C1QL1 | 7.1366 | 1.38E−09 |
| 30390 | SLC18A1 | 7.04751 | 3.52E−14 |
| 22823 | LOC728715 | 6.5801 | 8.79E−09 |
| 12456 | IGFBP5 | 6.15962 | 3.65E−05 |
| 27665 | PITX2 | 6.10679 | 6.79E−14 |
| 12655 | INSM2 | 5.18438 | 1.70E−09 |
| 12944 | KCNJ16 | 4.98753 | 8.89E−13 |
| 436 | ADCYAP1 | 4.94597 | 2.43E−09 |
| 31361 | SPON1 | 4.93795 | 4.69E−08 |
| 13857 | LMO3 | 4.83578 | 7.25E−08 |
| 13865 | LMX1A | 4.63407 | 1.51E−06 |
| 2543 | C20ORF56 | 4.4431 | 3.63E−13 |
| 12733 | IRX5 | 4.2929 | 1.45E−06 |
| 7988 | GNB3 | 4.13634 | 1.52E−10 |
| 32159 | TH | 4.08743 | 0.000370318 |
| 5346 | DLK1 | 4.02203 | 1.73E−05 |

TABLE 4-continued

Gene expression array data of significantly up-regulated and down-regulated genes at differentiation day 25 in SHH/FGF8/Chir treated Floor-plate based population over control LSB treated population.

| Column # | Column ID | Fold-Change | p-value |
|---|---|---|---|
| 31775 | SYT4 | 4.00669 | 0.000372793 |
| 9428 | HS.204481 | 3.88697 | 6.71E−09 |
| 6197 | ETS2 | 3.70155 | 3.07E−09 |
| 5036 | DDC | 3.61254 | 0.000194062 |
| 26250 | NR4A2 | 3.55879 | 9.29E−10 |
| 2867 | C6ORF141 | 3.48146 | 6.97E−09 |
| 26928 | OSBPL10 | 3.27941 | 3.81E−07 |
| 5372 | DMRTA2 | 3.26437 | 1.81E−08 |
| 33930 | XBP1 | 3.2414 | 0.000921089 |
| 27664 | PITX1 | 3.23009 | 1.10E−05 |
| 9819 | HS.388347 | 3.14523 | 8.26E−08 |
| 30239 | SHISA2 | 3.13411 | 4.23E−05 |
| 2743 | C3ORF58 | 3.10109 | 1.50E−06 |
| 623 | ALCAM | 3.00487 | 0.000307411 |
| 6533 | FAM46A | 2.99243 | 3.45E−05 |
| 28590 | PTPRO | 2.94164 | 4.45E−05 |
| 18750 | LOC643911 | 2.93448 | 1.14E−06 |
| 31669 | SULF2 | 2.92397 | 8.02E−05 |
| 5348 | DLL1 | 2.92274 | 8.36E−05 |
| 30066 | SERPINF1 | 2.76873 | 0.000156193 |
| 5349 | DLL3 | 2.75425 | 0.000173675 |
| 3186 | CALCA | 2.71125 | 2.10E−07 |
| 30590 | SLC39A8 | 2.67444 | 2.25E−05 |
| 32000 | TCF12 | 2.66777 | 1.46E−06 |
| 3941 | CGNL1 | 2.63848 | 0.00120585 |
| 32769 | TPH1 | 2.62647 | 1.95E−06 |
| 25941 | NENF | 2.55992 | 0.000599552 |
| 29509 | RPRM | 2.53138 | 0.00135525 |
| 32144 | TGFBR3 | 2.46754 | 8.27E−07 |
| 13689 | LDB2 | 2.40983 | 2.56E−05 |
| 2850 | C6ORF117 | 2.4009 | 0.000508473 |
| 31806 | TACSTD1 | 2.38661 | 0.00154495 |
| 24375 | MFNG | 2.31488 | 5.04E−05 |
| 5424 | DNAJC19 | 2.30405 | 4.42E−07 |
| 12986 | KCNS3 | 2.28802 | 0.000136062 |
| 27855 | PMP22 | 2.27371 | 1.36E−05 |
| 4003 | CHN2 | 2.26467 | 0.000550787 |
| 5691 | EBF3 | 2.26453 | 0.000571924 |
| 3187 | CALCB | 2.11359 | 2.49E−06 |
| 28325 | PROX1 | 2.08192 | 0.000135872 |
| 25218 | MNX1 | 2.05528 | 3.37E−06 |
| 6270 | F3 | 2.01261 | 5.71E−07 |
| 2245 | C18ORF10 | −2.00297 | 0.00129421 |
| 28546 | PTN | −2.003 | 0.000354472 |
| 5920 | EMID2 | −2.00456 | 1.77E−05 |
| 24405 | MGC11082 | −2.00498 | 2.75E−05 |
| 5949 | ENKUR | −2.00742 | 0.000107398 |
| 26398 | NUP93 | −2.01111 | 0.00124009 |
| 10837 | HS.545615 | −2.01378 | 2.65E−05 |
| 12688 | IQCC | −2.01383 | 0.00019749 |
| 6196 | ETS1 | −2.01751 | 0.000848186 |
| 27290 | PCSK5 | −2.02079 | 0.00122771 |
| 16112 | LOC100192378 | −2.0216 | 4.35E−05 |
| 19806 | LOC646345 | −2.02311 | 0.000183202 |
| 23846 | LRRIQ1 | −2.02718 | 0.000541683 |
| 27746 | PLCE1 | −2.02761 | 0.000217281 |
| 2727 | C3ORF39 | −2.03023 | 0.000131521 |
| 26072 | NLGN3 | −2.03154 | 2.45E−05 |
| 2770 | C4ORF22 | −2.03489 | 0.00113778 |
| 3491 | CCDC88C | −2.03515 | 0.00112864 |
| 25751 | NAV3 | −2.03716 | 8.63E−05 |
| 30413 | SLC22A17 | −2.03749 | 0.000703407 |
| 13014 | KDELC2 | −2.04133 | 0.00147391 |
| 27749 | PLCH1 | −2.0426 | 0.000234672 |
| 16489 | LOC284988 | −2.04353 | 0.000785305 |
| 9938 | HS.440518 | −2.04573 | 0.000285223 |
| 28076 | PPM1H | −2.04637 | 0.00038276 |
| 429 | ADCY3 | −2.05728 | 0.000712376 |
| 31199 | SORBS2 | −2.05812 | 8.31E−05 |
| 17624 | LOC441453 | −2.0676 | 3.05E−06 |
| 13793 | LIM2 | −2.07092 | 0.00040641 |
| 31165 | TUB | −2.07384 | 0.000187156 |
| 3462 | CCDC65 | −2.07613 | 0.00151516 |
| 4305 | COBL | −2.07819 | 0.000485834 |
| 6912 | FILIP1 | −2.07924 | 9.69E−05 |
| 5195 | DGCR6 | −2.07943 | 0.000935686 |
| 33905 | WSCD1 | −2.08212 | 0.00033792 |
| 12933 | KCNIP1 | −2.08721 | 3.72E−05 |
| 4933 | DACH2 | −2.09051 | 9.24E−05 |
| 25960 | NEUROG2 | −2.09361 | 0.00111856 |
| 25930 | NEK2 | −2.09683 | 0.00144313 |
| 3288 | CASP3 | −2.09925 | 0.000130992 |
| 12971 | KCNMB4 | −2.09934 | 0.00140267 |
| 3125 | CA14 | −2.10277 | 0.00147559 |
| 17153 | LOC399959 | −2.10829 | 0.000816932 |
| 15855 | LOC100134073 | −2.10866 | 0.000366572 |
| 6322 | NTM | −2.10973 | 0.000159062 |
| 7595 | GABRA2 | −2.11173 | 0.00169771 |
| 5618 | DUSP18 | −2.11289 | 8.90E−05 |
| 4289 | CNTFR | −2.11375 | 0.00132713 |
| 3760 | CDH8 | −2.11381 | 7.41E−05 |
| 3196 | CALM1 | −2.11418 | 0.00157715 |
| 13615 | LARGE | −2.11685 | 2.37E−05 |
| 32933 | TRIP6 | −2.11829 | 0.00047459 |
| 2242 | C17ORF97 | −2.12666 | 0.000851745 |
| 5478 | DOCK11 | −2.12763 | 0.000306132 |
| 7377 | FNDC4 | −2.13338 | 0.000482465 |
| 29672 | RYR3 | −2.13573 | 0.000392208 |
| 30669 | SLC7A6 | −2.13865 | 0.000299041 |
| 29816 | SCD5 | −2.14266 | 9.40E−05 |
| 12212 | HS6ST2 | −2.14751 | 0.00020473 |
| 4213 | CLSTN2 | −2.15117 | 2.14E−05 |
| 16924 | LOC389816 | −2.15626 | 4.60E−09 |
| 2102 | C15ORF26 | −2.15663 | 0.000242005 |
| 1103 | ARL4C | −2.16184 | 0.00049625 |
| 31151 | SNX10 | −2.16614 | 0.000623725 |
| 16382 | LOC255783 | −2.17123 | 0.000592438 |
| 30372 | SLC16A14 | −2.17701 | 0.000382805 |
| 13177 | KIAA1598 | −2.1779 | 0.000634174 |
| 28587 | PTPRM | −2.17848 | 0.000334455 |
| 8661 | HIST1H2AC | −2.18157 | 0.00018782 |
| 30015 | SEPT6 | −2.18483 | 0.00101243 |
| 6572 | FAM65B | −2.18593 | 1.46E−05 |
| 4614 | CSMD2 | −2.18777 | 0.000579739 |
| 19737 | LOC646168 | −2.18864 | 0.000417767 |
| 2429 | C1ORF53 | −2.19182 | 0.0017844 |
| 17855 | LOC641785 | −2.19315 | 0.000255891 |
| 5570 | DSCR6 | −2.20122 | 0.00137487 |
| 13835 | LIX1 | −2.20141 | 6.32E−06 |
| 23979 | MAF | −2.20457 | 6.38E−05 |
| 4734 | CTXN1 | −2.21039 | 0.0007813 |
| 2049 | C14ORF159 | −2.2127 | 0.000171696 |
| 30388 | SLC17A8 | −2.21639 | 0.000916084 |
| 26228 | NQO1 | −2.21974 | 0.000753734 |
| 23817 | LRRC46 | −2.22159 | 0.000756129 |
| 32380 | TMEM132D | −2.22662 | 0.000463067 |
| 2705 | C3ORF15 | −2.2299 | 0.000615847 |
| 27781 | PLEKHG1 | −2.23885 | 1.49E−05 |
| 29607 | RSPH9 | −2.24091 | 0.000109859 |
| 23965 | MAB21L1 | −2.24222 | 2.00E−05 |
| 25942 | NEO1 | −2.24511 | 2.27E−05 |
| 34157 | ZFP106 | −2.24688 | 0.00129693 |
| 33083 | TTC29 | −2.24927 | 0.000317648 |
| 3415 | CCDC19 | −2.25412 | 0.000638581 |
| 30209 | SH3GL2 | −2.2573 | 0.00175354 |
| 839 | ANKS1B | −2.25784 | 6.46E−05 |
| 3472 | CCDC74A | −2.25911 | 3.66E−05 |
| 27561 | PHTF1 | −2.26039 | 0.00113655 |
| 26505 | OPCML | −2.26062 | 2.34E−05 |
| 23859 | LRRTM4 | −2.26387 | 0.00050229 |
| 27040 | PACRG | −2.26701 | 8.08E−05 |
| 24318 | MELK | −2.27019 | 0.000423662 |
| 10017 | HS.452398 | −2.27201 | 0.000477927 |
| 9237 | HS.147562 | −2.27279 | 0.000798954 |
| 26976 | OTX1 | −2.27327 | 0.000877908 |
| 8046 | GOLSYN | −2.27724 | 0.000100581 |

TABLE 4-continued

Gene expression array data of significantly up-regulated and down-regulated genes at differentiation day 25 in SHH/FGF8/Chir treated Floor-plate based population over control LSB treated population.

| Column # | Column ID | Fold-Change | p-value |
| --- | --- | --- | --- |
| 1074 | ARHGEF6 | −2.27982 | 0.000748746 |
| 4639 | CSRNP3 | −2.28361 | 0.000213299 |
| 27547 | PHLDA1 | −2.28667 | 2.70E−05 |
| 3537 | CCNA1 | −2.28864 | 6.92E−05 |
| 26071 | NLGN2 | −2.29131 | 0.000215422 |
| 5325 | DKK3 | −2.29195 | 0.000372444 |
| 6326 | FAM108C1 | −2.29624 | 0.000567659 |
| 28721 | RAB3B | −2.30577 | 0.000211905 |
| 2372 | C1ORF158 | −2.3174 | 0.00184147 |
| 32499 | TMEM231 | −2.32173 | 0.000378145 |
| 5550 | DRD1IP | −2.3265 | 0.00129147 |
| 12785 | ITGB5 | −2.32837 | 0.00143999 |
| 30937 | SNORA79 | −2.32935 | 0.000394221 |
| 2538 | C20ORF46 | −2.34101 | 0.000827542 |
| 5939 | EMX2OS | −2.34991 | 1.28E−05 |
| 3153 | CACNA1E | −2.35127 | 0.000755994 |
| 28906 | RBKS | −2.35486 | 1.25E−05 |
| 3806 | CDRT4 | −2.36622 | 0.000173226 |
| 32129 | TFPI | −2.36876 | 0.000644776 |
| 5763 | EFHC1 | −2.36977 | 0.00112503 |
| 3746 | CDH18 | −2.37821 | 6.60E−06 |
| 33006 | TSHZ3 | −2.38415 | 0.00160322 |
| 6901 | FHOD3 | −2.38572 | 0.00106294 |
| 13805 | LIN28B | −2.38688 | 0.000393414 |
| 1806 | C10ORF107 | −2.39735 | 0.000750154 |
| 32034 | TCTEX1D1 | −2.40988 | 0.00160003 |
| 31146 | SNTN | −2.42893 | 0.000945171 |
| 30057 | SERPINB6 | −2.43305 | 1.01E−05 |
| 28580 | PTPRD | −2.43513 | 6.24E−05 |
| 28210 | PRDM8 | −2.44254 | 0.000113613 |
| 2614 | C22ORF15 | −2.45467 | 0.000112958 |
| 12892 | KBTBD9 | −2.45472 | 2.16E−06 |
| 6246 | EXT1 | −2.4653 | 0.000117948 |
| 25946 | NETO2 | −2.46601 | 0.000568595 |
| 493 | AFF2 | −2.4707 | 0.0012124 |
| 31610 | STOML3 | −2.48765 | 0.000560404 |
| 31577 | STIL | −2.49103 | 0.000199457 |
| 4826 | CYB5D1 | −2.49147 | 0.000128822 |
| 2078 | C14ORF45 | −2.49501 | 0.000787004 |
| 33501 | USP13 | −2.49771 | 6.06E−05 |
| 34226 | ZMYND10 | −2.50015 | 0.000105158 |
| 28507 | PTCHD1 | −2.50016 | 0.00120417 |
| 5322 | DKEZP781N1041 | −2.50483 | 0.000661286 |
| 3253 | CAPSL | −2.50626 | 0.000844682 |
| 14289 | LOC100129268 | −2.508 | 0.000176359 |
| 17551 | LOC441054 | −2.5088 | 0.00166136 |
| 26395 | NUP62CL | −2.51081 | 0.000373281 |
| 1776 | BTG3 | −2.51582 | 0.00131261 |
| 33005 | TSHZ2 | −2.51649 | 3.77E−05 |
| 4705 | CTNND2 | −2.52798 | 0.00038507 |
| 29792 | SCARNA11 | −2.53148 | 3.35E−05 |
| 4965 | DBC1 | −2.53221 | 0.000370596 |
| 32507 | TMEM31 | −2.53343 | 2.39E−06 |
| 1927 | C11ORF75 | −2.53649 | 0.000498243 |
| 6740 | FBXO15 | −2.54184 | 0.00139562 |
| 27370 | PDLIM1 | −2.54956 | 0.000681773 |
| 728 | AMPH | −2.55801 | 6.39E−06 |
| 33718 | VWC2 | −2.56363 | 0.000340976 |
| 13724 | LEPREL1 | −2.56798 | 4.43E−05 |
| 1057 | ARHGDIB | −2.573 | 5.20E−06 |
| 5765 | EFHD1 | −2.59294 | 0.000474204 |
| 3758 | CDH6 | −2.6075 | 0.000303268 |
| 7043 | FLJ23152 | −2.60944 | 0.000143522 |
| 31282 | SPATA17 | −2.61656 | 0.00020388 |
| 7106 | FLJ33590 | −2.61873 | 0.00025779 |
| 16264 | LOC151162 | −2.62005 | 0.000666466 |
| 32440 | TMEM178 | −2.62313 | 0.00011953 |
| 1987 | C12ORF69 | −2.62861 | 5.06E−06 |
| 2970 | C7ORF57 | −2.63494 | 0.000118643 |
| 23830 | LRRC6 | −2.63632 | 0.000197619 |
| 6173 | ESM1 | −2.63913 | 0.000368518 |
| 153 | ABAT | −2.64114 | 3.81E−06 |
| 2793 | C4ORF47 | −2.64571 | 0.00134045 |
| 2301 | C19ORF51 | −2.64617 | 7.44E−05 |
| 34155 | ZFHX4 | −2.66127 | 5.12E−06 |
| 5762 | EFHB | −2.66338 | 0.000148296 |
| 6920 | FJX1 | −2.66433 | 8.09E−05 |
| 12872 | KANK4 | −2.66744 | 0.000457332 |
| 26104 | NME5 | −2.66836 | 0.000118819 |
| 3148 | CACHD1 | −2.67846 | 0.000100474 |
| 25628 | MYO16 | −2.67972 | 8.67E−05 |
| 28838 | RAPGEF2 | −2.68049 | 7.06E−05 |
| 5553 | DRD4 | −2.68408 | 0.000500735 |
| 4087 | CITED2 | −2.68818 | 0.00192224 |
| 23790 | LRRC26 | −2.68889 | 2.44E−06 |
| 2631 | C22ORF42 | −2.69089 | 0.00039382 |
| 25564 | MXRA5 | −2.69302 | 0.000192861 |
| 12836 | JAZF1 | −2.70808 | 5.58E−05 |
| 13346 | KLHL29 | −2.71506 | 5.11E−06 |
| 25749 | NAV1 | −2.71696 | 0.000248061 |
| 29306 | RNF175 | −2.71799 | 3.04E−05 |
| 13815 | LINGO2 | −2.71868 | 2.30E−05 |
| 25208 | MMRN1 | −2.73481 | 0.000116097 |
| 3918 | CFDP1 | −2.73575 | 0.000150699 |
| 31242 | SP8 | −2.73862 | 5.04E−05 |
| 1311 | ATP1B3 | −2.7498 | 8.64E−05 |
| 25939 | NELL1 | −2.7509 | 0.00086776 |
| 32531 | TMEM51 | −2.77628 | 6.84E−06 |
| 15778 | LOC100133887 | −2.78135 | 1.17E−05 |
| 815 | ANKRD38 | −2.79552 | 0.000168264 |
| 33758 | WDR16 | −2.80194 | 0.000532777 |
| 12801 | ITM2C | −2.81062 | 7.32E−05 |
| 32847 | TRH | −2.84178 | 0.00148109 |
| 2881 | C6ORF165 | −2.84456 | 6.28E−05 |
| 15644 | LOC100133542 | −2.84572 | 9.65E−05 |
| 29811 | SCARNA8 | −2.84646 | 9.99E−06 |
| 33964 | XPR1 | −2.85352 | 5.49E−06 |
| 25940 | NELL2 | −2.86423 | 0.000248313 |
| 5455 | DNER | −2.87832 | 0.001272842 |
| 33807 | WDR63 | −2.88707 | 4.43E−05 |
| 3038 | C9ORF116 | −2.89396 | 0.000215965 |
| 2553 | C20ORF85 | −2.89405 | 7.84E−05 |
| 5531 | DPY19L1 | −2.90287 | 0.000183171 |
| 31955 | TBR1 | −2.90815 | 7.60E−06 |
| 8655 | HIST1H1C | −2.91043 | 9.46E−05 |
| 3401 | CCDC146 | −2.91057 | 0.000155147 |
| 31935 | TBC1D9 | −2.91662 | 6.93E−05 |
| 7421 | FOXJ1 | −2.94694 | 0.000577632 |
| 32783 | TPPP3 | −2.95648 | 0.000353912 |
| 5337 | DLG2 | −2.96987 | 1.13E−06 |
| 27810 | PLK4 | −2.98102 | 1.71E−06 |
| 24315 | MEIS2 | −3.03243 | 0.001099772 |
| 31243 | SPA17 | −3.03709 | 0.000523067 |
| 10979 | HS.551307 | −3.04712 | 1.13E−05 |
| 29794 | SCARNA13 | −3.05568 | 4.35E−05 |
| 32378 | TMEM132B | −3.06408 | 1.54E−06 |
| 2690 | C2ORF77 | −3.07752 | 4.19E−05 |
| 27660 | PITPNM1 | −3.09871 | 2.62E−05 |
| 32963 | TRPM3 | −3.10437 | 0.000937085 |
| 3640 | CD36 | −3.10624 | 0.000121554 |
| 26070 | NLGN1 | −3.1408 | 9.93E−05 |
| 5749 | EFCAB1 | −3.15705 | 0.000423897 |
| 3121 | CA10 | −3.15947 | 0.000537722 |
| 3215 | CAMK2N1 | −3.16181 | 0.000561888 |
| 8016 | GNRH1 | −3.16554 | 1.25E−05 |
| 13037 | KHDRBS3 | −3.16572 | 0.000269437 |
| 5681 | E2F7 | −3.17981 | 2.36E−07 |
| 8174 | GPR37 | −3.18311 | 2.85E−05 |
| 29510 | RPRML | −3.19177 | 0.000271322 |
| 4349 | COL4A6 | −3.1938 | 5.88E−05 |
| 27887 | PNOC | −3.19863 | 4.88E−05 |
| 1543 | BCAT1 | −3.20615 | 0.000858798 |
| 28813 | RALYL | −3.21662 | 0.000509498 |
| 0531 | SLC32A1 | −3.24737 | 0.0002618 |
| 5216 | MNS1 | −3.25707 | 0.000109366 |
| 3364 | CCDC109B | −3.26787 | 0.000147649 |

TABLE 4-continued

Gene expression array data of significantly up-regulated and down-regulated genes at differentiation day 25 in SHH/FGF8/Chir treated Floor-plate based population over control LSB treated population.

| Column # | Column ID | Fold-Change | p-value |
|---|---|---|---|
| 4004 | CHODL | −3.28962 | 0.00114785 |
| 965 | APOE | −3.29237 | 0.00155578 |
| 5764 | EFHC2 | −3.29611 | 0.000143319 |
| 29002 | RDH10 | −3.30034 | 0.000369857 |
| 29600 | RSHL3 | −3.30753 | 6.17E−05 |
| 12317 | HTRA1 | −3.31522 | 0.000437969 |
| 2398 | C1ORF194 | −3.31829 | 1.21E−05 |
| 5895 | ELMOD1 | −3.32218 | 0.000142072 |
| 3066 | C9ORF171 | −3.33251 | 4.78E−05 |
| 33592 | VAT1L | −3.3402 | 0.000247714 |
| 12399 | IFITM3 | −3.3542 | 0.0016376 |
| 8319 | PROM1 | −3.35504 | 5.84E−05 |
| 29034 | RELN | −3.43956 | 1.30E−05 |
| 2397 | C1ORF192 | −3.45738 | 0.000124675 |
| 586 | AKAP14 | −3.46559 | 1.94E−05 |
| 5032 | DDAH1 | −3.46896 | 1.42E−05 |
| 3766 | CDK2AP2 | −3.4706 | 3.31E−06 |
| 3652 | CD47 | −3.47334 | 6.18E−05 |
| 4283 | CNR1 | −3.48521 | 9.70E−05 |
| 12694 | IQCG | −3.4934 | 2.59E−05 |
| 10300 | HS.537002 | −3.49808 | 0.000142247 |
| 12506 | IL13RA2 | −3.50471 | 5.79E−05 |
| 28709 | RAB31 | −3.51372 | 7.79E−05 |
| 28536 | PTH2 | −3.54413 | 0.000188892 |
| 31283 | SPATA18 | −3.54742 | 5.71E−05 |
| 3071 | C9ORF24 | −3.55395 | 9.04E−05 |
| 7432 | FOXN4 | −3.57299 | 5.14E−09 |
| 27171 | PBX3 | −3.57487 | 0.000447274 |
| 32270 | TLE4 | −3.57637 | 7.16E−05 |
| 28981 | RCAN2 | −3.61105 | 0.000608216 |
| 32069 | TEKT1 | −3.61846 | 8.36E−05 |
| 17491 | LOC440585 | −3.62588 | 0.000175217 |
| 5660 | DYNLRB2 | −3.6297 | 6.28E−05 |
| 5938 | EMX2 | −3.66175 | 1.17E−06 |
| 24314 | MEIS1 | −3.68295 | 0.000402832 |
| 13856 | LMO2 | −3.74164 | 7.37E−06 |
| 6004 | EPHB1 | −3.77917 | 0.000119923 |
| 7504 | FSTL5 | −3.80048 | 0.000392914 |
| 1119 | ARMC3 | −3.82142 | 2.66E−05 |
| 31257 | SPAG6 | −3.86214 | 1.74E−05 |
| 7865 | GJA1 | −3.88524 | 0.000511853 |
| 3274 | CASC1 | −3.88963 | 2.00E−05 |
| 7696 | GAS1 | −3.95396 | 2.45E−07 |
| 7805 | GFRA2 | −4.00209 | 0.000116201 |
| 3050 | C9ORF135 | −4.09611 | 3.21E−05 |
| 23853 | LRRN3 | −4.2728 | 1.34E−05 |
| 29603 | RSPH1 | −4.35627 | 1.08E−05 |
| 6458 | FAM183A | −4.40302 | 2.73E−05 |
| 3220 | CAMKV | −4.47543 | 4.97E−05 |
| 27284 | PCP4 | −4.64191 | 1.37E−05 |
| 29723 | SAMD3 | −4.7132 | 2.41E−06 |
| 31223 | SOX3 | −4.74012 | 8.45E−06 |
| 29396 | ROPN1L | −4.86578 | 3.17E−06 |
| 29972 | SEMA3C | −5.03965 | 4.16E−05 |
| 3695 | CDC20B | −5.17405 | 5.72E−07 |
| 4298 | CNTNAP2 | −5.33902 | 4.01E−06 |
| 2006 | C13ORF30 | −5.4414 | 1.12E−06 |
| 33600 | VCAN | −5.47499 | 0.000917643 |
| 1936 | C11ORF88 | −5.55748 | 2.96E−06 |
| 30115 | SFRP2 | −6.27713 | 3.81E−08 |
| 27159 | PAX6 | −6.64236 | 3.94E−10 |
| 866 | ANXA1 | −7.3691 | 4.96E−06 |
| 3561 | CCNO | −9.3158 | 2.19E−08 |
| 13768 | LHX2 | −9.53566 | 3.56E−05 |

TABLE 5

Gene expression array data of significantly up-regulated and down-regulated genes at differentiation day 25 in SHH/FGF8/Chir treated Floor-plate based population over SHH/FGF8 only treated population.

| Column # | Column ID | Fold-Change | p-value |
|---|---|---|---|
| 32126 | TFF3 | 24.0181 | 3.37E−14 |
| 1209 | ASCL1 | 22.1637 | 1.69E−08 |
| 9374 | HS.19193 | 14.7045 | 1.42E−11 |
| 7395 | FOXA1 | 13.8748 | 2.30E−14 |
| 13865 | LMX1A | 10.953 | 4.33E−10 |
| 12456 | IGFBP5 | 9.56964 | 1.58E−06 |
| 4342 | COL3A1 | 9.49528 | 5.64E−06 |
| 12361 | ID3 | 9.45077 | 3.33E−08 |
| 27988 | POSTN | 9.10453 | 7.82E−11 |
| 7396 | FOXA2 | 8.85174 | 5.07E−15 |
| 3941 | CGNL1 | 8.71553 | 1.37E−08 |
| 30390 | SLC18A1 | 8.37911 | 4.77E−15 |
| 5689 | EBF1 | 8.02385 | 2.37E−06 |
| 2470 | C1QL1 | 7.76325 | 5.90E−10 |
| 22823 | LOC728715 | 7.73246 | 1.77E−09 |
| 27665 | PITX2 | 7.32855 | 7.16E−15 |
| 12655 | INSM2 | 7.04572 | 4.97E−11 |
| 26250 | NR4A2 | 6.75415 | 1.28E−13 |
| 8156 | GPR177 | 6.28979 | 1.08E−05 |
| 13857 | LMO3 | 6.20624 | 4.64E−09 |
| 33930 | XBP1 | 5.8436 | 6.74E−06 |
| 12944 | KCNJ16 | 5.71955 | 1.37E−13 |
| 27821 | PLS3 | 5.62251 | 8.45E−07 |
| 5372 | DMRTA2 | 5.61111 | 8.09E−12 |
| 7988 | GNB3 | 5.55425 | 2.56E−12 |
| 31669 | SULF2 | 5.51821 | 6.78E−08 |
| 33128 | TTR | 5.48234 | 2.88E−09 |
| 2543 | C20ORF56 | 5.42131 | 2.00E−14 |
| 32762 | TPBG | 5.30583 | 7.23E−05 |
| 436 | ADCYAP1 | 5.20834 | 1.29E−09 |
| 26977 | OTX2 | 5.10526 | 6.89E−06 |
| 3978 | CHGA | 5.07311 | 7.78E−07 |
| 32000 | TCF12 | 5.05883 | 1.27E−10 |
| 4003 | CHN2 | 4.53859 | 9.76E−08 |
| 2867 | C6ORF141 | 4.43629 | 1.97E−10 |
| 32417 | TMEM163 | 4.40645 | 3.65E−08 |
| 26245 | NR2F2 | 4.38488 | 8.32E−05 |
| 5036 | DDC | 4.37185 | 3.55E−05 |
| 6700 | FAT3 | 4.28732 | 4.74E−06 |
| 9428 | HS.204481 | 4.25031 | 1.93E−09 |
| 8288 | GRM8 | 4.16549 | 1.67E−06 |
| 28590 | PTPRO | 4.13365 | 8.06E−07 |
| 32159 | TH | 4.10876 | 0.000355952 |
| 31361 | SPON1 | 4.063 | 4.56E−07 |
| 34166 | ZFP36L1 | 4.05459 | 0.000219198 |
| 13689 | LDB2 | 3.9497 | 1.90E−08 |
| 32057 | TEAD2 | 3.94608 | 6.68E−06 |
| 12731 | IRX3 | 3.93674 | 0.000270763 |
| 28942 | RBM47 | 3.91109 | 0.000154758 |
| 30066 | SERPINF1 | 3.84276 | 3.72E−06 |
| 1666 | BMP7 | 3.83782 | 1.66E−05 |
| 25444 | MSX1 | 3.74709 | 3.45E−05 |
| 8593 | HES6 | 3.66092 | 5.43E−05 |
| 12149 | HS.7023 | 3.65165 | 0.000170814 |
| 30239 | SHISA2 | 3.60636 | 8.64E−06 |
| 9819 | HS.388347 | 3.52316 | 1.46E−08 |
| 7564 | FZD2 | 3.48734 | 3.69E−06 |
| 26928 | OSBPL10 | 3.44485 | 1.91E−07 |
| 27664 | PITX1 | 3.40016 | 5.92E−06 |
| 2743 | C3ORF58 | 3.31658 | 5.91E−07 |
| 30590 | SLC39A8 | 3.30002 | 1.28E−06 |
| 32144 | TGFBR3 | 3.28727 | 6.00E−09 |
| 18750 | LOC643911 | 3.2583 | 2.43E−07 |
| 17491 | LOC440585 | 3.24609 | 0.000469294 |
| 24375 | MFNG | 3.24122 | 3.31E−07 |
| 5346 | DLK1 | 3.21349 | 0.000161289 |
| 7562 | FZD1 | 3.15302 | 8.07E−08 |
| 3186 | CALCA | 3.14299 | 1.75E−08 |
| 27772 | PLEKHA5 | 3.09727 | 0.000150905 |
| 26335 | NUAK1 | 3.08699 | 1.10E−05 |
| 34155 | ZFHX4 | 3.05463 | 6.49E−07 |
| 27855 | PMP22 | 3.03785 | 1.12E−07 |
| 4491 | CPVL | 3.02972 | 0.000317992 |

TABLE 5-continued

Gene expression array data of significantly up-regulated and down-regulated genes at differentiation day 25 in SHH/FGF8/Chir treated Floor-plate based population over SHH/FGF8 only treated population.

| Column # | Column ID | Fold-Change | p-value |
|---|---|---|---|
| 7421 | FOXJ1 | 3.01784 | 0.000461499 |
| 2850 | C6ORF117 | 3.00725 | 3.47E−05 |
| 27105 | PAPSS2 | 2.97981 | 1.49E−05 |
| 12358 | ID1 | 2.94361 | 0.000160308 |
| 33004 | TSHZ1 | 2.93637 | 2.29E−07 |
| 5691 | EBF3 | 2.92465 | 2.26E−05 |
| 1086 | ARID5B | 2.92012 | 2.33E−06 |
| 32769 | TPH1 | 2.88914 | 4.24E−07 |
| 5424 | DNAJC19 | 2.87234 | 6.43E−09 |
| 6208 | EVI1 | 2.86069 | 2.04E−07 |
| 13858 | LMO4 | 2.85216 | 4.81E−05 |
| 12733 | IRX5 | 2.84963 | 0.000139911 |
| 5879 | ELF1 | 2.78573 | 1.43E−06 |
| 23752 | LRIG1 | 2.77491 | 0.000210665 |
| 23822 | LRRC4C | 2.77041 | 5.37E−07 |
| 4780 | CXCR4 | 2.72468 | 5.12E−07 |
| 27696 | PKNOX2 | 2.7166 | 1.59E−05 |
| 31514 | ST6GALNAC5 | 2.70116 | 0.00012729 |
| 32854 | TRIL | 2.66182 | 5.76E−06 |
| 7617 | GADD45G | 2.62149 | 0.000385727 |
| 5349 | DLL3 | 2.62131 | 0.000304562 |
| 8399 | GULP1 | 2.58556 | 2.34E−07 |
| 16419 | LOC283514 | 2.55654 | 7.18E−05 |
| 12986 | KCNS3 | 2.51225 | 3.59E−05 |
| 6270 | F3 | 2.50649 | 4.09E−09 |
| 32177 | THBS4 | 2.48547 | 9.17E−05 |
| 6457 | FAM181B | 2.48092 | 0.0001071 |
| 12644 | INPPL1 | 2.47363 | 7.08E−06 |
| 28624 | PVRL3 | 2.47112 | 3.32E−05 |
| 2885 | C6ORF173 | 2.45642 | 9.25E−05 |
| 25218 | MNX1 | 2.44999 | 9.15E−08 |
| 3835 | CEBPD | 2.44764 | 0.000160544 |
| 6197 | ETS2 | 2.43482 | 2.74E−06 |
| 8206 | GPR98 | 2.37781 | 0.000437636 |
| 30664 | SLC7A2 | 2.36837 | 5.80E−11 |
| 7853 | GINS2 | 2.3541 | 7.75E−05 |
| 29887 | SDC2 | 2.34674 | 3.00E−05 |
| 27402 | PDZRN4 | 2.29374 | 2.31E−06 |
| 16112 | LOC100192378 | 2.2867 | 4.57E−06 |
| 21088 | LOC650494 | 2.27924 | 4.94E−06 |
| 8583 | HERC5 | 2.27663 | 2.89E−07 |
| 1775 | BTG2 | 2.27014 | 6.72E−06 |
| 30719 | SLK | 2.24997 | 3.57E−05 |
| 19806 | LOC646345 | 2.232 | 3.69E−05 |
| 25137 | MKL2 | 2.22229 | 0.00012672 |
| 7610 | GABRR1 | 2.21011 | 2.33E−07 |
| 8573 | HEPACAM2 | 2.17226 | 1.17E−09 |
| 29151 | RHBDL3 | 2.16408 | 5.80E−05 |
| 27016 | P2RY5 | 2.16065 | 5.91E−06 |
| 30261 | SIAH3 | 2.14795 | 3.46E−05 |
| 30517 | SLC2A8 | 2.13975 | 8.81E−05 |
| 7457 | FREM1 | 2.12587 | 7.87E−08 |
| 1102 | ARL4A | 2.11255 | 0.000248586 |
| 29277 | RNF128 | 2.07512 | 8.41E−06 |
| 29124 | RGS16 | 2.06237 | 7.60E−05 |
| 8211 | GPRC5C | 2.04839 | 5.12E−05 |
| 26002 | NGF | 2.01869 | 9.29E−08 |
| 33375 | UCP2 | 2.00568 | 0.000336807 |
| 11039 | HS.553187 | −2.00024 | 0.000182185 |
| 7972 | GNAI1 | −2.00345 | 0.000400577 |
| 1241 | ASTN1 | −2.00503 | 0.000267753 |
| 29957 | SEL1L3 | −2.00817 | 9.40E−06 |
| 9721 | HS.348844 | −2.06728 | 9.46E−05 |
| 403 | ADAMTS5 | −2.09516 | 8.41E−07 |
| 5268 | DIRAS2 | −2.10442 | 0.000137286 |
| 1042 | ARHGAP22 | −2.11082 | 9.20E−05 |
| 24440 | MGC27121 | −2.11477 | 1.75E−08 |
| 28124 | PPP2R2C | −2.12982 | 0.000152152 |
| 2812 | C5ORF30 | −2.14976 | 2.66E−06 |
| 8046 | GOLSYN | −2.15553 | 0.000225269 |
| 7626 | GAGE12C | −2.16085 | 1.15E−07 |
| 728 | AMPH | −2.19127 | 7.33E−05 |
| 28104 | PPP1R1C | −2.2262 | 3.10E−07 |
| 28251 | PRKACB | −2.27738 | 6.28E−05 |
| 26252 | NR5A1 | −2.3262 | 1.83E−08 |
| 153 | ABAT | −2.33538 | 2.64E−05 |
| 28721 | RAB3B | −2.33887 | 0.000174687 |
| 31151 | SNX10 | −2.35266 | 0.000210353 |
| 26936 | OSBPL8 | −2.36481 | 0.000356878 |
| 30232 | SHC4 | −2.36756 | 5.88E−06 |
| 28689 | RAB15 | −2.37701 | 4.57E−05 |
| 31222 | SOX2OT | −2.37929 | 5.44E−06 |
| 10203 | HS.525171 | −2.37949 | 0.000112764 |
| 27287 | PCSK1N | −2.39396 | 0.000122619 |
| 30200 | SH3BGRL2 | −2.39696 | 0.000352607 |
| 23918 | LY6H | −2.3986 | 0.000426406 |
| 31543 | STAMBPL1 | −2.40424 | 0.000210764 |
| 12256 | HSPA12A | −2.4161 | 5.00E−06 |
| 12209 | HS3ST5 | −2.42056 | 1.64E−08 |
| 1764 | BTBD3 | −2.43171 | 9.02E−05 |
| 32742 | TOX2 | −2.47449 | 6.41E−06 |
| 896 | AP1S2 | −2.4814 | 0.000411095 |
| 13764 | LHFPL4 | −2.49494 | 0.000177306 |
| 12801 | ITM2C | −2.50635 | 0.000289334 |
| 1641 | BLCAP | −2.52288 | 0.000363648 |
| 30231 | SHC3 | −2.53075 | 2.70E−06 |
| 33964 | XPR1 | −2.55331 | 2.67E−05 |
| 28266 | PRKCE | −2.55567 | 1.75E−07 |
| 26521 | OPTN | −2.57271 | 0.000282119 |
| 5325 | DKK3 | −2.57389 | 8.27E−05 |
| 33325 | UBL3 | −2.58024 | 0.000136606 |
| 6859 | FGF13 | −2.58447 | 3.31E−05 |
| 32210 | THY1 | −2.60259 | 0.000107047 |
| 30015 | SEPT6 | −2.63038 | 0.000101624 |
| 30351 | SLC12A5 | −2.64265 | 0.000195945 |
| 607 | AKR1C4 | −2.66634 | 0.000217452 |
| 7635 | GAGE2B | −2.67196 | 4.87E−10 |
| 13177 | KIAA1598 | −2.67619 | 4.25E−05 |
| 1986 | C12ORF68 | −2.67913 | 0.000114615 |
| 25516 | MTSS1 | −2.69402 | 0.000290278 |
| 32535 | TMEM55A | −2.70095 | 5.71E−06 |
| 25864 | NDST3 | −2.72344 | 9.29E−06 |
| 33591 | VAT1 | −2.74928 | 0.000228555 |
| 26498 | ONECUT1 | −2.77372 | 1.86E−05 |
| 12634 | INPP1 | −2.79095 | 5.83E−05 |
| 5703 | ECEL1 | −2.83259 | 0.000107266 |
| 16740 | LOC387856 | −2.84534 | 0.000116969 |
| 5631 | DUSP6 | −2.85825 | 8.35E−05 |
| 31568 | STC1 | −2.8677 | 0.000365825 |
| 227 | ABLIM2 | −2.8948 | 2.50E−06 |
| 27415 | PELI2 | −2.9135 | 2.07E−05 |
| 2538 | C20ORF46 | −2.92994 | 6.05E−05 |
| 4639 | CSRNP3 | −2.9364 | 6.80E−06 |
| 31628 | STS-1 | −2.94215 | 9.63E−07 |
| 30210 | SH3GL3 | −2.94559 | 0.000343973 |
| 10017 | HS.452398 | −3.01786 | 1.26E−05 |
| 4705 | CTNND2 | −3.02031 | 4.91E−05 |
| 24516 | MGST1 | −3.02712 | 1.36E−06 |
| 4283 | CNR1 | −3.13389 | 0.000271812 |
| 13313 | KLF6 | −3.16185 | 3.73E−05 |
| 7613 | GAD1 | −3.18763 | 0.000116615 |
| 29400 | RORB | −3.1967 | 5.32E−08 |
| 27566 | PHYHIPL | −3.21046 | 3.97E−05 |
| 25628 | MYO16 | −3.21287 | 9.14E−06 |
| 25284 | MPPED2 | −3.23371 | 0.000114488 |
| 30531 | SLC32A1 | −3.23601 | 0.000270573 |
| 29034 | RELN | −3.32027 | 1.95E−05 |
| 26058 | NKX2-1 | −3.35392 | 4.84E−06 |
| 30114 | SFRP1 | −3.38198 | 0.00010787 |
| 4965 | DBC1 | −3.3928 | 1.25E−05 |
| 31763 | SYT1 | −3.47973 | 0.00017165 |
| 29624 | RTN1 | −3.48718 | 0.000208889 |
| 3121 | CA10 | −3.49466 | 0.000217475 |
| 24095 | MAP4 | −3.54296 | 0.000118613 |
| 9476 | HS.223856 | −3.61087 | 5.18E−05 |
| 32343 | TMEFF2 | −3.6559 | 1.52E−06 |

TABLE 5-continued

Gene expression array data of significantly up-regulated and down-regulated genes at differentiation day 25 in SHH/FGF8/Chir treated Floor-plate based population over SHH/FGF8 only treated population.

| Column # | Column ID | Fold-Change | p-value |
|---|---|---|---|
| 713 | AMHR2 | −3.65957 | 2.10E−08 |
| 28417 | PSD2 | −3.70127 | 0.000123589 |
| 7106 | FLJ33590 | −3.74166 | 4.19E−06 |
| 4386 | COPG2IT1 | −3.9994 | 7.98E−05 |
| 3207 | CALY | −4.03219 | 3.21E−06 |
| 30824 | SNCG | −4.48956 | 2.76E−06 |
| 5455 | DNER | −4.58982 | 1.95E−05 |
| 5550 | DRD1IP | −4.64486 | 5.89E−07 |
| 26253 | NR5A2 | −4.70942 | 1.65E−11 |
| 12954 | KCNK12 | −4.77483 | 2.25E−06 |
| 5352 | DLX1 | −4.89802 | 0.000316228 |
| 26332 | NTS | −4.92922 | 0.000411631 |
| 33565 | UTS2 | −5.26698 | 2.91E−07 |
| 3220 | CAMKV | −5.35563 | 1.08E−05 |
| 2631 | C22ORF42 | −5.4488 | 2.15E−07 |
| 29220 | RIT2 | −5.49937 | 9.53E−12 |
| 31359 | SPOCK2 | −5.66406 | 5.68E−06 |
| 12746 | ISLR2 | −5.6746 | 0.000247482 |
| 32591 | TMOD1 | −5.689 | 7.66E−12 |
| 3215 | CAMK2N1 | −5.84508 | 2.30E−06 |
| 33592 | VAT1L | −6.26024 | 7.74E−07 |
| 27971 | POMC | −6.74106 | 6.72E−05 |
| 26219 | NPTX2 | −7.85511 | 1.15E−05 |
| 25939 | NELL1 | −8.58778 | 1.80E−08 |
| 33624 | VGF | −8.61516 | 1.37E−05 |
| 31223 | SOX3 | −10.3701 | 8.71E−09 |
| 30314 | SIX6 | −12.5834 | 1.04E−12 |
| 26965 | OTP | −14.2469 | 6.08E−10 |
| 12743 | ISL1 | −21.0507 | 6.48E−05 |
| 31479 | SST | −21.3179 | 0.000281588 |

TABLE 6 shows an exemplary list of antibodies used as markers, including concentration (i.e. dilution) of antibodies used and exemplary sources of antibodies. In some embodiments, bound antibodies were identified with any of Alexa488, Alexa555 and Alexa647-conjugated secondary antibodies (Molecular Probes, Carlsbad, California). In some embodiments, biotinylated secondary antibodies were used to identify the bound primary antibodies followed by visualization via DAB (3,3'-Diaminobenzidine) chromogen.

| Antibody (primary) | Dilution | Source | Location |
|---|---|---|---|
| Human nuclear antigen | 1:100 | Millipore | Billerica, MA |
| Human cell adhesion molecule | 1:100 | Santa Cruz | Santa Cruz, CA |
| Tyrosine Hydroxylase (TH) | 1:1000/1:500 | Pel-Freez/ImmunoStar | Rogers, AR/Hudson, WI |
| β-tubulin III | 1:500/1:2000 | Covance | Littleton, CO/Princeton, NJ |
| Doublecortin | 1:100 | Millipore | Billerica, MA |
| Human specific Nestin | 1:300 | R&D | Minneapolis, MN |
| Nestin # 130 | 1:50 | R. McKay | NINDS, NIH |
| FoxA2 | 1:100 | Santa Cruz | Santa Cruz, CA |
| Pitx3 | 1:100 | Millipore | Billerica, MA |
| β-catenin | 1:100 | BD | Franklin Lakes, NJ |
| Collagen | 1:100 | Oncogene | LaJolla, CA |
| Cytokeratin | 1:100 | DAKO | Glostrup DK |
| Oct-4 | 1:200 | Santa Cruz | Billerica, MA |
| Ki-67 | 1:200/1:400 | Zymed/DAKO | San Francisco, CA |
| GABA polyclonal | 1:2000 | Sigma | St Louis, MI |
| Serotonin (5-HT) | 1:2000 | Sigma | St Louis, MI |
| GFAP polyclonal | 1:2000 | DAKO | Glostrup, DK |
| Calbindin | 1:300 | Abcam | Cambridge, MA |
| VMAT2 | 1:200 | Millipore | Billerica, MA |
| DAT | 1:1000/1:2000 | Millipore | Billerica, MA |
| GFP | 1:1000 | Molecular Probes | Carlsbad, CA |
| Girk2 | 1:200 | Abcam/Alomone | Cambridge, MA/Israel |
| FoxG1 | 1:100 | NeuraCell | Rensselaer, NY |
| Pax6 | 1:100 | Covance | Princeton, NJ |
| Otx2 | 1:2000 | Strategic Diagnostics | Newark, DE |
| Lmx1a | 1:2000 | Millipore | Pittsburgh, PA |
| Synapsin | 1:1000 | Sigma | St Louis, MI |
| Iba-1 | 1:200 | Millipore | Billerica, MA |
| ED-1 | 1:200 | Millipore | Pittsburgh, PA |
| Human NCAM (Eric-1) | 1:100 | Santa Cruz | Santa Cruz, CA |
| Human specific cytoplasm (SC-121) | 1:1000 | Stem Cells Inc. | Newark, CA |
| Nurr-1 | 1:1500 | Perseus Proteomics | Japan |

TABLE 7

Exemplary contemplated differentiation into DA neurons by cell type limits.

| Cell type | Marker | Assay Description | Proposed Limits |
|---|---|---|---|
| Midbrain FP/DA | FOXA2/LMX1A | IHC: Co-expression @ day 13 & day 25; validation by qRT-PCR | >50% |
| DA neuron precursor | FOXA2/TH; TH/NURR1 | IHC: Co-expression @ day 25 validation by qRT-PCR | >25% |
| Pluripotent cells | OCT-4; | IHC: @ day 13 & day 25; validation by qRT-PCR | <2% |
| Proliferating cells | Ki67 | IHC | <25% |
| (forebrain) precursor | FOXG1, PAX6 | IHC: @ day 13 & day 25; validation by qRT-PCR | <10% |
| DA neuron yield | TH/FOXA2 | IHC:: Co-expression @ day 25 out of hESC plated at day 0 | >1DA n/hESC |
| In vivo survival | TH/FOXA2 (in vivo) | Histology in vivo @ 4 weeks after grafting of 200k cells | >2,000/animal |

TABLE 8

Exemplary experiments to determine the role of certain factors for producing DA neurons.

| | LDN | SB | PURM | CHIR | SHH | BDNF | GDNF | AA | Dbc AMP | TGFB3 | DAPT |
|---|---|---|---|---|---|---|---|---|---|---|---|
| Control | +++ | +++ | +++ | +++ | +++ | +++ | +++ | +++ | +++ | +++ | +++ |
| Complete dropout | +++ | +++ | +++ | +++ | | | | | | | |
| +/−SHH | ++ | ++ | ++ | ++ | + | ++ | ++ | ++ | ++ | ++ | ++ |
| +/− BDNF | ++ | ++ | ++ | ++ | ++ | + | ++ | ++ | ++ | ++ | ++ |
| +/− GDNF | ++ | ++ | ++ | ++ | ++ | ++ | + | ++ | ++ | ++ | ++ |
| +/− AA | ++ | ++ | ++ | ++ | ++ | ++ | ++ | + | ++ | ++ | ++ |
| +/− dbcAMP | ++ | ++ | ++ | ++ | ++ | ++ | ++ | ++ | + | ++ | ++ |
| +/− TGFB3 | ++ | ++ | ++ | ++ | ++ | ++ | ++ | ++ | ++ | + | ++ |
| +/− DAPT | ++ | ++ | ++ | ++ | ++ | ++ | ++ | ++ | ++ | ++ | + |

TABLE 9

Exemplary methods for scaling up mDA neuron culture, in particular for use in producing GMP level cultures for use in the clinic.

| | Pilot scale (x3) | Intermediary scale (x ≥ 1) | Clinical scale |
|---|---|---|---|
| WCB thaw | 1 vial-1 × 10$^6$ on 6 cm dish | 7 vials-7 × 10$^6$ on 15 cm × 1 | 42 vials-7 × 10$^6$ per 15 cm × 6 |
| Passage 1 - clusters | 1:1-1:5 on 6 cm dishes | 1:1-1:5 on 15 cm dishes | 1:1-1:5 on 15 cm dishes |
| Passage 2 - clusters | 2 × 15 cm dishes | 6 × 15 cm dishes | 36 × 15 cm dishes |
| Passage 3 - Accutase (Neural induction) | 1 × 15 cm dish at high density (approximately 3.0 × 10$^7$ cells) | 3 × 15 cm dishes at high density (approximately 9.0 × 10$^7$ cells) | 18 × 15 cm dishes at high density (approximately 5.4 × 10$^8$ cells) |
| Passage 4 - Accutase (Day 15-20) | 1:1 | 1:1 | 1:1 |
| Cryopreservation (Day 25) | approximately 1.2 × 10$^8$, assume 50% loss after cryopreservation = approximately 6 × 10$^7$ viable cells | approximately 3.6 × 10$^8$, assume 50% loss after cryopreservation = approximately 1.8 × 10$^8$ viable cells | approximately 2.16 × 10$^9$, assume 50% loss after cryopreservation = approximately 1 × 10$^9$ viable cells |

TABLE 10

Exemplary in vivo assessment of hES line products - Graft composition.

| Cell type | Marker | Assay Description | Proposed Limits |
|---|---|---|---|
| DA neuron yield | TH/FOXA2 | Stereological assessment of total TH/FoxA2 cell number (IHC) in grafts | >5,000 per 200,000 grafted |
| Proliferation Index | Ki67 (MIB-1) | IHC for Ki67; percent of total cell number | <1% |
| Pluripotent cells | OCT-4/Nanog | IHC | <0.5% |
| Serotonergic neurons | 5-HT (serotonin) | IHC | <1% |
| Forebrain precursors | FOXG1; PAX6 | IHC | <10% |

TABLE 10-continued

Exemplary in vivo assessment of hES line products - Graft composition.

| Cell type | Marker | Assay Description | Proposed Limits |
|---|---|---|---|
| Teratoma derivatives | Myosin; cytokeratins; αfetoprotein | IHC | <1% |

TABLE 11

Exemplary in vivo assessment of hES line products - Behavioral Analyses.

| Test | Parameter | Assay Description | Proposed Limits |
|---|---|---|---|
| Amphetamine rotations (*) | Sum of rotations/min (ipsi-minus contralateral) | Turning behavior towards lesion side following intraperitoneal amphetamine injection | <1 rotation/min |
| Stepping Test | % contralateral step adjustments/total adjustments | Initiation of stepping movement using the limb contralateral to lesion side | 40-50% |
| Cylinder test | % use of ipsilateral limb/total | Spontaneous exploration with ipsi vs contralateral limb | Min. 20% improvement vs. pre-grafting |

(*) In some embodiments, rats exhibiting >6 rotations/min stably received grafts.

EXPERIMENTAL

The following examples serve to illustrate certain embodiments and aspects of the present invention and are not to be construed as limiting the scope thereof. In the experimental disclosures which follow, the following abbreviations apply: N (normal); M (molar); mM (millimolar); μM (micromolar); mol (moles); mmol (millimoles); (micromoles); nmol (nanomoles); pmol (picomoles); g (grams); mg (milligrams); μg (micrograms); ng (nanograms); pg (picograms); L and (liters); ml (milliliters); μl (microliters); cm (centimeters); mm (millimeters); μm (micrometers); nm (nanometers); U (units); min (minute); s and sec (second); deg (degree); pen (penicillin), strep (streptomycin) and ° C. (degrees Centigrade/Celsius).

Example I

Materials and Methods

Methods Summary:

Human ESC (H9, H1) and iPSC lines (2C6 and SeV6) were subjected to a modified Dual SMAD-inhibition (Chambers, et al. *Nat. Biotechnol.* 27:275-280 (2009), herein incorporated by reference) based floor plate induction (Fasano, et al., *Cell Stein Cell* 6:336-347 (2010), herein incorporated by reference) protocol. Exposure to SHH C25II, Purmorphamine, FGF8 and CHIR99021 were optimized for midbrain floor plate and yield of novel populations of DA neuron (see FIG. 1d). Following floor plate induction, further maturation (days 11-25 or longer than 25 days in culture up to at least 100 days in culture) was carried out in differentiation medium based on Neurobasal/B27 in the presence of DA neuron survival and maturation factors (Perrier, et al. *Proc Natl Acad Sci USA* 101:12543-8 (2004), herein incorporated by reference) such as AA, BDNF, GDNF, TGFβ and dbcAMP (see full methods for details). The resulting DA neuron population were subjected to extensive phenotypic characterization via immunocytochemistry, qRT-PCR, global gene expression profiling, HPLC analysis for the detection of dopamine and in vitro electrophysiological recordings. In vivo studies were performed in hemiparkinsonian rodents (mouse or rats injected with the 6OHDA toxin on one side of the animal's brain. The studies were carried out in adult NOD-SCID IL2Rgc mice (Jackson labs) and adult Sprague Dawley rats Taconic Farms, that received 6-hydroxydopamine lesions by stereotactic injections of the toxin as described previously as well as two adult rhesus monkeys that were treated with unilateral carotid injections of MPTP. DA neurons were injected stereotactically in the striata of the animals ($150 \times 10^3$ cells in mice, $250 \times 10^3$ cells in rats) and a total of $7.5 \times 10^6$ cells (distributed in 6 tracts; 3 on each side of brain) in monkeys. Behavioral assays were performed at monthly intervals post-grafting, including amphetamine mediated rotational analysis as well as a test for focal akinesia ("stepping test") and limb use (cylinder test). Rats and mice were sacrificed at 18-20 weeks and the primates at 1 month post grafting. Characterization of the grafts was performed via stereological analyses of cell number and graft volumes as well as a comprehensive phenotypic characterization via immunohistochemistry. Culture of undifferentiated human ES cells. hESC lines H9 (WA-09, XX, passages 27-55 from when 10/2009), H1 (WA-01, XY, passages 30-40 from when 6/2010) and iPS cell lines 2C6 (Kim, et al. *Cell Stem Cell* 8:695-706 (2011), herein incorporated by reference) (XY, passages 20-30) and SeV6 (XY, passages 20-30; derived from MRC-5 embryonic fibroblasts using non-integrating 4 factor Sendai vector system (Ban, et al. Proc. Natl. Acad. Sci. U.S.A (2011) 108(34):14234-14239:10.1073/pnas.1103509108, herein incorporated by reference) were maintained on mouse embryonic fibroblasts at plating concentrations estimated ranging from $0.5 \times 10^3$ per $cm^2$ to $100 \times 10^3$ per $cm^2$ based upon human ES cells which tend to cell cluster. (MEF, Global Stem, Rockville, Md.) in an optimal 20% knockout serum replacement (KSR, Invitrogen, Carlsbad, Calif.)-containing human ES cell medium (as described previously (Kim, et al. *Cell Stem Cell* 8:695-706 (2011), herein incorporated by reference). The use of knockout serum replacement may range from 0% to 40%.

Neural Induction.

For floor plate-based midbrain dopamine neuron induction, a modified version of the dual-SMAD inhibition (Chambers, et al. *Nat. Biotechnol.* 27:275-280 (2009), herein incorporated by reference) and floor plate induction (Fasano, et al. *Cell Stem Cell* 6:336-347 (2010), herein incorporated by reference) protocol was used based on timed exposure to LDN-193189 (100 nM (ranging in concentration from 0.5-50 µM, Stemgent, Cambridge, Mass.), SB431542 (10 µM (ranging in concentration from 0.5-50 µM, Tocris, Ellisville, Mich.), SHH C25II (100 ng/ml (ranging in concentration from 10-2000 ng/ml, R&D, Minneapolis, Minn.), Purmorphamine (2 µM (ranging in concentration from 10-500 ng/ml, Stemgent), FGF8 (100 ng/ml (ranging in concentration from 10-500 ng/ml, R&D) and CHIR99021 (CHIR; 3 µM (ranging in concentration from 0.1-10 µM, Stemgent). Note: for the floor plate induction protocol "SHH" treatment refers to exposure, i.e. contact, of cells to a combination of SHH C25II 100 ng/ml+Purmorphamine (2 µM). Cells were plated (35–40×10$^3$ cells/cm$^2$) and cultured for 11 days on matrigel or geltrex (used as purchased) (BD, Franklin Lakes, N.J.) in Knockout serum replacement medium (KSR) containing DMEM, 15% knockout serum replacement, 2 mM L-glutamine and 10-µM (ranging in concentration from 1-25 µM β-mercaptoethanol. KSR medium was gradually shifted to N2 medium starting on day 5 of differentiation, by mixing in ratios of 75% (KSR):25% (N2) on day 5-6, 50% (KSR):50% (N2) day 7-8 and 25% (KSR):75% (N2) on day 9-10, as described previously (Chambers, et al. *Nat. Biotechnol.* 27:275-280 (2009), herein incorporated by reference). On day 11, media was changed to Neurobasal medium/B27medium (1:50 dilution)/L-Glut (effective ranges 0.2-2 mM)) containing medium (NB/B27; Invitrogen) supplemented with CHIR (until day 13) and with BDNF (brain-derived neurotrophic factor, 20 ng/ml ranging from 5 to 100; R&D), ascorbic acid (AA; 0.2 mM (ranging in concentration from 0.01-1 mM), Sigma, St Louis, Mich.), GDNF (glial cell line-derived neurotrophic factor, 20 ng/ml (ranging in concentration from 1-200 ng/ml); R&D), TGFβ3 (transforming growth factor type β3, 1 ng/ml (ranging in concentration from 0.1-25 ng/ml); R&D), dibutyryl cAMP (0.5 mM (ranging in concentration from _0.05-2 mM); Sigma), and DAPT (10 nM (ranging in concentration from 0.5-50 nM); Tocris,) for 9 days. On day 20, cells were dissociated using Accutase® (Innovative Cell Technology, San Diego, Calif.) and replated under high cell density conditions (for example from 300-400 k cells/cm$^2$) on dishes pre-coated with polyornithine (PO); 15 µg/ml (ranging in concentration from 1-50 µg/ml)/Laminin (1 µg/ml) (ranging in concentration from 0.1-10 µg/ml)/Fibronectin (2 µg/ml (ranging in concentration from 0.1-20 µg/ml) in differentiation medium (NB/B27+BDNF, AA, GDNF, dbcAMP (ranging in concentration as described herein), TGFβ3 and DAPT (ranging in concentration as described herein) until the desired maturation stage for a given experiment.

For rosette-based DA neuron induction previously described protocols were followed in part (Perrier, et al. *Proc Natl Acad Sci USA* 101:12543-8 (2004), herein incorporated by reference) with at least one exception where dual-SMAD inhibition was used to accelerate the initial neural induction step. In brief, hESCs were induced towards neural fate by coculture with irradiated MS5 cells in KSR supplemented with SB431542 and Noggin (250 ng/ml (ranging in concentration from 10-1000 ng/ml); R&D), from day 2-8 and SHH+FGF8 from day 6-11 of differentiation. After 11 days in KSR, neural rosettes were manually isolated and cultured (P1 stage) in N2 medium supplemented with SHH, FGF8, BDNF and AA as described previously (Perrier, et al. *Proc Natl Acad Sci USA* 101:12543-8 (2004), herein incorporated by reference). After 5-7 days in P1 stage, rosettes were again harvested mechanically and triturated following incubation in Ca$^2$/Mg$^2$-free Hanks' balanced salt solution (HBSS) for 1 h and replated on polyornithine (PO)/Laminin/Fibronectin coated plates. Patterning with SHH/FGF8 was continued for 7 days at P2 stage followed by final differentiation in the presence of BDNF, AA, GDNF, TGFb3 and dbcAMP as described above until the desired maturation stage for a given experiment (typically 5-7 days for transplantation studies or 32 days for in vitro functional studies).

Gene Expression Analyses.

Total RNA was extracted during differentiation at days: 0, 1, 3, 5, 7, 9, 11, 13 and 25 from each condition of control LSB, LSB/SHH/FGF8 and LSB/SHH/FGF8/CHIR using the RNeasy kit (Qiagen, Valencia, Calif.). For microarray analysis, total RNA was processed by the MSKCC Genomic core facility and hybridized on Illumina Human ref-12 bead arrays according to the specifications of the manufacturer. Comparisons were performed among each days and conditions using the LIMMA package from Bioconductor (worldwideweb.bioconductor.org). Genes found to have an adjusted P-value<0.05 and a fold change greater than two were considered significant. Some of the descriptive microarray data analyses and presentation was performed using a commercially available software package (Partek Genomics Suite (version 6.10.0915)). For qRT-PCR analyses, total RNA at day 25 of each condition was reverse transcribed (Quantitech, Qiagen) and amplified material was detected using commercially available Taqman gene expression assays (Applied Biosystems, Carlsbad, Calif.) with the data normalized to HPRT. Each data point represents 9 technical replicates from 3 independent biological samples. Raw data of microarray studies are not yet available at GEO worldwideweb.ncbi.nlm.nih.gov/geo).

Animal Surgery.

Rodent and monkey procedures were performed following NIH guidelines, and were approved by the local Institutional Animal Care and Use Committee (IACUC), the Institutional Biosafety Committee (IBC) as well as the Embryonic Stem Cell Research Committee (ESCRO).

Mice.

NOD-SCID IL2Rgc null mice (20-35 g in weight; Jackson Laboratory, Bar Harbor, Me.) were anesthetized with Ketamine (90 mg/kg; Akorn, Decatur, Ill.) and Xylazine (4 mg/kg Fort Dodge, Iowa). 6-hydroxydopamine (10 µg (ranging in concentration from 0.1-20 µg) 6-OHDA (Sigma-Aldrich) was injected stereotactically into the striatum at the following coordinates (in millimeters): AP, 0.5 (from bregma; a skull suture used as reference for stereotactic surgery); ML, −2.0; DV, −3.0 (from dura a membrane covering the brain used for reference). Mice with successful lesions (an average of >6 rotations/minutes) were selected for transplantation. A total of 150×10$^3$ cells were injected in a volume of 1.5 µl into the striatum at the following coordinates (in mm): AP, 0.5; ML, −1.8; DV, 3.2. The mice were sacrificed 18 weeks post transplantation.

Rats.

Adult female Sprague-Dawley (Taconic, Hudson, N.Y.) rats (180-230 g) were anesthetized with Ketamine (90 mg/kg) and xylazine (4 mg/kg) during surgical procedures. Unilateral, medial forebrain bundle lesions of the nigrostriatal pathway were established by stereotaxic injection of 6-OHDA (3.6 mg/ml in 0.2% ascorbic acid and 0.9% saline, Sigma) at two sites (Studer, et al. *Nature Neurosci.* 1:290-295 (1998), herein incorporated by reference). Rats were selected for transplantation if amphetamine-induced rotation exceeded 6 rotations/min by 6-8 weeks post injection. 250×10$^3$ cells were transplanted into the striatum of each animal (Coordinates: AP+1.0 mm, ML −2.5 mm and V−4.7 mm; toothbar set at −2.5). Control rats received PBS instead. The surgical procedures were described previously (Studer, et al. *Nature Neurosci.* 1:290-295 (1998), herein incorporated by reference). Daily intraperitoneal injections of cyclosporine 15 mg/kg (Bedford Labs, Bedford, Ohio) were started 24 hours prior to cell grafting and continued until sacrifice, 20 weeks following cell grafting.

Primates.

Two adult (17-18 yr old; 10-12 kg; female) rhesus monkeys were rendered hemiparkinsonian via carotid MPTP administration followed by weekly I.V. MPTP administration to create a bilateral parkinsonian syndrome (Kordower, et al. *Science* 290:767-773 (2000), herein incorporated by reference). Both animals displayed parkinsonian symptoms consistent with a moderately-severe lesion based on behavioral analysis including crooked posture, dragging of leg and symptoms of rigor (inflexibility of movement), neglect (motor awareness to lateralized stimulus) and bradykinesia (slow movement inflation). These parameters can be assessed in monkeys using a modified parkinsonian clinical rating scale (CRS). On the day of transplantation surgery, animals were tranquilized with ketamine (3.0 mg/kg, IM) and dexdomitor (0.02-0.04 mg/kg IM), intubated to maintain a stable airway and anesthetized with isoflurane. They were then placed into a stereotaxic frame for surgery. Both rhesus monkeys underwent a single surgery with three intracranial injections of human floor plate-derived DA cultures based on stereotaxic coordinates (Paxinos, et al. *The Rhesus Monkey Brain in Stereotaxic Coordinates* (Academic Press, 2000), herein incorporated by reference). Bilateral injections of cells (10 ul/injection; 125,000 cell/ul) were performed at three sites (1-posterior caudate, 2-pre-commissural putamen and overlying white matter) for a total volume of 30 µl per hemisphere. An infusion pump attached to a stereotaxic micromanipulator was utilized to deliver the cells at a rate of 1 µl/min though a 50 µl Hamilton syringe with 28 G needle. After the injections were completed, the needle was left in place for an additional 2-5 minutes to allow the infusate to diffuse off the needle tip before slowly retracting the syringe. Immediately following surgery, the animals received analgesics (buprenex, 0.01 mg/kg IM, BID for 72 hours post surgery; meloxicam, 0.1 mg/kg SQ, SID for 72 hours post surgery) as well as an antibiotic (cephazolin, 25 mg/kg IM, BID) until 72-hours post-surgery. The animals received cyclosporine A (Neoral, Sandimmune) orally (30 mg/kg tapered to 15 mg/kg) once daily beginning 48-hrs prior to surgery until sacrifice, one month following transplantation.

Behavioral Assays.

Amphetamine-induced rotations (mice and rats) and the stepping test (rat) were carried out before transplantation and 4, 8, 12, 18 weeks after transplantation. Rotation behavior in mice was recorded 10 min after i.p. injection of d-amphetamine (10 mg/kg, Sigma) and recorded for 30 minutes. Rotation behavior in rats was recorded 40 min after i.p. injection of d-amphetamine (5 mg/kg) and automatically assessed by the TSE VideoMot2 system (Germany). The data were presented as the average number of rotations per minute. The stepping test was modified from Blume, et al. *Exp. Neurol.* 219:208-211 (2009) and Crawley, et al. *What's Wrong With My Mouse: Behavioral Phenotyping of Transgenic and Knockout Mice* (Wiley-Liss, 2000), all of which are herein incorporated by reference. In brief, each rat was placed on a flat surface; its hind legs were lifted by gently holding up the tail to allow the forepaws alone to touch the table. The experimenter pulled the rat backwards 1 meter at a steady pace. Adjusting step numbers from both contralateral and ipsilateral forepaws were counted. Data was presented as the percentage of contralateral/(contralateral+ipsilateral) adjusting steps. The cylinder test was performed by placing each animal in a glass cylinder and counting the number of ipsilateral versus contralateral paw touches (out of 20 touches) to the wall of the cylinder as described previously (Tabar, et al. *Nature Med.* 14:379-381 (2008), herein incorporated by reference). Tissue Processing. Mice and Rats: Animals (mice and rats) received overdoses of Pentobarbital intraperitoneally (50 mg/kg) to induce deep anesthesia and were perfused in 4% paraformaldehyde (PFA). Brains were extracted, post-fixed in 4% PFA then soaked in 30% sucrose solutions for 2-5 days. They were sectioned on a cryostat after embedding in O.C.T. compound (Sakura-Finetek, Torrance, Calif.).

Primates:

Animals were sacrificed under deep anesthesia with ketamine (10 mg/kg, Intramuscular (IM)) and pentobarbital (25 mg/kg, intravenous (IV)) via cardiac perfusion with heparinized 0.9% saline followed by fresh cold 4% PFA fixative (pH7.4). Immediately following primary fixation, brains were removed from the skull and post-fixed in 4% PFA, free-floating, for 24-36 hrs. They were then rinsed and re-suspended in 10% sucrose on a slow shaker at 4° C., and allowed to "sink". The process was then repeated in 20% sucrose followed by 30% sucrose. Whole brains were cut coronally into 40 µm serial sections on a frozen sledge microtome and stored free-floating in cryopreservative medium at −20° Celcius.

Immunohistochemistry:

Cells were fixed in 4% PFA and blocked with 1% bovine serum albumin (BSA) with 0.3% Triton. Brain tissue sections were washed in cold PBS and processed similarly. Primary antibodies were diluted in 1-5% BSA or Normal Goat Serum and incubated according to manufacturer recommendations. A comprehensive list of antibodies and sources is provided as Table 6. Appropriate Alexa488, Alexa555 and Alexa647-conjugated secondary antibodies (Molecular Probes, Carlsbad, Calif.) were used with 4',6-diamidino-2-phenylindole (DAPI) nuclear counterstain (Thermo Fisher, Rockford, Ill.). For some analyses biotinylated secondary antibodies were used followed by visualization via DAB (3,3'-Diaminobenzidine) chromogen. HPLC Analysis. Reversed-phase HPLC with electrochemical detection for measuring levels of dopamine, Homovanillic acid (HVA) and DOPAC (3,4-Dihydroxy-Phenylacetic Acid) was performed as described previously (Roy, et al. *Nature Med.* 12:1259-1268 (2006); Studer, et al. *Brain Res. Bull.* 41:143-150 (1996), all of which are herein incorporated by reference). Culture samples were collected in perchloric acid at day 65 of differentiation. For some experiments DA was measured directly in the medium using the same detection system but following aluminum extraction of dopamine and its metabolites using a commercially available kit as described previously (Studer, et al. *Brain Res. Bull.* 41:143-150 (1996), herein incorporated by reference). Electrophysiological recordings: Cultures were transferred to a recording chamber on an upright microscope equipped with a 40× water-immersion objective (Eclipse E600FN; Nikon); cultures were perfused with saline containing in mM: 125 NaCl, 2.5 KCl, 25 NaHCO$_3$, 1.25 NaH$_2$PO$_4$, 2 CaCl, 1 MgCl$_2$, and 25 glucose (34° C.; saturated with 95%

$O_2$-5% $CO_2$; pH 7.4; 298 mOsm/L). The saline flow rate was 2-3 ml/min running through an in-line heater (SH-27B with TC-324B controller; Warner Instruments). Neurons were visualized by video microscopy with a cooled-CCD digital camera (CoolSNAP ES$^2$, Photometrics, Roper Scientific, Tucson, Ariz.). Cells selected for electrophysiological recordings had neuron-like shapes with fine branching neurites. Somatic whole-cell patch-clamp recordings in current clamp configuration were performed with a MultiClamp 700B amplifier (Molecular Devices). Signals were filtered at 1-4 kHz and digitized at 5-20 kHz with a Digidata 1440A (Molecular Devices). Recording patch electrodes were fabricated from filamented borosilicate glass (Sutter Instruments) pulled on a Flaming-Brown puller (P-97, Sutter Instruments) and had resistances of 4-6 MΩ in the bath. Electrodes were filled with internal solution containing in mM: 135 K-MeSO$_4$, 5 KCl, 5 HEPES, 0.25 EGTA, 10 phosphocroeatine-di(tris), 2 ATP-Mg, and 0.5 GTP-Na (pH 7.3, osmolarity adjusted to 290-300 mOsm/L). The amplifier bridge circuit was adjusted to compensate for electrode resistance and monitored. Electrode capacitance was compensated. When series resistance increased >20% during the recording, the data were discarded because increased resistance suggested a partial technical failure during recordings. Cell Counts and Stereological Analyses.

The percentages of marker positive cells at the floor plate (day 11) FIG. 1, midbrain dopamine neuron precursor (day 25), FIG. 2 and mature DA neuron stages (day 50 or later) FIGS. 3 and 11, were determined in samples derived from 3 independent experiments each. Images for quantification were selected in a uniform random manner and each image was scored first for the number of DAPI-positive nuclei, followed by counting the number of cells expressing the marker of interest. Data are presented as mean±SEM. Quantification of human cells (identified with anti-hNA) and TH+ neurons within grafts was performed on every tenth section where a graft was identifiable. Cell counts and graft volume was determined using the optical fractionator's probe and the Cavalieri estimator using the Stereo Investigator software (MBF bioscience, Vermont) as described previously in Tabar, et al. *Nat. Biotechnol.* 23:601-606 (2005), herein incorporated by reference. Data are presented as estimated total cell number and total graft volume+/−standard error of means (SEM).

The following formulations describe exemplary cell culture medium for use in developing embodiments of the present inventions.
hESC medium for maintenance (1 liter): 800 mL DMEM/F12, 200 mL of Knockout Serum Replacement, 5 mL of 200 mM L-Glutamine, 5 mL of Pen/Strep, 10 mL of 10 mM MEM minimum non-essential amino 15 acids solution, 55 μM of 13-mercaptoethanol, and bFGF (final concentration is 4 ng/mL).
KSR medium for hESC differentiation (1 liter): 820 mL of Knock out DMEM, 150 mL of Knock out Serum Replacement, 10 mL of 200 mM L-Glutamine, 10 mL of Pen/Strep, 10 mL of 10 mM MEM, and 55 μM of 13-mercaptoethanol.
N2 medium for hESC differentiation (1 liter): 985 ml dist. $H_2O$ with DMEM/F12 powder, 1.55 g of glucose (Sigma, cat. no. G7021), 2.00 g of sodium bicarbonate (Sigma, cat. no. S5761), putrescine (100 uL aliquot of 1.61 g dissolved in 100 mL of distilled water; Sigma, cat. no. P5780), progesterone (20 uL aliquot of 0.032 g dissolved in 100 mL 100% ethanol; Sigma, cat. no. P8783), sodium selenite (60 uL aliquot of 0.5 mM solution in distilled water; Bioshop Canada, cat. no. SEL888), and 100 mg of transferrin (Celliance/Millipore, cat. no. 4452-01), and 25 mg of insulin (Sigma, cat. no. I6634) in 10 mL of 5 mM NaOH.
Dulbecco's Modification of Eagles Medium (DMEM), with 10% FBS for preparing PMEF ((primary mouse embryo fibroblast (PMEF)) feeder cells) (1 liter): 885 mL of DMEM, 100 mL of FBS, 10 mL of Pen/Strep, and 5 mL of L-Glutamine.
Alpha Minimum Essential Medium (MEM) with 10% FBS for preparing MS-5 feeder cell medium (1 liter): 890 mL of Alpha MEM, 100 mL of FBS, 10 mL of Pen/Strep Gelatin solution (500 ml): Dissolve 0.5 g of gelatin in 500 ml of warm (50-60° C.) Milli-Q water. Cool to room temperature.

Example II

This example describes the discovery of small molecules and contact timing for providing directed differentiation of FOXA2+LMX1A+DA neurons of the present inventions.

The following is a brief summary of some of the experimental discoveries described herein: Treatment of Dual-SMAD inhibited cells with SHH agonists (purmorphamine+SHH) and FGF8 (S/F8) in the absence of CHIR99021 showed significantly lower expression of FOXA2 by day 11 and complete lack of LMX1A expression (FIG. 1*a,b*). The anterior marker OTX2 was robustly induced in LSB and LSB/S/F8/CHIR treated cultures, but not under LSB/S/F8 conditions (FIG. 1*a,c*).

The inventors previous used several other directed differentiation methods that resulted in cell populations containing DA-like neurons. These DA-like neurons were used in transplantation studies that resulted in concerns on the further use of these cells for therapeutic applications. For examples, procedures described in Perrier et al., 2004 and Fasano et al., 2010, including MS5 neural induction, resulted in rosette cell formation and were used to make Day 11 precursors, see FIGS. 2, 16 and 17 for examples, that were further used to derive DA-like neurons. These neurons resulted from a low percentage of the precursor cells in the resulting Day 11 cell populations. Transplantation studies that used these neurons showed poor post transplant viability and loss of the DA-like neuronal phenotype in addition to observations of post transplantation development of inappropriate neural types along with loss of growth control, which led to development of teratomas. See FIGS. 16 and 17.

Specifically, at P0 hESCs were contacted with molecules for beginning neural induction of Oct4+ cells into rosette cells using MS5 feeder cells (Perrier et al., 2004). At the P1 stage Rosette cells were expanded by contacting cells with additional molecules for differentiating cells into cells at stage P2 with specific expression patterns including Pax2+/En1+ DA progenitor cells and were further differentiated into TH+/En1+ DA neurons. These cells were used for engraftment in 6OHDA lesioned rats, immunosuppressed with Cyclosporin A. Those transplantation studies showed poor in vivo viability, loss of the TH+ phenotype, concerns about further growth into unwanted, possibly lethal, cells, i.e. teratomas, and growth of cells into inappropriate neural types that would cause additional medical problems for the patient.

There were very small numbers of surviving TH+ neuron at 4.5 moths after transplantation (<50 TH+ cells/animal) in grafts from rosette derived DA neuron precursors FIG. 16A. However, in contrast to TH+ cells, GFP marked cells (GFP was driven by a ubiquitous promoter) did survive quite well after transplantation. This suggests that most surviving cells following transplantation were neural cells of non-DA neuron identity (16B). Few graft-derived cells (hNA+ (green) co-express TH (red) again suggesting that most grafted human cells adopt a non-DA neuron phenotype FIG. 16C. Panels 16 D-E show that D-E, despite the very poor in vivo survival there was some (low and highly variable) improvement in a few behavioral assays such as amphetamine induced rotations (D), cylinder test and spontaneous rotations (E). Feeder-free neural induction was carried out as previously described (Chambers et al., 2009) but further modified to yield floor plate cells (Fasano et al., 2010). In the modified Dual-SMAD inhibition method for differentiating pluripotent cells into floor plate cells, the inventors' previously discovered that high concentrations of SHH were required for FP induction by day 11. For example, in some embodiments, Sonic C25II was added at 200 ng/ml. In some experiments, DKK-1 (R&D; 100 ng/ml) FGF8 (R&D; 50 ng/ml), Wnt-1 (Peprotech; 50 ng/ml) and retinoic acid (R&D; 1 mM) were added, See FIG. 17. However none of the resulting cell populations at day 11 using previous methods, contained the high percentage of FOXA2+/LMX1A+midbrain floor-plate progenitor cells using methods of the present inventions.

As shown herein, a cell population containing pluripotent cells was chosen by the inventors for a starting population and plated at Day 0. Cell are grown to near confluency prior to differentiation (between 60-100% confluence). These cells were contacted with Dual SMAD inhibitors (i.e. exposure to LDN-193189+SB431542="LSB") on Day 0. The inventors followed a cell population with regular feedings containing fresh LSB until Day 11 and discovered that some remaining cells were LMX1A+ but did not express FOXA2 (FIG. 1 a,b). The inventors plated duplicate starting cell populations then tested for cell types (i.e. gene/protein expression patterns) after contacting with mixtures containing any of the following SHH agonists (purmorphamine+ SHH) and FGF8 (S/F8) contacting the cells with different exposure regimens, i.e. contacting cells at Day 0, or Day 1, or Day 2, etc. for specific amounts of time, i.e. 24 hours, 48 hours, etc. Three primary exemplary culture conditions tested were 1) cells contacted with LDN/SB (LSB) on Day 0 then contacted with fresh LSB until Day 5, on Day 5 cells were contacted with fresh LDN without SB until Day 11, 2) cells contacted with LDN/SB (LSB) on Day 0 then contacted with fresh LSB until Day 5, on Day 5 cells were contacted with fresh LDN without SB until Day 11 while during this time cells were additionally contacted with fresh purmorphamine, SHH and FGF8 until Day 7 and 3) cells contacted with LDN/SB (LSB) on Day 0 then contacted with fresh LSB until Day 5, on Day 5 cells were contacted with fresh LDN without SB until Day 11 while during this time cells were additionally contacted with fresh purmorphamine, SHH and FGF8 until Day 7 while additionally contacted with fresh CHIR starting on Day 3 of culture until Day 11 with several variations of these primary conditions in order to determine optimal yield of cell types. Systematic comparisons of the three culture conditions (FIG. 1 d) were performed using global temporal gene expression profiling. See exemplary FIG. 8 and Tables 1-6. Hierarchical clustering of differentially expressed genes segregated the three treatment conditions by day 11 of differentiation (FIG. 8a). FOXA1, FOXA2 and several other SHH downstream targets including PTCH1 were amongst the most differentially regulated transcripts in LSB/S/F8/CHIR versus LSB treatment sets (FIG. 1e). Expression of LMX1A, NGN2, and DDC indicated establishment of midbrain DA neuron precursor fate already by day 11 (FIG. 1e,f). In contrast, LSB cultures by day 11 were enriched for dorsal forebrain precursor markers such as HES5, PAX6, LHX2, and EMX2. Direct comparison of LSB/S/F8/CHIR versus LSB/S/F8 treatment (FIG. 1f) confirmed selective enrichment for midbrain DA precursor markers in LSB/S/F8/CHIR group and suggested hypothalamic precursor identity in LSB/S/F8 treated cultures based on the differential expression of RAX1, SIX3, and SIX6 (see also POMC, OTP expression in FIG. 2d).

Exemplary lists of differentially expressed transcripts for day 11 are shown in Tables 1, 2 and day 25 in Tables 3-5 and gene ontology analysis FIG. 8b (DAVID; http://david.abc-c.ncifcrf.gov) confirmed enrichment for canonical WNT signaling upon CHIR treatment. Raw data are not yet available at GEO worldwideweb.ncbi.nlm.nih.gov/geo/ accession#: [TBD]). Comparative temporal analysis of gene expression for midbrain DA precursor markers (FIG. 1g) versus markers of anterior and ventral non-DA neuron fates (FIG. 1h) partitioned the three induction conditions into: i) LSB: dorsal forebrain; ii) LSB/S/F8: ventral/hypothalamic and iii) LSB/S/F8/CHIR: midbrain DA precursor identity.

Example III

Differentiation of DA neurons. For further differentiation, precursor cells were maintained in a medium promoting neuronal maturation (BAGCT—see material and methods). The following types of comparisons were made between the populations of differentiated cells resulting from previous methods and methods of the present inventions: A) Immunocytochemical analysis at day 50 of differentiation for TH in combination with LMX1A, FOXA2 and NURR1, B) Quantification of TH+, FOXA2+, LMX1+, and NURR1+ cells out of total cells comparing rosette-derived versus floor plate-derived (LSB/S/F8/CHIR) cultures. C) Quantification of the percentages of serotonin+ (5-HT), and GABA+ neuronal subtypes (non-DA neuron contaminants) at day 50 in floor plate and rosette-derived DA neuron cultures. And D) HPLC analysis for measuring dopamine and metabolites: Comparison of the DA, DOPAC and HVA levels between floor plate versus rosette-derived cultures. By day 25, three precursor cell populations yielded Tuj1+ neurons (FIG. 2a) and cells expressing TH, the rate-limiting enzyme in the synthesis of DA. However, LSB/S/F8/CHIR treatment yielded TH+ cells that co-expressed LMX1A and FOXA2 and displayed strong induction of the nuclear receptor NURR1 (NR4A2) (FIG. 2a,b). Comparing gene expression in day 13 versus day 25 cultures confirmed robust induction of other postmitotic DA neuron markers (FIG. 2c). Characterizing DA neuron identity at day 25 in comparison to LSB and LSB/S/F8 treated cultures confirmed enrichment for known midbrain DA neuron transcripts and identified multiple novel candidate markers (FIG. 2d, Tables 3-5, FIG. 8b). For example, the transcript most highly enriched in LSB/S/F8/CHIR (midbrain DA group) was TTF3, a gene not previously associated with midbrain DA neuron development, but highly expressed in the human substantia nigra (FIG. 8c; Allen Brain Atlas: http://human.brain-map.org).

Similar data were obtained for EBF-1, EBF-3 (FIG. 8c) as well as TTR, a known transcriptional target of FOXA2 in the liver. The data obtained during the development of the present inventions indicated enrichment of several PITX genes in midbrain DA precursor cells. PITX3, a classic marker of midbrain DA neurons, was also robustly expressed at day 25 of differentiation (FIG. 2e). Finally, both midbrain floor plate and DA neuron induction could be readily reproduced in independent hESC and hiPSC lines (FIG. 9). The data demonstrated herein showed that the LSB/S/F8/CHIR protocol as opposed to other tested protocols yields cells expressing a marker profile matching midbrain DA neuron fate.

In vitro and in vivo properties of floor plate-derived DA neurons were compared to DA-like neurons obtained via a neural rosette intermediate (FIGS. 10 and 16). Patterning of neural rosettes represents the currently most widely used strategy for deriving DA neurons from hPSCs. Both floor plate- and rosette-based protocols were efficient at generating TH+ neurons capable of long-term in vitro survival (day 50 of differentiation; FIG. 3a). However, the percentage of TH+ cells was significantly higher in floor plate-derived cultures (FIG. 3b). While TH+ cells in both protocols displayed co-expression of NURR1, floor plate-derived DA neurons co-expressed FOXA2 and LMX1A (FIG. 3a,b). Few GABA and serotonin (5-HT)-positive neurons were observed (FIG. 3c). DA, and its metabolites DOPAC and HVA, were present in cultures generated with either protocol, but DA levels were approximately 8 times higher in floor plate cultures (FIG. 3d,e). Midbrain DA neurons exhibited extensive fiber outgrowth and robust expression of mature neuronal markers including synapsin, dopamine transporter (DAT), and G-protein coupled, inwardly rectifying potassium channel (Kir3.2—also called GIRK2—expressed in substantia nigra pars compacta (SNpc) DA neurons) (FIG. 3f, FIG. 11). SNpc DA neurons in vivo exhibit an electrophysiological phenotype that differentiates them from most other neurons in the brain. In particular, they spike spontaneously at a slow (1-3 Hz) rate. Moreover, this slow spiking is accompanied by a slow, sub-threshold oscillatory potential. After 2-3 weeks in vitro, these same physiological features are displayed by SNpc DA neurons cultured from early postnatal mice. The DA neurons differentiated from hESCs consistently (4/4) displayed this distinctive physiological phenotype (FIG. 3g-i).

Maintenance of mDA neurons in vitro at d65 showed TH positive neurons are still expressing FoxA2 and extend long fibers typical for mDA neurons. FIG. 3A. DA release measurement by HPLC showed d65 old TH+ neurons are functional in vitro FIG. 3B.

Example IV

Engraftment of novel DA neuronal cell population in rodents, i.e. mice and rats containing damaged neurons.

One of the challenges in the field is the ability to generate hPSC-derived midbrain DA neurons that functionally engraft in vivo without the risk of neural overgrowth or inappropriate differentiation into non-midbrain neurons or develop teratomas. Based on fetal tissue transplantation studies, the inventors' contemplated that the time of cell cycle exit, marked by expression of NURR1, may be a suitable stage for grafting (approximately day 25 of differentiation—FIG. 2). Initial studies using day 25 cells in non-lesioned adult mice showed robust survival of hPSC-derived FOXA2+/TH+ neurons at 6 weeks after transplantation (FIG. 12). Survival of FOXA2+/TH+ cells long-term in Parkinsonian hosts without resulting in neural overgrowth was tested. To this end, 6-hydroxy-dopamine (6-OHDA) lesions (Tabar, et al. Nature Med. 14:379-381 (2008), herein incorporated by reference) were made in NOD-SCID IL2Rgc null mice, a strain that efficiently supports xenograft survival with particular sensitivity for exposing rare tumorigenic cells (Quintana, et al. Efficient tumour formation by single human melanoma cells. Nature 456:593-598 (2008), herein incorporated by reference). Both floor plate- and rosette-derived DA neuron cultures were grafted ($150 \times 10^3$/ animal) without prior purification in order to reveal potential contaminating cells with high proliferative potential. Four and a half months after transplantation floor plate-derived DA neuron grafts showed a well-defined graft core composed of TH+ cells co-expressing FOXA2 and the human specific marker hNCAM (FIG. 4a-c). Functional analysis showed a complete rescue of amphetamine-induced rotation behavior. In contrast, rosette-derived neuronal grafts showed few TH+ neurons, did not produce a significant reduction in rotation behavior (FIG. 4d) and displayed massive neural overgrowth (graft volume>20 mm$^3$; FIG. 13). Extensive overgrowth of rosette-derived neuronal cells used in grafting as reported herein was comparable to previous work with rosette-derived DA grafts from the inventors' group (Kim, et al. miR-371-3 Expression Predicts Neural Differentiation Propensity in Human Pluripotent Stem Cells. Cell Stem Cell 8:695-706 (2011), herein incorporated by reference) and others (Hargus, et al. Proceedings of the National Academy of Sciences of the United States of America 107:15921-15926 (2010), herein incorporated by reference). The overgrowth was likely due to the longer survival periods (4.5 months versus 6 weeks), lack of FACS purification prior to transplantation and choice of NOD-SCID IL2Rgc null host. The number of proliferating Ki67+ cells was minimal in floor plate-derived grafts (<1% of total cells), while rosette-derived grafts retained pockets of proliferating neural precursors. Neural overgrowth is thought to be caused by primitive anterior neuroectodermal cells within the graft (Elkabetz, et al. Genes Dev. 22:152-165 (2008); Aubry, et al. Proc. Natl. Acad. Sci. U.S.A. 105:16707-16712 (2008), herein incorporated by reference). This hypothesis was supported by the expression of the forebrain marker FOXG1 in rosette- but not floor plate-derived grafts. A small percentage of astroglial cells were present in both floor plate- and rosette-derived grafts, though most GFAP+ cells were negative for human markers indicating host origin (FIG. 13).

Results in NOD-SCID IL2Rgc null mice described herein demonstrated robust long-term survival of FOXA2+/TH+ neurons, complete reversal of amphetamine-induced rotation behavior and lack of any signs of neural overgrowth. However, some of these outcomes could be attributable to the specific use of NOD-SCID IL2Rgc null mice. To test this hypothesis, floor plate-derived DA neuron cultures ($250 \times 10^3$ cells) were transplanted in adult 6-OHDA lesioned rats immunosuppressed pharmacologically using cyclosporine A. Five months after transplantation graft survival was robust (FIG. 4e-h) with an average of more than 15,000 TH+ cells co-expressing FOXA2 (FIG. 4g), and human nuclear antigen (hNA) (FIG. 4e); TH+/hNCAM+ fibers emanated from the graft core into the surrounding host striatum (FIG. 4f). In addition to FOXA2, TH+ cells expressed midbrain DA neuron markers PITX3 and NURR1 (FIG. 4h-j). Behavioral analyses showed complete rescue of amphetamine-induced rotational asymmetry, in contrast to sham-grafted animals that did not show improvements (FIG. 4k). Grafted animals also showed improvements in the stepping test (FIG. 4l) measuring forelimb akinesia and in the cylinder test (FIG. 4m), assays that do not depend on pharmacological stimulation of the DA system. The late onset of recovery (approximately 3-4 months after transplantation) is expected for human DA neurons and depends on the rate of in vivo maturation such as the levels of DAT expression (FIG. 4n). The presence of TH+ cells expressing Kir3.2 channels (GIRK2) or calbindin indicate that both SNpc (A9) and ventral tegmental area (A10) DA neurons are present in the graft (FIG. 4o,p).

As in mice (FIG. 13), serotonergic and GABAergic cells were rare (<1% of total cells) in rat cells, as were the mostly host-derived GFAP+ glial cells (7% of total cells; (FIG. 14). While few serotonin+ neurons were detected in the graft, hNCAM-negative cells were observed that were likely host-derived serotonergic fibers (FIG. 14).

Example V

Engraftment of novel DA neuronal cell population in primates containing damaged neurons.

The results demonstrated herein showed excellent graft survival and behavioral outcome in two independent murine models. However, the number of DA neurons required in a mouse or rat brain represents a small fraction of the larger number of cells needed for engrafting in primates and humans. To test the scalability of this protocol, performed pilot grafting studies were done in two adult MPTP lesioned rhesus monkeys.

Batches of $50 \times 10^6$ transplantable DA neuron precursors were obtained by day 25 of differentiation using the floor plate-based protocol. Classic dose for inducing a Parkinson-like condition was though a 3 mg MPTP-HCL injected into the carotid artery (range 0.5-5 mg). This was followed by systemic injection of MPTP at 0.2 mg/kg IV of MPTP. Cells were injected at three locations (posterior caudate and pre-commissural putamen) on each side of the brain (6 tracts in total, $1.25 \times 10^6$ cells/tract), and the animals were immunosuppressed with cyclosporine-A. One side of the brain was injected with DA precursors from a GFP expressing subclone of H9, while the other side was engrafted with cells derived from unmarked H9 cells. Results showing engraftment of neurons in rhesus monkeys with continued FOX2A expression and TH production are shown in FIG. 4q-t. One month after transplantation, robust survival of midbrain DA neurons was observed based on expression of GFP (FIG. 15) and the human specific cytoplasmic marker (SC-121) (FIG. 4q). Each graft core was surrounded by a halo of TH+ fibers extending up to 3 mm into the host (FIG. 4r). The graft cores were composed of TH+ neurons co-expressing SC-121 (FIG. 4s) and FOXA2 (FIG. 4t). SC-121 and GFP negative areas within the graft contained Iba1+ host microglia (FIG. 15) indicating incomplete immunosuppression. In summary, engraftment of novel DA neuronal cell population in primates, i.e. adult MPTP (3 mg of MPTP-HCL (1-methyl-4-phenyl-1,2,3,6-tetrahydropyridine; ranging in concentration from 0.5-5 mg MPTP-HCl) lesioned rhesus monkeys containing a severe >95% loss of endogenous midbrain DA neurons. MPTP exposure caused observable changes and symptoms similar to Parkinson's disease in humans.

Example VI

Comparable differentiation potential towards midbrain DA neuron fate of PINK1 mutant PD-iPSC cells versus wild-type hES (or iPSC) cells.

This example described the discovery that large populations of midbrain DA neurons developed with characteristics of a PD patient's neurons when a PD patient's cell line, i.e. PINK1 mutant PD-iPSC cell, obtained in a manner that did not result in the destruction of an embryo, were used as the cell population for obtaining FOXA2/LIM1XA/TH+ DA neurons of the present inventions.

PINK1 Q456X mutant PD-iPSC line was differentiated using the novel floor-plate based midbrain DA neuron protocol (method) of the present inventions which yielded midbrain differentiation profiles comparable to those obtained from the iPSC H9 line. (FIG. 20). A-C) Immunocytochemical analysis of PINK1 mutant PD-iPSC line at day 11 of differentiation (midbrain precursor stage) for FOXA2 (red), LMX1A (green) and DAPI (blue) (A), day 25 of differentiation (early postmitotic DA neuronal stage) for FOXA2 (red) and TH (green) (B) and for NURR1 (red) and TH (green) (C). D-F) Same set of immunocytochemical analyses performed using H9 derived cells at day 11 of differentiation for FOXA2 (red), LMX1A (green) and DAPI (blue) (D), at day 25 of differentiation for FOXA2 (red) and TH (green) (E) and for NURR1 (red) and TH (green) (F).

PINK1 mutant PD-iPSC showed PD like phenotype of protein aggregation following long-term differentiation and maturation in vitro. The inventors discovered that PINK1 mutant PD-iPSC showed evidence of α-synuclein (major component of Lewy body on PD patience) expression in cytosol of TH+ DA neurons at day 55 of differentiation using the novel floor-plate based midbrain DA neuron induction protocol, (FIG. 21a-b). A, B) Immunocytochemical analysis of PINK1 mutant PD-iPSC line at day 55 of differentiation for α-synuclein (LB509, red), TH (green) and merged image (A) and α-synuclein (red) and ubiquitin (green) (B). These α-synuclein positive cells also showed high expression of ubiquitin (classical Lewy body marker). In contrast, DA neurons derived from control iPS line showed expression of normal synaptic (as opposed to cytosolic) α-synuclein expression and very low levels of Ubiquitin (FIG. 21c-d). C, D) Immunocytochemical analysis of control-iPSC line at day 55 of differentiation for α-synuclein (red) and TH (green) (C) and α-synuclein (red) and ubiquitin (green) (D).

Expression of aggregated form of α-synuclein. In the PD patient brain, dimerized insoluble forms of a-synulcein lead to aggregation in Lewy bodies. The dimerized form of α-synuclein shows phospholylation of Serine 129 on α-synuclein.

At the same day of differentiation, PINK1 mutant PD-iPSC derived cells showed strong expression for Ser129 phosphorylated α-synuclein in contrast to control-iPSC derived cells that showed very low levels of expression (FIG. 22). PINK1 mutant PD-iPSC derived cells showed strong expression for Ser129 phosphorylated α-synuclein in contrast to control-iPSC derived cells that showed very low levels of expression. A, B) Immunocytochemical analysis for Ser129 phosphorylated α-synuclein (green) and DAPI (blue) in PINK1 mutant PD-iPSC derived cells at day 55 of differentiation (A) and matched control-iPSC derived cells (B).

Differences in α-synuclein expression patterns are observed depending of differentiation protocol. The inventors contemplated that floor-plate derived "authentic" midbrain DA neurons showed PD specific vulnerability and corresponding, specific, in vitro phenotypes. DA neurons obtained using the classical MS5 stromal feeder based differentiation protocol (Perrier et al., PNAS 2004, herein incorporated by reference) yielded large numbers of TH+ neurons. However, based on data obtained during the development of the present inventions, the inventors showed that MS5 based TH+ cells were not authentic floorplate derived midbrain DA neurons. In cultures differentiated via the MS5 protocol, there were many α-synuclein positive cells. However, those cells did not co-express TH. Moreover, there was no difference in expression patterns between PD-iPSC and control-iPSC when using the MS5 differentiation strategy (FIG. 23a-b). These data indicate that α-synuclein is also expressed in other non-DA cell types and that such non-DA α-synuclein is unchanged in disease versus control-iPSC derived cells—particularly when using standard MS5 differentiation protocols. These are the DA-like rosette derived neurons reported in publications (e.g. Perrier PNAS 2004). Those MS5 based TH+ (=DA-like) cells are used for comparison in FIGS. 3, 10, 13 and 16. These data indicate that α-synuclein is also expressed in other non-DA cell types and that such non-DA α-synuclein is unchanged in disease versus control-iPSC derived cells, particularly when using standard MS5 differentiation protocols. Finally, the new floor plate based differentiation protocol described herein, yields large number of TH+ cells co-expressing α-synuclein. Those TH+ cells express α-synuclein in a cytosolic expression pattern. FIG. 24A, B) Immunocytochemical analysis for α-synuclein (LB509, red), TH (green) of PINK1 mutant PD-iPSC line at day 60 of MS5 based differentiation (A) and control-iPSC (B). C) Immunocytochemical analysis of PINK1 mutant PD-iPSC line at day 55 of floor-plate based differentiation for α-synuclein (red), TH (green).

Exemplary DA neurons derived from PINK1 mutant PD-iPSC are more vulnerable to toxic stimulation. PD-iPSC derived TH+ DA neurons derived via floor-plate based protocol were more vulnerable to toxin challenge (valinomycin: mitochondria ionophore, 5 uM (ranging in concentration from 1-10 uM), 48 hr) than control-iPSC derived cells. In contrast, TH+ neurons derived via the classic MS5 based protocol did not show differential vulnerability between PD- versus control-derived cells. (FIG. 24). A-F) Representative TH immunocytochemistry at day 60 of differentiation: Normal condition (no toxin treatment) for both PD- and control-iPSC derived cells obtained via floor-plate based protocol (A, PD-iPSC derived cells shown), nearly complete degeneration of TH+ DA neurons in PD-iPSC following toxin treatment (B), partially degenerated TH+ DA neurons from control-iPSC(C). Entire cell viability assay with alamar-blue after 48 hrs of valinomycin treatment also showed differential cell survival in a specific dose range for toxin challenge (5 and 10 uM) when comparing PD-iPSC and control iPSC (FIG. 25).

Normal condition both of PD- and control-iPSC derived cultures obtained via MS5 based protocol (D, PD-iPSC derived cells shown), TH+ neurons following toxin challenge in PD-iPSC (E), and control-iPSC derived cultures (F) obtained via MS5 protocol. G-H) low power images of immunocytochemistry for Tuj1 (red) and TH (green) by floor-plate based protocol at day 60 of differentiation: PD-iPSC of normal (G), versus toxin challenge (H) conditions and control iPSC of normal (I), versus toxin challenge (J) conditions. K-N) low power images of immunocytochemistry for Tuj1 (red) and TH (green) by MS5 based protocol at day 60 of differentiation: PD-iPSC of normal (K), versus toxin challenge (L) conditions and control iPSC of normal (M), versus toxin challenge (N) conditions.

Exemplary quantification of cell viability-dose response assay for toxin challenge. Cell viability assay with alamar-blue after 48 hrs of valinomycin treatment showed differential cell survival in a specific dose range for toxin challenge (5 and 10 uM) when comparing PD-iPSC and control iPSC (day 60 of floor-plate based differentiation). Note: this assay tests for overall cell death while the most dramatic effects were observed specifically in DA neurons (see FIG. 14). Therefore, alamar blue based quantification will likely underestimate the extent of the differential effect observed on DA neuron lineages.

References, herein incorporated by reference: Li, et al. *Nat. Biotechnol.* 23, 215-221 (2005); Perrier, et al. *Proc Natl Acad Sci US* 101, 12543-8 (2004); Perrier, et al. *Proc Natl Acad Sci USA* 101, 12543-8 (2004); Tabar, et al. *Nature Med.* 14, 379-381 (2008); Perrier, et al. *Proc Natl Acad Sci USA* 101, 12543-8 (2004); Wernig, et al. *Proc. Natl. Acad. Sci. U.S.A* 105, 5856-5861 (2008); Lindvall, et al. *J. Clin. Invest* 120, 29-40 (2010); Roy, et al. *Nature Med.* 12, 1259-1268 (2006); Elkabetz, et al. *Genes Dev.* 22, 152-165 (2008); Kittappa, et al. *PLoS. Biol.* 5, e325 (2007; Ferri, et al. *Development* 134, 2761-2769 (2007); Roelink, et al. *Cell* 76, 761-775 (1994); Liem, et al. *Cell* 82, 969-979 (1995); Fasano, et al. *Cell Stem Cell* 6, 336-347 (2010); Chambers, et al. *Nat. Biotechnol.* 27, 275-280 (2009); Muroyama, et al. *Genes Dev.* 16, 548-553 (2002); Joksimovic et al. *Nat Neurosci* 12, 125-131 (2009); Lyashenko, et al. *Nat. Cell Biol.* 13, 753-761 (2011); VanDunk, et al. *J. Neurosci.* 31, 6457-6467 (2011); Huang, et al. *Nat. Protoc.* 4, 44-57 (2009); Costa, et al. *Mol. Cell. Biol.* 9, 1415-1425 (1989); Elkabetz, et al. *Genes Dev.* 22, 152-165 (2008); Soldner, et al. *Cell* 136, 964-977 (2009); Guzman, et al. *J. Neurosci.* 29, 11011-11019 (2009); Nedergaard, et al. *J. Physiol* 466, 727-747 (1993); Ferrari, et al. *Eur. J. Neurosci.* 24, 1885-1896 (2006); Olanow, et al. *Trends Neurosci.* 19, 102-109 (1996); Zetterström, et al. *Science* 276, 248-250 (1997); Quintana, et al. *Nature* 456, 593-598 (2008); Kim, et al. diets Neural Differentiation Propensity in Human Pluripotent Stem Cells. *Cell Stem Cell* 8, 695-706 (2011); Hargu, et al. *Proceedings of the National Academy of Sciences of the United States of America* 107, 15921-15926 (2010); Aubry, et al. *Proc. Natl. Acad. Sci. U.S.A* 105, 16707-16712 (2008); Blume, et al., *Exp. Neurol.* 219, 208-211 (2009); Ban, et al., *Proc. Natl. Acad. Sci. U.S.A* (2011); Studer, et al., *Nature Neurosci.* 1, 290-295 (1998); Kordower, et al., *Science* 290, 767-773 (2000); Paxinos, et al., *The Rhesus Monkey Brain in Stereotaxic Coordinates* (Academic Press, 2000); Crawley, *What's Wrong With My Mouse: Behavioral Phenotyping of Transgenic and Knockout Mice* (Wiley-Liss, 2000); Studer, et al., *Brain Res. Bull.* 41, 143-150 (1996); Tabar, et al., *Nat. Biotechnol.* 23, 601-606 (2005); and Placantonakis, et al., *Stem Cells* 27, 521-532 (2009).

Example VII

Exemplary conditions were established for the in vivo recording of human pluripotent stem cell derived DA neurons in acute slice preparations; see exemplary results shown in FIG. 26.

Electrophysiological measurements are contemplated for use in acute slice preparations, i.e. from biopsies of engrafted areas. In one embodiment, A9- versus A10 type graft-derived DA neurons will be identified in vivo based on testing for the autonomouse pacemaking activity that is specific to A9-type dopamine neurons that are most affected in PD. In other words, A10 type neurons do not have pacemaking activity Conditions were established for the in vivo recording of human pluripotent stem cell derived DA neurons in acute slice preparations, see, FIG. 26. Specifically, grafted human DA neurons derived from pluripotent stem cells were measured for and discovered to have electrophysiological features typical of those seen in mouse substantia nigra pars compacta (SNpc), FIG. 26A where the top view shows reconstruction of a pacemaking neuron in the graft region. Bottom shows an exemplary photomicrograph of a brain slice taken from the rat into which the hES-derived neurons were injected 9 months prior; the graft is outlined; a higher magnification image is shown inset at the bottom. The slice was processed for tyrosine hydroxylase which shows up as white, FIG. 26B. Further, the top view shows an exemplary cell-attached patch recording from a putative DA neuron in the graft; Bottom shows an exemplary whole cell recording from the same cell. Recordings were made in the presence of glutamate and GABA receptor antagonists (50 µM AP5, 10 µM CNQX and 10 µM GABAzine) to eliminate synaptic input. These recordings demonstrated that the PS-derived neurons were autonomous pacemakers with normal intrasomatic voltage trajectories. Another neuron recorded in a graft sample had similar properties, FIG. 26C. For comparison, cell-attached and whole cell recordings from a dopaminergic neuron in SNpc of an adult mouse are shown. Abbreviations (CTx=cortex, STr=striatum, SNpc=substantia nigra pars compacta, DA=dopaminergic). This data shows in vivo functional studies in grafted rat striatum months after transplantation. Thus in some embodiments, in vivo functional studies on grafted tissue demonstrates recovery of substantia nigra pars compacta (SNpc).

Example VIII

Exemplary methods for identifying cell surface markers for use in methods of the present inventions. In particular, CD142 was identified with these methods.

Two main strategies to identify candidate surface markers: An unbiased gene expression screen in genetic reporter lines (FIG. 27a) that found several candidate markers, including a marker, termed DCSM1, that is selectively expressed in midbrain DA neurons and appears to specially marker A9-type DA neurons (FIG. 27b). A second strategy is the use of a CD cell surface marker screen in hESC derived DA neurons testing 242 commercially available antibodies in 96 well format (FIG. 27c,d). The results of such a screen (FIG. 27e) led to the identification of at least 5 validated markers enriched in midbrain DA neurons including CD142, a marker that selectively marks Nurr1+ DA neuron stage (FIG. 27f). With the use of the DA neuron cell procedure described herein, CD142 typically marked approximately 30% of the total cell population at day 25 of differentiation (FIG. 28a). Selectivity of CD142 for a Nurr1+ DA neuron stage was confirmed in multiple independent hESC and hiPSC lines (FIG. 28b). In addition to enriching for DA neurons, enrichment of CD142 positive cells resulted in selective depletion of undesired neuron subtypes such as GABA and Serotonergic neurons. (FIG. 28c-f). in vivo studies confirmed the ability of a CD142 positive cell population to give rise to high purity DA neuron grafts that overcame problems of contaminating GABA and Serotonergic neurons. While the grafting procedure that used unpurified cells already resulted in very few Serotonergic neurons, the use of CD142 based selection of precursor cells is contemplated to further reduce the risk of introducing serotonergic neurons, a contaminating cell type that was implicated in failed human fetal tissue grafting as the potential source of the undesirable fetal tissue graft-induced dyskinesias.

Example IX

This example describes methods for transformation of cells with human PST genes for increase PSA cell surface expression. This example also shows exemplary methods of using cells having increased PSA cell surface expression.

Specifically, this example shows engineered PST genes into hESCs for increasing PSA expression on DA neurons. A gene encoding the human polysialyl-transferase (hPST) was introduced into a hESC line (WA01) using a lentiviral vector (pLenty, Invitrogen). Twenty selected clones were expanded and analyzed for PST expression. PST-expressing hESC clones were differentiated to ensure that PST was not silenced in DA neurons. Quantification of PSA-NCAM at different stages of differentiation (day 0, 11, 25, and 50) was done using FACS analysis and immunofluorescence (Operetta). Positive clones were subjected to the suite of DA neuron QC parameters outlined in Table 7. At least 3 clones that retain high, uniform levels of PSA-NCAM during differentiation and perform well in the QC parameters (Table 7) will advance to assessment of the neurite outgrowth in PST-overexpressing hESC-derived DA neurons Selected control and PST-overexpressing hESC clones were differentiated into DA neurons using the standard protocol described herein, followed by cell fixation and analysis at days 25 and 50. The number and length of TH-positive fibers in such cultures were quantified with the Operetta High Content Microscope. The Neurite Analysis module in Harmony software 3.0 quantified neurite number and length, with or without PST, and the data was statistically analyzed using a two-way ANOVA. PST-overexpressing and control hESC clones that advance from in vitro studies above, were differentiated again into DA neurons and transplanted into a rat model of PD. Short-term grafts (4-6 weeks) to determine survival, PSA-NCAM expression and neurite outgrowth were done. For each clone that passed short-term in vivo parameters were subjected to long-term grafting studies. For those studies animals received half or a quarter of the standard ($200\times10^3$) dose of cells. These studies were to address whether increased PSA leads to increased long-term survival after transplantation (5 months), and whether smaller DA neuron numbers are capable of matching or outperforming the functional capacity of non-PST grafts transplanted at standard cell doses (not FIG. 27). In addition, complex behavioral assays sensitive to the extent of striatal reinnervation were monitored to further distinguish the functional potential of PST- versus control DA neuron grafts. The animals were sacrificed following completion of behavioral assays, and fiber outgrowth was quantitated using human specific antibodies NCAM and SC121 and antibodies against TH (see also not FIG. 29). The intensity and spread of the hNCAM+, SC121+ and TH+ graft was measured, as well as the percentage of human cells co-expressing DA neuron markers (TH, FOXA2) and PSA. The density of NCAM/TH+ halo of neurites emanating from the graft were quantified at different distances. Data was compared among groups using a two-way ANOVA with a Bonferroni post-hoc test. In addition, sections were examined for qualitative changes (e.g. branching, thickness, graft distribution and shape). In addition, some grafts will be processed for slice electrophysiological evaluation in terms of A9 phenotype, synapse formation with host striatum, as well as innervation by endogenous afferents.

Example X

The following example shows enhancement of polysialic acid expression that improved the function of ES-derived dopamine neuron grafts in Parkinsonian mice.

ES cells expressing GFP under control of Nurr1 promoter (Nurr1::GFP ES cells) were stably transduced with a lentiviral vector ubiquitously expressing polysialyltransferase (PST). Transduced cells showed a dramatic increase in PST mRNA as compared to controls (FIG. 30A). Expression of PST was observed to be sufficient for PSA synthesis on NCAM. Accordingly, PSA-NCAM expression was greatly increased in PST-modified cells at day 14 of DA neuron differentiation (FIG. 30B-E). Both the endogenous and induced cell surface PSA on ES-derived DA neurons could be removed (FIG. 30E) by a phage endoneuraminidase (endoN) that specifically cleaved PSA's unique alpha-2,8-linked sialic acid polymers. Surprisingly, PST transduction was not observed to affect expression of neuronal or midbrain markers in the GFP-purified DA neurons (FIG. 30F).

Other studies in 6OHDA-lesioned hemiparkinsonian mice showed that transplantation of approximately 100,000 ES-derived DA neuron precursors is required to produce robust functional recovery, as measured by the amphetamine-enhanced rotation test. In the present studies, sought to graft a sub-optimal number of cells in order to be able to assess augmentation by enhanced PSA expression. In order to transplant highly enriched DA neuron populations that are depleted for contaminating pluripotent cells, FACS-purified cultures at day 14 of differentiation for expression of Nurr1-driven GFP and for the absence of SSEA-1 expression (FIG. 31). Without PST overexpression, a reduction of the minimally effective graft size by half (55,000 Nurr1+ DA cells) failed to produce detectable behavioral recovery. By contrast, with enhanced PSA expression, the same number of Nurr1/PST DA neurons resulted in a significant correction of the PD behavioral impairment ($p<0.01$; two-way ANOVA), with complete recovery approximately 5 weeks after surgery (FIG. 32A). PSA removal prior to transplantation by incubation with endoN indicated the specificity of PSA's enhancement, in that the endoN treatment partially reversed the functional restitution obtained with Nurr1/PST (FIG. 32A).

To examine the characteristics of the grafted cells, animals were processed for immunohistochemistry two months after transplantation. There was a difference in the number of surviving Nurr1+ neurons, in that animals grafted with the PST-transduced line had on average twice as many GFP+ cells as animals grafted with control cells (9,300+/−1,400 vs. 4,230+/−1010 GFP+ cells per graft in PST versus control samples respectively; FIG. 32B, $p<0.05$, Student's t test). Furthermore, Nurr1/PST grafts also displayed higher levels of PSA expression in vivo (FIG. 32C,D). However, the proportions of cells expressing the midbrain DA markers TH and FoxA2 within the graft core were comparable for the Nurr1 and Nurr1/PST cells (TH: 62.0%+/−8.0 vs. 51.3%+/−7.0 $p=0.33$; FoxA2: 63.2%+/−8.6 vs. 55.4%+/−2.0, $p=0.3$, respectively; FIG. 32E).

Neuronal processes that emerged from the Nurr1 and Nurr1/PST cells showed comparable levels of TH, Girk2 (G-protein-coupled, inwardly rectifying potassium channel) and synapsin (FIG. 33A). Unlike other studies with transplanted Schwann cells (Ghosh, M., et al. Extensive cell migration, axon regeneration, and improved cells after spinal cord injury. Glia 60, 979-992 (2012)), enhanced PSA expression had little effect on migration of DA cells from the grafting site. However, there were clear changes in neurite outgrowth. As shown in FIG. 33B, there were more DA neuronal processes emerging from Nurr1/PST cells as compared to Nurr1+ controls. When the intensity of GFP and TH immunofluorescence was quantified in five successive 100 µm zones away from the transplant, Nurr1/PST grafts displayed a much higher relative density of processes (FIG. 33C,D; $p<0.01$ for both GFP and TH, two-way ANOVA). In quantifying this effect, normalized the relative density of processes to the density observed in the most proximal zone immediate to the graft core. Such normalization was required to compensate for the larger number of surviving cells in the Nurr1/PST grafts and to confirm a specific effect of PSA on neurite outgrowth. Specificity was also demonstrated when cell surface PSA was removed by endoN treatment prior to grafting. Thus pre-treatment with endoN reduced distal fiber outgrowth back to control levels (FIG. 33E).

These discoveries showed that at least some of the effects of PSA on graft function resulted from enhanced fiber innervation of striatum. Accordingly, there was a strong correlation between graft function and the relative extent of GFP-positive fiber outgrowth for example into zone IV (FIG. 33F; $p<0.001$, $r2=0.65$, $n=17$). Surprisingly, the fiber outgrowth/behavioral relationship was consistent for experimental groups (control, PSA enhanced, and endoN-treated), indicating that graft-host innervation was a parameter for behavior recovery in the mouse Parkinsonian model. Several factors contributed mechanistically to increased fiber outgrowth, such as enhanced penetration of the zone of reactive glia encapsulating the graft core, increased sprouting ability, improved outgrowth into the surrounding host tissue (e.g. easier growth cone translocation), and prevention of premature connections with host tissue in proximity to the graft core. The exemplary mechanisms are consistent with PSA's role in facilitating process outgrowth during normal development and in the adult nervous system.

The experiments described herein demonstrated the use of engineered PSA in DA neuron grafting which provided superior results compared to grafts from other types of cells. Data clearly indicated that PSA enhancement provided a significant augmentation of the ability of grafted DA neurons to innervate host striatum and attenuate PD functional deficits. Therefore clinical translation is contemplated comprising DA neurons of the present inventions for providing cells prior to transplantation. In some embodiments, the cells will be genetically manipulated for expressing PSA. In some embodiments, PST may be delivered directly to the cells via exposure to the purified enzyme and substrate, in vitro, prior to transplantation. In some embodiments, PSA strategy for human translation in PD grafting is contemplated to minimize the need for multiple injections and thereby reduce the surgical risks resulting from these multiple injections.

In other embodiments, this technology is contemplated for use on other cell types and species, for example, augmenting the migration of grafted Schwann cells in creating a bridge (for example, cell-cell communication) for re-growth of axons at the site of spinal cord injury.

The following are exemplary materials and methods used in this example.

Animals: Six-week old 129S3/SvImJ mice (Jackson Laboratory) were kept under controlled temperature with food and water available ad libitum. Experimental procedures were performed according to NIH and institutional animal use guidelines and approved by the local Institutional Animal Care and Use Committee (IACUC) and the Institutional Biosafety Committee (IBC).

6OHDA injection and amphetamine-induced test: Animals were anesthetized with sodium pentobarbital (10 mg/kg) and injected in the right striatum with 2 µl of 6OHDA (4 µg/µl in saline, 0.5% ascorbic acid). The injections were performed with a Hamilton syringe at coordinates: 0.5 mm posterior, 1.8 mm lateral relative to bregma and 2.5 mm ventral to brain surface. Before the surgery animals received a single i.p. injection of desipramine (25 mg/Kg, Sigma). Two weeks after surgery animals were scored in the amphetamine-induced rotation test. They were placed on 30 cm diameter clear plastic cylinders for half an hour after which they received a single i.p. injection of amphetamine (10 mg/Kg, Sigma). After 20 min, the number of ipsilateral/contralateral rotations was scored during another 20 mM. Animals were scored once a week for seven weeks then deeply anesthetized and perfused through the heart with PBS and 4% paraformaldehyde in 0.1 M phosphate buffer (PB, pH 7.4). Brains were removed and post-fixed overnight at 4° C. in 4% paraformaldehyde then vibratome sliced (Pelco-101, Ted Pella) in 40 µm-thick sagittal sections.

Cell differentiation and transplantation: A Nurr1::GFP BAC transgenic BAC mouse ES reporter cell line (i.e., GFP expression is driven by Nurr1 promoter) 5 was transduced with a lentivirus (pLenti, Invitrogen) containing the mouse PST gene under control of the CMV promoter. ES cells were propagated on mitomycin C-treated MEFs (StemCell Technologies) in DMEM (Invitrogen), 10% FBS (HyClone) supplemented with 1,400 units/ml LIF (ESGRO; Invitrogen), 2 mM L-glutamine, 1 mM β-mercaptoethanol, 100 U/ml penicillin and 100 µg/ml streptomycin (Invitrogen). DA differentiation was induced according to Barberi et al., Nat Biotechnol 21, 1200-1207 (2003), with modifications. Briefly, cells were differentiated on MS5 feeder cells in gelatin-coated dishes (10,000 cells/10 cm dish) and cultured for four days on serum replacement media (SRM). At day 4, Sonic hedgehog (SHH, 200 ng/ml) and FGF8 (100 ng/ml) were added. At day 7 of differentiation, the media was changed to N2 supplemented with SHH, FGF8 and bFGF (10 ng/ml). At day 11, terminal differentiation was induced by withdrawal of SHH, FGF8 and bFGF and the addition of ascorbic acid (AA, 200 µM) and BDNF (20 ng/ml).

Cells were harvested at day 14-15 with accutase treatment for 45 min, washed once with N2 and incubated with AlexaFluor-647 conjugated anti-SSEA-1 antibody (BD Pharmingen) for 25 mM. Cells were washed once with N2, resuspended in HEPES buffer with 0.1% BSA. DAPI was added to assess viability. FACS was performed with a MoFlo cell sorter and the population of interest was sorted for GFP fluorescence (Nurr1). The population positive for AlexaFluor-647 (SSEA-1) was negatively sorted. For GFP negative control, naïve J1 mouse ES-cells were used at the same differentiation stage.

Nurr1::GFP sorted cells were analyzed for viability and resuspended in N2 with BDN and AA to a final concentration of 55,000 cells/µl. One µl was injected into the lesioned mouse striatum with a 50 µm tipped fine glass capillary at coordinates: 0.3 mm posterior, 1.5 mm lateral from bregma and 2.2 mm ventral to the brain surface. An aliquot of the cell suspension was re-plated in matrigel-coated 6 mm dishes for further characterization.

For immunofluorescence analysis, cells were fixed with paraformaldehyde for 10 min at 40 C, washed twice with PBS, blocked with 5% BSA (0.1% Triton X-100 in PBS) and incubated with primary antibodies for 2 hrs at room temperature: rabbit anti-GFP (1:1000, Invitrogen), mouse IgM anti-PSA (1:2000, 5A5), mouse anti-NeuN (1:800, Chemicon), mouse anti-TH (1:1000, Sigma), goat anti-FoxA2 (1:800, Santa Cruz), goat anti-Engrailed (1:800, Santa Cruz). Cells were then incubated with Cy-conjugated secondary antibodies (1:1000, Jackson).

EndoN treatment: To remove PSA from NCAM, the night before harvesting, cells were treated with 20 units of endoN, a phage enzyme that specifically removes PSA 7-9. Cells were then harvested and injected as described before but were resuspended in N2 with BDNF and AA and 5 units of endoN. We previously assessed that the injection of the same amount of endoN alone into lesioned mice did not improve animal behavior.

PST mRNA and PSA-NCAM analysis in vitro: For Western blot analysis, cells were treated with WB buffer (PBS with 1% NP40, 150 mM NaCl, 1 mM EDTA, and 1× protease/phosphatase inhibitors added immediately before extraction, at pH of 7.4) and sonicated twice for 5 sec, centrifuged and resuspended in Laemli buffer (LB). Aliquots without LB were saved for protein determination. Equal amounts of protein were loaded into 6% sodium dodecyl sulfate-polyacrylamide gel electrophoresis gel (BioRad). Proteins were transferred by electrophoresis onto polyvinylidene membranes (Millipore). The membranes were blocked for 1-6 hr in 0.1% Triton X-100 TBS (TBS-T) with 5% non-fat dry milk and incubated overnight with anti-NCAM antibody (1:10,000, Santa Cruz) in TBS-T with 5% milk. Blots were then incubated with peroxidase-conjugated secondary antibody (1:10,000, Jackson) and detected with ECL detection method (Amersham Pharmacia Biotech). Protein levels were quantified using ImageJ software.

For qRT-PCR analysis, total RNA was extracted with Trizol (Sigma), reverse-transcribed (Qiagen) and amplified with 10 µl of 2×SYBR reaction mixture and 0.2 µM of forward and reverse primers to a final volume of 20 µl. For PSA-NCAM FACS analysis, cells were harvested with accutase treatment for 45 min, washed once and incubated with mouse IgM anti-PSA (1:250, 5A5) for 25 min on ice, washed once with N2 media and incubated with Cy3-conjugated anti-mouse-IgM (1:250, Jackson) for another 25 min on ice. Cells were washed once with N2 and resuspended with 0.1% BSA with 7AAD and analyzed in a FACS Calibur cell sorter. As control, no primary antibody was added.

Immunohistological and stereological procedures: Free floating coronal sections were blocked in 0.1% Triton X-100, 5% donkey serum in PBS for 30 min at room temperature and incubated 48 hrs at 4° C. with different antibodies: rabbit anti-GFP (1:300), chicken anti-GFP (1:200, Chemicon), mouse anti-TH (1:200), mouse IgM anti-PSA (1:1000), mouse anti-NeuN (1:400), goat anti-FoxA2 (1:300), rabbit anti-Girk2 (1:300, Alomone Labs), mouse anti-synapsin (1:200, BD Transduction Laboratories). Sections were then washed and incubated with secondary antibodies: Cy2, Cy3 and Cy5-conjugated donkey antibodies (1:400, Jackson). For PSA a Cy5-conjugated donkey anti-IgM was used (1:500 Jackson). Incubations were performed for 2 hrs at room temperature. Sections were washed twice in PBS and mounted in Mowiol (Calbiochem). One-in-three coronal sections of the brain were analyzed for each immunolabeling. Digital images were collected by a Zeiss LSM 510 laser scanning confocal microscope with three lasers (Argon 488, HeNe 543 and HeNe 633) with a c-Apochromat 40× objective (water-immersion). The number GFP+ and TH+ cells was counted in one-in-three sections encompassing the whole brain under a 40× objective, and the total number of cells/graft estimated. Double-labeled cells were analyzed in single optical planes through the entire z-axis.

For the analysis of the percentage of GFP/TH+ and GFP/FoxA2+ labeled cells, 100 GFP+ cells were analyzed for each marker. For process outgrowth analysis, confocal z-scans were performed at 0.8 µm intervals through the entire z-axis (20-40 µm) with a pinhole of 1 µm under a 40× objective. Sections were scanned from the injection site laterally until no processes were observed. 3-D projections encompassing the whole scanned area were sequentially matched. For GFP and TH intensity analysis, the entire scanned area was divided into five successive 100 µm zones away from the transplant and the intensities were measured using ImageJ software. Data were normalized to the intensity in the zone nearest the graft (zone I) to control for any potential differences in graft size.

Statistical analysis: Data are presented as the mean±standard error of the mean (SEM). Comparisons were performed using Student's t test or two-way analysis of variance (ANOVA) followed by Bonferroni post-hoc test. Linear regression analysis was performed and quantified using the Pearson correlation.

Example XI

The following example shows enzymatic engineering of PSA on hESC-derived DA neurons using the purified bacterial polysialyltransferase, PSTnm, to enhance transplant efficacy.

Although effective, PST gene transfection necessitated genetic modifications of hESCs with limited control over the duration of polysialylation. This example describes the discovery that external PSTnm induced PSA, instead of gene delivery, (see, FIG. 35). In FIG. 35A, PST treated Schwann cells (SC) (green line-middle line) had increased adhesion time while PSTnm-produced PSA inhibited adhesion. In particular, (A) PSTnm-produced PSA inhibits adhesion of Schwann cells in suspension to a Schwann cell monolayer even more effectively (red line-lowest line) than PSA produced by forced PST expression (green line-middle line). (B) PSA immunoblotting in ESC-derived HB9 motoneurons shows that control samples treated with PSTnm alone had undetectable levels of PSA. Incubation with PSTnm+CMP-sialic acid substrate produces a large PSA band, which is removed with endoN treatment. (C, D) Similar to effects obtained with the PST gene, polysialylation of these cells by PSTnm and substrate during differentiation enhances neurite outgrowth and cell migration (arrowheads). (E) PSA immunostaining of day-30 hESC-derived DA neurons. (F) This staining is significantly increased after treatment with PSTnm and substrate. (G) In vivo injection of PSTnm alone has no effect, while its co-administration with substrate (H) produces large amounts of PSA expression in mouse striatum.

Thus mature DA neurons externally treated with PSTnm is contemplated for use in the producing cells for engraftment. Both mammalian PST and PSTnm produced chemically identical chains of PSA. Increased PSA on hESC-derived DA neurons (FIG. 35F) should persist for several weeks, sufficient for DA fibers to exit graft core. Because PSTnm is removed prior to grafting, immunogenicity to this enzyme contaminating the grafted cells should not be factor.

PSTnm was produced from an engineered fragment with enhanced solubility and activity characteristics (Willis et al., Characterization of the alpha-2,8-polysialyltransferase from *Neisseria meningitidis* with synthetic acceptors, and the development of a self-priming polysialyltransferase fusion enzyme. Glycobiology 18, 177-186 (2008)). Cultures of hESC were induced to differentiate into DA neurons before PSTnm exposure, exposure to substrate or both. Cultures were examined at different time-points of exposure (10 min to 6 hrs) by quantitative immunofluorescence (Operetta) and western blotting to determine the speed and levels of polysialylation. Thus, Day 25 differentiated hESC-derived DA neurons will be incubated with the optimum concentrations of PSTnm and substrate using the conditions described herein. PSA+ mDA neurons will be transplanted in short- and long-term assays as described herein and in FIG. 29.

All publications and patents mentioned in the above specification are herein incorporated by reference. Various modifications and variations of the described method and system of the invention will be apparent to those skilled in the art without departing from the scope and spirit of the invention. Although the invention was described in connection with specific preferred embodiments, it should be understood that the invention as claimed should not be unduly limited to such specific embodiments. Indeed, various modifications of the described modes for carrying out the invention that are obvious to those skilled in cellular biology, neurobiology, cancer cell biology, molecular biology, biochemistry, chemistry, organic synthesis, or related fields are intended to be within the scope of the following claims.

The invention claimed is:

1. An in vitro method for differentiating pluripotent stem cells, comprising exposing a plurality of pluripotent stem cells to at least one inhibitor of TGFβ/Activin-Nodal signaling, at least one inhibitor of bone morphogenetic protein (BMP) signaling, at least two activators of Sonic hedgehog (SHH) signaling comprising purmorphamine and SHH C25II, and at least one inhibitor of glycogen synthase kinase 3β (GSK3β) signaling that activates wingless (Wnt) signaling,
   wherein the exposure of the cells to the at least one inhibitor of TGFβ/Activin-Nodal signaling and the at least one inhibitor of BMP signaling begins on day 0,
   wherein said cells are exposed to the at least one inhibitor of GSK3β signaling on the third ($3^{rd}$) day through the eleventh ($11^{th}$) day from the initial exposure of the cells to the at least one inhibitor of TGFβ/Activin-Nodal signaling and the at least one inhibitor of BMP signaling, and
   wherein said cells are exposed to the at least one inhibitor of TGFβ/Activin-Nodal signaling, the at least one inhibitor of BMP signaling, the at least two activators of SHH signaling, and the at least one inhibitor of GSK3β signaling in amounts effective to produce a cell population comprising at least about 10% differentiated cells expressing both forkhead box protein A2 (FOXA2) and LIM homeobox transcription factor 1 alpha (LMX1A).

2. The method of claim 1, wherein the initial exposure of the cells to the at least two activators of SHH signaling is between about 24 hours and about 36 hours from the initial exposure of the cells to the at least one inhibitor of TGFβ/Activin-Nodal signaling and the at least one inhibitor of BMP signaling.

3. The method of claim 1, wherein the exposure of the cells to the at least one inhibitor of GSK3β signaling is initiated between about 24 hours and about 36 hours from the initial exposure of the cells to the at least two activators of SHE signaling.

4. The method of claim 1, wherein said cell population comprises at least about 40% cells expressing FOXA and LMX1A.

5. The method of claim 1, wherein the pluripotent stem cells are selected from the group consisting of human, nonhuman primate or rodent embryonic stem cells, induced pluripotent stem cells and engineered pluripotent stem cells.

6. The method of claim 1, wherein the at least one inhibitor of TGFβ/Activin-Nodal signaling comprises 4-[4-(1,3-benzodioxol-5-yl)-5-(2-pyridinyl)-1H-imidazol-2-yl]benzamide (SB431542).

7. The method of claim 1, wherein the at least one inhibitor of GSK3β signaling comprises CHIR99021.

8. The method of claim 1, wherein the pluripotent stem cells:
   (a) are differentiated into cells that express both FOXA2 and LMX1A within about 11 days from the initial exposure of the cells to the at least one inhibitor of TGFβ/Activin-Nodal signaling; or
(b) are differentiated into dopamine neurons no later than 25 days from the initial exposure of the cells to the at least one inhibitor of TGFβ/Activin-Nodal signaling.

9. The method of claim 1, wherein
(a) the at least one inhibitor of TGFβ/Activin-Nodal signaling and the at least one inhibitor of BMP signaling are selected from the group consisting of LDN-193189, SB431542, Noggin, dorsomorphin, and combinations of two or more of the foregoing; and
(b) the at least two activators of SHH signaling are selected from the group consisting of recombinant SHH, purified SHH, Smoothened agonists (SAG), and combinations of two or more of the foregoing.

10. The method of claim 1, wherein the differentiated cells expressing FOXA2 and LMX1A do not express at least one marker selected from the group consisting of PAX6, HES5, EMX2 and LHX2.

11. The method of claim 1, comprising exposing the cells to an effective concentration of fibroblast growth factor 8 (FGF8) for up to about 144 hours from the initial exposure of the cells to the at least one inhibitor of TGFβ/Activin-Nodal signaling.

12. The method of claim 1, wherein said differentiated cells expressing FOXA2 and LMX1A are midbrain floor plate precursors.

13. The method of claim 1, wherein said cell population comprises at least about 50% differentiated cells expressing FOXA2 and LMX1A.

14. The method of claim 1, wherein said cell population comprises at least about 70% differentiated cells expressing FOXA2 and LMX1A.

* * * * *